US012698317B2

(12) United States Patent
Yu et al.

(10) Patent No.: US 12,698,317 B2
(45) Date of Patent: *Aug. 4, 2026

(54) MANUFACTURING PROCESS FOR MAKING T CELLS EXPRESSING CHIMERIC ANTIGEN RECEPTORS

(71) Applicant: CRISPR Therapeutics AG, Zug (CH)

(72) Inventors: Hui Yu, Cambridge, MA (US); Demetrios Kalaitzidis, Cambridge, MA (US); Siyuan Tan, Cambridge, MA (US)

(73) Assignee: CRISPR Therapeutics AG, Zug (CH)

( * ) Notice: Subject to any disclaimer, the term of this patent is extended or adjusted under 35 U.S.C. 154(b) by 185 days.

This patent is subject to a terminal disclaimer.

(21) Appl. No.: 17/098,212

(22) Filed: Nov. 13, 2020

(65) Prior Publication Data

US 2021/0139850 A1 May 13, 2021

Related U.S. Application Data

(60) Provisional application No. 62/934,991, filed on Nov. 13, 2019.

(51) Int. Cl.

| | |
|---|---|
| *C07K 14/705* | (2006.01) |
| *A61K 40/11* | (2025.01) |
| *A61K 40/31* | (2025.01) |
| *A61K 40/42* | (2025.01) |
| *C07K 16/28* | (2006.01) |
| *C07K 16/40* | (2006.01) |
| *C12N 5/0783* | (2010.01) |
| *C12N 9/22* | (2006.01) |
| *C12N 15/11* | (2006.01) |
| *C12N 15/90* | (2006.01) |

(52) U.S. Cl.
CPC ........ *C07K 14/70521* (2013.01); *A61K 40/11* (2025.01); *A61K 40/31* (2025.01); *A61K 40/4211* (2025.01); *A61K 40/4215* (2025.01); *C07K 14/70517* (2013.01); *C07K 14/70578* (2013.01); *C07K 16/2878* (2013.01); *C07K 16/40* (2013.01); *C12N 5/0636* (2013.01); *C12N 9/22* (2013.01); *C12N 15/11* (2013.01); *C12N 15/907* (2013.01); *A61K 2239/48* (2023.05); *C07K 2317/622* (2013.01); *C07K 2319/03* (2013.01); *C12N 2310/20* (2017.05); *C12N 2501/515* (2013.01); *C12N 2501/599* (2013.01); *C12N 2510/00* (2013.01)

(58) Field of Classification Search
CPC .................. C12N 5/0636; C12N 15/11; C12N 2501/515; C12N 2510/00; C07K 14/70517; C07K 2317/622
See application file for complete search history.

(56) References Cited

U.S. PATENT DOCUMENTS

| | | | |
|---|---|---|---|
| 7,083,785 | B2 | 8/2006 | Browning et al. |
| 7,435,596 | B2 | 10/2008 | Campana et al. |
| 7,446,179 | B2 | 11/2008 | Jensen et al. |
| 7,446,190 | B2 | 11/2008 | Sadelain et al. |
| 7,452,981 | B2 | 11/2008 | Wijdenes et al. |
| 7,491,390 | B2 | 2/2009 | Law et al. |
| 7,641,903 | B2 | 1/2010 | Law et al. |
| 7,662,387 | B2 | 2/2010 | Law et al. |
| 7,700,739 | B2 | 4/2010 | Lacy et al. |
| 7,741,465 | B1 | 6/2010 | Eshhar et al. |
| 7,771,720 | B2 | 8/2010 | Staunton et al. |
| 7,786,282 | B2 | 8/2010 | Prussak et al. |
| 7,888,121 | B2 | 2/2011 | Umov et al. |
| 8,067,546 | B2 | 11/2011 | McDonagh et al. |
| 8,124,738 | B2 | 2/2012 | Terret et al. |
| 8,337,838 | B2 | 12/2012 | Law et al. |
| 8,440,806 | B2 | 5/2013 | Wijdenes et al. |
| 8,535,678 | B2 | 9/2013 | Law et al. |
| 8,562,987 | B2 | 10/2013 | McDonagh et al. |
| 8,609,104 | B2 | 12/2013 | Law et al. |
| 8,629,257 | B2 | 1/2014 | Lacy et al. |
| 8,647,624 | B2 | 2/2014 | Law et al. |
| 8,663,642 | B2 | 3/2014 | Law et al. |
| 8,673,304 | B2 | 3/2014 | Wijdenes et al. |
| 8,697,359 | B1 * | 4/2014 | Zhang .................... C12N 15/85 435/6.13 |
| 8,834,882 | B2 | 9/2014 | Silence et al. |
| 8,871,908 | B2 | 10/2014 | Liu et al. |

(Continued)

FOREIGN PATENT DOCUMENTS

| | | |
|---|---|---|
| AU | 2014351557 A1 | 5/2016 |
| CN | 104910278 A | 9/2015 |

(Continued)

OTHER PUBLICATIONS

Abdelhakim et al., Role of αβ T cell depletion in Prevention of Graft versus Host Disease, Biomedicines, 2017, vol. 5, Issue 3, pp. 1-14 (Year: 2017).*
Graham et al., Allogenic CAR-T Cells: More than Ease of Access?, 2018, Cells, vol. 7, Issue 10, pp. 1-11 (Year: 2018).*
Rupp et al., CRISPR/Cas9-mediated PD-1 disruption enhances anti-tumor efficacy of human chimeric antigen receptor T cells, 2017, Nature Scientific Reports, vol. 7, Issue 737, pp. 1-10 (Year: 2017).*
Tey et al., Inducible caspase 9 suicide gene to improve the safety of allodepleted T cells after haploidentical stem cell transplantation, 2007, Biology of Blood and Marrow Transplantation, vol. 13, Issue 8, pp. 1-22 (Year: 2007).*

(Continued)

*Primary Examiner* — Jeffrey Stucker
*Assistant Examiner* — Brittney E Donoghue
(74) *Attorney, Agent, or Firm* — Casimir Jones, S.C.; J. Mitchell Jones

(57) ABSTRACT

Aspects of the present disclosure relate to methods for manufacturing genetically engineered T cells expressing a chimeric antigen receptor (CAR) that provide several improvements over conventional manufacturing methods, thereby enabling production of a robust supply of clinically useful CAR T-cell therapies.

40 Claims, 54 Drawing Sheets

Specification includes a Sequence Listing.

(56) References Cited

U.S. PATENT DOCUMENTS

| | | | |
|---|---|---|---|
| 8,956,828 B2 | 2/2015 | Bonini et al. | |
| 9,023,999 B2 | 5/2015 | Mori et al. | |
| 9,051,372 B2 | 6/2015 | Law et al. | |
| 9,102,737 B2 | 8/2015 | Chen et al. | |
| 9,120,854 B2 | 9/2015 | Ryan et al. | |
| 9,169,325 B2 | 10/2015 | Keler et al. | |
| 9,382,319 B2 | 7/2016 | Tso et al. | |
| 9,399,074 B2 | 7/2016 | Liu et al. | |
| 9,403,914 B2 | 8/2016 | Kubota | |
| 9,428,585 B2 | 8/2016 | McDonagh et al. | |
| 9,701,752 B2 | 7/2017 | McDonagh et al. | |
| 9,758,581 B2 | 9/2017 | Wijdenes et al. | |
| 9,765,148 B2 | 9/2017 | Silence et al. | |
| 9,765,149 B2 | 9/2017 | Silence et al. | |
| 9,889,160 B2 | 2/2018 | Jantz et al. | |
| 9,937,207 B2 | 4/2018 | Gregory et al. | |
| 10,166,255 B2 | 1/2019 | Moriarity et al. | |
| 10,266,850 B2 * | 4/2019 | Doudna | C12N 15/907 |
| 10,442,849 B2 | 10/2019 | Baeuerle et al. | |
| 10,584,352 B2 | 3/2020 | Duchateau et al. | |
| 10,729,725 B2 | 8/2020 | Terrett et al. | |
| 10,736,919 B2 | 8/2020 | Terrett et al. | |
| 10,857,184 B2 | 12/2020 | Terrett et al. | |
| 10,881,689 B2 | 1/2021 | Terrett et al. | |
| 2006/0051346 A1 | 3/2006 | Wijdenes | |
| 2008/0138343 A1 | 6/2008 | Law et al. | |
| 2009/0081239 A1 | 3/2009 | Staunton et al. | |
| 2009/0148942 A1 | 6/2009 | McDonagh et al. | |
| 2009/0208496 A1 | 8/2009 | Wijdenes et al. | |
| 2010/0129362 A1 | 5/2010 | Law et al. | |
| 2012/0034159 A1 | 2/2012 | Kindsvogel | |
| 2012/0045436 A1 | 2/2012 | McDonagh et al. | |
| 2012/0213771 A1 | 8/2012 | Keler et al. | |
| 2012/0294863 A1 | 11/2012 | Law et al. | |
| 2013/0039911 A1 | 2/2013 | Bedi et al. | |
| 2013/0122020 A1 | 5/2013 | Liu et al. | |
| 2013/0138586 A1 | 5/2013 | Jung et al. | |
| 2013/0287748 A1 | 10/2013 | June et al. | |
| 2014/0105915 A1 | 4/2014 | Algate et al. | |
| 2014/0112942 A1 | 4/2014 | Van Eenennaam et al. | |
| 2014/0178936 A1 | 6/2014 | McDonagh et al. | |
| 2014/0220008 A1 | 8/2014 | Wijdenes et al. | |
| 2014/0242700 A1 * | 8/2014 | Zhang | C12N 15/85 |
| | | | 435/325 |
| 2014/0349402 A1 | 11/2014 | Cooper et al. | |
| 2014/0357844 A1 | 12/2014 | Liu et al. | |
| 2015/0176013 A1 | 6/2015 | Musunuru et al. | |
| 2015/0266963 A1 | 9/2015 | Silence et al. | |
| 2015/0284467 A1 | 10/2015 | Lipp et al. | |
| 2015/0337047 A1 | 11/2015 | Keler et al. | |
| 2015/0368351 A1 | 12/2015 | Vu et al. | |
| 2016/0046724 A1 | 2/2016 | Brogdon et al. | |
| 2016/0289675 A1 | 10/2016 | Ryan et al. | |
| 2017/0022282 A1 | 1/2017 | McDonagh et al. | |
| 2017/0107286 A1 * | 4/2017 | Kochenderfer | C07K 14/70578 |
| 2017/0157176 A1 | 6/2017 | Wang et al. | |
| 2017/0173080 A1 | 6/2017 | Lee et al. | |
| 2017/0183418 A1 | 6/2017 | Galetto | |
| 2017/0226216 A1 | 8/2017 | Morgan et al. | |
| 2017/0233484 A1 | 8/2017 | Sussman et al. | |
| 2017/0267771 A1 | 9/2017 | Van Eenennaam et al. | |
| 2017/0281766 A1 | 10/2017 | Wiltzius | |
| 2017/0313759 A1 | 11/2017 | Batuwangala | |
| 2017/0320957 A1 | 11/2017 | Chen et al. | |
| 2017/0335281 A1 | 11/2017 | Loew et al. | |
| 2017/0342157 A1 | 11/2017 | McDonagh et al. | |
| 2017/0355776 A1 | 12/2017 | Xiao et al. | |
| 2017/0362297 A1 | 12/2017 | Marasco | |
| 2017/0369581 A9 | 12/2017 | Silence et al. | |
| 2018/0002435 A1 | 1/2018 | Sasu et al. | |
| 2018/0186878 A1 | 7/2018 | Rosenthal | |
| 2018/0201901 A1 | 7/2018 | Duchateau et al. | |
| 2018/0318435 A1 | 11/2018 | Pastan et al. | |
| 2018/0325955 A1 | 11/2018 | Terrett et al. | |
| 2019/0032049 A1 * | 1/2019 | Naldini | C12N 15/113 |
| 2019/0048060 A1 * | 2/2019 | Conway | C12N 15/907 |
| 2019/0136230 A1 * | 5/2019 | Sather | C12N 15/11 |
| 2019/0233528 A1 | 8/2019 | Srinivasan et al. | |
| 2019/0247433 A1 * | 8/2019 | Kalra | A61K 35/17 |
| 2019/0314413 A1 | 10/2019 | Terrett et al. | |
| 2019/0314414 A1 | 10/2019 | Terrett et al. | |
| 2019/0365808 A1 | 12/2019 | Terrett et al. | |
| 2019/0365809 A1 | 12/2019 | Terrett et al. | |
| 2020/0330518 A1 | 10/2020 | Terrett et al. | |
| 2020/0405761 A1 | 12/2020 | Terrett et al. | |
| 2020/0405764 A1 | 12/2020 | Terrett et al. | |

FOREIGN PATENT DOCUMENTS

| | | | | |
|---|---|---|---|---|
| CN | 106544321 A | 3/2017 | | |
| CN | 108192927 A * | 6/2018 | | A01K 67/0275 |
| CN | 109790517 A | 5/2019 | | |
| JP | 2015531242 A | 11/2015 | | |
| WO | WO 2004/073656 A2 | 9/2004 | | |
| WO | WO 2006/060878 A1 | 6/2006 | | |
| WO | WO 2006/113909 A2 | 10/2006 | | |
| WO | WO 2008/121420 A1 | 10/2008 | | |
| WO | WO 2011/059836 A2 | 5/2011 | | |
| WO | WO 2011/130434 A2 | 10/2011 | | |
| WO | WO 2012/004367 A1 | 1/2012 | | |
| WO | WO 2012/058460 A2 | 5/2012 | | |
| WO | WO 2012/079000 A1 | 6/2012 | | |
| WO | WO 2013/074916 A1 | 5/2013 | | |
| WO | WO 2013/138586 A1 | 9/2013 | | |
| WO | WO 2013/154760 A1 | 10/2013 | | |
| WO | WO 2013/176915 A1 | 11/2013 | | |
| WO | WO 2014/068079 A1 | 5/2014 | | |
| WO | WO 2014/122143 A1 | 8/2014 | | |
| WO | WO 2014/140374 A2 | 9/2014 | | |
| WO | WO 2014/158821 A1 | 10/2014 | | |
| WO | WO 2014/165119 A1 | 10/2014 | | |
| WO | WO 2014/165825 A2 | 10/2014 | | |
| WO | WO 2014/191128 A1 | 12/2014 | | |
| WO | WO 2015/120096 A2 | 8/2015 | | |
| WO | WO 2015/121454 A1 | 8/2015 | | |
| WO | WO 2015/134877 A1 | 9/2015 | | |
| WO | WO 2015/136001 A1 | 9/2015 | | |
| WO | WO 2015/158671 A1 | 10/2015 | | |
| WO | WO 2015/161276 A2 | 10/2015 | | |
| WO | WO 2015/164594 A1 | 10/2015 | | |
| WO | WO 2015/187528 A1 | 12/2015 | | |
| WO | WO 2015/188056 A1 | 12/2015 | | |
| WO | WO 2016/014789 A2 | 1/2016 | | |
| WO | WO 2016/025454 A2 | 2/2016 | | |
| WO | WO 2016/063264 A1 | 4/2016 | | |
| WO | WO 2016/069282 A1 | 5/2016 | | |
| WO | WO 2016/069283 A1 | 5/2016 | | |
| WO | WO 2016/073955 A2 | 5/2016 | | |
| WO | WO 2016/090320 A1 | 6/2016 | | |
| WO | WO 2016/094304 A2 | 6/2016 | | |
| WO | WO 2016/100985 A2 | 6/2016 | | |
| WO | WO-2016115179 A1 * | 7/2016 | | C12M 35/00 |
| WO | WO 2016/120216 A1 | 8/2016 | | |
| WO | WO 2016/151315 A1 | 9/2016 | | |
| WO | WO 2016/160721 A1 | 10/2016 | | |
| WO | WO 2016/164356 A1 | 10/2016 | | |
| WO | WO 2016/174652 A1 | 11/2016 | | |
| WO | WO 2016/183041 A2 | 11/2016 | | |
| WO | WO 2017/058850 A1 | 4/2017 | | |
| WO | WO 2017/062451 A1 | 4/2017 | | |
| WO | WO 2017/070429 A1 | 4/2017 | | |
| WO | WO 2017/075537 A1 | 5/2017 | | |
| WO | WO 2017/083511 A1 | 5/2017 | | |
| WO | WO 2017/093969 A1 | 6/2017 | | |
| WO | WO 2017/100176 A1 | 6/2017 | | |
| WO | WO 2017/106528 A1 | 6/2017 | | |
| WO | WO 2017/112859 A2 | 6/2017 | | |
| WO | WO 2017/130223 A1 | 8/2017 | | |
| WO | WO 2017/143069 A1 | 8/2017 | | |
| WO | WO 2017/149515 A1 | 9/2017 | | |
| WO | WO 2017/156484 A1 | 9/2017 | | |
| WO | WO 2017/177137 A1 | 10/2017 | | |
| WO | WO 2017/180993 A1 | 10/2017 | | |
| WO | WO 2017/186928 A1 | 11/2017 | | |

(56) References Cited

FOREIGN PATENT DOCUMENTS

| WO | WO 2017/189959 A1 | 11/2017 | | |
|----|----|----|----|----|
| WO | WO 2017/193107 A2 | 11/2017 | | |
| WO | WO 2017/210617 A2 | 12/2017 | | |
| WO | WO 2017/211900 A1 | 12/2017 | | |
| WO | WO 2017/222593 A1 | 12/2017 | | |
| WO | WO-2017222398 A1 * | 12/2017 | ........... | A61K 31/196 |
| WO | WO 2018/068257 A1 | 4/2018 | | |
| WO | WO 2018/073391 A2 | 4/2018 | | |
| WO | WO 2018/073393 A2 | 4/2018 | | |
| WO | WO 2018/115887 A1 | 6/2018 | | |
| WO | WO 2018/132479 A1 | 7/2018 | | |
| WO | WO-2018157072 A1 * | 8/2018 | ........... | C12N 5/0031 |
| WO | WO 2019/097305 A2 | 5/2019 | | |
| WO | WO 2019/152742 A1 | 8/2019 | | |
| WO | WO 2019/215500 A1 | 11/2019 | | |

OTHER PUBLICATIONS

Life Technologies, Dynabeads Human T-Activator CD3/CD28, 2011, pp. 1-2 (Retrieved from: https://assets.fishersci.com/TFS-Assets/LSG/manuals/11131D_32D_61D.pdf) (Year: 2011).*

Coeshott et al., Large-scale expansion and characterization of CD3+ T-cells in the Quantum Cell Expansion System, 2019, Journal of Translational Medicine, vol. 17, Issue 258, pp. 1-13 (Year: 2019).*

Ling et al., High-Efficiency Transduction of Primary Human Hematopoietic Stem/Progenitor Cells by AAV6 Vectors: Strategies for Overcoming Donor-Variation and Implications in Genome Editing, 2016, Nature Scientific Reports, vol. 6, Article 35495, pp. 1-8 (Year: 2016).*

Stemcell Technologies, Optimization of Human T Cell Expansion Protocol: Effects of Early Cell Dilution, 2018, Version 1.0.0 (Retrieved from: https://www.stemcell.com/optimization-of-human-t-cell-expansion-protocol-effects-of-early-cell-dilution.html) (Year: 2018).*

Mali et al., RNA-Guided Human Genome Engineering via Cas9, 2013, Science, vol. 339, pp. 823-826 (Year: 2013).*

Hendel et al., Chemically modified guide RNAs enhance CRISPR-Cas genome editing in human primary cells, 2015, Nature Biotechnology, vol. 33, No. 9, pp. 985-991 (Year: 2015).*

Medarex, 2007, Retrieved from: https://pipelinereview.com/index.php/2007041811096/Antibodies/Medarex-Presents-Preclinical-Data-Demonstrating-Potent-Anti-Tumor-Activity-of-Anti-CD19-and-Anti-CD70-Antibody-Drug-Conjugates-in-Cancer-Animal-Models.html (Year: 2007).*

Wang and Riviere, Clinical manufacturing of CAR T cells: foundation of a promising therapy, 2016, Molecular Therapy Oncolytics, vol. 3, pp. 1-8 (Year: 2016).*

Whisenant et al., The Activation-Induced Assembly of an RNA/Protein Interactome Centered on the Splicing Factor U2AF2 Regulates Gene Expression in Human CD4 T Cells, 2015, PLos ONE, Issue 10(12), pp. 1-3 (Year: 2015).*

Varshney et al., High-throughput gene targeting and phenotyping in zebrafish using CRIPSR/Cas9, 2015, Genome Research, vol. 25, pp. 1030-1042 (Year: 2015).*

Kumar et al., The CRISPR-Cas system for plant genome editing: advances and opportunities, 2015, Journal of Experimental Botany, vol. 66, No. 1, pp. 47-57 (Year: 2015).*

Ren et al., Multiplex Genome Editing to Generate Universal CAR T Cells Resistant to PD1 Inhibition, 2017, Clinical Cancer Research, vol. 23, Issue 9, pp. 2255-2266 (Year: 2017).*

Behr et al., In vivo delivery of CRISPR-Cas9 therapeutics: Progress and challenges, 2021, Chinese Pharmaceutical Association, vol. 11, Issue 8, pp. 2150-2171 (Year: 2021).*

Innovative Genomics Institute (IGI), Ribonucleoprotein complex (RNP), 2017, ages 1-4, retrieved from: https://innovativegenomics.org/glossary/ribonucleoprotein-complex-rnp/ (Year: 2017).*

Vocabulary, introduce, 2016, pp. 1-5, retrieved from: https://www.vocabulary.com/dictionary/introduce (Year: 2016).*

Thompson et al., The future of multiplexed eukaryotic genome engineering, 2018, ACS Chem Biol., vol. 13, Issue 2, pp. 313-325 (Year: 2018).*

Dai et al., One-step generation of modular CAR-T cells with AAV-Cpf1, 2019, Nature Methods, vol. 16, pp. 247-254 (Year: 2019).*

Eyquem et al., Targeting a CAR to the TRAC locus with CRISPR/Cas9 enhances tumour rejection. Nature. Mar. 2, 2017;543(7643):113-117. Epub Feb. 22, 2017.

Fraiietta et al., Determinants of response and resistance to CD19 chimeric antigen receptor (CAR) T cell therapy of chronic lymphocytic leukemia. Nature Medicine. 2018;24(5):563-71.

Jaspers et al., Development of Car T cells designed to improve antitumor efficacy and safety. Pharmacol Ther. Oct. 2017; 178:83-91. Epub Mar. 22, 2017.

Liu et al., CRISPR-Cas9-mediated multiplex gene editing in CAR-T cells. Cell Res. Jan. 2017;27(1):154-157. Epub Dec. 2, 2016.

MacLeod et al., Integration of a CD19 CAR into the TCR alpha chain locus streamlines production of alleogenic gene-edited CAR T cells. Molecular Therapy. 2017;25(4):949-61.

Maude et al., Chimeric antigen receptor T cells for sustained remissions in leukemia. The New England Journal of Medicine. 2014;371:1507-17.

Osborn et al., Evaluation of TCR gene editing achieved by TALENs, CRISPR/Cas9, and megaTAL nucleases. Molecular Therapy. 2016;24(3):570-81.

Poirot et al., Multiplex genome-edited T-cell manufacturing platform for "off-the-shelf" adoptive T-cell immunotherapies. Cancer Research. 2015;75(18):3853-64.

Ren et al., A versatile system for rapid multiplex genome-edited CAR T cell generation. Oncotarget. 2017;8 (10):17002-11.

Ren et al., Advancing chimeric antigen receptor T cell therapy with CRISPR/Cas9. Protein Cell. Sep. 2017;8(9):634-643. Epub Apr. 22, 2017.

Ren et al., Multiplex Genome Editing to Generate Universal CAR T Cells Resistant to PD1 Inhibition. Clin Cancer Res. May 1, 2017;23(9):2255-2266. Epub Nov. 4, 2016.

Torikai et al., A foundation for universal T-cell based immunotherapy: T cells engineered to express a CD19-specific chimeric-antigen-receptor and eliminate expression of endogenous TCR. Blood. Jun. 14, 2012;119(24):5697-705. Epub Apr. 24, 2012. Erratum in: Blood. Nov. 26, 2015;126(22):2527. Rabinovitch, Brian [corrected to Rabinovich, Brian].

Zah et al., T Cells Expressing CD19/CD20 Bispecific Chimeric Antigen Receptors Prevent Antigen Escape by Malignant B Cells. Cancer Immunol Res. Jun. 2016;4(6):498-508. doi: 10.1158/2326-6066.CIR-15-0231. Epub Apr. 8, 2016.

Lee et al., 323. Efficient Generation of CART Cells by Homology Directed Transgene Integration into the TCR-Alpha Locus. Mol Ther. May 2016;24(Supplement 1):S130. 1 page.

MacLeod et al., Generation of a Novel Allogeneic CAR T Cell Platform Utilizing an Engineered Meganuclease and AAV Donor Template to Achieve Efficient Disruption of T Cell Receptor Expression and Simultaneous Homology-Directed Insertion of a CD19 CAR. Mol Ther. May 2016;24(Supplement 1): S156. 1 page.

Rosenberg et al., Clinical Trial No. NCT00924326 "CAR T Cell Receptor Immunotherapy for Patients with B-cell Lymphoma". Sep. 22, 2018. 15 pages.

International Search Report and Written Opinion for International Application No. PCT/IB2020/060723, mailed Jan. 18, 2021, 9 Pages.

* cited by examiner

B2M(-)

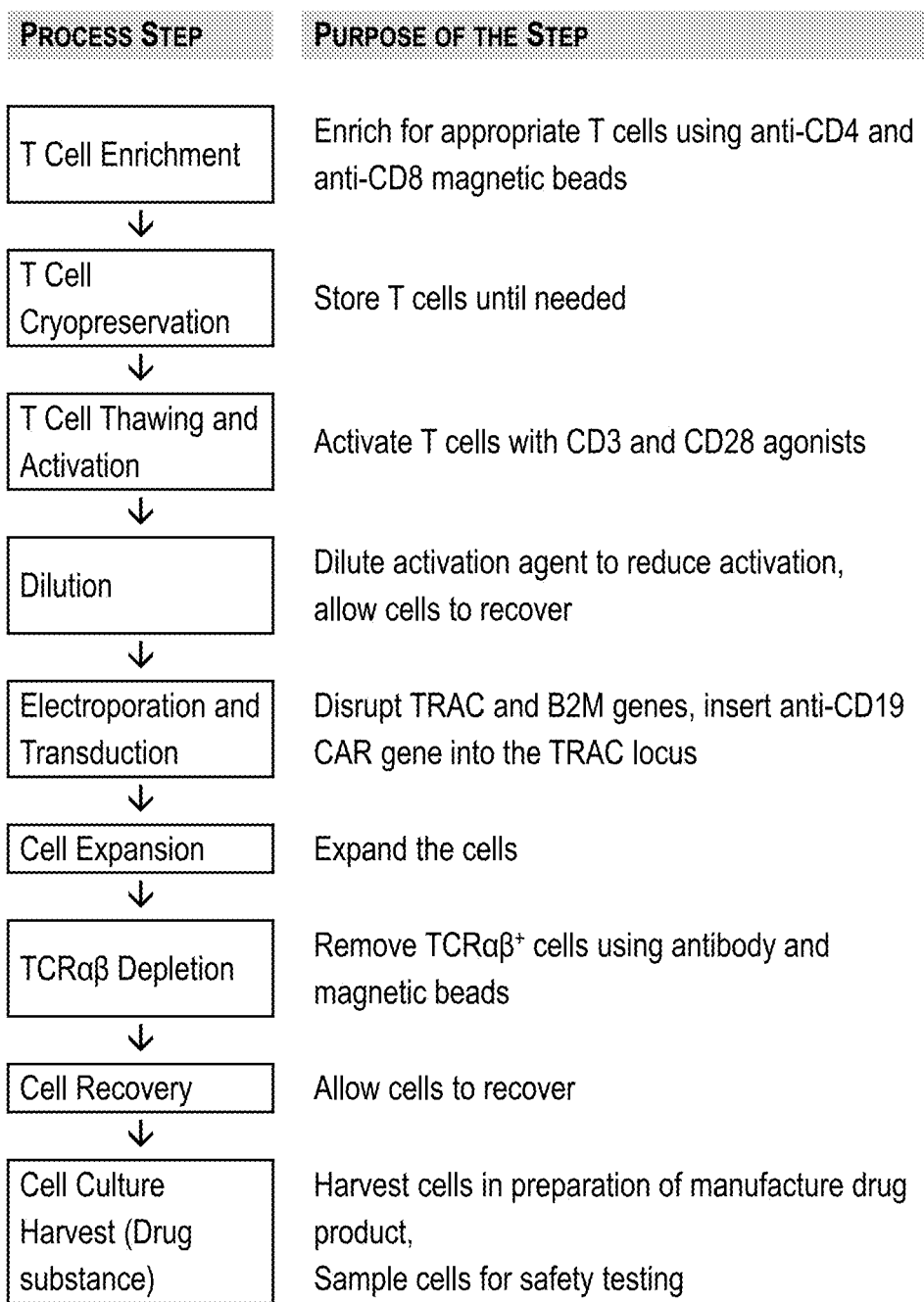

| PROCESS STEP | PURPOSE OF THE STEP |
|---|---|
| T Cell Enrichment | Enrich for appropriate T cells using anti-CD4 and anti-CD8 magnetic beads |
| T Cell Cryopreservation | Store T cells until needed |
| T Cell Thawing and Activation | Activate T cells with CD3 and CD28 agonists |
| Dilution | Dilute activation agent to reduce activation, allow cells to recover |
| Electroporation and Transduction | Disrupt TRAC and B2M genes, insert anti-CD19 CAR gene into the TRAC locus |
| Cell Expansion | Expand the cells |
| TCRαβ Depletion | Remove TCRαβ⁺ cells using antibody and magnetic beads |
| Cell Recovery | Allow cells to recover |
| Cell Culture Harvest (Drug substance) | Harvest cells in preparation of manufacture drug product, Sample cells for safety testing |

FIG. 7A

TCRαβ-     β2M-     DKO

TA-1 sgRNA (ug/mL)

TCRαβ-     β2M-     DKO

B2M-1 sgRNA (ug/mL)

CAR+%

TRAC-%

CTX110 CAR-T Cytotoxicity (24hr) in Raji Cells

- ◆ CTX110 reference
- ✳ CTX110 Day 5 replated
- ✳ CTX110 Day 6 replated
- ◆ CTX110 Day 7 replated
- ▲ CTX110 Positive Control

CTX110 CAR-T Cytotoxicity (24hr) in Raji Cells (plate 1)

- ◆ A. Day 7 – Unreplated CTX110
- ◆ B. UT control
- ✳ C. Day 3 – Replated CTX110
- ◆ D. Day 4 – Replated CTX110
- ✳ E. Day 5 – Replated CTX110
- ◆ F. Day 6 – Replated CTX110
- ✳ G. Day 7 – Replated CTX110
- CTX110 control_LF

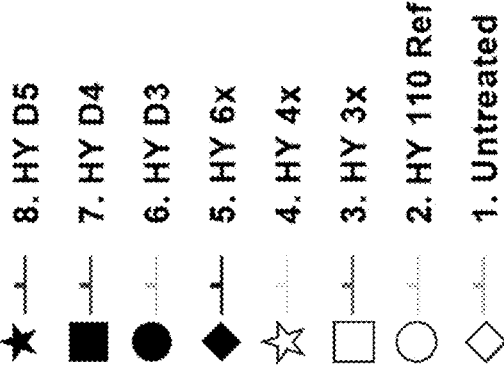
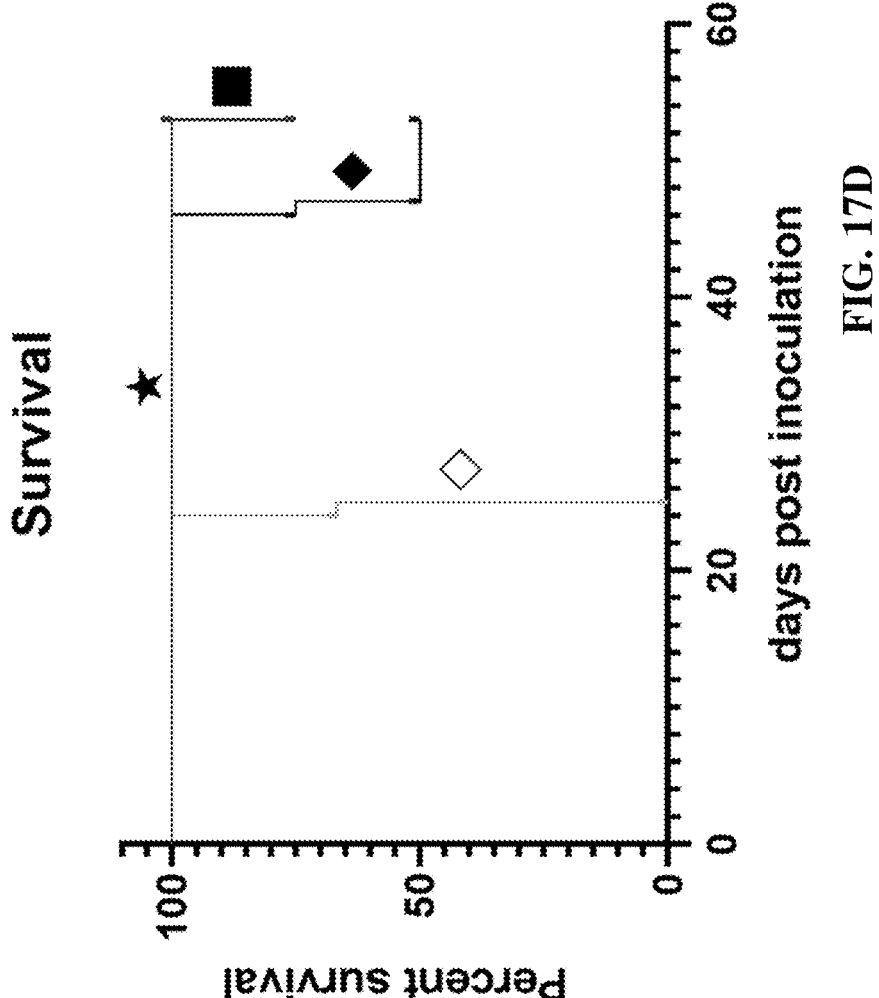
FIG. 17D

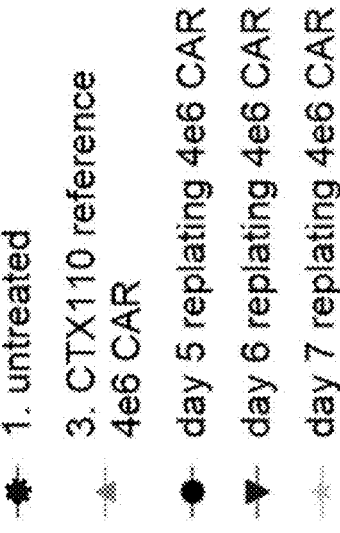
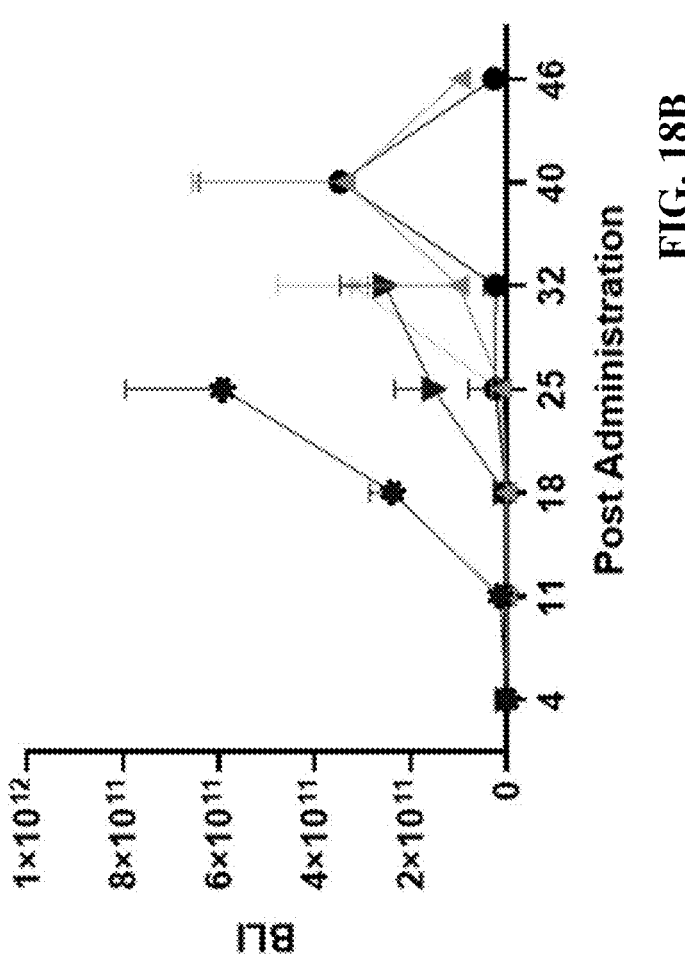
FIG. 18B

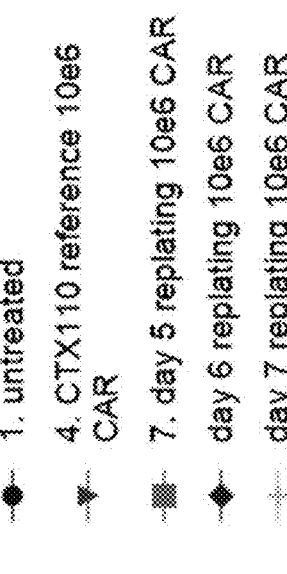
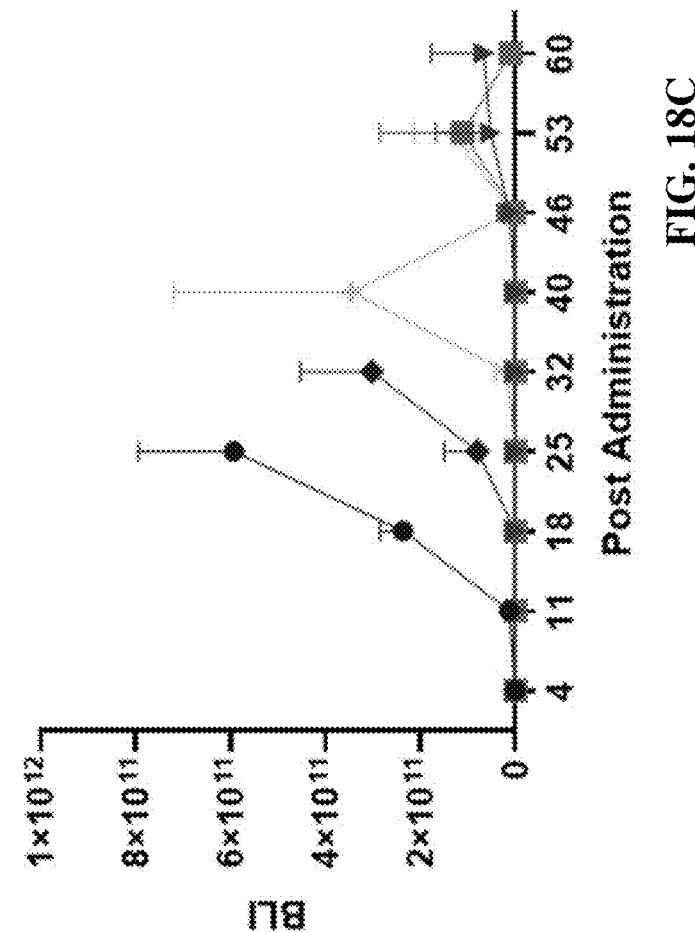
FIG. 18C

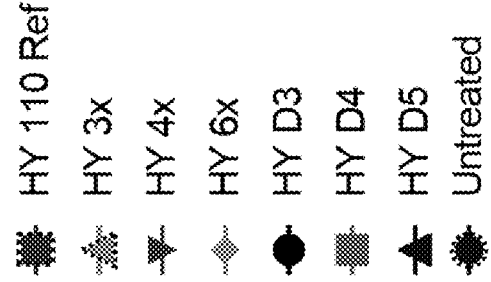
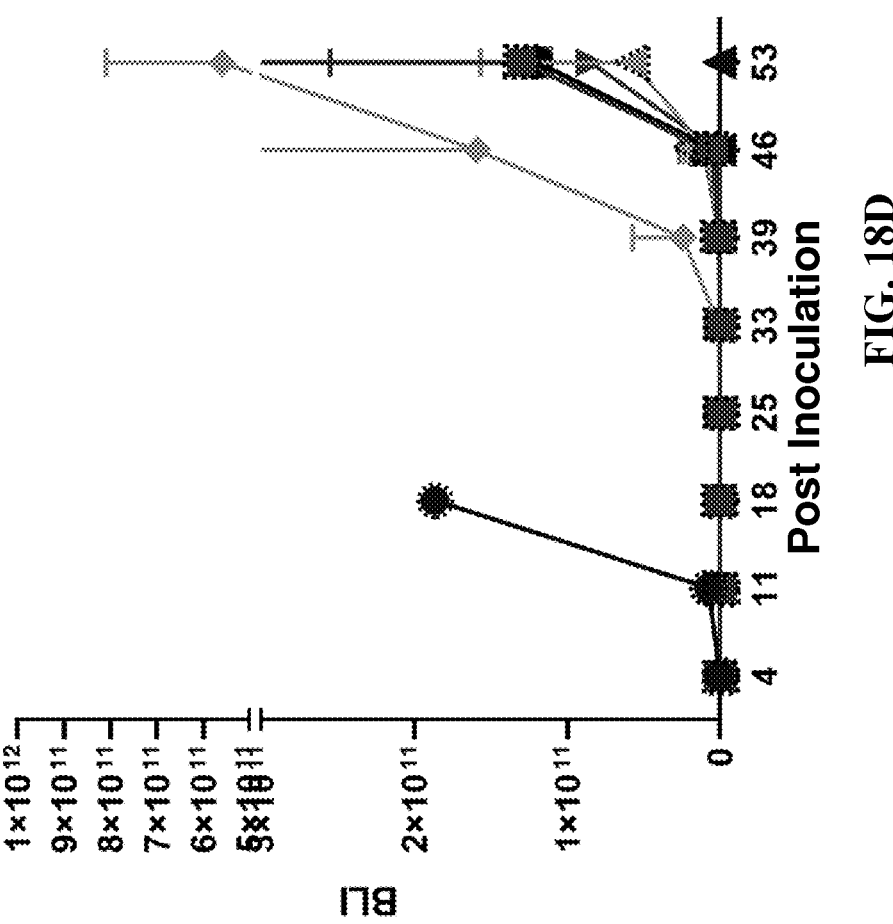
FIG. 18D

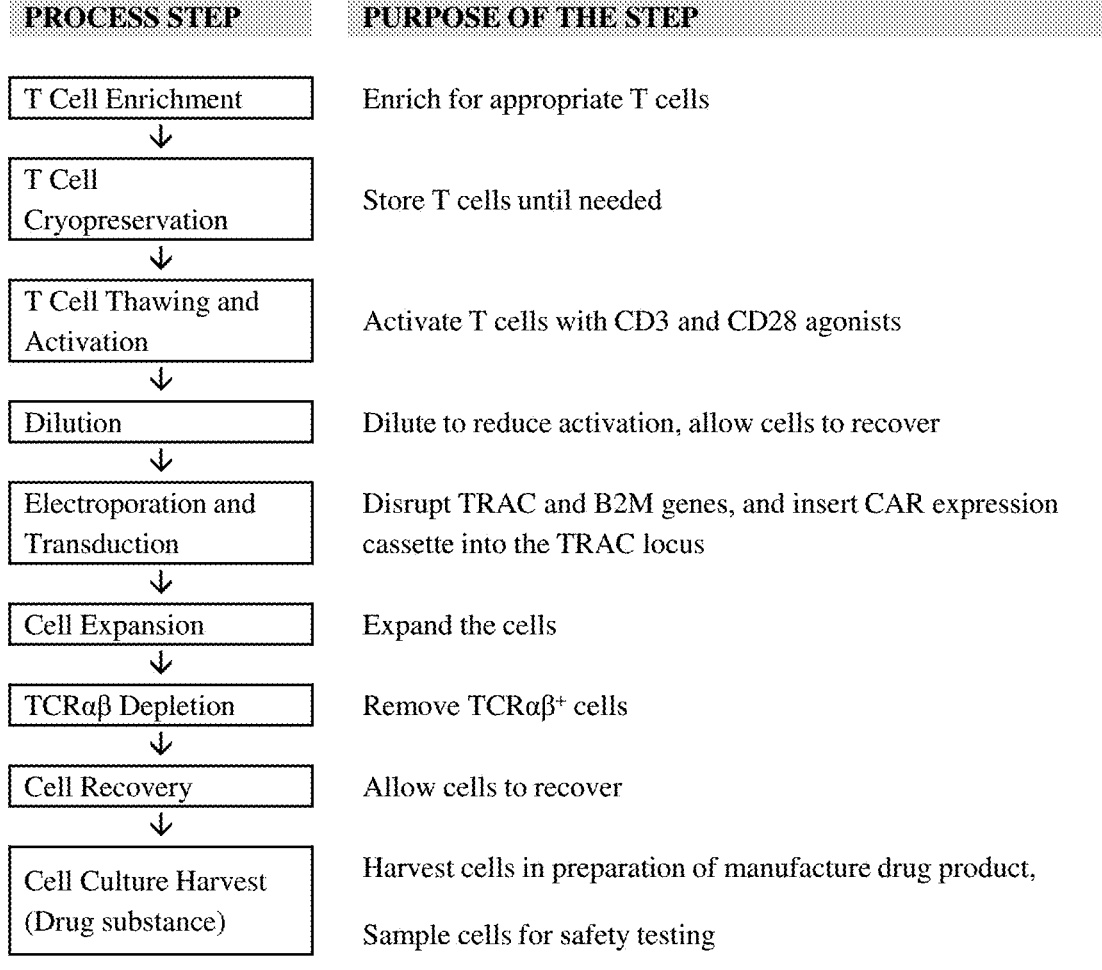

| PROCESS STEP | PURPOSE OF THE STEP |
|---|---|
| T Cell Enrichment | Enrich for appropriate T cells |
| T Cell Cryopreservation | Store T cells until needed |
| T Cell Thawing and Activation | Activate T cells with CD3 and CD28 agonists |
| Dilution | Dilute to reduce activation, allow cells to recover |
| Electroporation and Transduction | Disrupt TRAC and B2M genes, and insert CAR expression cassette into the TRAC locus |
| Cell Expansion | Expand the cells |
| TCRαβ Depletion | Remove TCRαβ⁺ cells |
| Cell Recovery | Allow cells to recover |
| Cell Culture Harvest (Drug substance) | Harvest cells in preparation of manufacture drug product, Sample cells for safety testing |

FIG. 19

IL2 Production in Culture Medium

DONOR 1 (~64% CAR)

Effector CAR-T cell : Target Cell ratio

DONOR 2 (~35% CAR)

Effector CAR-T cell : Target Cell ratio

DONOR 3 (~66% CAR)

Effector CAR-T cell : Target Cell ratio

Survival of Survival 4767: Donor #2

☐ ⟶ 1. Untreated

○ ⟶ 6. Donor #2, 1x

△ ⟶ 7. Donor #2, 2x

◇ ⟶ 8. Donor #2, 4x

Survival of Survival 4767: Donor #3

☐ ⟶ 1. Untreated

○ ⟶ 9. Donor #3, 1x

△ ⟶ 10. Donor #3, 2x

◇ ⟶ 11. Donor #3, 4x

MANUFACTURING PROCESS FOR MAKING T CELLS EXPRESSING CHIMERIC ANTIGEN RECEPTORS

CROSS-REFERENCE TO RELATED APPLICATIONS

This application claims the benefit of priority to U.S. Provisional Patent Application No. 62/934,991, filed Nov. 13, 2019, which is hereby incorporated by reference in its entirety.

SEQUENCE LISTING

The application contains a Sequence Listing that has been filed electronically in the form of a text file, created Nov. 13, 2020, and named "095136-0145-002US1_SEQ.TXT" (80,786 bytes), the contents of which are incorporated by reference herein in their entirety.

BACKGROUND

Chimeric antigen receptor (CAR) T-cell therapy has shown promising therapeutic effects in treating hematologic cancer. Typically, CAR-T cells are generated by genetic engineering of either patient immune cells (autologous) or immune cells from unrelated human donors (allogenic). Production of high-quality, clinical grade CAR-T cells is a prerequisite for the wide application of this technology. It is therefore of great interest to develop efficient manufacturing processes for large-scale production of CAR-T cells.

SUMMARY OF THE INVENTION

The present disclosure is based, at least in part, on the development of methods for manufacturing genetically engineered T cells expressing a chimeric antigen receptor (CAR) that provide several improvements over conventional manufacturing methods. Such improvements include, but are not limited to, improvements in consistency and effi-ciency of genetic modifications described herein, which allows production of a robust supply of clinically useful CAR T-cell therapies.

Accordingly, one aspect of the present disclosure provides a method for manufacturing genetically engineered T cells, the method comprising: (i) providing a first population of T cells; (ii) incubating the first population of T cells in the presence of a T cell activating agent in a cell culture vessel to produce a second population of T cells, wherein the second population of T cells comprises activated T cells; (iii) introducing into the activated T cells a first ribonucleopro-tein (RNP) complex comprising a first Cas9 enzyme and a first guide RNA (gRNA) targeting a T cell receptor alpha chain constant region (TRAC) gene, and a second RNP complex comprising a second Cas9 enzyme and a second gRNA targeting a β2M gene to produce a third population of T cells, wherein the third population of T cells comprises T cells having the TRAC gene disrupted and the β2M gene disrupted; (iv) incubating the third population of T cells with an adeno-associated viral (AAV) vector to produce a fourth population of T cells, wherein the fourth population of T cells comprises T cells expressing a chimeric antigen recep-tor (CAR), wherein the AAV vector comprises a nucleic acid sequence encoding the CAR, and wherein the CAR-encod-ing nucleic acid sequence is flanked by homologous sequences to the TRAC gene locus targeted by the first gRNA; (v) expanding the fourth population of T cells; (vi)

removing TCRαβ$^+$ T cells from the expanded T cells to produce a population of genetically engineered T cells, wherein the population of genetically engineered T cells comprises T cells expressing the CAR and having the TRAC gene and the β2M gene disrupted; and (vii) harvesting the population of genetically engineered T cells.

In some embodiments, the first population of T cells is derived from cryopreserved T cells enriched from human blood cells. In some embodiments, the first population of T cells is prepared by a process comprising: (a) obtaining blood cells from a human donor; and (b) enriching CD4$^+$ T cells and CD8$^+$ T cells. In some embodiments, (b) is performed using magnetic beads conjugated with anti-CD4 and/or anti-CD8 antibodies. In some embodiments, the first population of T cells has a cell viability of at least 80% and/or a purity of at least 80% of CD4$^+$ and CD8$^+$ T cells. In some embodiments, methods further comprise (c) cryo-preserving the enriched CD4$^+$ T cells and CD8$^+$ T cells produced in step (b).

In some embodiments, the T cell activating agent com-prises a CD3 agonist and a CD28 agonist attached to a nanomatrix particle. In some embodiments, step (ii) is performed by mixing the first population of T cells with the T cell activating agent in the cell culture vessel at a cell seeding density of about $2\times10^6$/cm$^2$ and a cell concentration of about $2\times10^6$ cells/mL; and incubating the mixture thus formed for about 48 hours. In some embodiments, the ratio of the T cell activating agent to medium in the mixture is about 1:12.5 (v/v).

In some embodiments, a method disclosed herein may further comprise diluting the T cell activating agent in the second population of T cells after step (ii) to reduce activa-tion and to allow cells to recover before step (iii).

In some embodiments, step (iii) is performed by elec-troporation. In some embodiments, step (iii) involves one electroporation event. In some embodiments, the first RNP complex and the second RNP complex are introduced into the activated T cells in the one electroporation event. In some embodiments, the amount of the first Cas9 enzyme in the first RNP complex is the same as the amount of the second Cas9 enzyme in the second RNA complex. In some embodiments, the concentration of the first Cas9 enzyme is about 0.15 mg/mL, the concentration of the second Cas9 enzyme is about 0.15 mg/mL, the concentration of the first gRNA targeting the TRAC gene is about 0.08 mg/mL, and the concentration of the second gRNA targeting the β2M gene is about 0.2 mg/mL. In some embodiments, the cell concentration in step (iii) is about $100\times10^6$ cells/mL to about $400\times10^6$ cells/mL. In some embodiments, the cell concen-tration in step (iii) is about $300\times10^6$ cells/mL. In other embodiments, the total cell number in each vessel used in step (iii) (e.g., electroporation) can be about $5\times10^8$ to about $1\times10^9$ cells, for example, about $7\times10^8$ cells. In some examples, multiple vessels may be used in step (iii) (e.g., electroporation), for example, about 5-10 vessels. In specific examples, as many as 7 vessels may be used in step (iii), which may contain about $1.5\times10^9$ to about $3\times10^9$ cells (e.g., about $2.1\times10^9$ cells or about $2.7\times10^9$ cells), e.g., for elec-troporation.

In some embodiments, the AAV vector has a multiplicity of infection (MOI) value of about 10,000 to about 80,000. In some embodiments, the MOI of the AAV vector is about 20,000. In some embodiments, the AAV vector is AAV serotype 6 (AAV6) vector.

In some embodiments, step (v) is performed by seeding the fourth population of T cells in a cell culture vessel at a seeding density of about $2\times10^5$ cells/cm$^2$ to about $7\times10^5$ cells/cm², and culturing the cells for about 6 days to about 12 days. In some embodiments, the fourth population of T cells may be seeded in a cell culture vessel at a seeding density of about 150,000 cells/cm² to about 600,000 cells/cm². In some embodiments, step (v) is performed by culturing the fourth population of T cells in a cell culture vessel at a seeding density of about $2\times10^5$ cells/cm² to about $5\times10^5$ cells/cm² for about 7 days to about 9 days. In some embodiments, step (v) is performed by seeding the fourth population of T cells in a cell culture vessel at a seeding density of about $3\times10^5$ cells/cm² to about $5\times10^5$ cells/cm². In some embodiments, the cell culture vessel is a static cell culture vessel (also referred interchangeably herein as a static culture vessel) allowing for cell expansion for about 10 days to about 12 days without medium change. In some embodiments, the cell culture vessel is a static cell culture vessel allowing for cell expansion for about 7 days to about 9 days without medium change. In some embodiments, step (vi) is performed by contacting the expanded cells to beads on which anti-TCRαβ antibodies are immobilized, and collecting unbound cells.

In some embodiments, the first Cas9 enzyme, the second Cas9 enzyme, or both are *Streptococcus pyogenes* Cas9 nuclease (spCas9). In some embodiments, the first Cas9 enzyme and the second Cas9 enzyme are the same. In some embodiments, the first Cas9 enzyme comprises the amino acid sequence of SEQ ID NO: 1, and/or wherein the second Cas9 enzyme comprises the amino acid sequence of SEQ ID NO: 1. In some embodiments, the first gRNA targeting the TRAC gene comprises a spacer sequence of SEQ ID NO: 4. In some embodiments, the first gRNA targeting the TRAC gene comprises the nucleotide sequence of SEQ ID NO: 2. In some embodiments, the second gRNA targeting the β2M gene comprises a spacer sequence of SEQ ID NO: 8. In some embodiments, the second gRNA targeting the β2M gene comprises the nucleotide sequence of SEQ ID NO: 6. In some embodiments, the first gRNA, the second gRNA, or both comprise one or more 2'-O-methyl phosphorothioate modification.

In some embodiments, the CAR comprises an extracellular domain targeting a cancer antigen, a transmembrane domain, a co-stimulatory domain, and a CD3z cytoplasmic signaling domain. In some embodiments, the extracellular domain comprises a single-chain variable fragment (scFv), the transmembrane domain is derived from CD8a, and/or the co-stimulatory domain is derived from CD28 and/or 4-1BB. In some embodiments, the CAR binds CD19. In some embodiments, the CAR comprises the amino acid sequence of SEQ ID NO: 37. In some embodiments, the CAR binds BCMA. In some embodiments, the CAR comprises the amino acid sequence of SEQ ID NO: 61.

Aspects of the present disclosure provide a genetically engineered T cell population, which is produced by a method described herein.

The details of one or more embodiments of the invention are set forth in the description below. Other features or advantages of the present invention will be apparent from the following drawings and detailed description of several embodiments, and also from the appended claims.

DETAILED DESCRIPTION OF THE DRAWINGS

FIGS. 1A-1B include diagrams showing activation and expansion of T cells under various conditions. FIG. 1A: a graph showing T cell activation measured as percent of cells expressing CD25 and/or CD69. FIG. 1B: a graph showing that the expression level of CD25 is correlated to the cell expansion rate. The expression level of CD25 was measured as the mean florescent intensity (MFI) of CD25.

FIGS. 2A-2D include diagrams showing editing efficiency and CAR expression in T cells prepared in a small scale manufacturing process in which T cells were activated in a static culture vessel using optimized conditions described herein. T cells were manufactured in parallel in a T-flask as a control. UT: untreated T cells; EP: mock electroporated T cells; Flask: T cells in T-flask; and Vessel: T cells in static culture vessel. FIG. 2A: a graph showing TCRαβ knockout efficiency in T cells. FIG. 2B: a graph showing β2M knockout efficiency in T cells. FIG. 2C: a graph showing double knockout (DKO) efficiency in T cells. FIG. 2D: a graph showing CAR percent (CAR %) expression in T cells.

FIG. 3 is a diagram showing T cell expansion post editing of T cells prepared in a small scale manufacturing process. UT: untreated T cells; EP: mock electroporated T cells; Flask: T cells in T-flask; and Vessel: T cells in static culture vessel.

FIGS. 4A-4F include diagrams showing editing efficiency and CAR expression in T cells that were electroporated at different cell concentrations. UT: untreated T cells; D3: editing efficiency on day 3; D6: editing efficiency on day 6; D9: editing efficiency on day 9; and D12: editing efficiency on day 12. FIG. 4A: a graph showing β2M knockout efficiency in T cells electroporated at cell concentrations of $100\times10^6$ cells/mL to $300\times10^6$ cells/mL. FIG. 4B: a graph showing TCRαβ knockout efficiency in T cells electroporated at cell concentrations of $100\times10^6$ cells/mL to $300\times10^6$ cells/mL. FIG. 4C: a graph showing CAR percent (CAR %) expression in T cells electroporated at cell concentrations of $100\times10^6$ cells/mL to $300\times10^6$ cells/mL. FIG. 4D: a graph showing β2M knockout efficiency in T cells electroporated at cell concentrations of $200\times10^6$ cells/mL to $400\times10^6$ cells/mL. FIG. 4E: a graph showing TCRαβ knockout efficiency in T cells electroporated at cell concentrations of $200\times10^6$ cells/mL to $400\times10^6$ cells/mL. FIG. 4F: a graph showing CAR percent (CAR %) expression in T cells electroporated at cell concentrations of $200\times10^6$ cells/mL to $400\times10^6$ cells/mL.

FIGS. 5A-5B include diagrams showing CAR⁺ expression in T cells transduced with varying MOI. FIG. 5A: a graph showing CAR⁺ expression in T cells transduced with MOI ranging from 1.25K to 80K. UT: untreated T cells; D3: CAR⁺ expression 3 days after transduction; D6: CAR⁺ expression 6 days after transduction; D10: CAR⁺ expression 10 days after transduction; and D13: CAR⁺ expression 13 days after transduction. FIG. 5B: a graph showing CAR⁺ expression in T cells measured 11 days after transduced with MOI ranging from 0.12K to 23K. P.C.: positive control; EP: electroporation only control; and Iso Type: CAR positive isotype replaced with goat IgG.

FIGS. 6A-6C include diagrams showing effects of cell seeding density on expansion of edited T cells. FIG. 6A: a graph showing cell number during expansion. FIG. 6B: a graph showing cell density during expansion. FIG. 6C: a graph showing fold expansion during expansion.

FIGS. 7A-7E include diagrams showing data from manufacturing of genetically engineered T cells expressing an anti-CD19 directed chimeric T cell antigen receptor (CTX110). FIG. 7A includes a flow chart of an illustrative manufacturing process for making T cells expressing an anti-CD19 CAR, in accordance with some embodiments of the technology described herein. FIGS. 7B-7C include diagrams showing CAR⁺ expression in T cells transduced with varying MOI. FIG. 7B: a graph showing CAR⁺ expression in T cells transduced with rAAV-138 MOI ranging from OK to 80K. FIG. 7C: a graph showing CAR$^+$ expression in T cells transduced with rAAV-138 MOI ranging from OK to 80K. Transduction with rAAV-138 MOI of 20K was used as a positive control. FIGS. 7D-7E include diagrams showing editing efficiency in T cells electroporated with RNP complexes formed from different concentrations of sgRNA targeting TCR (TA-1 sgRNA) or sgRNA targeting B2M (B2M-1 sgRNA). TCRαβ$^-$: percent of cells having TCRαβ edits; β2M$^-$: percent of cells having β2M edits; and double knockout (DKO): percent of cells having TCRαβ edits and β2M edits. FIG. 7D: a graph showing knockout efficiency in T cells electroporated with RNP complexes formed using 37.5 μg/mL to 300 μg/mL of TA-1. FIG. 7E: a graph showing knockout efficiency in T cells electroporated with RNP complexes formed using 37.5 μg/mL to 300 μg/mL of B2M-1.

FIGS. 8A-8G include diagrams showing data from manufacturing of genetically engineered T cells expressing an anti-BCMA directed chimeric T cell antigen receptor (CTX120). FIG. 8A includes a flow chart of an illustrative manufacturing process for making T cells expressing an anti-BCMA CAR, in accordance with some embodiments of the technology described herein. FIG. 8B: a graph showing CAR$^+$ expression in T cells transduced with increasing MOI. FIG. 8C: a graph showing levels of exhaustion markers detected in CTX120. FIG. 8D: a graph showing levels of memory markers detected in CD8$^+$ T cells of CTX120. FIG. 8E: a graph showing levels of memory markers detected in CD4$^+$ T cells of CTX120. FIG. 8F: a graph showing production of IFNγ upon co-culture of CTX120 with BCMA$^+$ tumor cells. FIG. 8G: a graph showing tumor killing upon co-culture of CTX120 with BCMA$^+$ tumor cells.

FIGS. 9A and 9B provide graphs of cell concentration per mL as a function of days of expansion post editing.

FIGS. 10A and 10B provide graphs of calculated cell number as a function of days of expansion post editing.

FIGS. 11A and 11B provide graphs of percentage cell viability as a function of days of expansion post editing.

FIGS. 12A-12C provide graphs of depicting editing efficiency including CAR$^+$ % (FIG. 12A), TRAC$^-$ % (FIG. 12B) and β2M$^-$ % (FIG. 12C) assessed in the various replating and low-plating groups.

FIGS. 13A and 13B provide the ratio of CD4$^+$ and CD8$^+$ cells in the various replated cell populations.

FIGS. 14A-14F provide bar graphs depicting the assessment of memory cell subtype markers in the replated populations. The cells in the replated populations were assessed as naïve T cells, central memory (CM) T cells, effector memory (EM) T cells and terminal effector (TE) T cells.

FIGS. 15A-15F provide bar graphs depicting the assessment of exhaustion markers in the replated populations of CAR$^+$, CD4$^+$/CAR+, and CD8$^+$/CAR$^+$ cells. The three exhaustion markers assayed were PD1, LAGS and TIM3.

FIGS. 16A-16C provide graphs showing the ability of the CAR-T cells in replated and low-plating density groups to kill CD19 positive Raji target cells in vitro, which was assessed using a flow cytometry-based cytotoxicity assay.

FIGS. 17A-17D provide graphs showing the percentage of survival of tumor cells as a function of days post inoculation at three different doses of CAR cells in vivo.

FIGS. 18A-18D provides graphs showing the tumor mass in mice as a function of days post inoculation at three dose of CAR cells in vivo.

FIG. 19 shows a flow chart illustrating one embodiment of the present disclosure.

Figure 21A:
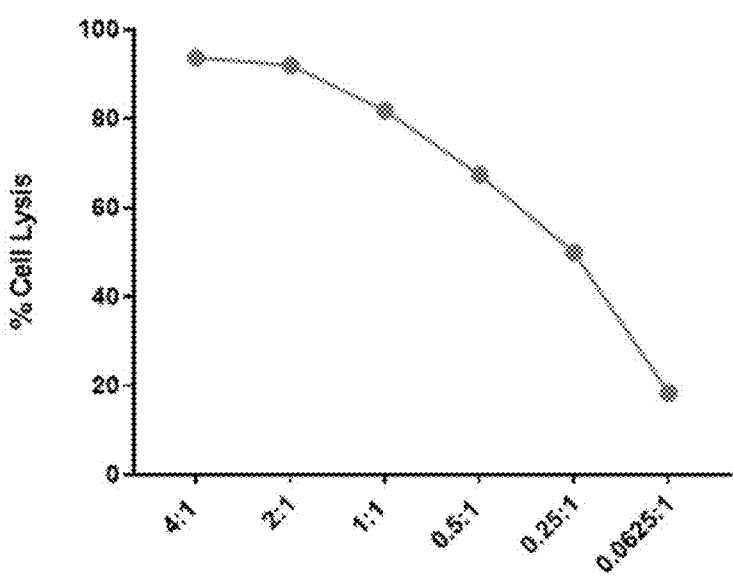
Figure 21B:
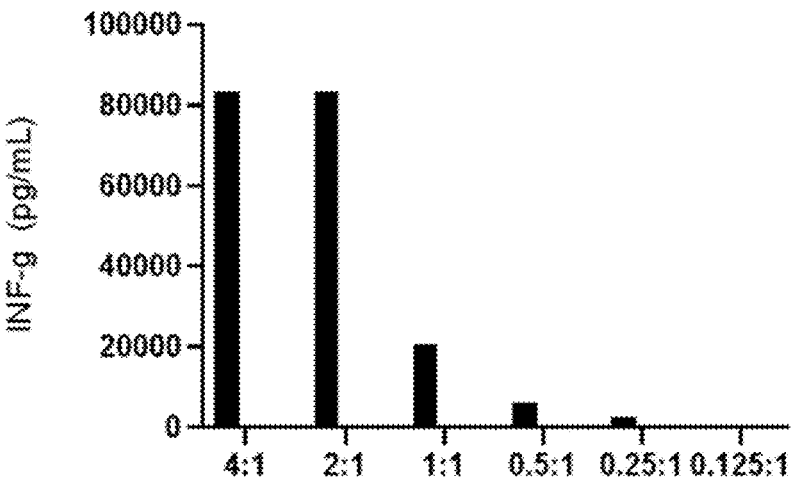
Figure 21C:
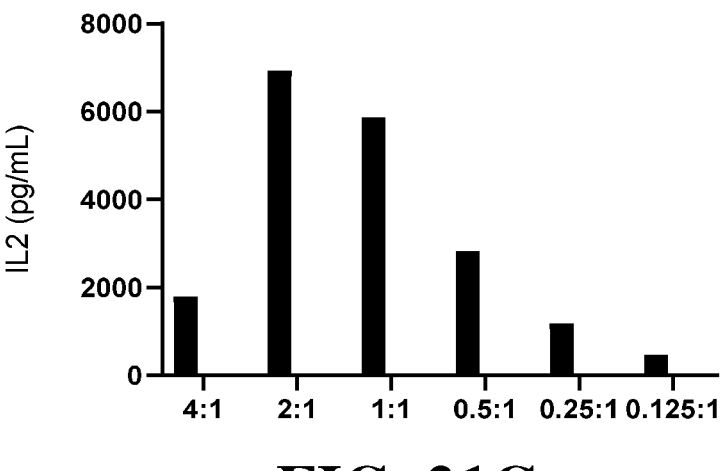

FIGS. 21A-21C show the results of an assay control experiment measuring cell lysis and cytokine production in vitro. The assay used CTX110 CAR-T cells thawed from frozen stock. The T-cells were 80% CAR$^+$ day 6 post HDR.

Figure 22A:
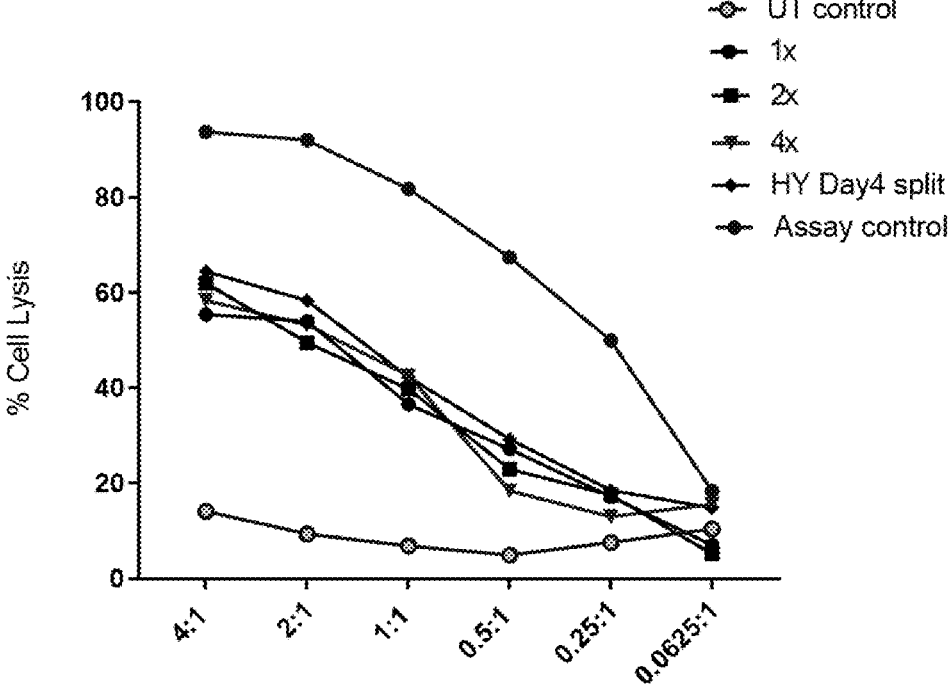
Figure 22B:
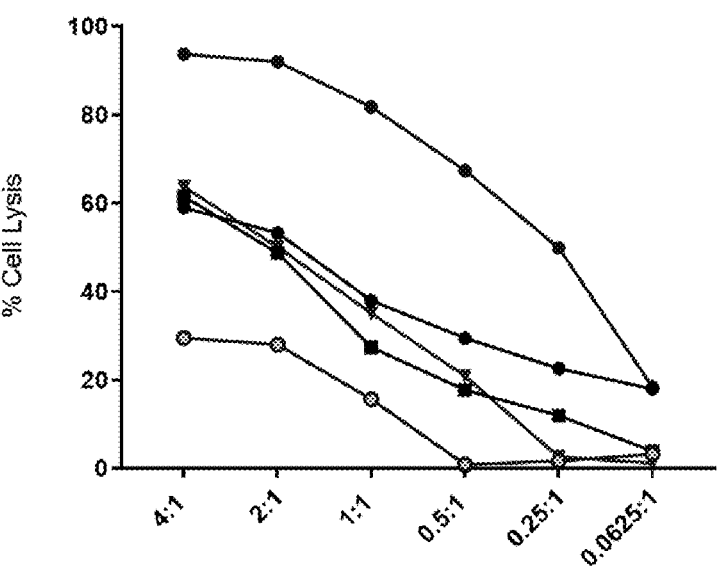
Figure 22C:
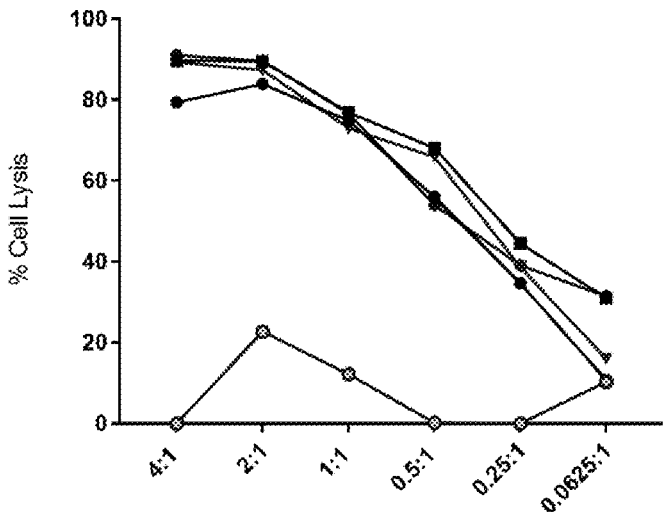

FIGS. 22A-22C show the results of an in vitro efficacy analysis showing that T-cells derived from each of the three donors had varying degrees of in vitro efficacy among 1×, 2× and 4× culture conditions.

Figure 23A:
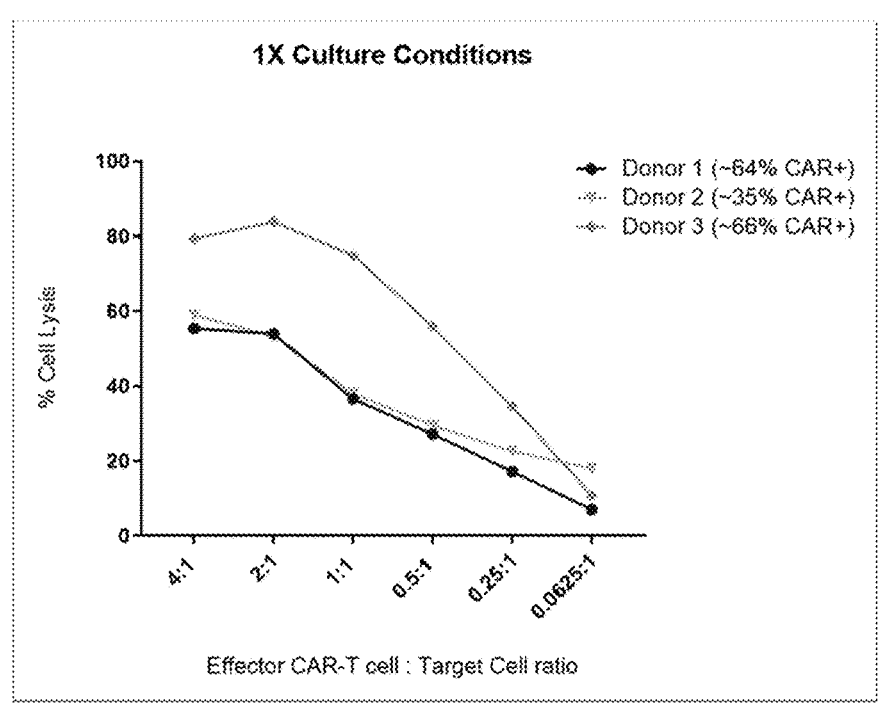
Figure 23B:
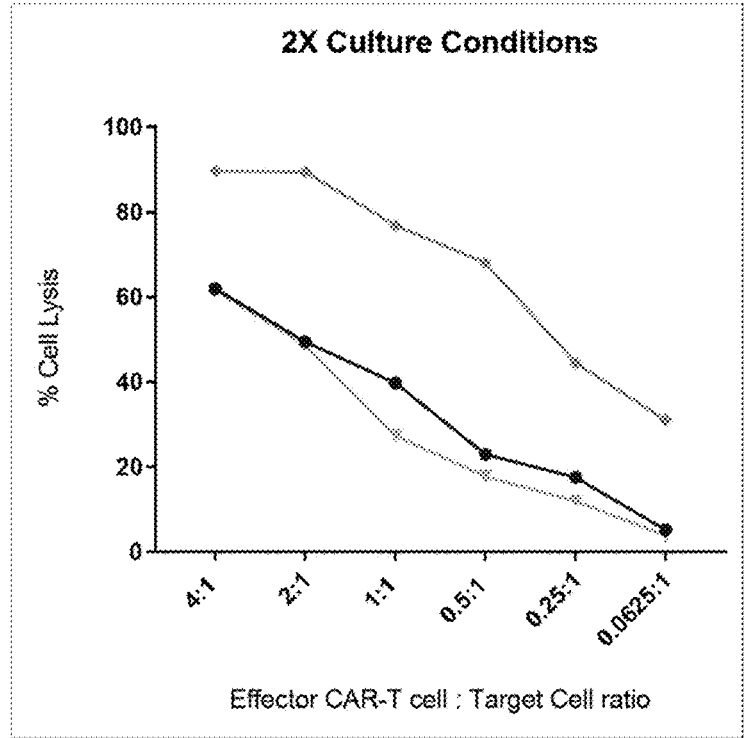
Figure 23C:
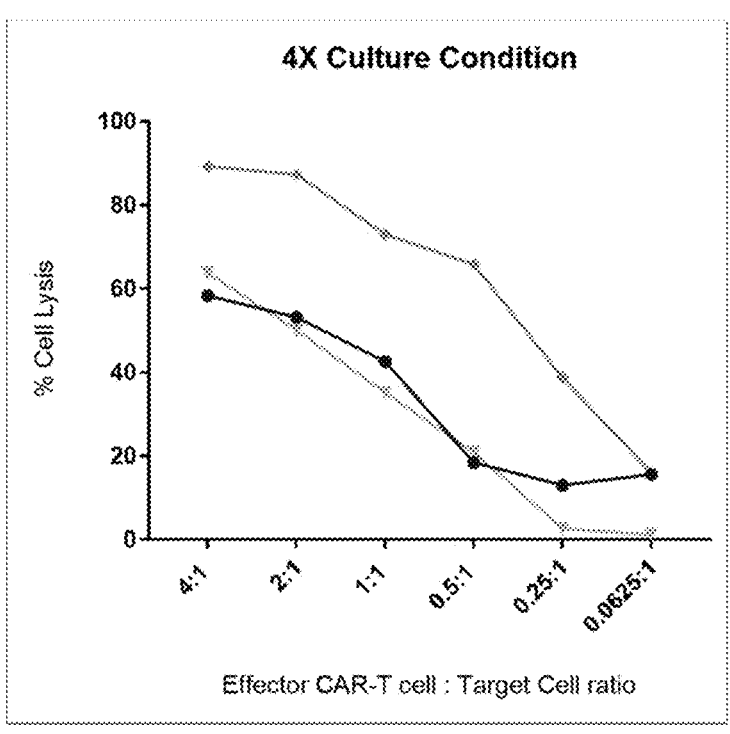

FIGS. 23A-23C show the results of an analysis of cell lysis at different cell concentrations, demonstrating that cells derived from donors 1 and 2 showed similar responses despite differing percentages of CAR$^+$ cells.

Figure 24A:
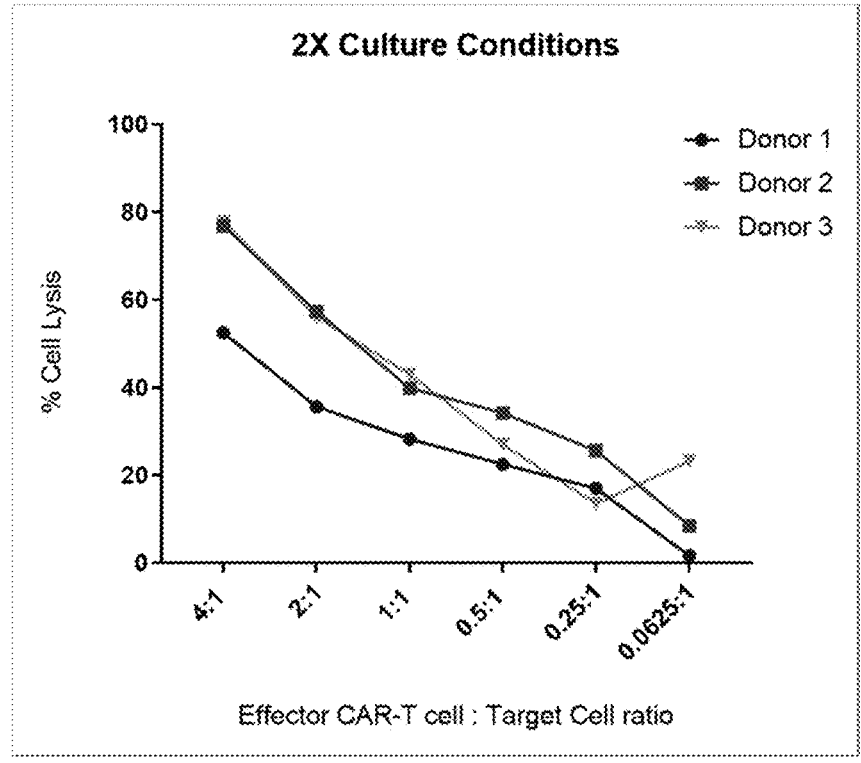
Figure 24B:
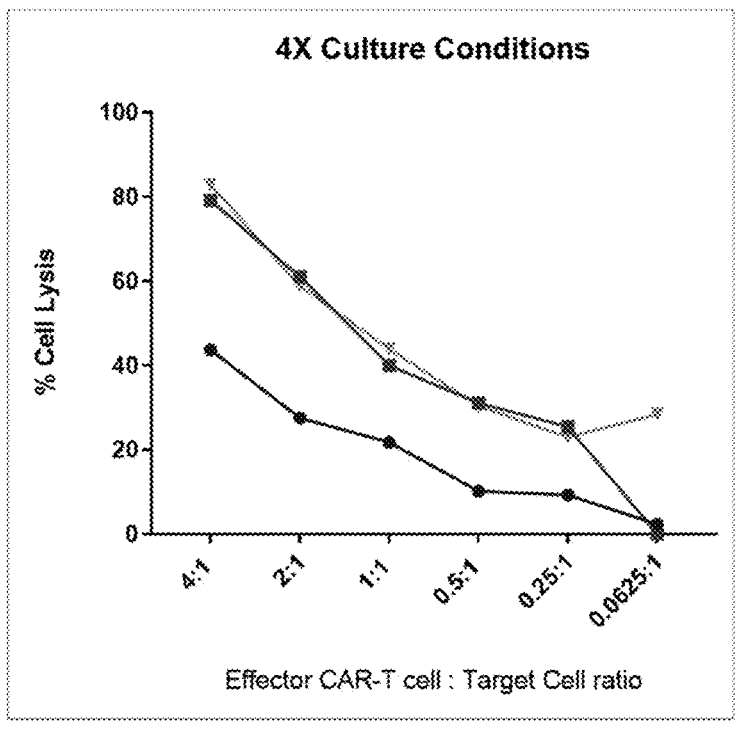

FIGS. 24A-24B show the results of an analysis of cell lysis from the three donors when normalized for CAR$^+$ cells. Donors 2 and 3 behaved similarly in the assay when CAR cells were normalized. The assay was repeated with 2×CAR-T cell number for donor 2 at the same E:T ratios.

Figure 25A:
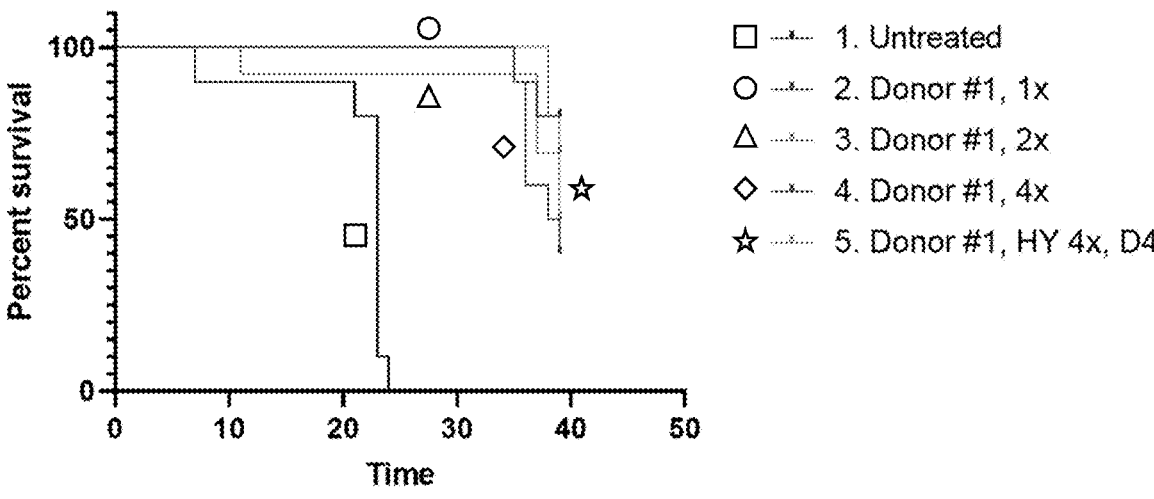
Figure 25B:
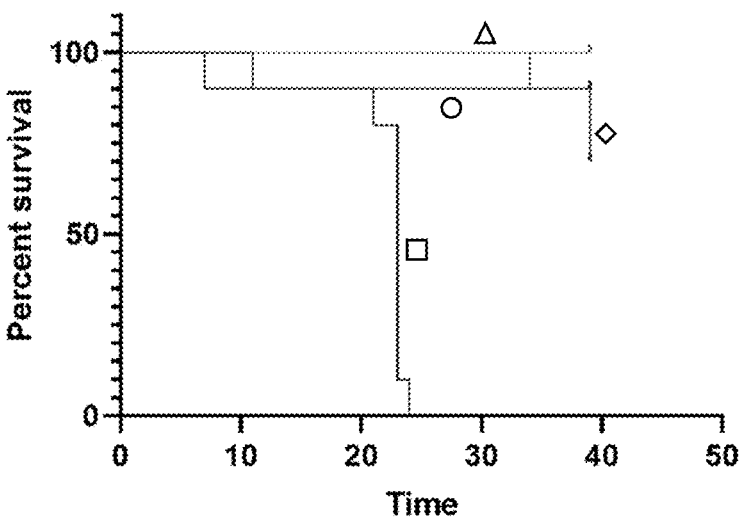
Figure 25C:
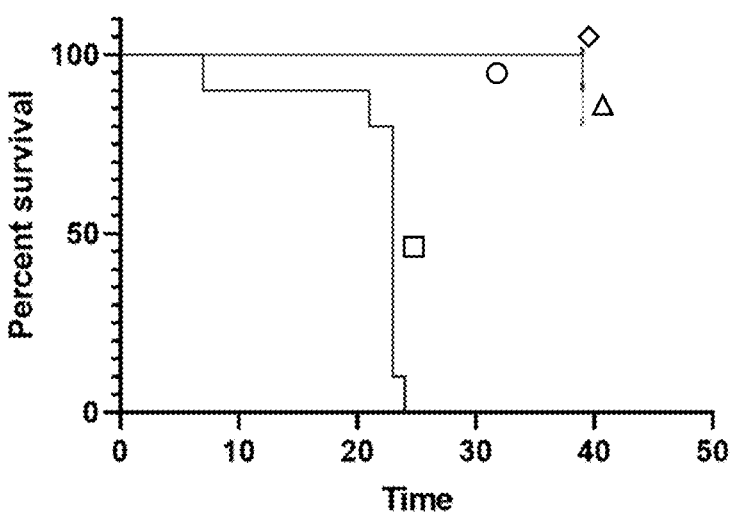

FIGS. 25A-25C provide survival curves showing the percentage of survival of mice as a function of days post inoculation of CAR cells for all three donors and expansion conditions in vivo.

Figure 26A:
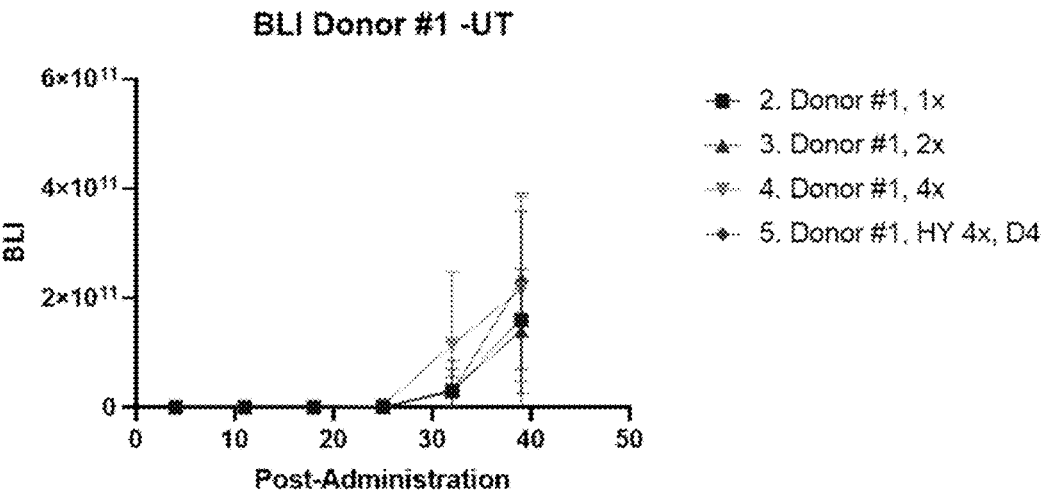
Figure 26B:
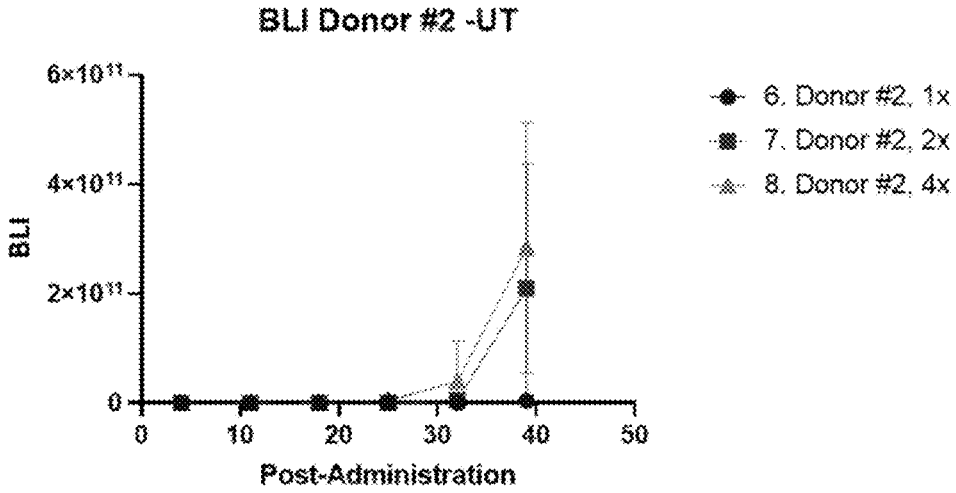
Figure 26C:
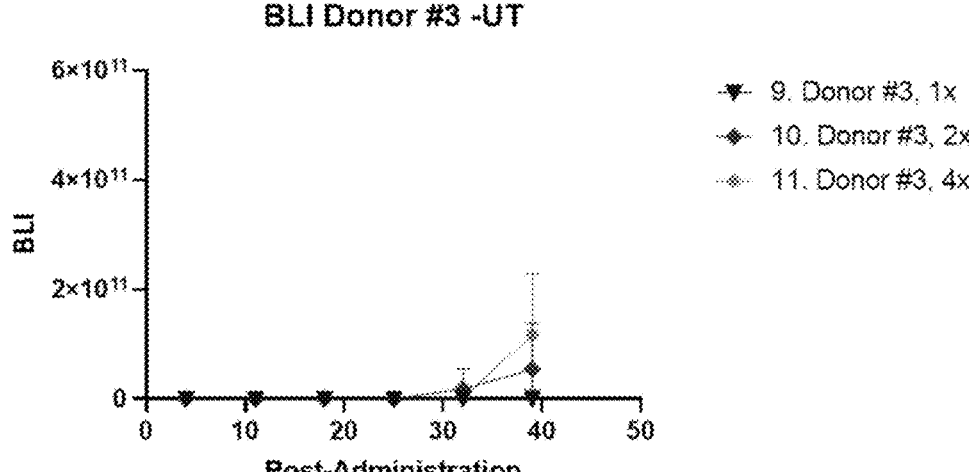

FIGS. 26A-26C provide graphs showing the tumor mass in mice as a function of days post inoculation of CAR cells from all three donors and expansion conditions in vivo.

DETAILED DESCRIPTION OF THE INVENTION

The present disclosure is based, at least in part, on the development of improved manufacturing processes for producing CAR-T cells, particularly allogenic CAR-T cells, including improved conditions for one or more steps of the manufacturing processes. The improved manufacturing processes disclosed herein led to at least the following advantageous outcomes:

(a) Improved T cell purity and improved T cell viability resulting from the improved T cell enrichment conditions provided herein.

(b) Improved consistency and improved efficiency for producing CAR-expressing T cells resulting from the improved T cell transduction conditions provided herein.

(c) Improved consistency and improved efficiency of TRAC gene and β2M gene disruptions in T cells resulting from the improved CRISPR-Cas9-mediated gene editing conditions provided herein.

(d) Increased supply of CAR T-cell therapy resulting from decreased production times and decreased production costs provided by the improved manufacturing processes described herein.

(e) Reduced variability of manufactured drug product resulting from production of uniform and high quality CAR T-therapies using the improved manufacturing processes described herein.

(f) Simplified AAV transduction condition while maintaining high CAR expression level in T cells.

Accordingly, provided herein are methods for manufacturing genetically engineered T cells expressing a CAR construct, such as a CAR construct targeting a cancer antigen, for example, CD19 or BCMA, and having TRAC and β2M gene knocked-out. The genetically engineered T cell populations produced by methods described herein, and therapeutic uses thereof are also within the scope of the present disclosure.

I. Manufacturing Genetically Engineered T Cells

Aspects of the present disclosure provide methods for manufacturing genetically engineered T cells comprising a disrupted beta-2-microglobulin (β2M) gene, and a disrupted T cell receptor alpha chain constant region (TRAC) gene, and an inserted nucleic acid encoding a chimeric antigen receptor (CAR).

Disruption of the β2M gene and the TRAC gene renders the genetically engineered T cell non-alloreactive and suitable for allogeneic transplantation. Insertion of a nucleic acid encoding a CAR enables the genetically engineered T cell to express the CAR on its surface where it targets the genetically engineered T cell to cancer cells.

Accordingly, methods for manufacturing genetically engineered T cells disclosed herein, in some embodiments, involve the use of CRISPR-Cas9 gene editing to disrupt expression of TRAC and β2M, and the use of adeno-associated virus (AAV) transduction to insert a nucleic acid encoding a CAR.

In general, the method for manufacturing CAR-T cells disclosed herein may comprise: (i) enriching CD4$^+$/CD8$^+$ T cells from a suitable human immune cell source, (ii) activating the enriched CD4$^+$/CD8$^+$ T cells, and (iii) genetically engineering the activated T cells to produce CAR-T cells having disrupted TRAC and B2M genes; and harvesting the genetically engineered T cells for therapeutic uses. When needed, the enriched CD4$^+$/CD8$^+$ T cells may be stored via cryopreservation for future use. Alternatively or in addition, the genetically engineered T cells may be expanded in vitro prior to harvesting. TCRαβ$^+$ T cells may be depleted from the CAR-T cell population thus produced.

(i) T Cell Enrichment

Any of the manufacturing methods disclosed herein may use human blood cells as the starting material. For example, T cells can be obtained from a unit of blood collected from a subject using techniques known to a skilled person, such as sedimentation, e.g., FICOLL™ separation. Alternatively, the T cells for use in making the genetically engineered T cells may be derived from stem cells (e.g., HSCs or iPSCs) via in vitro differentiation. In some embodiments, blood cells can be obtained from an individual human donor. In other embodiments, blood cells can be obtained from multiple human donors (e.g., 2, 3, 4, or 5 human donors).

In some examples, leukopak samples from a suitable human donor may be used. As known in the art, a leukopak sample is an enriched leukapheresis product collected from peripheral blood. It typically contains a variety of blood cells including monocytes, lymphocytes, platelets, plasma, and red cells. The human donor preferably is a healthy human donor. For example, a human donor candidate may be subject to screening for HBV, HCV, HIV, HTLV, WNV, *Trypanosoma cruzi*, and/or CMV. A human subject showing negative results in the screening may be used as a donor for blood cells.

The sources of T-cells that find use in the present methods is not particularly limited. In some embodiments, T cells from a T cell bank can be used as the starting material in any of the manufacturing methods disclosed herein. A T cell bank may comprise T cells with genetic editing of certain genes (e.g., genes involved in cell self renewal, apoptosis, and/or T cell exhaustion or replicative senescence) to improve T cell persistence in cell culture. A T cell bank may be produced from bonafide T cells, for example, non-transformed T cells, terminally differentiated T cells, T cells having stable genome, and/or T cells that depend on cytokines and growth factors for proliferation and expansion. Alternatively, such a T cell bank may be produced from precursor cells such as hematopoietic stem cells (e.g., iPSCs), e.g., in vitro culture. In some examples, the T cells in the T cell bank may comprise genetic editing of one or more genes involved in cell self-renewal, one or more genes involved in apoptosis, and/or one or more genes involved in T cell exhaustion, so as to disrupt or reduce expression of such genes, leading to improved persistence in culture. Examples of the edited genes in a T cell bank include, but are not limited to, Tet2, Fas, CD70, Regnase-1, or a combination thereof. Compared with the non-edited T counterpart, T cells in a T cell bank may have enhanced expansion capacity in culture, enhanced proliferation capacity, greater T cell activation, and/or reduced apoptosis levels.

Suitable T cells can be enriched from human blood cells using conventional methods or methods disclosed herein. T cells for use in making the genetically engineered T cells may express one or more of the T cell markers, including, but not limited to a CD4$^+$, CD8$^+$, or a combination thereof. In some embodiments, CD4$^+$ T cells can be enriched from human blood cells. In other embodiments, CD8$^+$ T cells can be enriched. In specific examples, both CD4$^+$ and CD8$^+$ T cells are purified from human blood cells.

CD4$^+$ T cells and/or CD8$^+$ T cells can be isolated from a suitable blood cell source, such as those described herein, using any method known in the art or those disclosed herein, for example, using antibodies capable of binding to specific cell-surface biomarkers for the target T cells, e.g., antibodies specific to CD4 and/or antibodies specific to CD8. In some embodiments, enriching CD4$^+$ T cells and CD8$^+$ T cells can be performed using anti-CD4 and anti-CD8 antibodies conjugated to magnetic beads. A cell population comprising CD4$^+$ and CD8$^+$ T cells can be incubated with such magnetic beads under suitable conditions for a suitable period allowing for binding of the target T cells to the magnetic beads via the antibodies conjugated to the beads. Non-bound cells can be washed and CD4$^+$ and CD8$^+$ T cells bound to the beads can be collected using routine methods.

The enriched T cells (e.g., CD4$^+$ T cells and CD8$^+$ T cells) may be evaluated for features such as cell viability and/or purity of the target T cells following routine practice. In some embodiments, the T cell population from the enrichment step disclosed here may have a cell viability of at least about 80% (e.g., at least about 85%, at least about 90%, at least about 95%, or above). Alternatively or in addition to, the enriched T cell population may have a purity of at least about 80% of the target T cells (e.g., CD4$^+$ and/or CD8$^+$ T cells), for example, at least about 85%, at least about 90%, at least about 95%, at least about 97%, about 98% or higher. Alternatively or in addition to, the enriched T cell population may have a purity of at least about 70% of the target T cells (e.g., CD4$^+$ and/or CD8$^+$ T cells), for example, at least about 75%, at least about 80%, at least about 85%, at least about 90%, at least about 95%, at least about 97%, about 98% or higher.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The enriched T cell population (which is also within the scope of the present disclosure) may be used immediately for further processing as disclosed herein. Alternatively, the enriched T cell population may be stored under suitable conditions for future use, for example, via cryopreservation. Prior to further processing, cryopreserved T cells can be thawed following routine procedures. Cell viability of the thawed cells can be assessed to determine whether the thawed cells are suitable for further processing.

(ii) T Cell Activation

The enriched T cells may be subject to T cell activation to allow for proliferation and expansion of the enriched CD4$^+$/CD8$^+$ T cells. The T cell activation step used in any of the methods disclosed herein may involve T cell activation conditions disclosed herein that provide high T cell activation efficiency. Further, the activated T cells obtained therefrom would exhibit high gene editing efficiencies and great rates of T cell expansion post editing. See Examples below.

In some embodiments, T cell activation can be achieved using a T cell activating agent or agents, for example, agents that stimulates a CD3/TCR-mediated signaling pathway and/or a co-stimulatory molecule (e.g., CD28) mediated signaling pathway. For example, a T cell activating agent may be a CD3 agonist (e.g., an agonistic anti-CD3 antibody) and activates the CD3/TCR-mediated cell signaling pathway. Alternatively or in addition, a T cell activating agent may be a CD28 agonist (e.g., an anti-CD28 antibody) and activate the co-stimulatory signaling pathway mediated by CD28. Any of the T cell activating agents for use in the method disclosed herein may be conjugated to a support member, such as a nanomatrix particle. In specific examples, the T cell activating agent for use in the method disclosed herein may comprise an anti-CD3 antibody and an anti-CD28 antibody, which may be conjugated to nanomatrix particles. In some embodiments, the T cell activating agent comprises a CD3 agonist and a CD28 agonist attached to a nanomatrix particle. In some embodiments, the CD3 agonist and a CD28 agonist are attached to the same nanomatrix particle. In some embodiments, the CD3 agonist and a CD28 agonist are attached to different nanomatrix particles.

To achieve T cell activation, the enriched T cells as disclosed herein (e.g., CD4$^+$/CD8$^+$ T cells) may be placed in a cell culture vessel at a suitable cell seeding density and a suitable cell concentration and incubated in the presence of any of the T cell activating agents disclosed herein for a suitable period to induce T cell activation.

In some instances, ratios of the T cell activating agent to the cell culture medium in the cell culture vessel may range from about 1:10 (v/v) to about 1:15 (v/v). In some examples, the ratio of the T cell activating agent to the cell culture medium in the cell culture vessel may be about 1:10 (v/v), about 1:10.5 (v/v), about 1:11 (v/v), about 1:11.5 (v/v), about 1:12 (v/v), about 1:12.5 (v/v), about 1:13 (v/v), about 1:13.5 (v/v), about 1:14 (v/v), about 1:14.5 (v/v), or about 1:15 (v/v). In specific examples, the ratio of the T cell activating agent to the culture medium in the cell culture vessel is about 1:12.5 (v/v).

Alternatively or in addition, a suitable cell seeding density may be about $1.5 \times 10^6$ to $2.5 \times 10^6$ (e.g., $2 \times 10^6$/cm$^2$) and a suitable cell concentration may be about $1.5 \times 10^6$ to $2.5 \times 10^6$ (e.g., $2 \times 10^6$/ml). The cells may be incubated with the T cell activating agent for about 42-54 hours, for example, about 48 hours.

In some embodiments, the cell culture vessel may be a static culture vessel, which would allow for relatively large-scale production of the genetically engineered T cells as disclosed herein. Compared to conventional cell culture flasks, static cell culture vessels allow T cells to reside on a highly gas permeable membrane submerged under medium that supplies oxygen and nutrients to the T cells without mixing or shaking. Static culture vessels allow T cell manufacturing without medium change. Accordingly, in some embodiments, the T cell activation process in any of the methods disclosed herein may involve no medium change.

When needed, the activating agent may be removed from the cell culture vessel or diluted prior to the follow-on gene editing events to minimize any potential impact that the activating agent may confer during gene editing. In some embodiments, the activating agent can be removed from the cell culture vessel using routine methods, e.g., centrifugation. Alternatively, the activating agent may be diluted in the cell culture vessel prior to gene editing, e.g., diluted by addition of media to the cell culture vessel.

In some embodiments, the activated T cells derived from any of the T cell activation processes disclosed herein may be cultured overnight (e.g., about 16 hours) to allow T cells to recover prior to gene editing. In some instances, the activated T cell culture may still contain the T activating agent. In other instances, the activated T cells may have little or no presence of the T cell activating agent.

(iii) CRISPR-CAS9-Mediated Gene Editing of Activated T Cells

The activated T cells prepared by any of the procedures disclosed herein may subject to gene editing to knock out host response related genes, for example, the TRAC gene and/or the β2M gene, via, for example, CRISPR-Cas9 gene editing technology.

The TRAC gene encodes a component of the TCR complex. Disruption of the TRAC gene leads to loss of function of the TCR and renders the engineered T cell non-alloreactive and suitable for allogeneic transplantation, minimizing the risk of graft versus host disease. The β2M gene encodes a common (invariant) component of the major histocompatibility complex (MHC) I complexes. Disrupting the β2M gene can prevent host versus therapeutic allogeneic T cells responses. Knocking out both the TRAC gene and the β2M gene would result in production of allogeneic T cells for use in cell therapy.

CRISPR-Cas9-Mediated Gene Editing System

The CRISPR-Cas9 system is a naturally-occurring defense mechanism in prokaryotes that has been repurposed as an RNA-guided DNA-targeting platform used for gene editing. It relies on the DNA nuclease Cas9, and two noncoding RNAs, crisprRNA (crRNA) and trans-activating RNA (tracrRNA), to target the cleavage of DNA. CRISPR is an acronym for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see, e.g., Koonin et al., (2017) Curr Opin Microbiol 37:67-78).

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the crRNA, if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

(i) Cas9

In some embodiments, the Cas9 (CRISPR associated protein 9) endonuclease is used in a CRISPR method for making the genetically engineered T cells as disclosed herein. The Cas9 enzyme may be one from *Streptococcus pyogenes*, although other Cas9 homologs may also be used. It should be understood that wild-type Cas9 may be used or modified versions of Cas9 may be used (e.g., evolved versions of Cas9, or Cas9 orthologues or variants), as provided herein. In some embodiments, Cas9 comprises a *Streptococcus pyogenes*-derived Cas9 nuclease protein that has been engineered to include C- and N-terminal SV40 large T antigen nuclear localization sequences (NLS). The resulting Cas9 nuclease (sNLS-spCas9-sNLS) is a 162 kDa protein that is produced by recombinant *E. coli* fermentation and purified by chromatography. The spCas9 amino acid sequence can be found as UniProt Accession No. Q99ZW2, which is provided herein as SEQ ID NO: 1.

(ii) Guide RNAs (gRNAs)

CRISPR-Cas9-mediated gene editing as described herein includes the use of a guide RNA or a gRNA. As used herein, a "gRNA" refers to a genome-targeting nucleic acid that can direct the Cas9 to a specific target sequence within a TRAC gene or a β2M gene for gene editing at the specific target sequence. A guide RNA comprises at least a spacer sequence that hybridizes to a target nucleic acid sequence within a target gene for editing, and a CRISPR repeat sequence.

An exemplary gRNA targeting a TRAC gene is provided in SEQ ID NO: 2. See also International Application No. PCT/IB2018/001619, filed May 11, 2018, which published as WO 2019/097305A2, the relevant disclosures of which are incorporated by reference herein for the subject matter and purpose referenced herein. Other gRNA sequences may be designed using the TRAC gene sequence located on chromosome 14 (GRCh38: chromosome 14: 22,547,506-22,552,154; Ensembl; ENSG00000277734). In some embodiments, gRNAs targeting the TRAC genomic region and Cas9 create breaks in the TRAC genomic region resulting Indels in the TRAC gene disrupting expression of the mRNA or protein.

In some embodiments, gRNAs targeting the TRAC genomic region create Indels in the TRAC gene comprising at least one nucleotide sequence selected from the sequences in Table 9. In some embodiments, gRNA (SEQ ID NO: 2) targeting the TRAC genomic region create Indels in the TRAC gene comprising at least one nucleotide sequence selected from the sequences in Table 9.

An exemplary gRNA targeting a β2M gene is provided in SEQ ID NO: 6. See also International Application No. PCT/IB2018/001619, filed May 11, 2018, which published as WO 2019/097305A2, the relevant disclosures of which are incorporated by reference herein for the subject matter and purpose referenced herein. Other gRNA sequences may be designed using the β2M gene sequence located on Chromosome 15 (GRCh38 coordinates: Chromosome 15: 44,711,477-44,718,877; Ensembl: ENSG00000166710). In some embodiments, gRNAs targeting the β2M genomic region and RNA-guided nuclease create breaks in the β2M genomic region resulting in Indels in the β2M gene disrupting expression of the mRNA or protein.

In some embodiments, gRNAs targeting the β2M genomic region create Indels in the β2M gene comprising at least one nucleotide sequence selected from the sequences in Table 10. In some embodiments, gRNA (SEQ ID NO: 6) targeting the β2M genomic region create Indels in the β2M gene comprising at least one nucleotide sequence selected from the sequences in Table 10.

In Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid (e.g., gRNA) is a double-molecule guide RNA. In some embodiments, the genome-targeting nucleic acid (e.g., gRNA) is a single-molecule guide RNA.

A double-molecule guide RNA comprises two strands of RNA molecules. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (referred to as a "sgRNA") in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins. A single-molecule guide RNA in a Type V system comprises, in the 5' to 3' direction, a minimum CRISPR repeat sequence and a spacer sequence.

The "target sequence" is in a target gene that is adjacent to a PAM sequence and is the sequence to be modified by Cas9. The "target sequence" is on the so-called PAM-strand in a "target nucleic acid," which is a double-stranded molecule containing the PAM-strand and a complementary non-PAM strand. One of skill in the art recognizes that the gRNA spacer sequence hybridizes to the complementary sequence located in the non-PAM strand of the target nucleic acid of interest. Thus, the gRNA spacer sequence is the RNA equivalent of the target sequence.

For example, if the TRAC target sequence is 5'-AGAGCAACAGTGCTGTGGCC-3' (SEQ ID NO: 11), then the gRNA spacer sequence is 5'-AGAGCAACAGUGCUGUGGCC-3' (SEQ ID NO: 5). In another example, if the β2M target sequence is 5'-GC-TACTCTCTCTTTCTGGCC-3' (SEQ ID NO: 13), then the gRNA spacer sequence is 5'-GCUACUCUCUC-UUUCUGGCC-3' (SEQ ID NO: 9). The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM recognizable by a Cas9 enzyme used in the system. The spacer may perfectly match the target sequence or may have mismatches. Each Cas9 enzyme has a particular PAM sequence that it recognizes in a target DNA. For example, *S. pyogenes* recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length. In some embodiments, the target nucleic acid sequence has 20 bases immediately 5' of the first nucleotide of the PAM. For example, in a sequence comprising 5'-NNNNNNNNNNNNNNNNNNNNNRG-3', the target nucleic acid can be the sequence that corresponds to the Ns, wherein N can be any nucleotide, and the underlined NRG sequence is the *S. pyogenes* PAM.

A spacer sequence in a gRNA is a sequence (e.g., a 20 nucleotide sequence) that defines the target sequence (e.g., a DNA target sequences, such as a genomic target sequence) of a target gene of interest. An exemplary spacer sequence of a gRNA targeting a TRAC gene is provided in SEQ ID NO: 4. An exemplary spacer sequence of a gRNA targeting a β2M gene is provided in SEQ ID NO:8.

The guide RNA disclosed herein may target any sequence of interest via the spacer sequence in the crRNA. In some embodiments, the degree of complementarity between the spacer sequence of the guide RNA and the target sequence in the target gene can be about 60%, 65%, 70%, 75%, 80%, 85%, 90%, 95%, 97%, 98%, 99%, or 100%. In some embodiments, the spacer sequence of the guide RNA and the target sequence in the target gene is 100% complementary. In other embodiments, the spacer sequence of the guide RNA and the target sequence in the target gene may contain up to 10 mismatches, e.g., up to 9, up to 8, up to 7, up to 6, up to 5, up to 4, up to 3, up to 2, or up to 1 mismatch.

Non-limiting examples of gRNAs that may be used as provided herein are provided in International Application No. PCT/IB2018/001619, filed May 11, 2018, which published as WO 2019/097305A2, and International Application No. PCT/IB2019/000500, filed May 10, 2019, which published as WO/2019/215500. the relevant disclosures of each of the prior applications are herein incorporated by reference for the purposes and subject matter referenced herein. For any of the gRNA sequences provided herein, those that do not explicitly indicate modifications are meant to encompass both unmodified sequences and sequences having any suitable modifications.

The length of the spacer sequence in any of the gRNAs disclosed herein may depend on the CRISPR/Cas9 system and components used for editing any of the target genes also disclosed herein. For example, different Cas9 proteins from different bacterial species have varying optimal spacer sequence lengths. Accordingly, the spacer sequence may have 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the spacer sequence may have 18-24 nucleotides in length. In some embodiments, the targeting sequence may have 19-21 nucleotides in length. In some embodiments, the spacer sequence may comprise 20 nucleotides in length.

In some embodiments, the gRNA can be a sgRNA, which may comprise a 20 nucleotide spacer sequence at the 5' end of the sgRNA sequence. In some embodiments, the sgRNA may comprise a less than 20 nucleotide spacer sequence at the 5' end of the sgRNA sequence. In some embodiments, the sgRNA may comprise a more than 20 nucleotide spacer sequence at the 5' end of the sgRNA sequence. In some embodiments, the sgRNA comprises a variable length spacer sequence with 17-30 nucleotides at the 5' end of the sgRNA sequence. Examples are provided in Table 8 in Example 7.

In some embodiments, the sgRNA comprises no uracil at the 3' end of the sgRNA sequence. In other embodiments, the sgRNA may comprise one or more uracil at the 3' end of the sgRNA sequence. For example, the sgRNA can comprise 1-8 uracil residues, at the 3' end of the sgRNA sequence, e.g., 1, 2, 3, 4, 5, 6, 7, or 8 uracil residues at the 3' end of the sgRNA sequence.

Any of the gRNAs disclosed herein, including any of the sgRNAs, may be unmodified. Alternatively, it may contain one or more modified nucleotides and/or modified backbones. For example, a modified gRNA such as an sgRNA can comprise one or more 2'-O-methyl phosphorothioate nucleotides, which may be located at either the 5' end, the 3' end, or both.

In certain embodiments, more than one guide RNAs can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

It should be understood that more than one suitable Cas9 and more than one suitable gRNA can be used in methods described herein, for example, those known in the art or disclosed herein. In some embodiments, methods comprise a Cas9 enzyme and/or a gRNA known in the art. Examples can be found in, e.g., International Application No. PCT/IB2018/001619, filed May 11, 2018, which published as WO 2019/097305A2, and International Application No. PCT/IB2019/000500, filed May 10, 2019, which published as WO/2019/215500, the relevant disclosures of each of the prior applications are herein incorporated by reference for the purposes and subject matter referenced herein.

CRISPR-Cas9-Mediated Gene Editing of TRAC and B2M Genes

In some embodiments, the activated T cells as disclosed herein may subject to gene editing of both the TRAC gene and β2M gene via CRISPR-Cas9-mediated gene editing under conditions disclosed herein, which would result in higher and more consistent gene editing efficiencies compared to those provided by conventional conditions. Further, the TRAC⁻/β2M⁻ T cells obtained from the gene editing process disclosed herein showed high expression level of a chimeric antigen receptor (CAR) when a viral vector coding for the CAR construct is delivered into the TRAC⁻/β2M⁻ T cells.

The Cas9 enzyme and the gRNAs targeting the TRAC gene and β2M gene may form one or more ribonucleoprotein (RNP) complexes, which can be delivered into the activated T cells as disclosed herein. RNPs are useful for gene editing, at least because they minimize the risk of promiscuous interactions in a nucleic acid-rich cellular environment and protect the RNA from degradation. Methods for forming RNPs are known in the art.

The CRISPR-Cas9-mediated gene editing process may involve two ribonucleoprotein complexes. The first RNP complex comprises a first Cas9 enzyme and a guide RNA (gRNA) targeting a TRAC gene. The second RNP complex comprises a second Cas9 enzyme and a gRNA targeting a β2M gene. In some examples, the two RNP complexes may comprise different Cas9 enzymes. In other examples, the two RNP complexes comprise the same Cas9 enzyme. In specific examples, the Cas9 enzyme of SEQ ID NO:1 can be used in both the first and second RNPs.

In some embodiments, the two RNP complexes may contain the same amount of the Cas9 enzyme. For example, both RNP complexes may comprise about 0.1-0.3 mg/ml (e.g., about 0.1-0.2 mg/ml) of the Cas9 enzyme (e.g., the Cas9 enzyme of SEQ ID NO:1). In some examples, each of the RNP complexes may comprise about 0.15 mg/ml of the Cas9 enzyme, which may be the Cas9 enzyme of SEQ ID NO:1.

In other embodiments, the two RNP complexes may contain different amounts of the Cas9 enzyme. In some examples, the RNP complex targeting the TRAC gene may comprise a higher amount of the Cas9 enzyme relative to the RNP complex targeting the β2M gene. Alternatively, the RNP complex targeting the β2M gene may comprise a higher amount of the Cas9 enzyme relative to the RNP complex targeting the TRAC gene.

The two RNP complexes may comprise the same amount of the gRNAs (one targeting TRAC and the other targeting β2M). Alternatively, the two RNP complexes may comprise different amounts of the gRNAs. For example, the amount of the gRNA targeting the TRAC gene may range from about 0.035 mg/ml to about 0.8 mg/ml, for example, about 50 µg/ml to about 80 µg/ml. In specific examples, the amount of the gRNA targeting the TRAC gene is about 0.08 mg/ml. Alternatively or in addition, the amount of the gRNA targeting the β2M gene may range from about 0.075 mg/ml to about 0.3 mg/ml, for example, about 0.1 mg/ml to about 0.3 mg/ml. In specific examples, the amount of the gRNA targeting the β2M gene is about 0.2 mg/ml.

In specific examples, the RNP complex targeting the TRAC gene may comprise about 0.15 mg/ml Cas9 (e.g., the Cas9 of SEQ ID NO:1) and about 0.08 mg/ml of a gRNA targeting the TRAC gene (e.g., the gRNA of TA-1). Alternatively or in addition, the RNP complex targeting the β2M gene may comprise about 0.15 mg/ml Cas9 (e.g., the Cas9 of SEQ ID NO:1) and about 0.2 mg/ml of a gRNA targeting the β2M gene (e.g., the gRNA of B2M-1).

In some embodiments, the two RNPs may be introduced into the activated T cell via electroporation sequentially, i.e., via two electroporation event. Alternatively, the two RNPs may be introduced into the activated T cells simultaneously, i.e., via one electroporation event. In this case, the two RNPs may be combined to form a mixture prior to the electroporation event.

Any of the RNPs disclosed herein may be introduced into the activated T cells by mixing the RNP(s) with a suitable amount of the activated T cells and the mixture thus formed is subject to electroporation under suitable conditions allowing for delivery of the RNPs into the cells. In some instances, the suitable amount of the activated T cells may range from about $100 \times 10^6$ cells/mL to about $300 \times 10^6$ cells/mL. For example, suitable amount of the T cells for the electroporation step may range from about $200 \times 10^6$ cells/mL to about $300 \times 10^6$ cells/mL. In some examples, the concentration of the activated T cells may be about $100 \times 10^6$ cells/mL. In some embodiments, the concentration of activated T cells may be about $200 \times 10^6$ cells/mL. In some embodiments, the concentration of activated T cells may be about $300 \times 10^6$ cells/mL.

In some embodiments, the suitable amount of the activated T cells may range from about $1 \times 10^8$ to about $1 \times 10^{10}$ cells, e.g., about $5 \times 10^8$ to about $8 \times 10^9$ cells, about $1 \times 10^9$ to about $5 \times 10^9$ cells, or about $1 \times 10^9$ to about $3 \times 10^9$ cells.

The T cells for use in electroporation may be placed in multiple cell cassettes, depending upon the electroporation instrument used. Suitable electroporation instruments are known to those skilled in the art and could include static and flow electroporators, including the Lonza Nucleofector, Maxcyte GT, and MaxCyte GTx. In some instances, multiple cell cassettes may be used in an electroporation process. More details are provided in Example 10 below.

In specific examples, the two RNPs disclosed above, comprising about 0.3 mg/ml of the Cas9 enzyme in total (e.g., the Cas9 enzyme of SEQ ID NO:1), about 0.08 mg/ml of the gRNA of TA-1, and about 0.2 mg/ml of the gRNA of B2M-1, may be mixed with the activated T cells in the amount of about $100 \times 10^6$ cells/mL to about $300 \times 10^6$ cells/ mL (e.g., about 300×10$^6$ cells/mL). The mixture is then subject to electroporation for delivery of the RNPs into the T cells.

After electroporation, the cells may be cultured in a fresh medium or electroporation buffer for a suitable period for recovery. Gene editing efficiency may be performed following routine practice. The genetically edited T cells thus produced may be subjected to viral vector transduction for delivery of a nucleic acid configured for CAR expression.

(iv) T Cell Transduction

The genetically edited T cells, having TRAC and β2M genes knocked out, may be subject to transduction with a viral vector such as an adeno-associated viral (AAV) vector that comprises a nucleic acid sequence encoding a chimeric antigen receptor (CAR) to produce a population of T cells expressing the CAR.

Chimeric Antigen Receptor (CAR)

A chimeric antigen receptor (CAR) refers to an artificial immune cell receptor that is engineered to recognize and bind to an antigen expressed by undesired cells, for example, disease cells such as cancer cells. A T cell that expresses a CAR polypeptide is referred to as a CAR T cell. CARs have the ability to redirect T-cell specificity and reactivity toward a selected target in a non-MHC-restricted manner. The non-MHC-restricted antigen recognition gives CAR-T cells the ability to recognize an antigen independent of antigen processing, thus bypassing a major mechanism of tumor escape. Moreover, when expressed on T-cells, CARs advantageously do not dimerize with endogenous T-cell receptor (TCR) alpha and beta chains.

There are various generations of CARs, each of which contains different components. First generation CARs join an antibody-derived scFv to the CD3zeta (ζ or z) intracellular signaling domain of the T-cell receptor through hinge and transmembrane domains. Second generation CARs incorporate an additional co-stimulatory domain, e.g., CD28, 4-1BB (41BB), or ICOS, to supply a costimulatory signal. Third-generation CARs contain two costimulatory domains (e.g., a combination of CD27, CD28, 4-1BB, ICOS, or OX40) fused with the TCR CD3ζ chain. Maude et al., *Blood.* 2015; 125(26):4017-4023; Kakarla and Gottschalk, *Cancer J.* 2014; 20(2):151-155). Any of the various generations of CAR constructs is within the scope of the present disclosure.

Generally, a CAR is a fusion polypeptide comprising an extracellular domain that recognizes a target antigen (e.g., a single-chain variable fragment (scFv) of an antibody or other antibody fragment) and an intracellular domain comprising a signaling domain of the T-cell receptor (TCR) complex (e.g., CD3ζ) and, in most cases, a co-stimulatory domain. (Enblad et al., Human Gene Therapy. 2015; 26(8): 498-505). A CAR construct may further comprise a hinge and transmembrane domain between the extracellular domain and the intracellular domain, as well as a signal peptide at the N-terminus for surface expression. Examples of signal peptides include MLLLVTSLLLCELPHPAFLLIP (SEQ ID NO: 44) and MALPVTALLLPLALLLHAARP (SEQ ID NO: 75). Other signal peptides may be used.

(a) Antigen Binding Extracellular Domain

The antigen-binding extracellular domain is the region of a CAR polypeptide that is exposed to the extracellular fluid when the CAR is expressed on cell surface. In some instances, a signal peptide may be located at the N-terminus to facilitate cell surface expression. In some embodiments, the antigen binding domain can be a single-chain variable fragment (scFv, which may include an antibody heavy chain variable region (V$_H$) and an antibody light chain variable region (V$_L$) (in either orientation). In some instances, the V$_H$ and V$_L$ fragment may be linked via a peptide linker. The linker, in some embodiments, includes hydrophilic residues with stretches of glycine and serine for flexibility as well as stretches of glutamate and lysine for added solubility. The scFv fragment retains the antigen-binding specificity of the parent antibody, from which the scFv fragment is derived. In some embodiments, the scFv may comprise humanized V$_H$ and/or V$_L$ domains. In other embodiments, the V$_H$ and/or V$_L$ domains of the scFv are fully human.

The antigen-binding extracellular domain may be specific to a target antigen of interest, for example, a pathologic antigen such as a tumor antigen. In some embodiments, a tumor antigen is a "tumor associated antigen," referring to an immunogenic molecule, such as a protein, that is generally expressed at a higher level in tumor cells than in non-tumor cells, in which it may not be expressed at all, or only at low levels. In some embodiments, tumor-associated structures, which are recognized by the immune system of the tumor-harboring host, are referred to as tumor-associated antigens. In some embodiments, a tumor-associated antigen is a universal tumor antigen, if it is broadly expressed by most types of tumors. In some embodiments, tumor-associated antigens are differentiation antigens, mutational antigens, overexpressed cellular antigens or viral antigens. In some embodiments, a tumor antigen is a "tumor specific antigen" or "TSA," referring to an immunogenic molecule, such as a protein, that is unique to a tumor cell. Tumor specific antigens are exclusively expressed in tumor cells, for example, in a specific type of tumor cells.

In some examples, the CAR constructs disclosed herein comprise a scFv extracellular domain capable of binding to CD19. In some examples, the CAR constructs disclosed herein comprise a scFv extracellular domain capable of binding to BCMA. Examples of anti-CD19 CAR and anti-BCMA CAR are provided in Examples below.

(b) Transmembrane Domain

The CAR polypeptide disclosed herein may contain a transmembrane domain, which can be a hydrophobic alpha helix that spans the membrane. As used herein, a "transmembrane domain" refers to any protein structure that is thermodynamically stable in a cell membrane, preferably a eukaryotic cell membrane. The transmembrane domain can provide stability of the CAR containing such.

In some embodiments, the transmembrane domain of a CAR as provided herein can be a CD8 transmembrane domain. In other embodiments, the transmembrane domain can be a CD28 transmembrane domain. In yet other embodiments, the transmembrane domain is a chimera of a CD8 and CD28 transmembrane domain. Other transmembrane domains may be used as provided herein. In some embodiments, the transmembrane domain is a CD8a transmembrane domain containing the sequence of:

```
                                    (SEQ ID NO: 49)
FVPVFLPAKPTTTPAPRPPTPAPTIASQPLSLRPEACRPAAG

GAVHTRGLDFACDIYIWAPLAGTCGVLLLSLVITLYCNHRNR;
or
```

```
                                    (SEQ ID NO: 31)
IYIWAPLAGTCGVLLLSLVITLY.
```

Other transmembrane domains may also be used.

(c) Hinge Domain

In some embodiments, a hinge domain may be located between an extracellular domain (comprising the antigen binding domain) and a transmembrane domain of a CAR, or between a cytoplasmic domain and a transmembrane domain of the CAR. A hinge domain can be any oligopeptide or polypeptide that functions to link the transmembrane domain to the extracellular domain and/or the cytoplasmic domain in the polypeptide chain. A hinge domain may function to provide flexibility to the CAR, or domains thereof, or to prevent steric hindrance of the CAR, or domains thereof.

In some embodiments, a hinge domain may comprise up to 300 amino acids (e.g., 10 to 100 amino acids, or 5 to 20 amino acids). In some embodiments, one or more hinge domain(s) may be included in other regions of a CAR. In some embodiments, the hinge domain may be a CD8 hinge domain. Other hinge domains may be used.

(d) Intracellular Signaling Domains

Any of the CAR constructs contain one or more intracellular signaling domains (e.g., CD3ζ, and optionally one or more co-stimulatory domains), which are the functional end of the receptor. Following antigen recognition, receptors cluster and a signal is transmitted to the cell.

CD3ζ is the cytoplasmic signaling domain of the T cell receptor complex. CD3ζ contains three (3) immunoreceptor tyrosine-based activation motif (ITAM)s, which transmit an activation signal to the T cell after the T cell is engaged with a cognate antigen. In many cases, CD3ζ provides a primary T cell activation signal but not a fully competent activation signal, which requires a co-stimulatory signaling.

In some embodiments, the CAR polypeptides disclosed herein may further comprise one or more co-stimulatory signaling domains. For example, the co-stimulatory domains of CD28 and/or 4-1BB may be used to transmit a full proliferative/survival signal, together with the primary signaling mediated by CD3ζ. In some examples, the CAR disclosed herein comprises a CD28 co-stimulatory molecule. In other examples, the CAR disclosed herein comprises a 4-1BB co-stimulatory molecule. In some embodiments, a CAR includes a CD3ζ signaling domain and a CD28 co-stimulatory domain. In other embodiments, a CAR includes a CD3ζ signaling domain and 4-1BB co-stimulatory domain. In still other embodiments, a CAR includes a CD3ζ signaling domain, a CD28 co-stimulatory domain, and a 4-1BB co-stimulatory domain.

It should be understood that methods described herein encompasses more than one suitable CAR that can be used to produce genetically engineered T cells expressing the CAR, for example, those known in the art or disclosed herein. Examples can be found in, e.g., PCT/IB2018/001619, filed May 11, 2018, which published as WO 2019/097305A2, the relevant disclosures of which are incorporated by reference herein for the purpose and subject matter referenced herein. In another example, the CAR binds CD19 (also known as a "CD19 CAR" or an "anti-CD19 CAR"). The amino acid sequence of an exemplary CAR that binds CD19 is provided in SEQ ID NO: 37 (see Example 7 below, Table 11). In yet another example, the CAR binds BCMA (also known as a "BCMA CAR" or an "anti-BCMA CAR"). The amino acid sequence of an exemplary CAR that binds to BCMA is provided in SEQ ID NO: 61 (see Example 8 below, Tables 16 and 17).

AAV Vectors for Delivery of CAR Constructs to T Cells

A nucleic acid encoding a CAR construct can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV for use in delivering the CAR-coding nucleic acid is AAV serotype 6 (AAV6).

Adeno-associated viruses are among the most frequently used viruses for gene therapy for several reasons. First, AAVs do not provoke an immune response upon administration to mammals, including humans Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

A nucleic acid encoding a CAR can be designed to insert into a genomic site of interest in the host T cells. In some embodiments, the target genomic site can be in a safe harbor locus.

In some embodiments, a nucleic acid encoding a CAR (e.g., via a donor template, which can be carried by a viral vector such as an adeno-associated viral (AAV) vector) can be designed such that it can insert into a location within a TRAC gene to disrupt the TRAC gene in the genetically engineered T cells and express the CAR polypeptide. Disruption of TRAC leads to loss of function of the endogenous TCR. For example, a disruption in the TRAC gene can be created with an endonuclease such as those described herein and one or more gRNAs targeting one or more TRAC genomic regions. Any of the gRNAs specific to a TRAC gene and the target regions can be used for this purpose, e.g., those disclosed herein.

In some examples, a genomic deletion in the TRAC gene and replacement by a CAR coding segment can be created by homology directed repair or HDR (e.g., using a donor template, which may be part of a viral vector such as an adeno-associated viral (AAV) vector). In some examples, the gRNA target sequence, or portion thereof, is deleted (e.g., SEQ ID NO: 17). In some embodiments, a disruption in the TRAC gene can be created with an endonuclease as those disclosed herein and one or more gRNAs targeting one or more TRAC genomic regions, and inserting a CAR coding segment into the TRAC gene.

A donor template as disclosed herein can contain a coding sequence for a CAR. In some examples, the CAR-coding sequence may be flanked by two regions of homology to allow for efficient HDR at a genomic location of interest, for example, at a TRAC gene using CRISPR-Cas9 gene editing technology. In this case, both strands of the DNA at the target locus can be cut by a CRISPR Cas9 enzyme guided by gRNAs specific to the target locus. HDR then occurs to repair the double-strand break (DSB) and insert the donor DNA coding for the CAR. For this to occur correctly, the donor sequence is designed with flanking residues which are complementary to the sequence surrounding the DSB site in the target gene (hereinafter "homology arms"), such as the TRAC gene. These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced into a cell as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLY)).

A donor template, in some embodiments, can be inserted at a site nearby an endogenous promoter (e.g., downstream or upstream) so that its expression can be driven by the endogenous promoter. In other embodiments, the donor template may comprise an exogenous promoter and/or enhancer, for example, a constitutive promoter, an inducible promoter, or tissue-specific promoter to control the expression of the CAR gene. In some embodiments, the exogenous promoter is an EF1α promoter. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

T Cell Transduction

A suitable amount of any of the viral vectors such as an AAV vector, which encodes a CAR construct disclosed herein (e.g., an anti-CD19 CAR or an anti-BCMA CAR) may be incubated with a suitable amount of T cells, such as the genetically edited T cells disclosed herein for a suitable period to allow for entry of the viral vector into the T cells. For example, the transduction process may involve the use of a range of optimized multiplicity of infection (MOI) that increases percentages of CAR+ T cells. In some instances, the MOI of an AAV vector in the transduction process may range from about 1,000 to about 150,000, such as from about 10,000 to about 80,000. In some examples, the MOI of the AAV vector used in the transduction process may be about 1,000 to about 150,000, about 5,000 to about 100,000, about 10,000 to about 100,000, about 10,000 to about 90,000, about 10,000 to about 80,000, about 10,000 to about 70,000, about 10,000 to about 60,000, about 10,000 to about 50,000, about 10,000 to about 40,000, about 10,000 to about 30,000, about 10,000 to about 20,000, about 20,000 to about 80,000, about 30,000 to about 80,000, about 40,000 to about 80,000, about 50,000 to about 80,000, about 60,000 to about 80,000, or about 70,000 to about 80,000. In some examples, the MOI of the AAV vector used in the transduction process may be about 1,000, about 2,500, about 5,000, about 10,000, about 15,000, about 20,000, about 25,000, about 30,000, about 31,000, about 32,000, about 33,000, about 34000, about 35,000, about 40,000, about 50,000, about 60,000, about 70,000, about 80,000, about 90,000, about 100,000, about 110,000, about 120,000, about 130,000, about 140,000, or about 150,000.

In some embodiments, the AAV vector encodes an anti-CD19 CAR (e.g., as disclosed in Example 7 below) and the MOI of such an AAV vector for use in the transduction process is about 20,000. In other embodiments, the AAV vector encodes an anti-BCMA CAR (e.g., as disclosed in Example 8 below) and the MOI of such an AAV vector for use in the transduction process is about 20,000.

After transduction, the T cells may be cultured in a suitable cell culture medium for a suitable period for recovery. The genetically engineered T cells, having TRAC and B2M genes knocked-out and expressing the CAR, may be expanded in vitro as disclosed below.

(v) T Cell Expansion

The genetically engineered T cells as disclosed herein may be expanded in vitro under suitable conditions to produce a population of genetically engineered T cells to a clinically relevant scale. Cell culture conditions used in this expansion step intend to, at least in part, achieve higher final cell densities in shorter incubation periods (thereby reducing manufacturing cost) and higher potent T cells for use in cell therapy. Potency may be indicated by various T cell functions, e.g., proliferation, target cell killing, cytokine production, activation, migration, and combinations thereof.

In some embodiments, the T cell expansion step may be performed by seeding a population of T cells (e.g., the genetically engineered T cells as disclosed herein) in a cell culture vessel at a seeding density of about 150,000 cells/cm² to about 600,000 cells/cm² in a cell vessel. For example, the T cells may be seeded at about 300,000 cells/cm² to about 500,000 cells/cm², in a cell vessel. In some aspects, the T cell expansion is performed by seeding a population of T cells in a cell culture vessel at a seeding density of at least about 60,000 cells/cm², at least about 62,500 cells/cm², or at least about 83,000 cells/cm². In some aspects, the T cell expansion is performed by seeding a population of T cells in a cell culture vessel at a seeding density of at least about 150,000 cells/cm², or at least about 250,000 cells/cm², or at least about 300,000 cells/cm², or at least about 400,000 cells/cm², or at least about 500,000 cells/cm², or at least about 600,000 cells/cm². In some aspects, the seeding density is about 250,000 cells/cm². In other aspects, the seeding density is about 500,000 cells/cm². In other aspects, the seeding density is about 600,000 cells/cm².

In some embodiments, the T cell expansion step may be performed by seeding a population of T cells (e.g., the genetically engineered T cells as disclosed herein) in a cell culture vessel at a seeding density of about 2×10⁵ cells/cm² to about 7×10⁵ cells/cm², and culturing the cells for about 6 days to about 12 days. In some examples, the T cell expansion is performed by seeding a population of T cells in a cell culture vessel at a seeding density of about 2×10⁵ cells/cm² to about 7×10⁵ cells/cm², about 2×10⁵ cells/cm² to about 5×10⁵ cells/cm², about 2×10⁵ cells/cm² to about 4×10⁵ cells/cm², 2×10⁵ cells/cm² to about 3×10⁵ cells/cm², 3×10⁵ cells/cm² to about 5×10⁵ cells/cm², or 4×10⁵ cells/cm² to about 5×10⁵ cells/cm², and culturing the cells for about 6 days to about 12 days, about 6 days to about 11 days, about 6 days to about 10 days, about 6 days to about 9 days, about 6 days to about 8 days, about 6 days to about 7 days, about 7 days to about 12 days, about 7 days to about 11 days, about 7 days to about 10 days, about 7 days to about 9 days, about 7 days to about 8 days, about 8 days to about 12 days, about 8 days to about 9 days, about 9 days to about 12 days, about 10 days to about 12 days, or about 11 days to about 12 days. In some embodiments, the T cell expansion is performed by seeding a population of T cells in a cell culture vessel at a seeding density of about $3 \times 10^5$ cells/cm$^2$ to about $5 \times 10^5$ cells/cm$^2$ and culturing the cells for about 7 days to about 9 days.

In some embodiments, the T cell expansion step may include replating the cell culture (i.e., splitting the cell culture into new culture vessels). In some embodiments, the cell culture can be replated at day 3, 4, 5, 6, or 7 post editing at a 1:4 ratio (1 vessel split into 4 new vessels) for further expansion.

T cell expansion may be performed in a static culture vessel, which allows expansion of the T cells without medium change. For example, T cells can be expanded in a static culture vessel for at about 7 days to about 12 days, or at about 7 days to about 9 days without medium change.

(vi) Depletion of TCRαβ$^+$ T Cells

In some embodiments, TCRαβ$^+$ T cells may be depleted from the expanded T cell population disclosed herein to produce a population of allogenic T cells for use in cell therapy. As used herein, "TCRαβ$^+$ T cell depletion" refers to depleting TCRαβ$^+$ T cells from a population of cells comprising such. Following TCRαβ$^+$ T cell depletion, the resultant T cell population may have a substantially low level of TCRαβ$^+$ T cell (e.g., less than 3% in the total cell population, or less than 2%, less than 1%, or less than 0.5% in the total cell population). In some examples, the resultant T cell population may be free of TCRαβ$^+$ T cell, i.e., presence of TCRαβ$^+$ T cell is not dateable via a conventional method (e.g., in an immune assay using an antibody binding to TCRαβ$^+$ or by flow cytometry).

TCRαβ$^+$ T cell depletion may be performed using an agent that recognizes TCRαβ$^+$ T cells to capture the TCRαβ$^+$ T cells, thereby separating them from those lacking TCRαβ$^+$, e.g., by performing a magnetic cell separation. Such methods may be carried out by contacting the expanded T cells disclosed above to beads on which anti-TCRαβ antibodies are immobilized, and collecting unbound cells. Unbound cells (those lacking TCRαβ$^+$) thus collected may be cultured to allow cell recovery prior, for example, unbound cells may be cultured overnight to allow cells to recover.

(vii) Harvest of Genetically Engineered T Cells

The genetically engineered T cells produced by any of the methods disclosed herein can then be harvested for therapeutic uses using conventional methods known in the art. For example, harvesting genetically engineered T cells may comprise collecting cells from which TCRαβ$^+$ has been depleted. The harvested population of genetically engineered T cells may be used as the drug substance. As used herein, a "drug substance" refers to a population of genetically engineered T cells that may be administered to patients. The drug substance may be formulated for therapeutic uses, e.g., formulated in storage media (e.g., CryoStor CS5) and cryopreserved for future use.

Drug substance may be tested for one or more contaminants, e.g., mycoplasma, human viruses (e.g., HIV, HBV, HCV, CMV), and bacterial endotoxins. Alternatively, or in addition to, drug substance may be tested for sterility. Contamination free drug substance may be aliquoted into individual patient doses. Alternatively, or in addition to, contamination free drug substance may be stored for therapeutic use.

Accordingly, aspects of the present disclosure provide a population of genetically engineered T cells (drug substance). The population of genetically engineered T cells has a disrupted TRAC gene, a disrupted β2M gene, and a nucleic acid encoding a CAR, e.g., those described herein. In some embodiments, the CAR binds an antigen expressed on a pathological cell. In some embodiments, the CAR binds CD19. In some embodiments, the CAR binds BCMA.

In some embodiments, at least 30%, at least 40%, at least 50%, at least 60%, at least 70%, at least 80%, at least 90%, or at least 95% of the population of genetically engineered T cells produced by methods described herein express a CAR. In other aspects, these cells that express a CAR further do not express a detectable level of surface TCR and/or a detectable level of surface β2M.

In other embodiments, where at least 30% of the population of genetically engineered T cells produced by methods described herein express a CAR, that population of cells comprises not more than about 1.0%, not more than about 0.5%, not more than about 0.4%, or not more than about 0.15% T cells that express surface TCR (e.g., TCRα/β$^+$ cells).

In other embodiments, where at least 30% of the population of genetically engineered T cells produced by methods described herein express a CAR, that population of cells comprises not more than about 50%, not more than about 40%, or not more than about 30%, T cells that express surface β2M.

Also within the scope of the present disclosure is a genetically engineered T cell population produced by methods described herein comprising a Cas9 enzyme, a gRNA targeting a TRAC gene, a gRNA targeting a β2M gene, and an AAV vector comprising a nucleic acid sequence encoding a CAR (e.g., a CD19 CAR or a BCMA CAR).

II. Therapeutic Applications

A population of genetically engineered T cells produced by methods described herein may be administered to a subject for therapeutic purposes, for example, treatment of a cancer targeted by the CAR construct expressed by the population of genetically engineered T cells.

A subject may be any subject for whom diagnosis, treatment, or therapy is desired. In some embodiments, the subject is a mammal. In some embodiments, the subject is a human.

Non-limiting examples of cancers that may be treated using a genetically engineered T cell population produced by methods described herein include, but are not limited to, multiple myeloma, leukemia (e.g., T cell leukemia, B-cell acute lymphoblastic leukemia (B-ALL), and/or chronic lymphocytic leukemia (C-CLL)), lymphoma (e.g., B-cell non-Hodgkin's lymphoma (B-NHL), Hodgkin's lymphoma, and/or T cell lymphoma), and/or clear cell renal cell carcinoma (ccRCC), pancreatic cancer, gastric cancer, ovarian cancer, cervical cancer, breast cancer, renal cancer, thyroid cancer, nasopharyngeal cancer, non-small cell lung (NSCLC), glioblastoma, and/or melanoma.

Administering may include placement (e.g., transplantation) of the genetically engineered T cell population into a subject by a method or route that results in at least partial localization of the genetically engineered T cell population at a desired site, such as a tumor site, such that a desired effect(s) can be produced. The genetically engineered T cell population can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment. For example, in some aspects described herein, an effective amount of the genetically engineered T cell population can be administered via a systemic route of administration, such as an intraperitoneal or intravenous route.

In some embodiments, the genetically engineered T cell population is administered systemically, which refers to the administration of a population of cells other than directly into a target site, tissue, or organ, such that it enters, instead, the subject's circulatory system and, thus, is subject to metabolism and other like processes. Suitable modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

An effective amount refers to the amount of a genetically engineered T cell population needed to prevent or alleviate at least one or more signs or symptoms of a medical condition (e.g., cancer), and relates to a sufficient amount of a genetically engineered T cell population to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

An effective amount of a genetically engineered T cell population may comprise at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof.

The efficacy of a treatment using the genetically engineered T cell population manufactured as described herein can be determined by one of ordinary skill in the art. A treatment is considered "effective", if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

Genetically engineered T cell populations manufactured as described herein may also be used in combination therapies. For example, the genetically engineered T cell population manufactured as described herein may be co-used with other therapeutic agents, for treating the same indication, or for enhancing efficacy of the genetically engineered T cell population and/or reducing side effects of the genetically engineered T cell population.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985; *Transcription and Translation* (B. D. Hames & S. J. Higgins, eds. (1984; *Animal Cell Culture* (R. I. Freshney, ed. (1986; *Immobilized Cells and Enzymes* (1RL Press, (1986; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described may be more fully understood, the following examples are set forth. The examples described in this application are offered to illustrate the methods and compositions provided herein and are not to be construed in any way as limiting their scope.

Example 1: Identification of Optimized Conditions for T Cell Enrichment

This Example reports identification of optimized conditions for T cell enrichment, using an automated cell processing system to enrich CD4$^+$ and CD8$^+$ T cells from leukopaks.

Methods

Leukopak and Buffer Preparation

Human leukopaks were collected from HemaCare or Stem Express and processed for T cells enrichment. PBS/EDTA Buffer (phosphate buffered saline, pH 7.2, supplemented with 1 mM EDTA) was supplemented with 0.5% Human Serum Albumin (HSA) and used for processing, priming, washing, and elution during T cell selection.

The leukopak donors were screened for the following:

Hepatitis B Surface Antigen (HBsAg EIA)

Hepatitis C Virus Antibody (Anti-HCV EIA)

Human Immunodeficiency Virus Antibody (HIV 1/2 plus 0)

Human T-Lymphotropic Virus Antibody (HTLV-I/II)

HIV-1/HCV/HBV Nucleic Acid Testing

WNV Nucleic Acid Testing

*Trypanosoma Cruzi* Antibody (Selective Chagas Disease Testing, a single lifetime test per donor)

HIV/HBV/HCV

CMV

Donors showing positive results of any of the above tests were excluded. Demographic information of the donors used in the Examples disclosed herein is shown in Table 1.

28 for separation. CD4$^+$ and CD8$^+$ T cells were captured and further eluted into the target bag in processing buffer.

Cell Count and Viability

Cell count and viability assessment were performed with COUNTESS® II (Life Technologies, Cat: AMQAX1000) using a default profile. Cells (20 μL) were mixed with Trypan blue (20 μL) by pipetting up and down a few times without introducing bubbles. Cell/Trypan blue mixture (10 μL) was loaded into COUNTESS® II cell counting chamber slides.

Flow Cytometry

About 1×10$^6$ total nuclei cells were blocked with 5 μL of human TruStain FcX™ in 95 μL of staining buffer (0.5% Bovine Serum Albumin (BSA)/DPBS)) at room temperature (RT) for 10 minutes. Cells were further incubated with Pacific blue-conjugated anti-human CD45 antibody (1:50), BV510-conjugated anti-human CD3 antibody (1:50), APC-Cy7-conjugated anti-human CD4 antibody (1:50), PE-Cy7-conjugated anti-human CD8 antibody (1:50), APC-conjugated anti-human CD19 antibody (1:50), FITC-conjugated anti-human CD56 antibody (1:50) and PE-conjugated anti-human CD33 antibody (1:50) at 4° C. for 30 minutes. Then, 1 mL of Ammonium-Chloride-Potassium (ACK) lysis buffer containing 5 μL 7-amino-actinomycin D (7-AAD) viability staining solution was applied to each sample. After incubation with ACK lysing buffer at RT for 10 minutes, cells were acquired with NovoCyte-3000 flow cytometer.

TABLE 1

| | | | | | | | | | |
|---|---|---|---|---|---|---|---|---|---|
| Donor demographic and hematology parameters. All donors were male. | | | | | | | | | |
| Batch | Supplier | Donor source ID | Age | Donor weight (lb) | BMI | Ethnicity | ABO/Rh | Product volume (mL) | WBC (×10$^9$) | Lymphocyte % |
| 1 | HemaCare | D327083 | 26 | 144 | 19.0 | Hispanic/Latino | O-POS | 279 | 9.77 | 79 |
| 2 | HemaCare | 141402 | 29 | 160 | 22.9 | Caucasian | A-POS | 302 | 13.59 | 75.9 |
| 3 | HemaCare | 141121 | 26 | 154 | 24.8 | Hispanic | O-POS | 250 | 8.75 | 74.7 |
| 4 | HemaCare | 136723 | 20 | 130 | 20.9 | Caucasian | A-POS | 305 | 12.81 | 70.1 |
| 5 | HemaCare | D64140 | 28 | 272 | 42.6 | Hispanic/Latino | A-POS | 339 | 21.36 | 81.1 |
| 6 | Stem Express | D001003864 | 33 | 176 | 24.0 | Caucasian | A-POS | 140 | 8.14 | 70.9 |
| 7 | HemaCare | 141722 | 20 | 135 | 19.9 | Hispanic | O-POS | 308 | 13.24 | 78.5 |
| 8 | HemaCare | D327737 | 36 | 200 | 26.4 | African American | B-POS | 310 | 14.57 | 81.3 |
| 9 | HemaCare | D326737 | 31 | 225 | 29.7 | African American | AB-POS | 314 | 10.99 | 77.9 |

Leukopak Hematology Analysis with Sysmex

Samples from incoming leukopaks were processed for hematology analysis with Sysmex XP300 (Sysmex, Serial No: B0628) following manufacturer's instructions. White blood cell (WBC) count was used to calculate the total cell mass loaded into the automated cell processing system.

T cell Enrichment

Process buffer, leukopak, CD4 microbeads, and CD8 microbeads were loaded in the automated cell processing system prior to starting the run. Cells were washed and labeled in the chamber and directed to the magnet column Results White Blood Cells (WBCs) in Leukopak Samples WBC in the tested leukopaks ranged from 8.14×10$^9$ to 21.36×10$^9$ cells with lymphocyte number ranging from 5.77×10$^9$ to 17.32×10$^9$.

CD4 and CD8 Enrichment—Purity, Viability, Cell Recovery, and Yield

Among the 9 batches tested, four were evaluated with program A and five were evaluated with program B. All batches yielded T cells with >90% purity and with >90% viability (Table 2). Cell recovery from program A was 31% whereas cell recovery from program B was 55.69%.

TABLE 2

| | | | | Target Cell | | | |
| Batch | Program | Leukopak CD3 % | Non-Target Cell CD3 % | Cell Number ($\times 10^9$) | CD3 % | Viability (%) | Recovery (%) |
|---|---|---|---|---|---|---|---|
| 1 | A | 73.20 | 50.80 | 1.32 | 96.20 | 96.50 | 29.24 |
| 2 | | 72.30 | 60.40 | 2.76 | 96.30 | 93.50 | 27.00 |
| 3 | | 64.90 | 46.00 | 2.32 | 96.80 | 95.00 | 39.15 |
| 4 | | 63.50 | 55.00 | 2.59 | 89.70 | 94.00 | 30.77 |
| | Avg (A) | 68.48 | 53.05 | 2.25 | 94.75 | 94.75 | 31.54 |
| 5 | B | 70.30 | 15.70 | 6.00 | 94.50 | 93.00 | 39.75 |
| 6 | | 56.00 | 3.17 | 2.14 | 92.80 | 96.00 | 47.10 |
| 7 | | 69.00 | 16.80 | 4.68 | 96.60 | 93.00 | 49.10 |
| 8 | | 59.40 | 15.20 | 6.82 | 92.60 | 96.00 | 75.87 |
| 9 | | 55.50 | 11.20 | 3.88 | 93.60 | 98.00 | 61.65 |
| | Avg (B) | 62.04 | 12.41 | 4.70 | 94.02 | 95.20 | 54.69 |

Taken together, these results demonstrate that T cells from healthy donor (HD) leukopaks were enriched with high purity (>90%) and high viability (>90%) for CD4$^+$ and CD8$^+$ T cells.

Example 2: Identification of Optimized Conditions for T Cell Activation

This Example reports identification of optimized conditions for T cell activation, using a colloidal polymeric nanomatrix conjugated to recombinant humanized CD3 and CD28 agonists.

Identification of Optimized Conditions for T Cell Activation in a Static Culture Vessel In brief, cryopreserved T cells from healthy donor leukopaks were thawed, and activated with recombinant humanized CD3 and CD28 agonists conjugated to a polymeric nanomatrix for 48 hours in a T-flask as a control or a static culture vessel. T cell activation was evaluated by monitoring the surface expression of cell activation marker CD25 and CD69, and by monitoring cell proliferation. Various T cell activation conditions for activation in static culture vessels were tested including cell seeding density, medium volume, and recombinant humanized CD3 and CD28 agonists conjugated to a polymeric nanomatrix concentration ("CD3/CD28 agonists") (Table 3). T cell activation was evaluated by monitoring the surface expression of cell activation marker CD25 and CD69, and by monitoring cell proliferation. T cell activation in a T-flask was used as a positive control (PC) (Table 3).

TABLE 3

| | | | | | | CD3/CD28 agonists to |
| Condition | Vessel | cell number per cm$^2$ | Volume of Medium (mL) | cell density per mL | CD3/CD28 agonists (µl per $1 \times 10^6$ cells) | Medium ratio |
|---|---|---|---|---|---|---|
| 1 | Static | $1.00 \times 10^7$ | 8 | $2.50 \times 10^6$ | 40 | 1:10 |
| 2 | Vessel | $1.00 \times 10^7$ | 4 | $5.00 \times 10^6$ | 40 | 1:5 |
| 3 | | $1.00 \times 10^7$ | 2 | $1.00 \times 10^7$ | 40 | 1:2.5 |
| 4 | | $1.00 \times 10^7$ | 4 | $5.00 \times 10^6$ | 8 | 1:25 |
| 5 | | $1.00 \times 10^7$ | 2 | $1.00 \times 10^7$ | 4 | 1:25 |
| 6 | | $2.00 \times 10^6$ | 4 | $1.00 \times 10^6$ | 40 | 1:25 |
| 7 | | $2.00 \times 10^6$ | 2 | $2.00 \times 10^6$ | 40 | 1:12.5 |
| 8 | | $2.00 \times 10^6$ | 2 | $2.00 \times 10^6$ | 20 | 1:12.5 |
| Positive Control (PC) | T-Flask | | 10 | $1.00 \times 10^6$ | 40 | 1:25 |

Figure 1A:
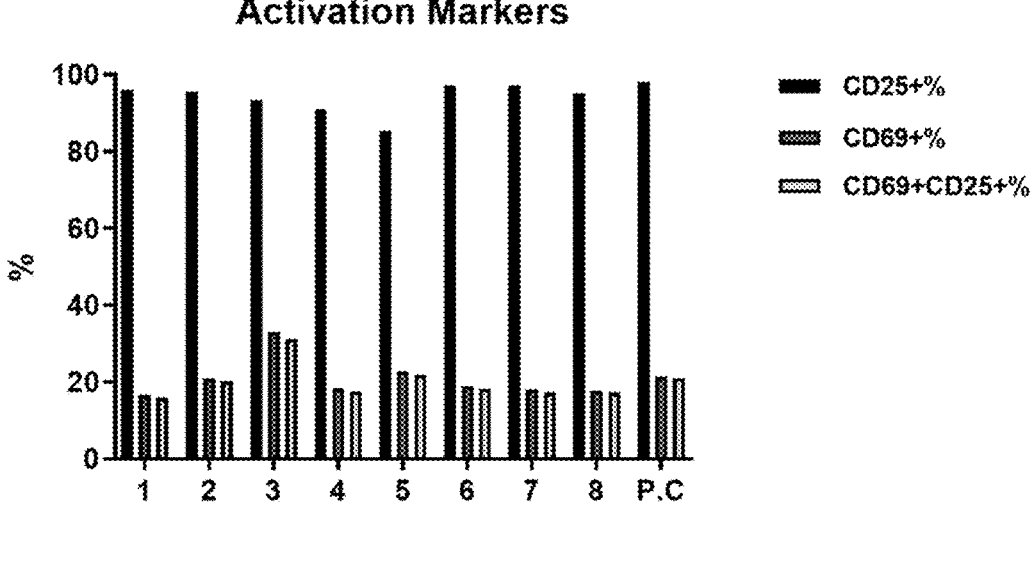

As shown in FIG. 1A, the percentage of cells expressing CD25 and CD69 were similar among the conditions tested. A slightly higher (~10% higher) population of $CD69^+$ cells and CD25+CD69+ cells were observed in condition 3 (FIG. 1A).

Figure 1B:
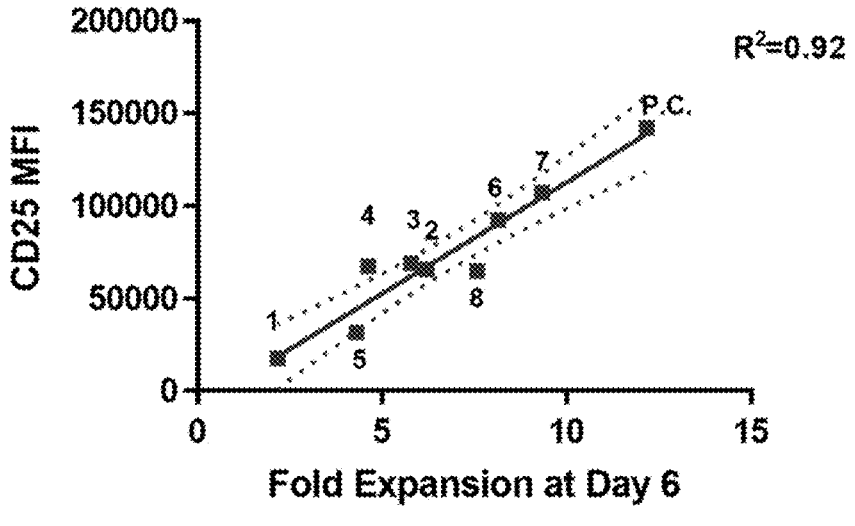

The cell expansion rate, however, was not correlated with the expression level of CD69 but rather, it was correlated with the expression level of CD25, as measured by the mean florescent intensity (MFI) of CD25 (FIG. 1B). Among the conditions tested, condition 7 had the most similar correlation between CD25 MFI and cell expansion when compared to that of the positive control (FIG. 1B). CD25 and CD69 are T-cell activation markers, where early upregulation and late upregulation are correlated with activation status.

In sum, these results demonstrate that Condition 7 in Table 3 led to superior T cell activation effect (Condition 7: $2.00 \times 10^6$ cells/cm$^2$; $2.00 \times 10^6$ cells/mL; 40 µL of colloidal polymeric nanomatrix conjugated to recombinant humanized CD3 and CD28 agonists/$1 \times 10^6$ cells; and 1:12.5 colloidal polymeric nanomatrix conjugated to recombinant humanized CD3 and CD28 agonists to medium ratio) in a static culture vessel.

Validation of Optional T Cell Activation Conditions in a Small-Scale Manufacturing Process Next, the identified T cell activation conditions (Condition 7: $2.00 \times 10^6$ cells/cm$^2$; $2.00 \times 10^6$ cells/mL; 40 µL of colloidal polymeric nanomatrix conjugated to recombinant humanized CD3 and CD28 agonists/$1 \times 10^6$ cells; and 1:12.5 colloidal polymeric nanomatrix conjugated to recombinant humanized CD3 and CD28 agonists to medium ratio) were tested in a small scale manufacturing process (in a static culture vessel) and the activated T cells were investigated for their gene editing efficiency with respect to expression of a chimeric antigen receptor (CAR), T cell receptor alpha chain constant region (TRAC) knock-out, and/or beta-2-microglobulin (β2M) knock-out. Activation and editing of T cells in a T-flask (Flask) was compared to that in a static cell culture vessel (Vessel). TRAC and β2M electroporated T cells (EP) and untreated T cells (UT) were used as controls.

Small Scale Manufacturing Process

Cryovials were retrieved from liquid nitrogen storage and were thawed in a water bath until a small amount of frozen material remained. Cells were then added dropwise to a 10× volume of full growth medium (X-VIVO™ 15 (Lonza), 5% Human AB Serum, 100 U/mL IL2, 100 U/mL IL7), and pelleted by centrifugation at 300 g for 10 minutes at room temperature. Cells were resuspended to a concentration of $1 \times 10^6$ cells/mL and subjected to colloidal polymeric nanomatrix conjugated to recombinant humanized CD3 and CD28 agonists-mediated activation, which improved downstream modification. In brief, isolated T cells were activated with recombinant CD3 and CD28 covalently attached to a colloidal polymeric nanomatrix. The colloidal polymeric nanomatrix conjugated to recombinant humanized CD3 and CD28 agonists was applied to cells at a 1:25 ratio or 40 µL per $1 \times 10^6$ cells in a nontreated flask. Cells were maintained in the colloidal polymeric nanomatrix conjugated to recombinant humanized CD3 and CD28 agonists for 2 days in an incubator at 37° C., 5% CO$_2$ for 48 hours. Following incubation, cells are centrifuged at 300 g for 10 minutes at room temperature. Cell pellets were then resuspended in full growth media and cultured overnight at a concentration of $1 \times 10^6$ cells/mL prior to gene modification.

Following overnight culture in full media without the colloidal polymeric nanomatrix conjugated to recombinant humanized CD3 and CD28 agonists, total cell numbers and cell viability were quantified by addition of Trypan blue and counting on the COUNTESS® cytometer. Then, cells were centrifuged at 300 g for 10 minutes at room temperature. Cell pellets were washed in 10 mL of electroporation buffer and centrifuged again. While cells were being centrifuged, ribonucleoprotein (RNP) complexes were prepared. Two separate RNP complexes were formed. One RNP was formed containing B2M sgRNA and Cas9 at concentrations of 150 µg/mL and 150 µg/mL, respectively. The other RNP was formed containing TCR sgRNA and Cas9 at concentrations of 150 µg/mL and 150 µg/mL respectively. RNP complexes containing sgRNAs and Cas9 were formed by incubation at room temperature for 10 minutes. One RNP complex was formed containing Cas9 (Cas9; SEQ ID NO: 1) and a gRNA targeting the β2M gene (B2M-1; SEQ ID NO: 6), and the other RNP complex was formed containing Cas9 (Cas9; SEQ ID NO: 1) and a gRNA targeting the TCR gene (TA-1; SEQ ID NO: 2). Following centrifugation, cell pellets were resuspended in electroporation buffer to a concentration of $400 \times 10^6$ cells/mL. Using the resulting cell suspension, further dilutions were generated bearing final cell concentrations of $300 \times 10^6$ cells/mL, $200 \times 10^6$ cells/mL, $150 \times 10^6$ cells/mL, and $100 \times 10^6$ cells/mL. Separate RNP complexes were combined and pipetted into electroporation cuvettes. Cells at the varying concentrations were added to the RNP complexes and pipetted up and down 5 times.

Cells were electroporated using a transfection system based on flow electroporation. Once each individual cuvette was electroporated, the cell and RNP solution was aliquoted into a non-treated 12-well plate, with each well containing 500 µL of X-VIVO™ 15 media (without Human AB serum, IL2 and IL7). Cells were allowed to rest for 20 minutes in the incubator. Total cell numbers and cell viability were quantified by addition of Trypan blue and counting on the COUNTESS® cytometer or NC-200.

Based on total cell numbers after resting, cells may need to be further diluted with X-VIVO™ 15 (without Human AB serum, IL2 or IL7) to reach the desired concentration. Total cell numbers are needed to calculate the volume of AAV needed to perform the transduction.

$$\text{µL of AAV needed} = (\text{Total cell numbers})(\text{desired MOI (i.e., 20,000)})/(\text{virus vgc/mL (i.e., } 1.5 \times 10^{13}))$$

AAV and cell suspension was mixed and allowed to incubate in a non-treated flask at 37° C. and 5% CO$_2$ for 1 hour. The entire volume, including AAV, was added to a static culture vessel containing 100 mL of full media. The static culture vessel was incubated for 3 days to allow cell expansion.

After electroporation, each well of a static culture vessel was filled with 100 mL of full growth media. Gene modified cells were seeded at a concentration of $5 \times 10^5$ cells/mL to $1 \times 10^6$ cells/mL in full growth media. IL2 or IL7 were replenished every three to four days to a final working concentration of 100 U/mL. Total cell numbers were quantified every three to four days by addition of Trypan blue and counting on the COUNTESS® cytometer. Cells were maintained in culture for nine to twelve days after electroporation to achieve maximal total cell numbers based on a saturation concentration of $30 \times 10^6$ cells/mL. Once cells reached this threshold, depletion of any remaining unedited cells that expressed TCR alpha or beta was performed to remove these cellular impurities.

During the expansion phase in a static culture vessel, cells may reach a plateau phase, thereby attaining a maximal number of cells in the static culture vessel. At this stage, the total cell population comprised 6% or less of TCR alpha and beta positive expressing cells. TCR alpha and beta positive cells may be depleted from the population because they may contribute to graft versus host response. Volume reduction was performed on the static culture vessel to remove 90% of the volume, with the remaining 10% of the volume containing cells. Cells were loaded into a transfer bag which was sterile welded to the tubing set used to perform the depletion. TCR alpha and beta positive cells were removed from the main population using a TCR alpha beta depletion kit comprising biotin anti-TCR alpha beta, which may be captured by anti-biotin beads. Cells depleted of TCR alpha beta positive were eluted into the target bag and are transferred back into a static culture vessel and cultured for an additional day. Cells were then cryopreserved in CS5 and stored at −145° C.

Cells fresh from culture or thawed from cryovials were washed in staining buffer and centrifuged at 1500 rpm for 5 minutes. As a negative control, $1 \times 10^6$ cells were incubated with Fab-Biotin or IgG-Biotin antibodies. Cells were washed with staining buffer and incubated with mouse anti-IgG to capture excess primary antibodies. Cells were washed again and incubated with the full panel of secondary plexes using a transfection system based on flow electroporation. After electroporation, the cells were transduced with a rAAV vector for expressing an anti-CD19 CAR (anti-CD19 CAR; SEQ ID NO: 53) at multiplicity of infection (MOI) of 20,000 and expanded. Knockout efficiency of TCRαβ and β2M, anti-CD19 CAR expression, and cell expansion were assessed during cell expansion. TCRαβ depletion was performed using the automated cell processing system. Process buffer, cell product, and a TCRαβ kit that includes anti-TCRα/β monoclonal antibodies conjugated to biotin were loaded in the automated cell processing system prior to the run. Cells were washed and labeled in the chamber and directed to the magnet column for separation. Unbound cells (TCRαβ⁻) were collected into the target bag in processing buffer.

The cells thus obtained were analyzed by flow cytometry to examine T cell activation efficiency (as represented by CD25⁺ %, CD69⁺ % and fluorescence intensity or MFI), gene editing efficiency (αβ % and β2M %), TCDαβ depletion efficiency, and CAR expression efficiency. See Table 4 below.

TABLE 4

| Panel | Purpose | Unconjugated Antibody | Unconjugated Antibody |
|---|---|---|---|
| T cell activation panel | T cell activation status: CD25%, CD25 mean fluorescence intensity (MFI), CD69% | | CD45-Pacific Blue; CD5-FITC; CD4-APC-Cy7; CD3-BV510; CD4-APC-Cy7; CD8-Percp5.5; CD25-PE; CD69-APC; 7-AAD |
| CAR full panel (In-process) | Editing outcome and TCRαβ depletion efficiency: αβ⁻%, β2M⁻% and CAR⁺% | Biotin-Anti-Mouse Fab' | CD45-Pacific Blue; CD5-FITC; CD4-APC-Cy7; CD8-Percp5.5; TCRab-PE; B2M-PE-Cy7; Live-Dead-HV500 |
| CAR reduced panel (Post Thaw) | Editing outcome: CAR⁺% | Biotin-Anti-Mouse Fab' | CD45-Pacific Blue; Streptavidin-APC; Live-Dead-HV500 |
| TCR panel (Post thaw) | Editing outcome: TCRαβ⁻%, β2M⁻% | | CD45-Pacific Blue; CD5-FITC; CD4-APC-Cy7; CD8-Percp5.5; TCRab-PE; B2M-PE-Cy7; Live-Dead-HV500 |

*(Flow panels for flow cytometry.)* antibodies (CD45, CD5, CD4, CD8, B2M, TCR, Streptavidin-APC) and viability dye. Cells were washed a final time with staining buffer and run on the flow cytometer to capture various stained populations.

Flow cytometry was used to quantify the diverse populations present in in-process samples as well as cryopreserved product. The gating strategy described herein was used to differentiate subpopulations. In brief, the strategy used is based on initially gating the lymphocyte population, selecting singlet cell populations, and gating CD45⁺ or CD5⁺ populations. Editing efficiency was determined by visualizing B2M⁻ and TRAC⁻ stained cells as a proportion of the parental CD45⁺ or CD5⁺ population. Similarly, ratios of CD4 and CD8 subpopulations were plotted as a proportion of the CD45⁺ or CD5⁺ population. Isotype controls were used to set the gate for CAR⁺ expression in the APC channel.

Results

In the small-scale manufacturing process disclosed herein, T cells were activated in a static culture vessel and in a T-flask under the same activation conditions (Condition 7) and the resultant activated T cells were then electroporated in the presence of two ribonucleoprotein (RNP) com- Briefly, a total $0.5 \times 10^6$ to $1 \times 10^6$ cells were incubated in primary un-conjugated antibody for CAR full panel and CAR reduced panel at 4° C. for 20 min. Unbound antibody was removed by washing with 1 mL of staining buffer (DPBS/0.5% BSA), and then cells were incubated with 1 µg control mouse IgG in 100 µL of staining buffer at room temperature (RT) for 10 min. Then, cells were stained with conjugated antibodies (all panels) including LIVE/DEAD™ Fixable Dead Cell Stain (Thermo Fisher) (except for T cell activation panel) at 4° C. for 30 min protected from light. After incubation, cells were washed with staining buffer and resuspended in staining buffer except for T cell activation panel, which was resuspended in staining buffer containing 7-AAD.

Figure 2A:
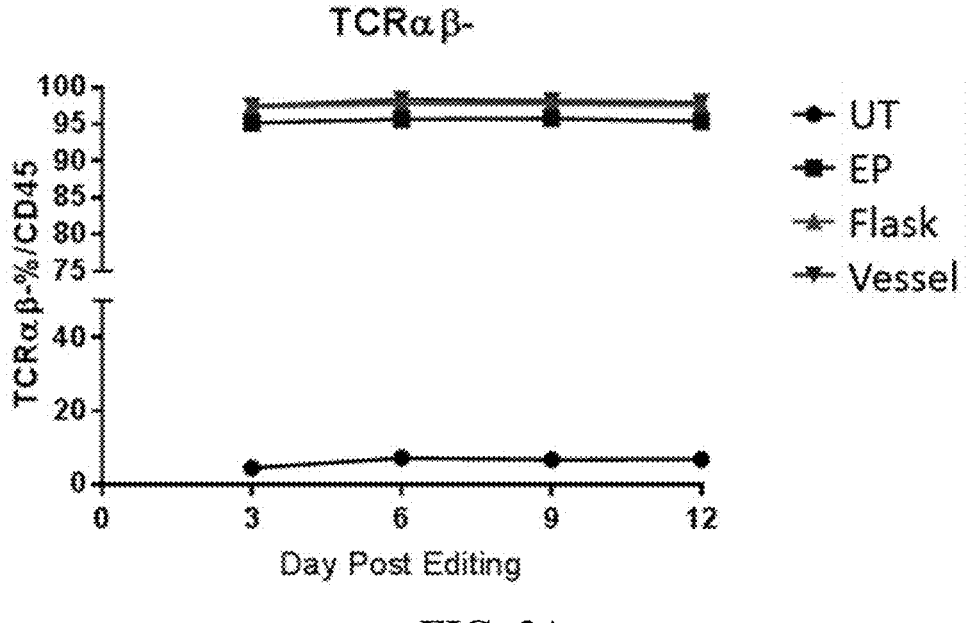
Figure 2B:
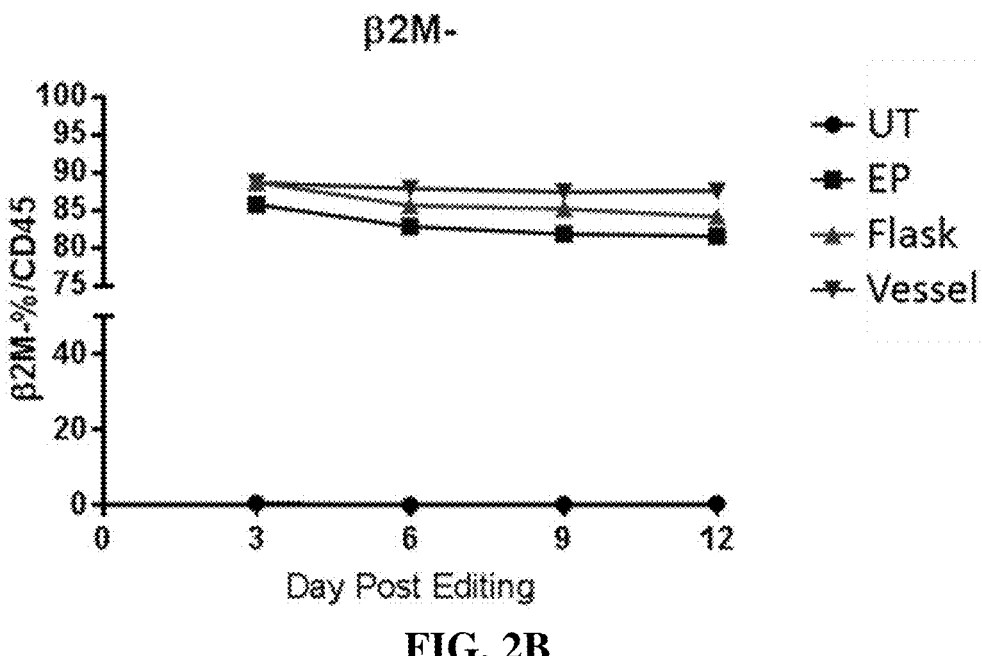
Figure 2C:
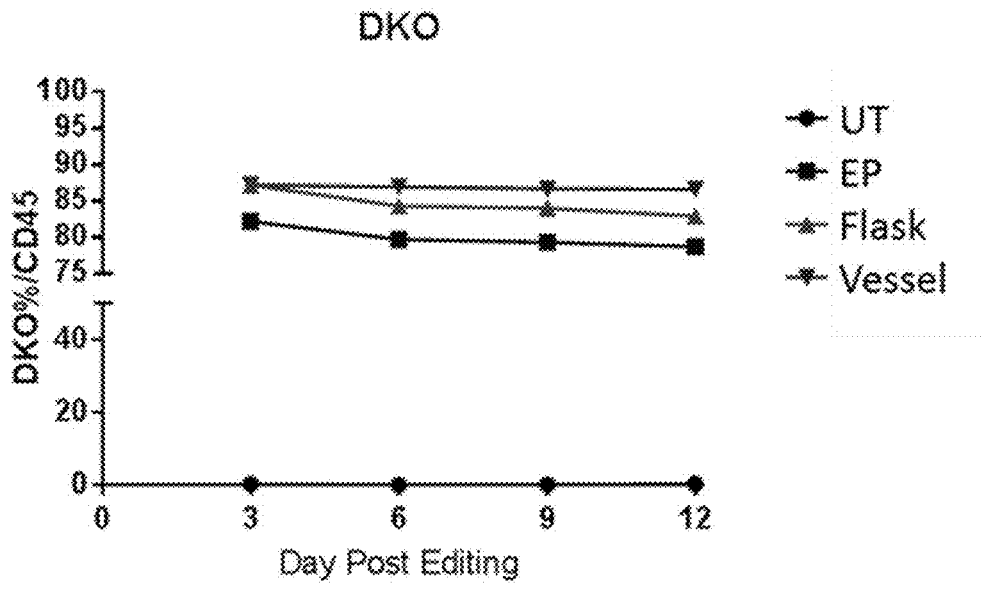
Figure 2D:
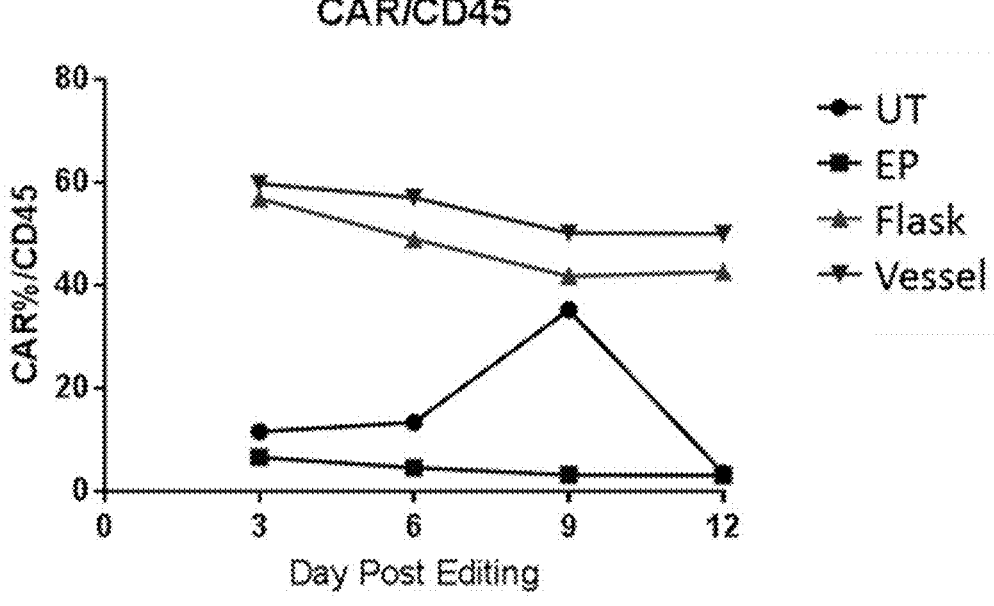

T cells activated in the static culture vessel showed comparable or higher TCRαβ and β2M knockout efficiency, and CAR % expression as compared to T cells activated in the T-flask (FIGS. 2A-2D). Editing remained persistent over a 12-day time period in which editing efficiency was monitored (FIGS. 2A-2D). An elevated level of CAR % expression in untreated T cells (UT) on day 9 resulted from a technical issue during flow cytometry and was inconsistent with the CAR % expression measured on days 3, 6, and 12 (FIG. 2D).

Figure 3:
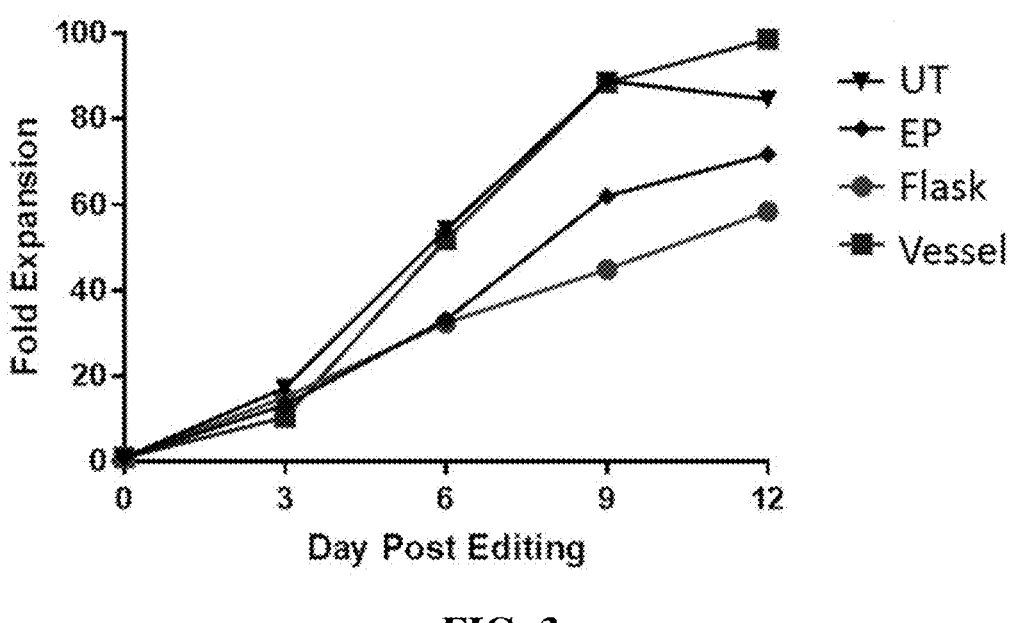

T cells activated in the static culture vessel showed significantly higher fold expansion post editing compared to T cells activated in T-flasks (98.66 fold compared to 58.46 fold; FIG. 3). Fold expansion post editing of untreated T cells (84.61 fold) and mock electroporated T cells (71.77 fold) was higher than that observed for T cells activated in the T-flask (58.46 fold), but lower than that observed for T cells activated in the static culture vessel (98.66 fold) (FIG. 3).

Taken together, these results demonstrate that the identified optimal conditions for T cell activation showed similar high T cell activation efficiency in a small scale manufacturing process (represented by a static culture vessel) as compared with a control T-flask. Further, the resultant activated T cells produced in the static culture vessel showed comparable or higher editing efficiency, CAR expression efficiency, and greater cell expansion post editing compared to activated T cells manufactured in T-flasks.

Example 3: Identification of Optimized Conditions for T Cell Electroporation

This Example reports identification of optimized conditions for gene editing of T cells via electroporation, including the range of T cell concentrations for optimal CRISPR-Cas9-dependent gene editing at the TRAC and the $\beta$2M loci. In this Example, fixed concentrations of gsRNA and Cas9 were introduced into increasing T cell concentrations by electroporation, and editing efficiency was determined by flow cytometry.

Cell Concentrations of $100\times10^6$ Cells/mL to $300\times10^6$ Cells/mL Permits Efficient Editing Using a fixed concentration of B2M sgRNA (B2M-1; SEQ ID NO: 6), TRAC sgRNA (TA-1, SEQ ID NO: 2) and CAS9 (SEQ ID NO: 1) at 150 µg/mL, 150 µg/mL and 300 µg/mL respectively, electroporation was performed with an increasing cell concentration ($100\times10^6$ cells/mL to $400\times10^6$ cells/mL). Editing efficiency was monitored every three days after gene editing using flow cytometry. Concentrations in each sample are summarized in Table 5.

TABLE 5

| Cell concentrations for electroporation. | | | | | |
|---|---|---|---|---|---|
| Cell Concentration ($10^6$/mL) | B2M-1 256117 (µg/mL) | TA-1 256116 (µg/mL) | CAS9 E0417 (µg/mL) | Cassette | Volume (µL) |
| 100 | 150 | 150 | 150 | 100 µL volume | 100 |
| 150 | 150 | 150 | 150 | 100 µL volume | 100 |
| 200 | 150 | 150 | 150 | 100 µL volume | 100 |
| 300 | 150 | 150 | 150 | 100 µL volume | 100 |
| 200 | 150 | 150 | 150 | 100 µL volume | 50 |
| 300 | 150 | 150 | 150 | 100 µL volume | 50 |
| 400 | 150 | 150 | 150 | 100 µL volume | 50 |

Figure 4A:
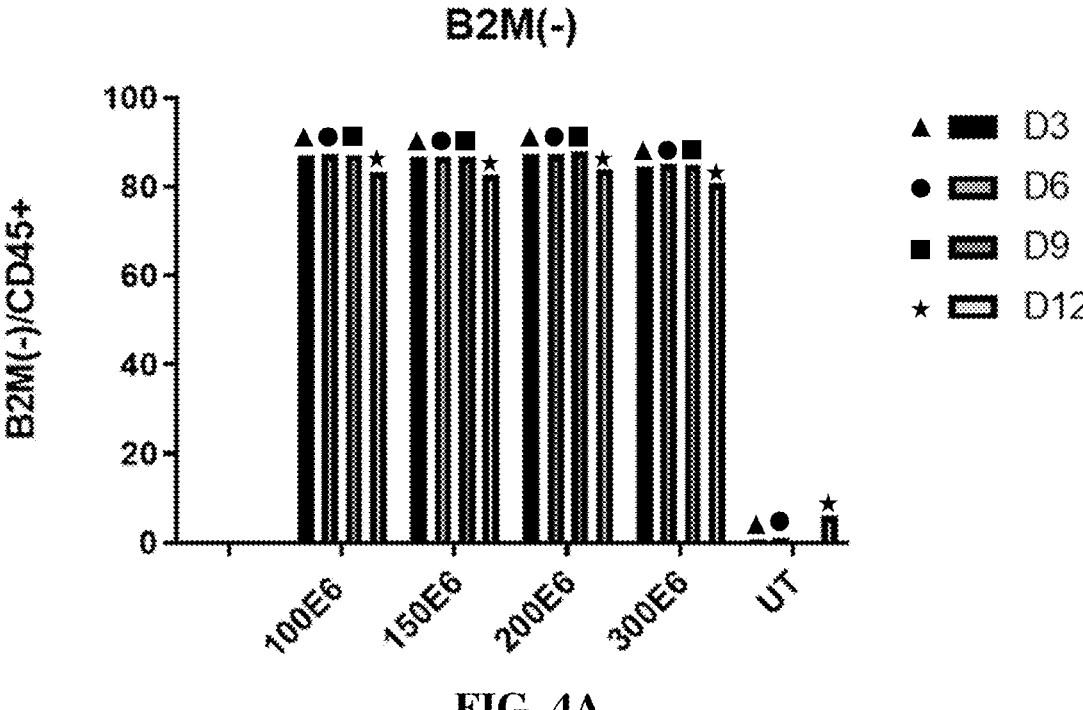
Figures 4B, 4C:
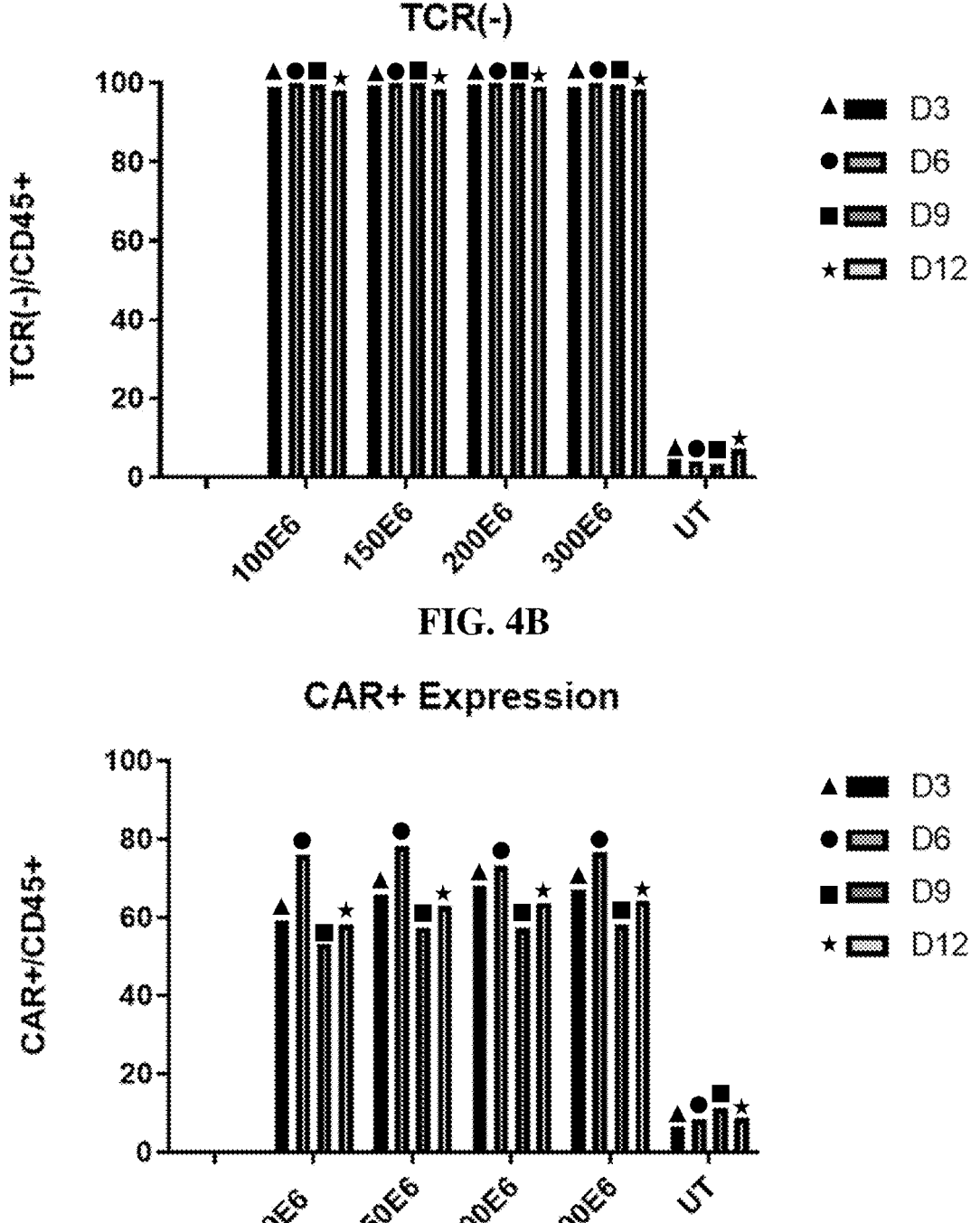
Figure 4D:
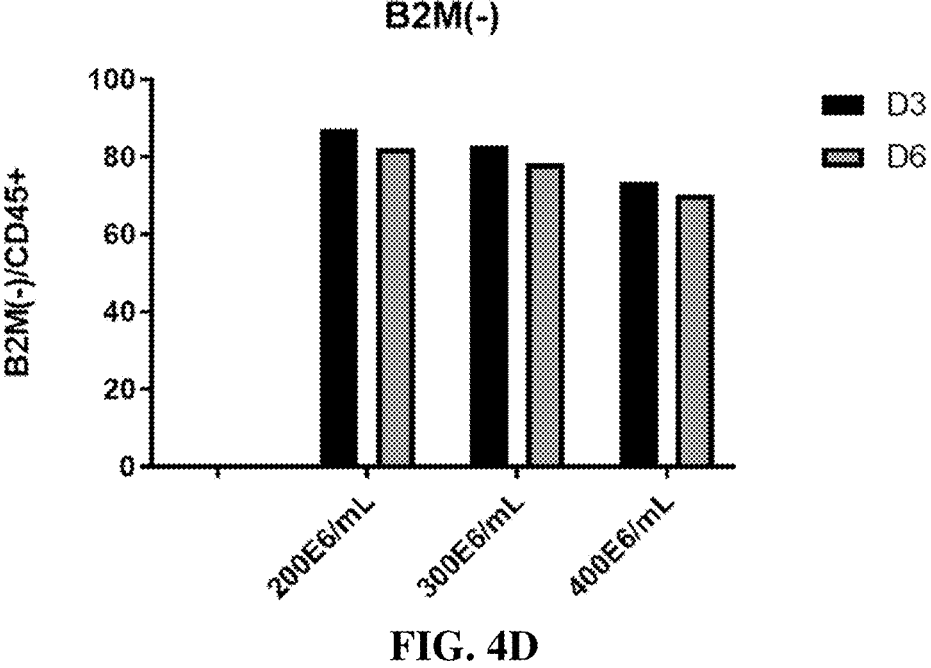
Figure 4E:
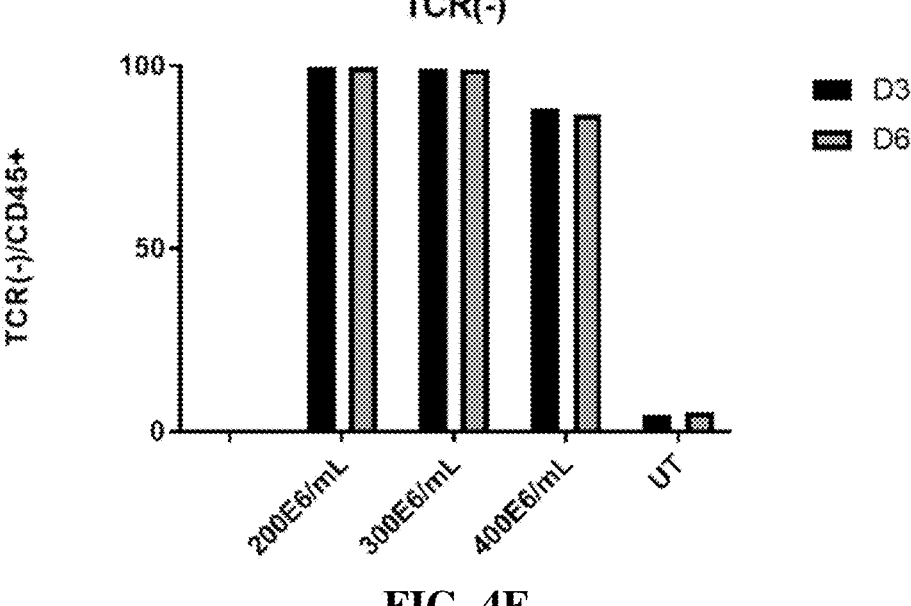
Figure 4F:
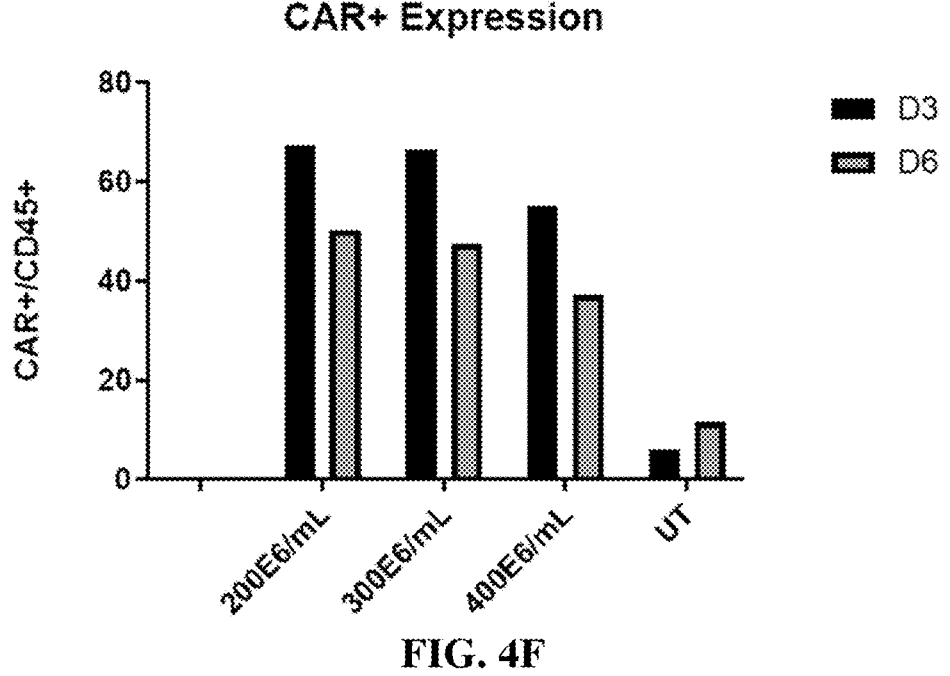

At cell concentrations ranging from $100\times10^6$ cells/mL to $300\times10^6$ cells/mL, B2M(−) and TCR(−) subpopulations in edited cells were >80% and >98%, respectively (FIGS. 4A-4B). CAR$^+$ expression was >40% when cells were electroporated at concentrations ranging from $100\times10^6$ cells/mL to $300\times10^6$ cells/mL (FIG. 4C). For a cell concentration of $400\times10^6$ cells/mL, B2M(−) and TCR(−) subpopulations were <80% and <87%, respectively (FIGS. 4D-4E). CAR$^+$ expression was also slightly reduced in cells electroporated at a density of $400\times10^6$ cells/mL (FIG. 4F).

In sum, these results demonstrate that a range of cell concentration between $100\times10^6$ cells/mL to $300\times10^6$ cells/mL allows efficient editing at the endogenous $\beta$2M and TCR loci.

Example 4: Identification of Optimized Conditions for T Cell Transduction

This Example reports identification of the range of MOI for optimal T cell transduction of an rAAV vector coding for a chimeric antigen receptor, leading to CAR$^+$ expression in T cells. In this Example, T cells were transduced by the rAAV vector with increasing MOI, and CAR$^+$ expression was quantified by flow cytometry.

In brief, cryopreserved T cells from healthy donor leukopak were thawed and activated for 48 hours. Cells were electroporated in bulk at a cell concentration of $1\times10^6$ in the presence of RNP complexes comprising Cas9 and sgRNA targeting TCR (TA-1; SEQ ID NO: 2/Cas9; SEQ ID NO: 1), and Cas9 and sgRNA targeting $\beta$2M (B2M-1; SEQ ID NO: 6/Cas9; SEQ ID NO: 1), with 150 µg/mL of sgRNA and 150 µg/mL in each complex (Table 6). See also Examples 1-3 above.

Following electroporation, cells were resuspended and allowed to rest in the incubator for 20 minutes. Electroporated cells were then separated into various aliquots and transduced with increasing MOI of rAAV for 1 hour at 37° C. (Table 6). CAR$^+$ expression was determined by flow cytometry after electroporation and transduction on days 3, 6, 10, and 13.

TABLE 6

| T cell transduction conditions tested. | | | | | |
|---|---|---|---|---|---|
| | B2M-1 256162 (µg/mL) | TA-1 256161 (µg/mL) | CAS9 E0417 (µg/mL) | Cuvette | Volume | MOI (vg/cell) |
| 1 | 150 | 150 | 150 | 400 µL volume | 400 | 80K |
| 2 | 150 | 150 | 150 | 400 µL volume | 400 | 40K |
| 3 | 150 | 150 | 150 | 400 µL volume | 400 | 20K |
| 4 | 150 | 150 | 150 | 400 µL volume | 400 | 10K |
| 5 | 150 | 150 | 150 | 400 µL volume | 400 | 5K |
| 6 | 150 | 150 | 150 | 400 µL volume | 400 | 1.25K |
| 7 | Untreated | Untreated | Untreated | NA | NA | NA |

Figure 5A:
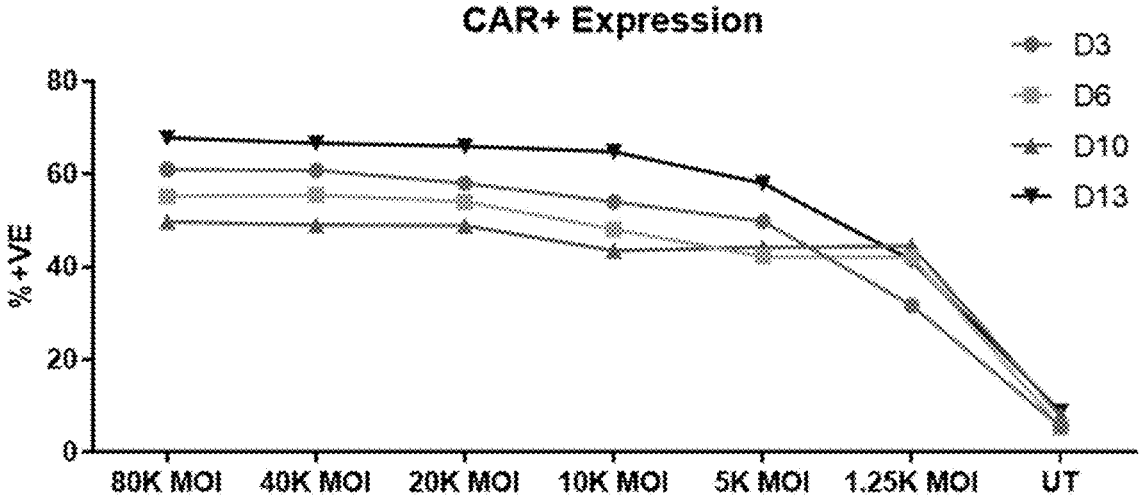
Figure 5B:
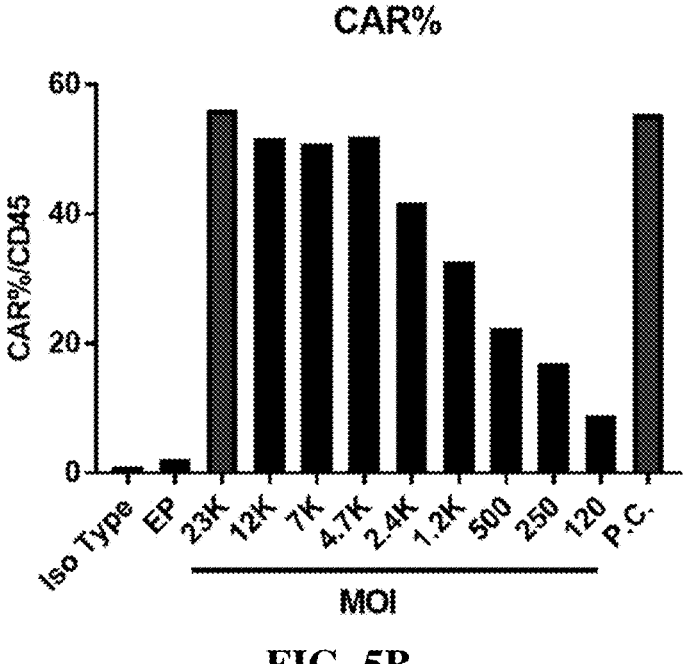

As shown in FIG. 5A, a MOI of 20K was sufficient to achieve CAR$^+$ expression of at least 50% over the time period tested. CAR$^+$ expression was saturated at MOIs of 10K, 20K, 40K, and 80K (FIG. 5A). Varying MOI had no effect on cell viability and cell expansion (data not shown). Differences in CAR$^+$ expression were not due to inefficiencies in gene editing, as bulk electroporation was performed, and B2M and TRAC knockdown was consistent across all samples, with the exception of untreated cells (data not shown). MOIs between 1.25K and 10K appeared to correlate linearly with decreased CAR$^+$ expression (FIG. 5A). Additional experiments in which T cells were incrementally transduced at MOI between OK to 23K showed a linear correlation between CAR$^+$ expression and MOIs in the range of 0.12K to 4.7K (FIG. 5B).

Taken together, these results demonstrate that CAR$^+$ expression was saturated in T cells transduced at an MOI between 10K and 80K, and that CAR$^+$ expression was linearly correlated to MOI in T cells transduced at an MOI between 0.12K and 4.7K.

Example 5: Identification of Optimized Conditions for T Cell Expansion

This Example reports identification of optional cell seeding densities for superior T cell expansion. In this Example, T cells were seeded at increasing densities and cell expansion was monitored over time.

In brief, cryopreserved T cells from healthy donor leukopak were thawed and activated for 48 hours. Cells were then electroporated in the presence of RNP complexes comprising Cas9 and sgRNA targeting TCR (TA-1; SEQ ID NO: 2/Cas9; SEQ ID NO: 1) and Cas9 and sgRNA targeting β2M (B2M-1; SEQ ID NO: 6/Cas9; SEQ ID NO: 1), with 150 μg/mL of sgRNA and 150 μg/mL in each complex. After electroporation, cells were transduced with the rAAV at MOI of 20,000, and then expanded in a static culture vessel. See Examples 1-4 above for details.

After editing, cells were seeded in a static culture vessel at $5 \times 10^4$ cells/cm$^2$ (50,000), $1 \times 10^5$ cells/cm$^2$ (100,000), $2 \times 10^5$ cells/cm$^2$ (200,000), $3 \times 10^5$ cells/cm$^2$ (300,000), and $5 \times 10^5$ cells/cm$^2$ (500,000) for expansion of up to 12 days. Cell count and viability were assessed every 3 days. Fold expansion was calculated as the ratio of ending cell number and starting cell number.

Figure 6A:
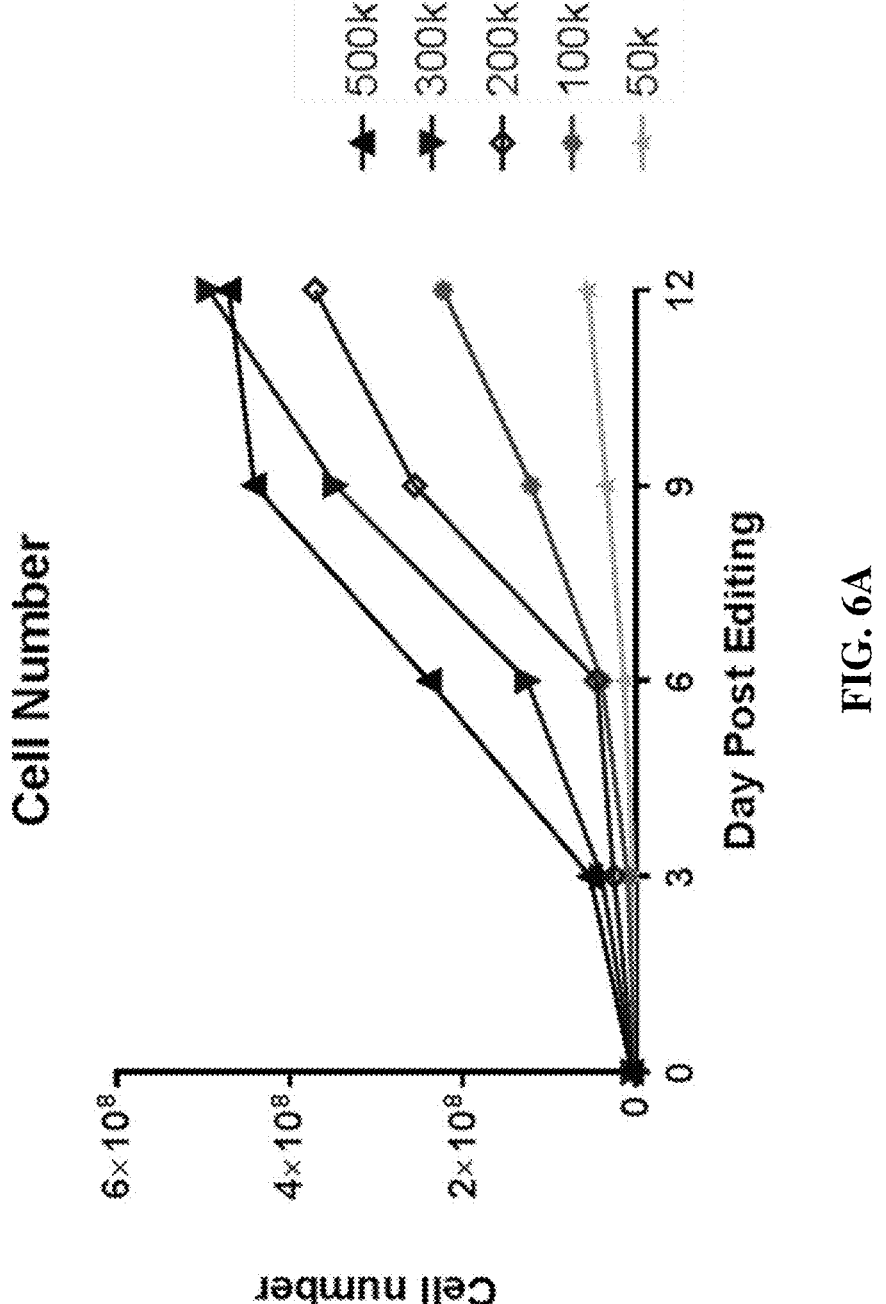
Figure 6B:
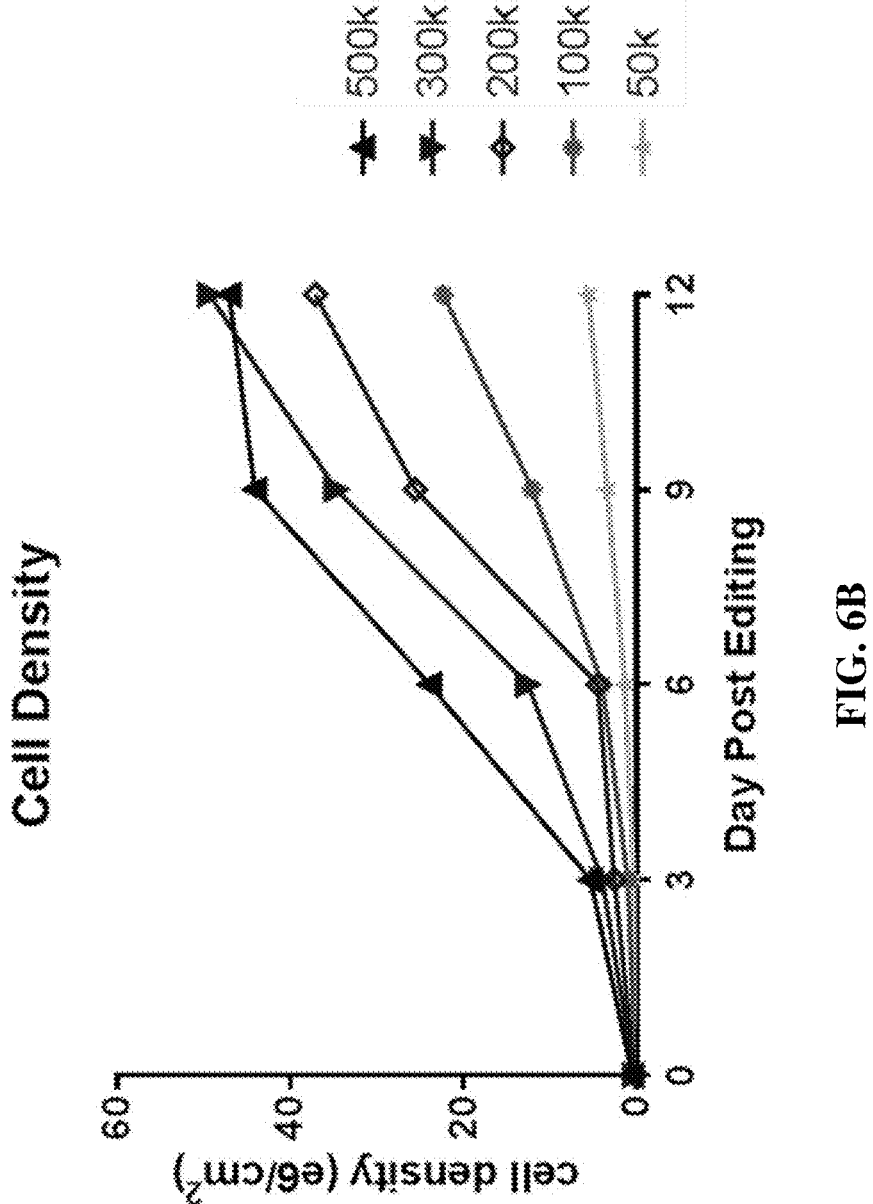

As shown in FIGS. 6A-6B, cells seeded at a density of $5 \times 10^5$ cells/cm$^2$ reached a growth plateau in 9 days. By day 12, cells seeded at a density of $3 \times 10^5$/cm$^2$ reached cell numbers comparable to those reached by cells seeded at $5 \times 10^5$ cells/cm$^2$ on day 9 (FIGS. 6A-6B). Cells seeded at ablation of TCRαβ expression in >90% of T cells. To minimize the potential of graft versus host disease (GvHD), the remaining TCRαβ$^+$ T cells may be further reduced through a TCRαβ$^+$ depletion process.

In brief, cells were incubated with biotin conjugated-TCRαβ antibody and anti-biotin microbeads. After removal of excess unbound antibody and microbeads, cells were passed through a magnet column, and labeled TCRαβ$^+$ cells were captured on the column. Unbound TCRαβ$^-$ cells are eluted into a target bag with 0.5% HSA in PBS/EDTA buffer. Eluted cells were cultured overnight to allow cell recovery, and then harvested for drug product formulation.

Four batches of CAR-expressing T cell product were processed for TCRαβ depletion. Three batches were generated from a full scale process, and one batch (CTX110-18-01) was generated from a medium size process. Input cell number varied from $7.4 \times 10^9$ cells to $32.0 \times 10^9$ cells due to donor variation and expansion scale (Table 7). Post depletion cell number recovery ranged from 75% to 113.33% (Table 7). Cell number recovery of 100% or 113% may have been caused by an under estimation of input cell number (Table 7). Viability of input and output cells were above 90%, except input cells from the CTX110-18-01 batch (84.5%) (Table 7). Average percent of TCRαβ$^+$ in input cells and output cells was 2.06% and 0%, respectively.

TABLE 7

TCRαβ Depletion of Four Batches of Drug Product.

Figure 6C:
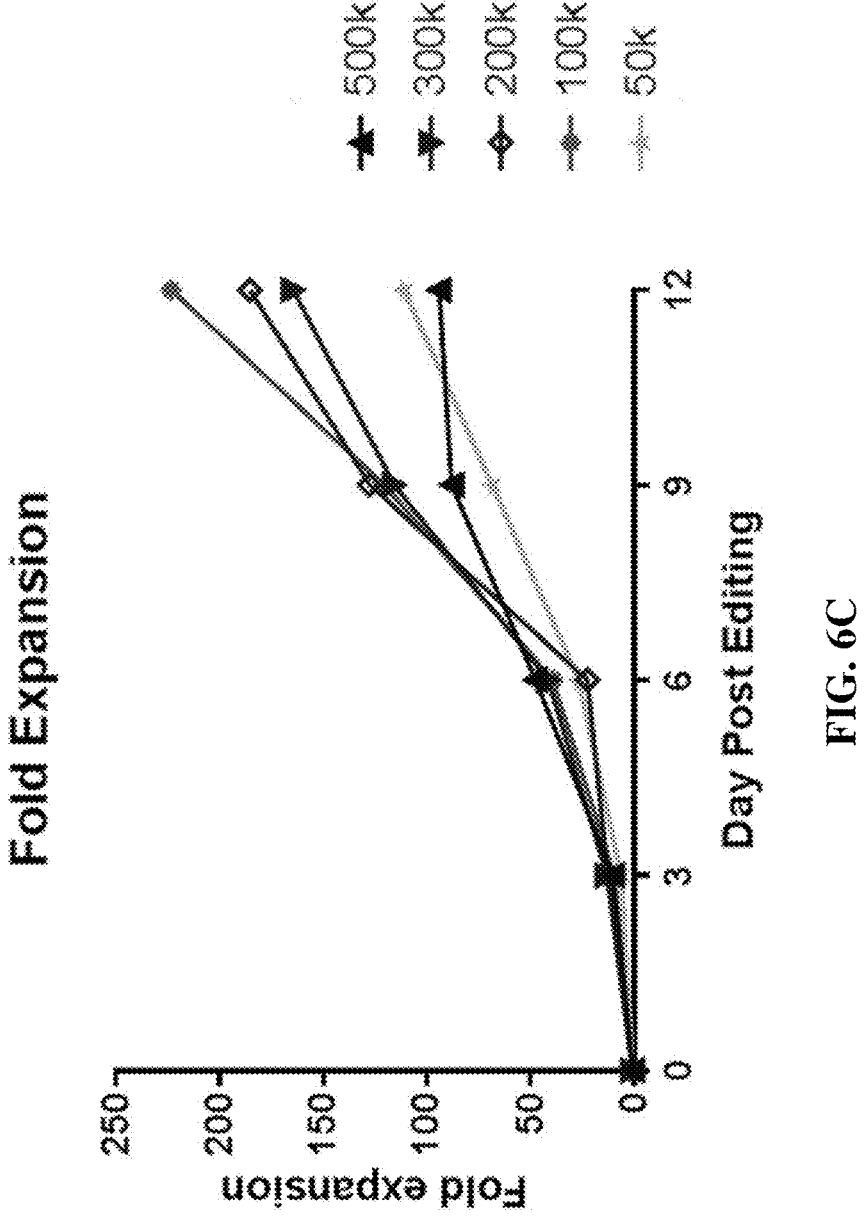

| Batch | Input Cells | | | | Output Cells | | | | TCRαβ+ |
| | Cell number (×10⁹) | Viability (%) | TCRαβ+ % | TCRαβ+ cell number (×10⁹) | Cell number (×10⁹) | Viability (%) | Cell Recovery (%) | TCRαβ+ % | cell number (×10⁹) |
|---|---|---|---|---|---|---|---|---|---|
| CTX110-18-01 | 7.40 | 84.50 | 1.98 | 0.15 | 6.32 | 93.00 | 85.41 | 0.000 | 0.00 |
| CTX110-18-02 | 32.00 | 93.50 | 0.71 | 0.23 | 24.00 | 96.00 | 75.00 | 0.000 | 0.00 |
| CTX110-18-03 | 8.48 | 93.50 | 2.76 | 0.23 | 9.61 | 97.00 | 113.33 | 0.000 | 0.00 |
| CTX110-18-04 | 14.30 | 92.00 | 2.78 | 0.40 | 14.40 | 96.00 | 100.70 | 0.003 | 0.00 |
| Average | 15.55 | 90.88 | 2.06 | 0.25 | 13.58 | 95.50 | 93.61 | 0.00 | 0.00 | densities of $2 \times 10^5$ cells/cm$^2$ and $1 \times 10^5$ cells/cm$^2$ showed modest expansion without reaching a growth plateau by day 12 (FIGS. 6A-6B). Among the tested seeding densities, the lowest levels of proliferation were observed for cells seeded at a density of $5 \times 10^4$ cells/cm$^2$ cells (FIGS. 6A-6B). Cells seeded at a density of $1 \times 10^5$ cells/cm$^2$ showed more robust fold expansion rate (223.4 fold) compared to cells seeded at densities of $2 \times 10^5$ cells/cm$^2$ (185.5 fold) and $3 \times 10^5$ cells/cm$^2$ (164.6 fold) (FIG. 6C), although they resulted in smaller total cells. Fold expansion rate for cells seeded at either $5 \times 10^5$ cells/cm$^2$ and $5 \times 10^4$ cells/cm$^2$ were around 100-fold (FIG. 6C).

In sum, these results demonstrate that a range of cell seeding densities between $3 \times 10^5$ cells/cm$^2$ to $5 \times 10^5$ cells/cm$^2$ provided efficient T cell expansion post editing.

Example 6: Identification of Optimized Conditions for TCRαβ Depletion

This Example reports identification of conditions for optimal depletion of TCRαβ$^+$ cells that remain after editing. CRISPR-Cas9-mediated gene-editing typically leads to an In sum, these results demonstrate efficient depletion of TCRαβ from CAR-expressing T cells in which the TRAC gene and the β2M gene has been genetically disrupted.

Example 7: Manufacturing Process Development for Making Genetically Engineered T Cells Expressing an Anti-CD19 CAR and Having Genetically Disrupted TRAC and β2M Genes (CTX110)

Overview

CTX110 is a CD19-directed T cell immunotherapy comprised of allogeneic T cells that are genetically modified ex vivo using CRISPR/Cas9 (Clustered Regularly Interspaced Short Palindromic Repeats/CRISPR associated protein 9) gene editing components (sgRNA and Cas9 nuclease).

The modifications include targeted disruption of the TRAC and β2M genes. The disruption of the TRAC locus results in loss of expression of the T cell receptor (TCR) and is intended to reduce the probability of Graft versus Host Disease (GvHD), while the disruption of the β2M locus results in lack of expression of the major histocompatibility complex type I (MHC I) proteins and is intended to improve persistence by reducing the probability of host rejection. The addition of the anti-CD19 CAR directs the modified T cells towards CD19-expressing tumor cells.

The CAR is composed of an anti-CD19 scFv, the CD8 transmembrane domain, a CD28 co-stimulatory domain, and a CD3 signaling domain. Expression of the CTX110 CAR is driven by the EF-1α promoter.

Figure 7B:
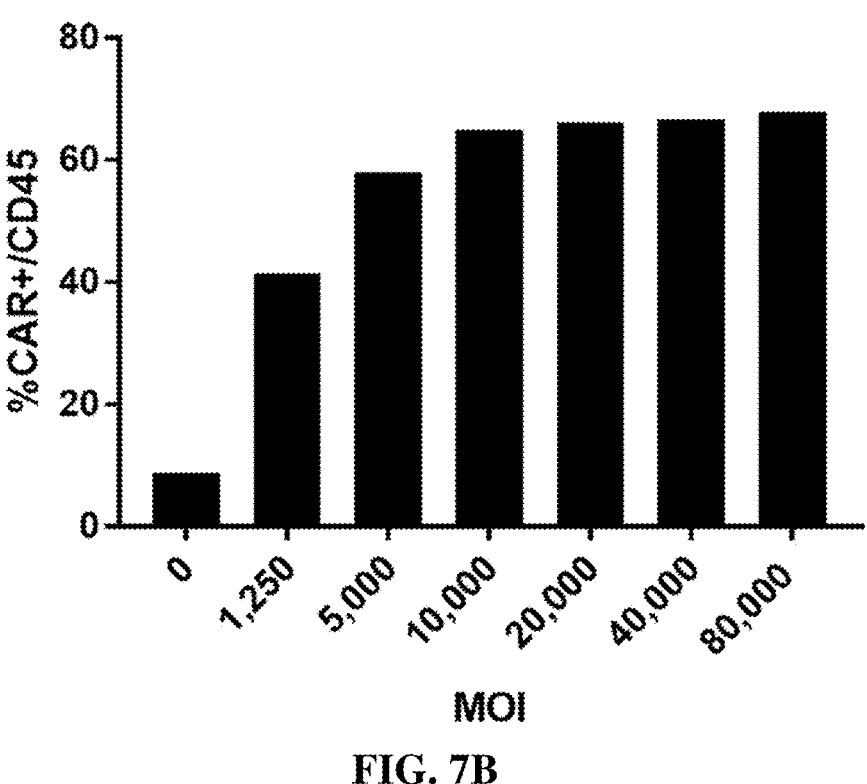

An exemplary manufacturing process for CTX110 is depicted in FIG. 7A.

Evolution of Manufacturing Process

The CTX110 manufacturing process was performed at three production scales including research scale, development scale, and clinical scale. The Research Scale Process was performed at small scale, and the Research Scale Process was scaled up and transferred for Development Scale Process and Clinical Scale Process. Initial development campaigns (4 lots) were conducted using laboratory-grade starting materials for the drug substance for feasibility and adjustment of the operating parameters. Subsequently, use of GMP-sourced starting materials (sgRNAs, Cas9 and rAAV-138) and quantitative acceptance criteria were implemented for the Clinical Scale Process, which is operationally identical to the Development Scale Process.

Selection of the Starting Materials

The starting materials for production of CTX110 include:
leukopaks collected from healthy donors,
bacterially-derived Cas9 nuclease,
two single guide RNAs (sgRNA), TA-1 which targets the TRAC locus and β2M-1 which targets the β2M locus, and
the recombinant AAV-6 vector (rAAV-138), which encodes the anti-CD19 CAR gene.

Structure information for the components used in making the genetic modifications of CTX110, as well as edited TRAC and β2M gene loci, is provided below:

```
Amino acid sequence of Cas9
nuclease (SEQ ID NO: 1):
MDKKYSIGLDIGTNSVGWAVITDEYKVPSKKF

KVLGNTDRHSIKKNLIGALLEDSGETAEATRL

KRTARRRYTRRKNRICYLQEIFSNEMAKVDDS

FFHRLEESFLVEEDKKHERHPIFGNIVDEVAY

HEKYPTIYHLRKKLVDSTDKADLRLIYLALAH

MIKFRGHFLIEGDLNPDNSDVDKLFIQLVQTY

NQLFEENPINASGVDAKAILSARLSKSRRLEN

LIAQLPGEKKNGLFGNLIALSLGLTPNEKSNE

DLAEDAKLQLSKDTYDDDLDNLLAQIGDQYAD

LFLAAKNLSDAILLSDILRVNTEITKAPLSAS

MIKRYDEHHQDLTLLKALVRQQLPEKYKEIFF

DQSKNGYAGYIDGGASQEEFYKFIKPILEKMD

GTEELLVKLNREDLLRKQRTFDNGSIPHQIHL

GELHAILRRQEDFYPFLKDNREKIEKILTFRI

PYYVGPLARGNSRFAWMTRKSEETITPWNFEE

VVDKGASAQSFIERMTNFDKNLPNEKVLPKHS

LLYEYFTVYNELTKVKYVTEGMRKPAFLSGEQ
```

```
KKAIVDLLEKTNRKVTVKQLKEDYFKKIECFD

SVEISGVEDRFNASLGTYHDLLKIIKDKDFLD

NEENEDILEDIVLTLTLFEDREMIEERLKTYA

HLFDDKVMKQLKRRRYTGWGRLSRKLINGIRD

KQSGKTILDFLKSDGFANRNFMQLIHDDSLTF

KEDIQKAQVSGQGDSLHEHIANLAGSPAIKKG

ILQTVKVVDELVKVMGRHKPENIVIEMARENQ

TTQKGQKNSRERMKRIEEGIKELGSQILKEHP

VENTQLQNEKLYLYYLQNGRDMYVDQELDINR

LSDYDVDHIVPQSFLKDDSIDNKVLTRSDKNR

GKSDNVPSEEVVKKMKNYWRQLLNAKLITQRK

FDNLTKAERGGLSELDKAGFIKRQLVETRQIT

KHVAQILDSRMNTKYDENDKLIREVKVITLKS

KLVSDERKDFQFYKVREINNYHHAHDAYLNAV

VGTALIKKYPKLESEFVYGDYKVYDVRKMIAK

SEQEIGKATAKYFFYSNIMNFEKTEITLANGE

IRKRPLIETNGETGEIVWDKGRDFATVRKVLS

MPQVNIVKKTEVQTGGFSKESILPKRNSDKLI

ARKKDWDPKKYGGFDSPTVAYSVLVVAKVEKG

KSKKLKSVKELLGITIMERSSFEKNPIDFLEA

KGYKEVKKDLIIKLPKYSLFELENGRKRMLAS

AGELQKGNELALPSKYVNFLYLASHYEKLKGS

PEDNEQKQLFVEQHKHYLDEIIEQISEFSKRV

ILADANLDKVLSAYNKHRDKPIREQAENIIHL

FTLTNLGAPAAFKYFDTTIDRKRYTSTKEVLD

ATLIHQSITGLYETRIDLSQLGGD
```

TABLE 8

| sgRNA Sequences and Target Gene Sequences. | | | |
| --- | --- | --- | --- |
| | | | SEQ ID NO: |
| sgRNA Sequences | | | |
| TRAC sgRNA (TA-1) | Modified | A*G*A*GCAACA GUGCUGUGGCCg uuuuagagcuag aaauagcaaguu aaaauaaggcua guccguuaucaa cuugaaaaagug gcaccgagucgg ugcU*U*U* U | 2 |
| | Unmodified | AGAGCAACAGUG CUGUGGCCguuu uagagcuagaaa uagcaaguuaaa auaaggcuaguc cguuaucaacuu | 3 |

TABLE 8-continued sgRNA Sequences and Target Gene Sequences.

| | | | SEQ ID NO: |
|---|---|---|---|
| | | gaaaaaguggca ccgagucggugc UUUU | |
| TRAC sgRNA spacer | Modified | A*G*A*GCAACA GUGCUGUGGCC | 4 |
| | Unmodified | AGAGCAACAGUG CUGUGGCC | 5 |
| β2M sgRNA (B2M-1) | Modified | G*C*U*ACUCUC UCUUUCUGGCCg uuuuagagcuag aaauagcaaguu aaaauaaggcua guccguuaucaa cuugaaaaagug gcaccgagucgg ugcU*U*U*U | 6 |
| | Unmodified | GCUACUCUCUCU UUCUGGCCguuu uagagcuagaaa uagcaaguuaaa auaaggcuaguc cguuaucaacuu gaaaaaguggca ccgagucggugc UUUU | 7 |
| β2M sgRNA spacer | Modified | G*C*U*ACUCUC UCUUUCUGGCC | 8 |
| | Unmodified | GCUACUCUCUCU UUCUGGCC | 9 |

Target Sequences (PAM)

| | | | |
|---|---|---|---|
| TRAC sgRNA | AGAGCAACAGTG CTGTGGCC (TGG) | | 10 |
| TRAC sgRNA | AGAGCAACAGTG CTGTGGCC | | 11 |
| β2M sgRNA | GCTACTCTCTCTT TCTGGCC (TGG) | | 12 |
| β2M sgRNA | CCTACTCTCTCTT TCTGGCC | | 13 |

Exemplary sgRNA Formulas

| | | | |
|---|---|---|---|
| sgRNA sequence | nnnnnnnnnnnnnnnnnnnng uuuuagagcuagaaauagcaa guuaaaauaaggcuaguccgu uaucaacuugaaaaaguggca ccgagucggugcuuuu | | 14 |
| sgRNA sequence | nnnnnnnnnnnnnnnnnnnng uuuuagagcuagaaauagcaa guuaaaauaaggcuaguccgu uaucaacuugaaaaaguggca ccgagucggugc | | 15 |
| sgRNA sequence | n(17-30)guuuuagagcuag aaauagcaaguuaaaauaagg cuaguccguuaucaacuugaa aaaguggcaccgagucggug cu(1-8) | | 16 |

*indicates a nucleotide with a 2'-O-methyl phosphorothioate modification
"n" refers to the spacer sequence at the 5' end

TABLE 9

Edited TRAC Gene Sequence

| Description | Sequence (Deletions indicated by dashes (-);insertions indicated by bold) | SEQ ID NO: |
|---|---|---|
| TRAC gene edit | AA--------------------GAGC AACAAATCTGACT | 17 |
| TRAC gene edit | AAGAGCAACAGTGCTGT-GCCTGGAGC AACAAATCTGACT | 18 |
| TRAC gene edit | AAGAGCAACAGTG-------CTGGAGC AACAAATCTGACT | 19 |
| TRAC gene edit | AAGAGCAACAGT------GCCTGGAGC AACAAATCTGACT | 20 |
| TRAC gene edit | AAGAGCAACAGTG------------- -------CTGACT | 21 |
| TRAC gene edit | AAGAGCAACAGTGCTGTGGGCCTGGAG CAACAAATCTGACT | 22 |
| TRAC gene edit | AAGAGCAACAGTGC--TGGCCTGGAGC AACAAATCTGACT | 23 |
| TRAC gene edit | AAGAGCAACAGTGCTGTGTGCCTGGAG CAACAAATCTGACT | 24 |

TABLE 10

Edited β2M Gene Sequence.

| Description | Sequence (Deletions indicated by dashes (-); insertions indicated by bold) | SEQ ID NO: |
|---|---|---|
| β2M gene-edit | CGTGGCCTTAGCTGTGCTCGCGCTACTCTC TCTTTCT-GCCTGGAGGCTATCCAGCGTGA GTCTCTCCTACCCTCCCGCT | 25 |
| β2M gene-edit | CGTGGCCTTAGCTGTGCTCGCGCTACTCTC TCTTTC--GCCTGGAGGCTATCCAGCGTGA GTCTCTCCTACCCTCCCGCT | 26 |
| β2M gene-edit | CGTGGCCTTAGCTGTGCTCGCGCTACTCTC TCTTT-----CTGGAGGCTATCCAGCGTGA GTCTCTCCTACCCTCCCGCT | 27 |
| β2M gene-edit | CGTGGCCTTAGCTGTGCTCGCGCTACTCTC TCTTTCTGGATAGCCTGGAGGCTATCCAGC GTGAGTCTCTCCTACCCTCCCGCT | 28 |
| β2M gene-edit | CGTGGCCTTAGCTGTGCTCGC--------- ---------------GCTATCCAGCGTGA GTCTCTCCTACCCTCCCGCT | 29 |
| β2M gene-edit | CGTGGCCTTAGCTGTGCTCGCGCTACTCTC TCTTTCTGTGGCCTGGAGGCTATCCAGCGT GAGTCTCTCCTACCCTCCCGCT | 30 |

TABLE 11

| Name Description | Sequence | SEQ ID NO: |
|---|---|---|
| CD8a transmembrane domain | IYIWAPLAGTCGVLLLSLVITLY | 31 |
| CD28 nucleotide sequence | TCAAAGCGGAGTAGGTTGTTGCATTCCGATTACATGAATATGACT CCTCGCCGGCCTGGGCCGACAAGAAAACATTACCAACCCTATGCC CCCCCACGAGACTTCGCTGCGTACAGGTCC | 32 |
| CD28 amino acid sequence | SKRSRLLHSDYMNMTPRRPGPTRKHYQPYAPPRDFAAYRS | 33 |
| CD3-zeta nucleotide sequence | CGAGTGAAGTTTTCCCGAAGCGCAGACGCTCCGGCATATCAGCAA GGACAGAATCAGCTGTATAACGAACTGAATTTGGGACGCCGCGAG GAGTATGACGTGCTTGATAAACGCCGGGGGAGAGACCCGGAAATG GGGGGTAAACCCCGAAGAAAGAATCCCCAAGAAGGACTCTACAAT GAACTCCAGAAGGATAAGATGGCGGAGGCCTACTCAGAAATAGGT ATGAAGGGCGAACGACGACGGGGAAAAGGTCACGATGGCCTCTAC CAAGGGTTGAGTACGGCAACCAAAGATACGTACGATGCACTGCAT ATGCAGGCCCTGCCTCCCAGA | 34 |
| CD3-zeta amino acid sequence | RVKFSRSADAPAYQQGQNQLYNELNLGRREEYDVLDKRRGRDPEM GGKPRRKNPQEGLYNELQKDKMAEAYSEIGMKGERRRGKGHDGLY QGLSTATKDTYDALHMQALPPR | 35 |
| Anti-CD19 CAR FMC63-28Z (FMC63-CD8[tm]-CD28[co-stimulatory domain]-CD3z) Nucleic Acid | ATGCTTCTTTTGGTTACGTCTCTGTTGCTTTGCGAACTTCCTCAT CCAGCGTTCTTGCTGATCCCCGATATTCAGATGACTCAGACCACC AGTAGCTTGTCTGCCTCACTGGGAGACCGAGTAACAATCTCCTGC AGGGCAAGTCAAGACATTAGCAAATACCTCAATTGGTACCAGCAG AAGCCCGACGGAACGGTAAAACTCCTCATCTATCATACGTCAAGG TTGCATTCCGGAGTACCGTCACGATTTTCAGGTTCTGGGAGCGGA ACTGACTATTCCTTGACTATTTCAAACCTCGAGCAGGAGGACATT GCGACATATTTTTGTCAACAAGGTAATACCCTCCCTTACACTTTC GGAGGAGGAACCAAACTCGAAATTACCGGGTCCACCAGTGGCTCT GGGAAGCCTGGCAGTGGAGAAGGTTCCACTAAAGGCGAGGTGAAG CTCCAGGAGAGCGGCCCCGGTCTCGTTGCCCCCAGTCAAAGCCTC TCTGTAACGTGCACAGTGAGTGGTGTATCATTGCCTGATTATGGC GTCTCCTGGATAAGGCAGCCCCCCGCGAAAGGGTCTTGAATGGCTT GGGGTAATATGGGGCTCAGAGACAACGTATTATAACTCCGCTCTC AAAAGTCGCTTGACGATAATAAAAGATAACTCCAAGAGTCAAGTT TTCCTTAAAATGAACAGTTTGCAGACTGACGATACCGCTATATAT TATTGTGCTAAACATTATTACTACGGCGGTAGTTACGCGATGGAT TATTGGGGGCAGGGGACTTCTGTCACAGTCAGTAGTGCTGCTGCC TTTGTCCCGGTATTTCTCCCAGCCAAACGACCACGACTCCCGCC CCGCGCCCTCCGACACCCGCTCCCACCATCGCCTCTCAACCTCTT AGTCTTCGCCCCGAGGCATGCCGACCCGCCGCCGGGGGTGCTGTT CATACGAGGGGCTTGGACTTCGCTTGTGATATTTACATTTGGGCT CCGTTGGCGGGTACGTGCGGCGTCCTTTTGTTGTCACTCGTTATT ACTTTGTATTGTAATCACAGGAATCGCTCAAAGCGGAGTAGGTTG TTGCATTCCGATTACATGAATATGACTCCTCGCCGGCCTGGGCCG ACAAGAAAACATTACCAACCCTATGCCCCCCCACGAGACTTCGCT GCGTACAGGTCCCGAGTGAAGTTTTCCCGAAGCGCAGACGCTCCG GCATATCAGCAAGGACAGAATCAGCTGTATAACGAACTGAATTTG GGACGCCGCGAGGAGTATGACGTGCTTGATAAACGCCGGGGGAGA GACCCGGAAATGGGGGGTAAACCCCGAAGAAAGAATCCCCAAGAA GGACTCTACAATGAACTCCAGAAGGATAAGATGGCGGAGGCCTAC TCAGAAATAGGTATGAAGGGCGAACGACGACGGGGAAAAGGTCAC GATGGCCTCTACCAAGGGTTGAGTACGGCAACCAAAGATACGTAC GATGCACTGCATATGCAGGCCCTGCCTCCCAGA | 36 |
| Anti-CD19 CAR FMC63-28Z (FMC63-CD8[tm]-CD28 [co-stimulatory domain]-CD3z) Amino Acid | MLLLVTSLLLCELPHPAFLLIPDIQMTQTTSSLSASLGDRVTISC RASQDISKYLNWYQQKPDGTVKLLIYHTSRLHSGVPSRFSGSGSG TDYSLTISNLEQEDIATYFCQQGNTLPYTEGGGTKLEITGSTSGS GKPGSGEGSTKGEVKLQESGPGLVAPSQSLSVTCTVSGVSLPDYG VSWIRQPPRKGLEWLGVIWGSETTYYNSALKSRLTIIKDNSKSQV FLKMNSLQTDDTAIYYCAKHYYYGGSYAMDYWGQGTSVTVSSAAA FVPVFLPAKPTTTPAPRPPTPAPTIASQPLSLRPEACRPAAGGAV HTRGLDFACDIYIWAPLAGTCGVLLLSLVITLYCNHRNRSKRSRL LHSDYMNMTPRRPGPTRKHYQPYAPPRDFAAYRSRVKFSRSADAP AYQQGQNQLYNELNLGRREEYDVLDKRRGRDPEMGGKPRRKNPQE GLYNELQKDKMAEAYSEIGMKGERRRGKGHDGLYQGLSTATKDTY DALHMQALPPR | 37 |
| Left ITR (5' ITR) (alternate) | CCTGCAGGCAGCTGCGCGCTCGCTCGCTCACTGAGGCCGCCCGGG CGTCGGGCGACCTTTGGTCGCCCGGCCTCAGTGAGCGAGCGAGCG CGCAGAGAGGGAGTGGCCAACTCCATCACTAGGGGTTCCT | 38 |

TABLE 11-continued

Sequences of Anti-CD19 CAR Construct Components

| Name Description | Sequence | SEQ ID NO: |
|---|---|---|
| Right ITR (3' ITR) (alternate) | AGGAACCCCTAGTGATGGAGTTGGCCACTCCCTCTCTGCGCGCTC GCTCGCTCACTGAGGCCGGGCGACCAAAGGTCGCCCGACGCCCGG GCTTTGCCCGGGCGGCCTCAGTGAGCGAGCGAGCGCGCAGCTGCC TGCAGG | 39 |
| TRAC-LHA (800 bp) | GAGATGTAAGGAGCTGCTGTGACTTGCTCAAGGCCTTATATCGAG TAAACGGTAGTGCTGGGGCTTAGACGCAGGTGTTCTGATTTATAG TTCAAAACCTCTATCAATGAGAGAGCAATCTCCTGGTAATGTGAT AGATTTCCCAACTTAATGCCAACATACCATAAACCTCCCATTCTG CTAATGCCCAGCCTAAGTTGGGGAGACCACTCCAGATTCCAAGAT GTACAGTTTGCTTTGCTGGGCCTTTTTCCCATGCCTGCCTTTACT CTGCCAGAGTTATATTGCTGGGGTTTTGAAGAAGATCCTATTAAA TAAAAGAATAAGCAGTATTATTAAGTAGCCCTGCATTTCAGGTTT COTTGAGTGGCAGGCCAGGCCTGGCCGTGAACGTTCACTGAAATC ATGGCCTCTTGGCCAAGATTGATAGCTTGTGCCTGTCCCTGAGTC CCAGTCCATCACGAGCAGCTGGTTTCTAAGATGCTATTTCCCGTA TAAAGCATGAGACCGTGACTTGCCAGCCCCACAGAGCCCCGCCCT TGTCCATCACTGGCATCTGGACTCCAGCCTGGGTTGGGGCAAAGA GGGAAATGAGATCATGTCCTAACCCTGATCCTCTTGTCCCACAGA TATCCAGAACCCTGACCCTGCCGTGTACCAGCTGAGAGACTCTAA ATCCAGTGACAAGTCTGTCTGCCTATTCACCGATTTTGATTOTCA AACAAATGTGTCACAAAGTAAGGATTCTGATGTGTATATCACAGA CAAAACTGTGCTAGACATGAGGTCTATGGACTTCA | 40 |
| TRAC-RHA (800 bp) | TGGAGCAACAAATCTGACTTTGCATGTGCAAACGCCTTCAACAAC AGCATTATTCCAGAAGACACCTTCTTCCCCAGCCCAGGTAAGGGC AGCTTTGGTGCCTTCGCAGGCTGTTTCCTTGCTTCAGGAATGGCC AGGTTCTGCCCAGAGCTCTGGTCAATGATGTCTAAAACTCCTCTG ATTGGTGGTCTCGGCCTTATCCATTGCCACCAAAACCCTCTTTTT ACTAAGAAACAGTGAGCCTTGTTCTGGCAGTCCAGAGAATGACAC GGGAAAAAAGCAGATGAAGAGAAGGTGGCAGGAGAGGGCACGTGG CCCAGCCTCAGTCTCTCCAACTGAGTTCCTGCCTGCCTGCCTTTG CTCAGACTGTTTGCCCCTTACTGCTCTTCTAGGCCTCATTCTAAG CCCCTTCTCCAAGTTGCCTCTCCTTATTTCTCCCTGTCTGCCAAA AAATCTTTCCCAGCTCACTAAGTCAGTCTCACGCAGTCACTCATT AACCCACCAATCACTGATTGTGCCGGCACATGAATGCACCAGGTG TTGAAGTGGAGGAATTAAAAAGTCAGATGAGGGGTGTGCCCAGAG GAAGCACCATTCTAGTTGGGGGAGCCCATCTGTCAGCTGGGAAAA GTCCAAATAACTTCAGATTGGAATGTGTTTTAACTCAGGGTTGA AAAACAGCTACCTTCAGGACAAAAGTCAGGGAAGGGCTCTCTGAA GAAATGCTACTTGAAGATACCAGCCCTACCAAGGGCAGGGAGAGG ACCCTATAGAGGCCTGGGACAGGAGCTCAATGAGAAAGG | 41 |
| EF1α | GGCTCCGGTGCCCGTCAGTGGGCAGAGCGCACATCGCCCACAGTC CCCGAGAAGTTGGGGGGAGGGGTCGGCAATTGAACCGGTGCCTAG AGAAGGTGGCGCGGGGTAAACTGGGAAAGTGATGTCGTGTACTGG CTCCGCCTTTTTCCCGAGGGTGGGGGAGAACCGTATATAAGTGCA GTAGTCGCCGTGAACGTTCTTTTTCGCAACGGGTTTGCCGCCAGA ACACAGGTAAGTGCCGTGTGTGGTTCCCGCGGGCCTGGCCTCTTT ACGGGTTATGGCCCTTGCGTGCCTTGAATTACTTCCACTGGCTGC AGTACGTGATTCTTGATCCCGAGCTTCGGGTTGGAAGTGGGTGGG AGAGTTCGAGGCCTTGCGCTTAAGGAGCCCCTTCGCCTCGTGCTT GAGTTGAGGCCTGGCCTGGGCGCTGGGGCCGCCGCGTGCGAATCT GGTGGCACCTTCGCGCCTGTCTCGCTGCTTTCGATAAGTCTCTAG CCATTTAAAATTTTTGATGACCTGCTGCGACGCTTTTTTTCTGGC AAGATAGTCTTGTAAATGCGGGCCAAGATCTGCACACTGGTATTT CGGTTTTTGGGGCCGCGGGCGGCGACGGGGCCCGTGCGTCCCAGC GCACATGTTCGGCGAGGCGGGGCCTGCGAGCGCGGCCACCGAGAA TCGGACGGGGGTAGTCTCAAGCTGGCCGGCCTGCTCTGGTGCCTG GCCTCGCGCCGCCGTGTATCGCCCCGCCCTGGGCGGCAAGGCTGG CCCGGTCGGCACCAGTTGCGTGAGCGGAAAGATGGCCGCTTCCCG GCCCTGCTGCAGGGAGCTCAAAATGGAGGACGCGGCGCTCGGGAG AGCGGGCGGGTGAGTCACCCACACAAAGGAAAAGGGCCTTTCCGT CCTCAGCCGTCGCTTCATGTGACTCCACGGAGTACCGGGCGCCGT CCAGGCACCTCGATTAGTTCTCGAGCTTTTGGAGTACGTCGTCTT TAGGTTGGGGGGAGGGGTTTTATGCGATGGAGTTTCCCCACACTG AGTGGGTGGAGACTGAAGTTAGGCCAGCTTGGCACTTGATGTAAT TCTCCTTGGAATTTGCCCTTTTTGAGTTTGGATCTTGGTTCATTC TCAAGCCTCAGACAGTGGTTCAAAGTTTTTTTCTTCCATTTCAGG TGTCGTGA | 42 |

TABLE 11-continued

| Name Description | Sequence | SEQ ID NO: |
|---|---|---|
| Sequences of Anti-CD19 CAR Construct Components | | |
| GM-CSF signal peptide | ATGCTTCTTTTGGTTACGTCTCTGTTGCTTTGCGAACTTCCTCAT CCAGCGTTCTTGCTGATCCCC | 43 |
| GM-CSF signal peptide | MLLLVTSLLLCELPHPAFLLIP | 44 |
| Anti-CD19 scFv | GATATTCAGATGACTCAGACCACCAGTAGCTTGTCTGCCTCACTG GGAGACCGAGTAACAATCTCCTGCAGGGCAAGTCAAGACATTAGC AAATACCTCAATTGGTACCAGCAGAAGCCCGACGGAACGGTAAAA CTCCTCATCTATCATACGTCAAGGTTGCATTCCGGAGTACCGTCA CGATTTTCAGGTTCTGGGAGCGGAACTGACTATTCCTTGACTATT TCAAACCTCGAGCAGGAGGACATTGCGACATATTTTTGTCAACAA GGTAATACCCTCCCTTACACTTTCGGAGGAGGAACCAAACTCGAA ATTACCGGGTCCACCAGTGGCTCTGGGAAGCCTGGCAGTGGAGAA GGTTCCACTAAAGGCGAGGTGAAGCTCCAGGAGAGCGGCCCCGGT CTCGTTGCCCCCAGTCAAAGCCTCTCTGTAACGTGCACAGTGAGT GGTGTATCATTGCCTGATTATGGCGTCTCCTGGATAAGGCAGCCC CCGCGAAAGGGTCTTGAATGGCTTGGGGTAATATGGGGCTCAGAG ACAACGTATTATAACTCCGCTCTCAAAAGTCGCTTGACGATAATA AAAGATAACTCCAAGAGTCAAGTTTTCCTTAAAATGAACAGTTTG CAGACTGACGATACCGCTATATATTATTGTGCTAAACATTATTAC TACGGCGGTAGTTACGCGATGGATTATTGGGGGCAGGGGACTTCT GTCACAGTCAGTAGT | 45 |
| CD19 scFv amino acid sequence Linker underlined | DIQMTQTTSSLSASLGDRVTISCRASQDISKYLNWYQQKPDGTVK LLIYHTSRLHSGVPSRFSGSGSGTDYSLTISNLEQEDIATYFCQQ GNTLPYTFGGGTKLEITGSTSGSGKPGSGEGSTKGEVKLQESGPG LVAPSQSLSVTCTVSGVSLPDYGVSWIRQPPRKGLEWLGVIWGSE TTYYNSALKSRLTIIKDNSKSQVFLKMNSLQTDDTAIYYCAKHYY YGGSYAMDYWGQGTSVTVSS | 46 |
| CD8a extracellular + CD8a transmembrane + 5' Linker (underlined) | GCTGCTGCCTTTGTCCCGGTATTTCTCCCAGCCAAACCGACCACG ACTCCCGCCCCGCGCCCTCCGACACCCGCTCCCACCATCGCCTCT CAACCTCTTAGTCTTCGCCCCGAGGCATGCCGACCCGCCGCCGGG GGTGCTGTTCATACGAGGGGCTTGGACTTCGCTTGTGATATTTAC ATTTGGGCTCCGTTGGCGGGTACGTGCGGCGTCCTTTTGTTGTCA CTCGTTATTACTTTGTATTGTAATCACAGGAATCGC | 47 |
| CD8a extracellular + CD8a transmembrane (without linker) | TTTGTCCCGGTATTTCTCCCAGCCAAACCGACCACGACTCCCGCC CCGCGCCCTCCGACACCCGCTCCCACCATCGCCTCTCAACCTCTT AGTCTTCGCCCCGAGGCATGCCGACCCGCCGCCGGGGGTGCTGTT CATACGAGGGGCTTGGACTTCGCTTGTGATATTTACATTTGGGCT CCGTTGGCGGGTACGTGCGGCGTCCTTTTGTTGTCACTCGTTATT ACTTTGTATTGTAATCACAGGAATCGC | 48 |
| CD8a extracellular + CD8a transmembrane | FVPVFLPAKPTTTPAPRPPTPAPTIASQPLSLRPEACRPAAGGAV HTRGLDFACDIYIWAPLAGTCGVLLLSLVITLYCNHRNR | 49 |
| CD19 VH | EVKLQESGPGLVAPSQSLSVTCTVSGVSLPDYGVSWIRQPPRKGL EWLGVIWGSETTYYNSALKSRLTIIKDNSKSQVFLKMNSLQTDDT AIYYCAKHYYYGGSYAMDYWGQGTSVTVSS | 50 |
| CD19 VL | DIQMTQTTSSLSASLGDRVTISCRASQDISKYLNWYQQKPDGTVK LLIYHTSRLHSGVPSRFSGSGSGTDYSLTISNLEQEDIATYFCQQ GNTLPYTFGGGTKLEIT | 51 |
| CD19 linker | GSTSGSGKPGSGEGSTKG | 52 |
| rAAV | CCTGCAGGCAGCTGCGCGCTCGCTCGCTCACTGAGGCCGCCCGGG CGTCGGGCGACCTTTGGTCGCCCGGCCTCAGTGAGCGAGCGAGCG CGCAGAGAGGGAGTGGCCAACTCCATCACTAGGGGTTCCTGCGGC CGCACGCGTGAGATGTAAGGAGCTGCTGTGACTTGCTCAAGGCCT TATATCGAGTAAACGGTAGTGCTGGGGCTTAGACGCAGGTGTTCT GATTTATAGTTCAAAACCTCTATCAATGAGAGAGCAATCTCCTGG TAATGTGATAGATTTCCCAACTTAATGCCAACATACCATAAACCT CCCATTCTGCTAATGCCCAGCCTAAGTTGGGGAGACCACTCCAGA TTCCAAGATGTACAGTTTGCTTTGCTGGGCCTTTTTCCCATGCCT GCCTTTACTCTGCCAGAGTTATATTGCTGGGGTTTTGAAGAAGAT CCTATTAAATAAAAGAATAAGCAGTATTATTAAGTAGCCCTGCAT TTCAGGTTTCCTTGAGTGGCAGGCCAGGCCTGGCCGTGAACGTTC ACTGAAATCATGGCCTCTTGGCCAAGATTGATAGCTTGTGCCTGT CCCTGAGTCCCAGTCCATCACGAGCAGCTGGTTTCTAAGATGCTA TTTCCCGTATAAAGCATGAGACCGTGACTTGCCAGCCCCACAGAG | 53 |

TABLE 11-continued

| Sequences of Anti-CD19 CAR Construct Components | | |
|---|---|---|
| Name Description | Sequence | SEQ ID NO: |
| | CCCCGCCCTTGTCCATCACTGGCATCTGGACTCCAGCCTGGGTTG | |
| | GGGCAAAGAGGGAAATGAGATCATGTCCTAACCCTGATCCTCTTG | |
| | TCCCACAGATATCCAGAACCCTGACCCTGCCGTGTACCAGCTGAG | |
| | AGACTCTAAATCCAGTGACAAGTCTGTCTGCCTATTCACCGATTT | |
| | TGATTCTCAAACAAATGTGTCACAAAGTAAGGATTCTGATGTGTA | |
| | TATCACAGACAAAACTGTGCTAGACATGAGGTCTATGGACTTCAG | |
| | GCTCCGGTGCCCGTCAGTGGGCAGAGCGCACATCGCCCACAGTCC | |
| | CCGAGAAGTTGGGGGGAGGGGTCGGCAATTGAACCGGTGCCTAGA | |
| | GAAGGTGGCGCGGGGTAAACTGGGAAAGTGATGTCGTGTACTGGC | |
| | TCCGCCTTTTTCCCGAGGGTGGGGGAGAACCGTATATAAGTGCAG | |
| | TAGTCGCCGTGAACGTTCTTTTTCGCAACGGGTTTGCCGCCAGAA | |
| | CACAGGTAAGTGCCGTGTGTGGTTCCCGCGGGCCTGGCCTCTTTA | |
| | CGGGTTATGGCCCTTGCGTGCCTTGAATTACTTCCACTGGCTGCA | |
| | GTACGTGATTCTTGATCCCGAGCTTCGGGTTGGAAGTGGGTGGGA | |
| | GAGTTCGAGGCCTTGCGCTTAAGGAGCCCCTTCGCCTCGTGCTTG | |
| | AGTTGAGGCCTGGCCTGGGCGCTGGGGCCGCCGCGTGCGAATCTG | |
| | GTGGCACCTTCGCGCCTGTCTCGCTGCTTTCGATAAGTCTCTAGC | |
| | CATTTAAAATTTTTGATGACCTGCTGCGACGCTTTTTTTCTGGCA | |
| | AGATAGTCTTGTAAATGCGGGCCAAGATCTGCACACTGGTATTTC | |
| | GGTTTTTGGGGCCGCGGGCGGCGACGGGGCCCGTGCGTCCCAGCG | |
| | CACATGTTCGGCGAGGCGGGGCCTGCGAGCGCGGCCACCGAGAAT | |
| | CGGACGGGGGTAGTCTCAAGCTGGCCGGCCTGCTCTGGTGCCTGG | |
| | CCTCGCGCCGCCGTGTATCGCCCCGCCCTGGGCGGCAAGGCTGGC | |
| | CCGGTCGGCACCAGTTGCGTGAGCGGAAAGATGGCCGCTTCCCGG | |
| | CCCTGCTGCAGGGAGCTCAAAATGGAGGACGCGGCGCTCGGGAGA | |
| | GCGGGCGGGTGAGTCACCCACACAAAGGAAAAGGGCCTTTCCGTC | |
| | CTCAGCCGTCGCTTCATGTGACTCCACGGAGTACCGGGCGCCGTC | |
| | CAGGCACCTCGATTAGTTCTCGAGCTTTTGGAGTACGTCGTCTTT | |
| | AGGTTGGGGGGAGGGGTTTTATGCGATGGAGTTTCCCCACACTGA | |
| | GTGGGTGGAGACTGAAGTTAGGCCAGCTTGGCACTTGATGTAATT | |
| | CTCCTTGGAATTTGCCCTTTTTGAGTTTGGATCTTGGTTCATTCT | |
| | CAAGCCTCAGACAGTGGTTCAAAGTTTTTTTCTTCCATTTCAGGT | |
| | GTCGTGACCACCATGCTTCTTTTGGTTACGTCTCTGTTGCTTTGC | |
| | GAACTTCCTCATCCAGCGTTCTTGCTGATCCCCGATATTCAGATG | |
| | ACTCAGACCACCAGTAGCTTGTCTGCCTCACTGGGAGACCGAGTA | |
| | ACAATCTCCTGCAGGGCAAGTCAAGACATTAGCAAATACCTCAAT | |
| | TGGTACCAGCAGAAGCCCGACGGAACGGTAAAACTCCTCATCTAT | |
| | CATACGTCAAGGTTGCATTCCGGAGTACCGTCACGATTTTCAGGT | |
| | TCTGGGAGCGGAACTGACTATTCCTTGACTATTTCAAACCTCGAG | |
| | CAGGAGGACATTGCGACATATTTTTGTCAACAAGGTAATACCCTC | |
| | CCTTACACTTTCGGAGGAGGAACCAAACTCGAAATTACCGGGTCC | |
| | ACCAGTGGCTCTGGGAAGCCTGGCAGTGGAGAAGGTTCCACTAAA | |
| | GGCGAGGTGAAGCTCCAGGAGAGCGGCCCCGGTCTCGTTGCCCCC | |
| | AGTCAAAGCCTCTCTGTAACGTGCACAGTGAGTGGTGTATCATTG | |
| | CCTGATTATGGCGTCTCCTGGATAAGGCAGCCCCCGCGAAAGGGT | |
| | CTTGAATGGCTTGGGGTAATATGGGGCTCAGAGACAACGTATTAT | |
| | AACTCCGCTCTCAAAAGTCGCTTGACGATAATAAAAGATAACTCC | |
| | AAGAGTCAAGTTTTCCTTAAAATGAACAGTTTGCAGACTGACGAT | |
| | ACCGCTATATATTATTGTGCTAAACATTATTACTACGGCGGTAGT | |
| | TACGCGATGGATTATTGGGGGCAGGGGACTTCTGTCACAGTCAGT | |
| | AGTGCTGCTGCCTTTGTCCCGGTATTTCTCCCAGCCAAACCGACC | |
| | ACGACTCCCGCCCCGCGCCCTCCGACACCCGCTCCCACCATCGCC | |
| | TCTCAACCTCTTAGTCTTCGCCCCGAGGCATGCCGACCCGCCGCC | |
| | GGGGGTGCTGTTCATACGAGGGGCTTGGACTTCGCTTGTGATATT | |
| | TACATTTGGGCTCCGTTGGCGGGTACGTGCGGCGTCCTTTTGTTG | |
| | TCACTCGTTATTACTTTGTATTGTAATCACAGGAATCGCTCAAAG | |
| | CGGAGTAGGTTGTTGCATTCCGATTACATGAATATGACTCCTCGC | |
| | CGGCCTGGGCCGACAAGAAAACATTACCAACCCTATGCCCCCCCA | |
| | CGAGACTTCGCTGCGTACAGGTCCCGAGTGAAGTTTTCCCGAAGC | |
| | GCAGACGCTCCGGCATATCAGCAAGGACAGAATCAGCTGTATAAC | |
| | GAACTGAATTTGGGACGCCGCGAGGAGTATGACGTGCTTGATAAA | |
| | CGCCGGGGGAGAGACCCGGAAATGGGGGGTAAACCCCGAAGAAAG | |
| | AATCCCCAAGAAGGACTCTACAATGAACTCCAGAAGGATAAGATG | |
| | GCGGAGGCCTACTCAGAAATAGGTATGAAGGGCGAACGACGACGG | |
| | GGAAAAGGTCACGATGGCCTCTACCAAGGGTTGAGTACGGCAACC | |
| | AAAGATACGTACGATGCACTGCATATGCAGGCCCTGCCTCCCAGA | |
| | TAATAATAAAATCGCTATCCATCGAAGATGGATGTGTGTTGGTTT | |
| | TTTGTGTGTGGAGCAACAAATCTGACTTTGCATGTGCAAACGCCT | |
| | TCAACAACAGCATTATTCCAGAAGACACCTTCTTCCCCAGCCCAG | |
| | GTAAGGGCAGCTTTGGTGCCTTCGCAGGCTGTTTCCTTGCTTCAG | |
| | GAATGGCCAGGTTCTGCCCAGAGCTCTGGTCAATGATGTCTAAAA | |
| | CTCCTCTGATTGGTGGTCTCGGCCTTATCCATTGCCACCAAAACC | |
| | CTCTTTTTTACTAAGAAACAGTGAGCCTTGTTCTGGCAGTCCAGAG | |
| | AATGACACGGGAAAAAAGCAGATGAAGAGAAGGTGGCAGGAGAGG | |
| | GCACGTGGCCCAGCCTCAGTCTCTCCAACTGAGTTCCTGCCTGCC | |

TABLE 11-continued

| Sequences of Anti-CD19 CAR Construct Components | | |
|---|---|---|
| Name<br>Description | Sequence | SEQ<br>ID NO: |
| | TGCCTTTGCTCAGACTGTTTGCCCCTTACTGCTCTTCTAGGCCTC<br>ATTCTAAGCCCCTTCTCCAAGTTGCCTCTCCTTATTTCTCCCTGT<br>CTGCCAAAAAATCTTTCCCAGCTCACTAAGTCAGTCTCACGCAGT<br>CACTCATTAACCCACCAATCACTGATTGTGCCGGCACATGAATGC<br>ACCAGGTGTTGAAGTGGAGGAATTAAAAAGTCAGATGAGGGGTGT<br>GCCCAGAGGAAGCACCATTCTAGTTGGGGGAGCCCATCTGTCAGC<br>TGGGAAAAGTCCAAATAACTTCAGATTGGAATGTGTTTTAACTCA<br>GGGTTGAGAAAACAGCTACCTTCAGGACAAAAGTCAGGGAAGGGC<br>TCTCTGAAGAAATGCTACTTGAAGATACCAGCCCTACCAAGGGCA<br>GGGAGAGGACCCTATAGAGGCCTGGGACAGGAGCTCAATGAGAAA<br>GGTAACCACGTGCGGACCGAGGCTGCAGCGTCGTCCTCCCTAGGA<br>ACCCCTAGTGATGGAGTTGGCCACTCCCTCTCTGCGCGCTCGCTC<br>GCTCACTGAGGCCGGGCGACCAAAGGTCGCCCGACGCCCGGGCTT<br>TGCCCGGGCGGCCTCAGTGAGCGAGCGAGCGCGCAGCTGCCTGCA<br>GG | |
| LHA to RHA | GAGATGTAAGGAGCTGCTGTGACTTGCTCAAGGCCTTATATCGAG<br>TAAACGGTAGTGCTGGGGCTTAGACGCAGGTGTTCTGATTTATAG<br>TTCAAAACCTCTATCAATGAGAGAGCAATCTCCTGGTAATGTGAT<br>AGATTTCCCAACTTAATGCCAACATACCATAAACCTCCCATTCTG<br>CTAATGCCCAGCCTAAGTTGGGGAGACCACTCCAGATTCCAAGAT<br>GTACAGTTTGCTTTGCTGGGCCTTTTTCCCATGCCTGCCTTTACT<br>CTGCCAGAGTTATATTGCTGGGGTTTTGAAGAAGATCCTATTAAA<br>TAAAAGAATAAGCAGTATTATTAAGTAGCCCTGCATTTCAGGTTT<br>CCTTGAGTGGCAGGCCAGGCCTGGCCGTGAACGTTCACTGAAATC<br>ATGGCCTCTTGGCCAAGATTGATAGCTTGTGCCTGTCCCTGAGTC<br>CCAGTCCATCACGAGCAGCTGGTTTCTAAGATGCTATTTCCCGTA<br>TAAAGCATGAGACCGTGACTTGCCAGCCCCACAGAGCCCGCCCT<br>TGTCCATCACTGGCATCTGGACTCCAGCCTGGGTTGGGGCAAAGA<br>GGGAAATGAGATCATGTCCTAACCCTGATCCTCTTGTCCCACAGA<br>TATCCAGAACCCTGACCCTGCCGTGTACCAGCTGAGAGACTCTAA<br>ATCCAGTGACAAGTCTGTCTGCCTATTCACCGATTTTGATTCTCA<br>AACAAATGTGTCACAAAGTAAGGATTCTGATGTGTATATCACAGA<br>CAAAACTGTGCTAGACATGAGGTCTATGGACTTCAGGCTCCGGTG<br>CCCGTCAGTGGGCAGAGCGCACATCGCCCACAGTCCCCGAGAAGT<br>TGGGGGGAGGGGTCGGCAATTGAACCGGTGCCTAGAGAAGGTGGC<br>GCGGGGTAAACTGGGAAAGTGATGTCGTGTACTGGCTCCGCCTTT<br>TTCCCGAGGGTGGGGGAGAACCGTATATAAGTGCAGTAGTCGCCG<br>TGAACGTTCTTTTTCGCAACGGGTTTGCCGCCAGAACACAGGTAA<br>GTGCCGTGTGTGGTTCCCGCGGGCCTGGCCTCTTTACGGGTTATG<br>GCCCTTGCGTGCCTTGAATTACTTCCACTGGCTGCAGTACGTGAT<br>TCTTGATCCCGAGCTTCGGGTTGGAAGTGGGTGGGAGAGTTCGAG<br>GCCTTGCGCTTAAGGAGCCCCTTCGCCTCGTGCTTGAGTTGAGGC<br>CTGGCCTGGGCGCTGGGGCCGCCGCGTGCGAATCGGTGGCACCT<br>TCGCGCCTGTCTCGCTGCTTTCGATAAGTCTCTAGCCATTTAAAA<br>TTTTTGATGACCTGCTGCGACGCTTTTTTTCTGGCAAGATAGTCT<br>TGTAAATGCGGGCCAAGATCTGCACACTGGTATTTCGGTTTTTGG<br>GGCCGCGGGCGGCGACGGGGCCCGTGCGTCCCAGCGCACATGTTC<br>GGCGAGGCGGGGCCTGCGAGCGCGGCCACCGAGAATCGGACGGGG<br>GTAGTCTCAAGCTGGCCGGCCTGCTCTGGTGCCTGGCCTCGCGCC<br>GCCGTGTATCGCCCCGCCCTGGGCGGCAAGGCTGGCCCGGTCGGC<br>ACCAGTTGCGTGAGCGGAAAGATGGCCGCTTCCCGGCCCTGCTGC<br>AGGGGAGCTCAAAATGGAGGACGCGGCGCTCGGGAGAGCGGGCGGG<br>TGAGTCACCCACACAAAGGAAAAGGGCCTTTCCGTCCTCAGCCGT<br>CGCTTCATGTGACTCCACGGAGTACCGGGCGCCGTCCAGGCACCT<br>CGATTAGTTCTCGAGCTTTTGGAGTACGTCGTCTTTAGGTTGGGG<br>GGAGGGGTTTTATGCGATGGAGTTTCCCCACACTGAGTGGGTGGA<br>GACTGAAGTTAGGCCAGCTTGGCACTTGATGTAATTCTCCTTGGA<br>ATTTGCCCTTTTTGAGTTTGGATCTTGGTTCATTCTCAAGCCTCA<br>GACAGTGGTTCAAAGTTTTTTCTTCCATTTCAGGTGTCGTGACC<br>ACCATGCTTCTTTTGGTTACGTCTCTGTTGCTTTGCGAACTTCCT<br>CATCCAGCGTTCTTGCTGATCCCCGATATTCAGATGACTCAGACC<br>ACCAGTAGCTTGTCTGCCTCACTGGGAGACCGAGTAACAATCTCC<br>TGCAGGGCAAGTCAAGACATTAGCAAATACCTCAATTGGTACCAG<br>CAGAAGCCCGACGGAACGGTAAAACTCCTCATCTATCATACGTCA<br>AGGTTGCATTCCGGAGTACCGTCACGATTTTCAGGTTCTGGGAGC<br>GGAACTGACTATTCCTTGACTATTTCAAACCTCGAGCAGGAGGAC<br>ATTGCGACATATTTTTGTCAACAAGGTAATACCCTCCCTTACACT<br>TTCGGAGGAGGAACCAAACTCGAAATTACCGGGTCCACCAGTGGC<br>TCTGGGAAGCCTGGCAGTGGAGAAGGTTCCACTAAAGGCGAGGTG<br>AAGCTCCAGGAGAGCGGCCCCGGTCTCGTTGCCCCCAGTCAAAGC<br>CTCTCTGTAACGTGCACAGTGAGTGGTGTATCATTGCCTGATTAT<br>GGCGTCTCCTGGATAAGGCAGCCCCCGCGAAAGGGTCTTGAATGG<br>CTTGGGGTAATATGGGCTCAGAGACAACGTATTATAACTCCGCT<br>CTCAAAAGTCGCTTGACGATAATAAAAGATAACTCCAAGAGTCAA | 54 |

TABLE 11-continued

| Sequences of Anti-CD19 CAR Construct Components | | |
|---|---|---|
| Name Description | Sequence | SEQ ID NO: |
| | GTTTTCCTTAAAATGAACAGTTTGCAGACTGACGATACCGCTATA | |
| | TATTATTGTGCTAAACATTATTACTACGGCGGTAGTTACGCGATG | |
| | GATTATTGGGGGCAGGGGACTTCTGTCACAGTCAGTAGTGCTGCT | |
| | GCCTTTGTCCCGGTATTTCTCCCAGCCAAACCGACCACGACTCCC | |
| | GCCCCGCGCCCTCCGACACCCGCTCCCACCATCGCCTCTCAACCT | |
| | CTTAGTCTTCGCCCCGAGGCATGCCGACCCGCCGCCGGGGGTGCT | |
| | GTTCATACGAGGGGCTTGGACTTCGCTTGTGATATTTACATTTGG | |
| | GCTCCGTTGGCGGGTACGTGCGGCGTCCTTTTGTTGTCACTCGTT | |
| | ATTACTTTGTATTGTAATCACAGGAATCGCTCAAAGCGGAGTAGG | |
| | TTGTTGCATTCCGATTACATGAATATGACTCCTCGCCGGCCTGGG | |
| | CCGACAAGAAAACATTACCAACCCTATGCCCCCCCACGAGACTTC | |
| | GCTGCGTACAGGTCCCGAGTGAAGTTTTCCCGAAGCGCAGACGCT | |
| | CCGGCATATCAGCAAGGACAGAATCAGCTGTATAACGAACTGAAT | |
| | TTGGGACGCCGCGAGGAGTATGACGTGCTTGATAAACGCCGGGGG | |
| | AGAGACCCGGAAATGGGGGGTAAACCCCGAAGAAAGAATCCCCAA | |
| | GAAGGACTCTACAATGAACTCCAGAAGGATAAGATGGCGGAGGCC | |
| | TACTCAGAAATAGGTATGAAGGGCGAACGACGACGGGGAAAAGGT | |
| | CACGATGGCCTCTACCAAGGGTTGAGTACGGCAACCAAAGATACG | |
| | TACGATGCACTGCATATGCAGGCCCTGCCTCCCAGATAATAATAA | |
| | AATCGCTATCCATCGAAGATGGATGTGTGTTGGTTTTTTGTGTGT | |
| | GGAGCAACAAATCTGACTTTGCATGTGCAAACGCCTTCAACAACA | |
| | GCATTATTCCAGAAGACACCTTCTTCCCCAGCCCAGGTAAGGGCA | |
| | GCTTTGGTGCCTTCGCAGGCTGTTTCCTTGCTTCAGGAATGGCCA | |
| | GGTTCTGCCCAGAGCTCTGGTCAATGATGTCTAAAACTCCTCTGA | |
| | TTGGTGGTCTCGGCCTTATCCATTGCCACCAAAACCCTCTTTTTA | |
| | CTAAGAAACAGTGAGCCTTGTTCTGGCAGTCCAGAGAATGACACG | |
| | GGAAAAAAGCAGATGAAGAGAAGGTGGCAGGAGAGGGCACGTGGC | |
| | CCAGCCTCAGTCTCTCCAACTGAGTTCCTGCCTGCCTGCCTTTGC | |
| | TCAGACTGTTTGCCCCTTACTGCTCTTCTAGGCCTCATTCTAAGC | |
| | CCCTTCTCCAAGTTGCCTCTCCTTATTTCTCCCTGTCTGCCAAAA | |
| | AATCTTTCCCAGCTCACTAAGTCAGTCTCACGCAGTCACTCATTA | |
| | ACCCACCAATCACTGATTGTGCCGGCACATGAATGCACCAGGTGT | |
| | TGAAGTGGAGGAATTAAAAAGTCAGATGAGGGGTGTGCCCAGAGG | |
| | AAGCACCATTCTAGTTGGGGGAGCCCATCTGTCAGCTGGGAAAAG | |
| | TCCAAATAACTTCAGATTGGAATGTGTTTTAACTCAGGGTTGAGA | |
| | AAACAGCTACCTTCAGGACAAAAGTCAGGGAAGGGCTCTCTGAAG | |
| | AAATGCTACTTGAAGATACCAGCCCTACCAAGGGCAGGGAGAGGA | |
| | CCCTATAGAGGCCTGGGACAGGAGCTCAATGAGAAAGG | |

(i) Cell Editing Performance Across Healthy Donors

T cells from healthy donors (male, n=10) were isolated from leukopaks and frozen in cryotubes. Editing efficiency was evaluated on thawed cells of each donor using the following concentrations of the gene-editing components: Cas9 (300 µg/mL), TA-1 (75 µg/mL), and B2M-1 (150 µg/mL and 200 µg/mL).

Greater than 40% of the edited cells from all donors expressed CAR. β2M and TRAC knockout rates were greater than 80% and 95% of the total cell population, respectively (Table 12). All of the T cell isolations across donors were deemed acceptable for CTX110 manufacturing, indicating a robust production process.

TABLE 12

| Editing Outcomes across 10 Male Donors. | | | | | | | |
|---|---|---|---|---|---|---|---|
| Donor | Blood Type | Age | BMI | % TCRαβ⁻ | % B2M⁻ | % CAR⁺ | Fold Expansion |
| TA-1 = 75 µg/mL, B2M-1 = 150 µg/mL, Cas9 = 300 µg/mL | | | | | | | |
| 1 | A+ | 49 | 40.1 | 99.00 | 89.00 | 46.30 | 13.41 |
| 2 | A+ | 28 | 42.6 | 99.99 | 95.00 | 68.20 | 62.64 |
| 3 | A+ | 36 | 29 | 99.00 | 85.00 | 66.30 | 63.00 |
| 4 | A+ | 33 | 24 | 99.96 | 91.00 | 53.10 | 42.16 |
| TA-1 = 75 µg/mL, B2M-1 = 200 µg/mL, Cas9 = 300 µg/mL | | | | | | | |
| 40 | A− | 19 | 25.2 | 95.00 | 82.33 | 49.00 | 53.57 |
| 41 | A+ | 31 | 24 | 98.00 | 86.33 | 59.67 | 76.07 |
| 43 | O+ | 29 | 25.7 | 96.00 | 81.67 | 59.00 | 69.83 |
| A | O+ | 23 | 24.4 | 98.00 | 86.67 | 63.00 | 63.53 |
| 44 | O+ | 30 | 26.5 | 98.00 | 83.00 | 60.00 | 76.37 |
| 45 | A+ | 35 | 27.2 | 97.00 | 84.33 | 62.00 | 59.40 |

TABLE 12-continued

| | | | | Editing Outcomes across 10 Male Donors. | | | |
|---|---|---|---|---|---|---|---|
| Donor | Blood Type | Age | BMI | % TCRαβ⁻ | % B2M⁻ | % CAR⁺ | Fold Expansion |
| | Average | | | 98.00 | 86.43 | 58.66 | 58.00 |
| | SD | | | 1.54 | 3.98 | 6.78 | 17.72 |
| | % CV | | | 1.57 | 4.61 | 11.55 | 30.56 |

Abbreviations.
B2M = β2 microglobulin, BMI = Body mass index, CAR = Chimeric antigen receptor, CV = Coefficient of variation, SD = Standard deviation, TCRαβ = T cell receptor alpha chain + T cell receptor beta chain.

(ii) Cas9 Nuclease

The Cas9 nuclease of SEQ ID NO:1 was used in this Example. The results, summarized in Table 14 below, indicate that similar levels of TCRαβ⁻ and B2M⁻ cells were present, as well as double-negative cells.

(iii) rAAV-138 Vector rAAV-138 vector as disclosed above was used for evaluation of the impact of MOI to achieve desired CAR⁺ expression. Cells were transduced with increasing MOI and CAR⁺ expression was quantified. See Example 4 above. The data, presented in FIG. 7B, support the selection of a MOI of 20,000.

Figure 7C:
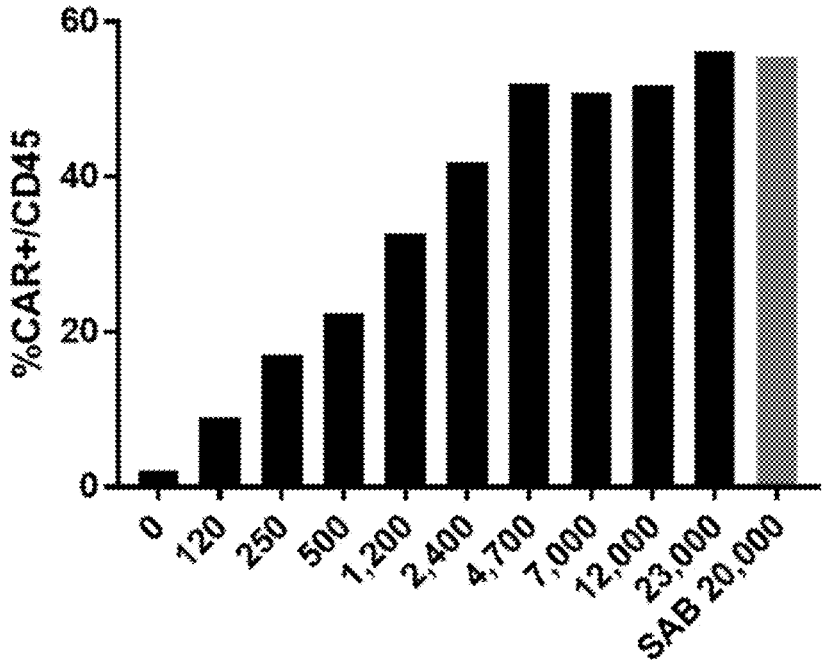

For scale-up development, a study was conducted to verify the suitability of the selected MOI with the starting materials noted above. Cells were transduced at MOIs ranging from 0 to 23,000. After electroporation and viral infection followed by 11 days of expansion, CAR⁺ expression was quantified by flow cytometry. The results are presented in FIG. 7C. CAR⁺ expression, which is AAV dose-dependent, ranged from 2.1% CAR+ at MOI of 0 to 56.2% CAR⁺ at MOI of 23,000. CAR⁺ expression saturated at MOI of 4,700.

CAR expression for cells infected with the GMP rAAV-138 (MOI of 23,000) was comparable to that obtained with the non-GMP vector (MOI of 20,000), 56.2% and 55.4%, respectively. The MOI of 20,000 was selected for scale-up manufacture.

(iv) In Situ Formation of the Ribonucleoprotein Complex (RNP)

Using a fixed concentration of cells, electroporation was performed with increasing concentrations of RNP complexes formed by incubation of Cas9 (SEQ ID NO: 1) with a sgRNA targeting TCR (TA-1, SEQ ID NO: 2) and a sgRNA targeting β2M (B2M-1; SEQ ID NO 6). In situ formation of the TA-1/Cas9 and β2M/Cas9 complexes was evaluated using a final combined concentration of 300 μg/mL Cas9 nuclease (equivalent to a final concentration of 150 μg/mL Cas9 nuclease combined with each guide). Final concentrations of TA-1 and B2M-1 varied from 37.5 μg/mL to 300 μg/mL.

Figure 7D:
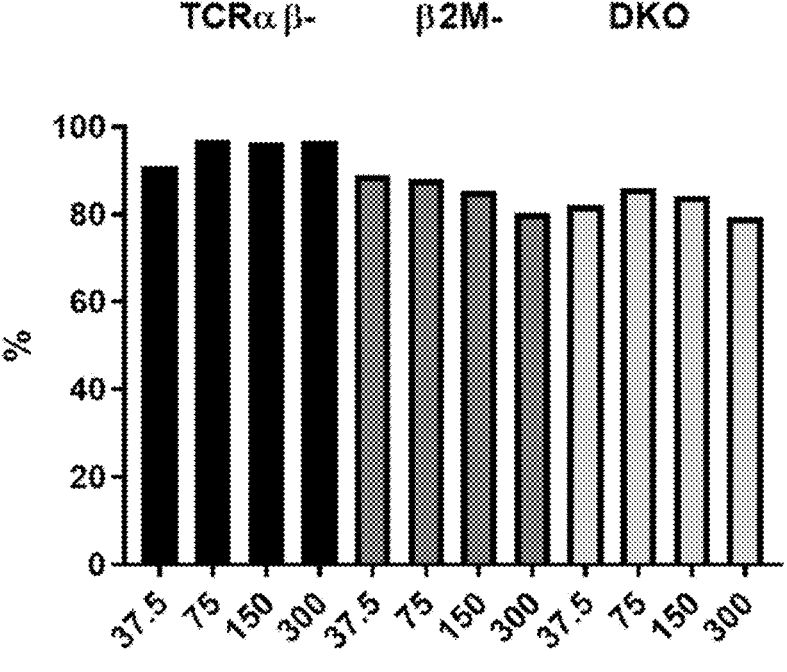
Figure 7E:
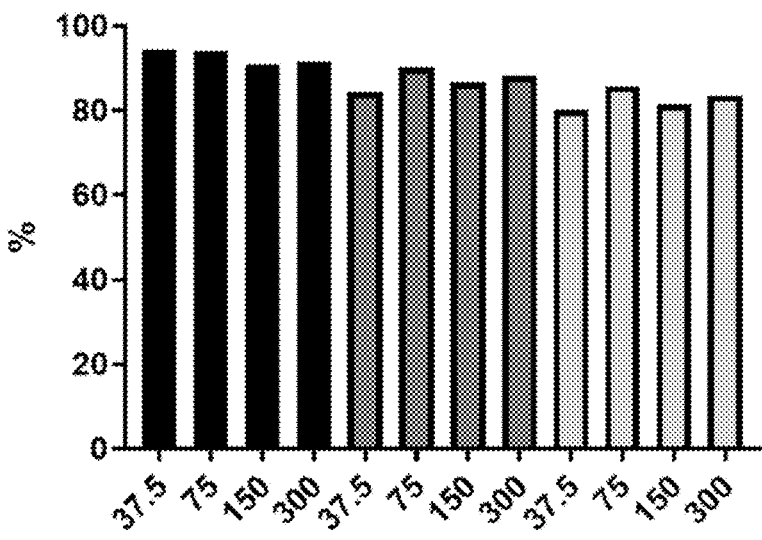

As shown in FIG. 7D, TA-1 sgRNA concentrations from 37.5 μg/mL to 75 μg/mL resulted in higher editing of TCRαβ. TA-1 sgRNA concentrations from 150 μg/mL or 300 μg/mL did not provide additional editing of TCRαβ, and decreased editing of B2M. Among the concentrations tested, 75 μg/mL of TA-1 sgRNA provided the highest efficiency for editing of TCRαβ, β2M, and TCRαβ and β2M double knockout (DKO). As shown in FIG. 7E, B2M-1 sgRNA concentrations from 75 μg/mL to 150 μg/mL resulted in higher editing of β2M suggesting that efficient editing may be achieved using a concentration of B2M-1 sgRNA that is higher than the concentration of TA-1 sgRNA.

In sum, these results demonstrate efficient editing of T cells using final concentrations of Cas9, TA-1 sgRNA, and B2M-1 sgRNA of 0.3 mg/mL, 0.08 mg/mL, and 0.2 mg/mL, respectively. To achieve these concentrations, TA-1 sgRNA/Cas9 and B2M-1 sgRNA/Cas9 mixtures were prepared at molar ratios of 2.7:1 and 6.7:1, respectively.

To determine the percent of free Cas9 detected in RNP complexes, TA-1 sgRNA (TA-1; SEQ ID NO: 2) and Cas9 (Cas9; SEQ ID NO: 1), and B2M-1 sgRNA (B2M-1; SEQ ID NO: 6) and Cas9 (Cas9; SEQ ID NO: 1) mixtures were prepared at molar ratios of 2.7:1 and 6.7:1, respectively. Mixtures were incubated for 10 minutes and then analyzed by CEX HPLC to quantify the amount of free Cas9. As shown in Table 13, the low percent of free Cas9 detected in the mixtures suggests that RNP complexes were efficiently formed.

TABLE 13

| Percent of Free Cas9 in RNP Complexes. | |
|---|---|
| | Free Cas9 (%) |
| B2M-1 | 16 ± 2 (n = 9) |
| TA-1 | 3 ± 2 (n = 9) |

These results demonstrate that incubation of Cas9 and sgRNA results in the majority of Cas9 comprised within the RNP complex.

Development of Manufacturing Process (i) Research Process

A total of 22 research lots were produced by Research Scale Processes using T cells from 17 healthy volunteers. Conditions identified for the Research Scale Process were verified and adjusted for scale-up to perform the Development Scale Process. Finally, GMP-sourced critical starting materials were evaluated for the preparation of clinical materials in the Clinical Scale Process. Effectively, the Development Scale Process and Clinical Scale Process are operationally identical.

The research scale process followed the same steps as the process illustrated in FIG. 7A. Briefly, T cells from either frozen vials of PBMC (Lots 1-14, 16, 21, 22) or frozen T cells enriched from leukapheresis products (Lots 12-15, 17-20) were activated with colloidal nanomatrix particles conjugated to CD3/CD28 agonists for 2-3 days in "T-cell media" consisting of X-VIVO™ 15 without gentamicin or phenol red, 5% human AB serum, rhIL-2 and rhIL-7. On the $2^{nd}$ or $3^{rd}$ day, the colloidal polymeric nanomatrix conjugated to recombinant humanized CD3 and CD28 agonists was either diluted with fresh media or removed by washing the cells and centrifugation. On the next day, T cells were electroporated with Cas9 and sgRNAs using electroporation-based transfection systems, including a transfection system based on flow electroporation.

Approximately 20-60 minutes after electroporation, cells were left untreated or infected with AAV6 rAAV-138 at a MOI of either 20,000 or 50,000 genocopies per cell. After approximately 1 hour of infection, cells were washed and plated in T-cell media.

Approximately 1 week after genome editing, cells were assessed for TCRαβ/β2M knockout and CAR expression by flow cytometry. The percentage of cells that were TCRαβ⁻, B2M⁻, CD4⁺, CD8⁺ and CAR⁺ was subsequently calculated.

The percentage of cells that lost surface expression of the TCRαβ and B2M after gene editing, and that expressed cell-surface detectable CAR was evaluated by flow cytometry for each process (Table 14). Across the research lots (n=22), 43±16% (18-72%) of the cells achieved the desired surface expression of the anti-CD19 CAR, while also exhibiting surface loss of TCRαβ (98±0.66%, 97-99%) and B2M (79±9.6%, 54-86%) (Table 14). Similar results were obtained for the Development Scale Process and Clinical Scale Process (Table 14). On average the percentage of cells that were fully edited (TCRαβ⁻ B2M⁻CAR⁺) in the research lots was 31±13% (15-59%).

CD3ζ surface expression is dependent on the formation of a complex with the TCR. As such, it serves as a functional biochemical marker for loss of the TCR in addition to that of TCRαβ. Loss of CD3 surface expression averaged 96±3.5% (85-99%) in the research lots.

CD4/CD8 frequencies for subpopulations were compared to control T cells processed by electroporation with no gene-editing components. For research lots, edited cells (TCRαβ⁻ B2M⁻ CAR⁺, Lots 1-11, 16-22) contained, on average, 50±12% CD4 cells and 45±14% CD8 cells. Electroporated and control T cells (Lots 1-11, 16-21) contained 57±12% CD4 cells and 40±12% CD8 cells. No statistically-significant differences were observed between CD4 or CD8 frequencies when comparing edited to control T cells (unpaired 2-tailed Students t-test).

(ii) Development and Clinical Processes

The Research Process was transferred to a GMP facility, for scale-up and manufacture of the clinical material. Conditions identified for the Research Process were verified and adjusted for scale-up (Development Process). Finally, GMP-sourced critical starting materials were evaluated (Clinical Process) for the preparation of clinical materials. Effectively, the Development and Clinical Processes are operationally identical. Results are presented in Table 14 below.

(iii) Comparability of Gene Editing Across the Manufacturing Processes

The comparison of results from the clinical lots to the research process and initial scale-up and non-clinical lots is presented in Table 14.

TABLE 14

| Results Across Manufacturing Processes. | | | |
|---|---|---|---|
| Parameter | Research Scale Process | Development Scale Process | Clinical Scale Process |
| Cell Viability (%) | N.D. | 86.4 ± 7.1 | 92.5 (average, n = 2) |
| % CAR⁺ T Cells | 43.0 ± 16.0 | 49.0 ± 12.7 | 58.0 ± 12.0 |
| CD3ζ | 96 ± 3.5 | N.D. | N.D. |
| % TCRαβ⁻ | 98.0 ± 0.7 | 99.8 ± 0.2 | 99.8 ± 0.1 |
| % B2M⁻ | 79.0 ± 9.6 | 84.8 ± 1.6 | 83.9 ± 1.1 |

Evaluation of the Process Parameters

The manufacturing operating parameters were evaluated in a series of small-scale and full-scale experiments, which are summarized in Table 15.

TABLE 15

| Process Development Study Results | |
|---|---|
| Parameter | Results and Conclusions |
| T Cell Enrichment | |
| CD4_CD8 T cell Isolation with the automated cell processing system | T cells isolated using a CD4_CD8 enrichment program were of high purity and viability |
| T Cell Activation | |
| T cell activation in a gas permeable rapid expansion system: Cell density, cell concentration, colloidal polymeric nanomatrix conjugated to recombinant humanized CD3 and CD28 agonists dose and dilution | Conditions below were identified to achieve desirable editing and cell expansion for CTX110 manufacture: 1) cell seeding density: 2 × 10⁶/cm² 2) cell seeding concentration: 2 × 10⁶/mL 3) colloidal polymeric nanomatrix conjugated to recombinant humanized CD3 and CD28 agonists: 40 µL/1 × 10⁶ cells 4) 10X colloidal polymeric nanomatrix conjugated to recombinant humanized CD3 and CD28 agonists dilution 48 hours post-activation Electroporation and Transduction |
| Concentration of sgRNAs and Cas9 | TA-1 sgRNA concentrations from 37.5 to 150 µg/mL, B2M-1 sgRNA concentrations from 75 to 150 µg/mL and Cas9 concentration of 300 µg/mL, achieves comparable TCRαβ and B2M editing efficiency. The following conditions were selected for the final manufacturing process: 0.08 mg/ml TA-1, 0.2 mg/nl B2M-1 and 0.3 mg/ml Cas9 |
| Cell concentration | Cell concentrations ranging from 100-400 × 10⁶ cells/mL were incubated with fixed concentrations of RNP (B2M-1, TA-1 gRNAs and Cas9 at 150 µg/mL, 150 µg/mL and 300 µg/mL, respectively). At cell concentrations of 100-300 × 10⁶ cells/mL, B2M-and TCRαβ-subpopulations were > 80% and > 98% respectively. |

TABLE 15-continued

Process Development Study Results

| Parameter | Results and Conclusions |
|---|---|
|  | At a cell concentration of $400 \times 10^6$ cells/mL, the B2M-and TCRαβ-subpopulations were < 80% and < 87%, demonstrating lower efficiency. |
| Impact of EP medium during electroporation | Comparable TCRαβ and B2M editing efficiency and CAR expression were achieved with up to 10% medium during electroporation, indicating no negative impact of residual medium on CTX110 editing. |
| rAAV-138 transduction | The clinical AAV transduction process includes:<br>1) removal of wash step before and after AAV transduction<br>2) Cell density of AAV Transduction: $10 \times 10^6$/mL<br>3) AAV MOI: 20,000 (determined on a lot by lot basis)<br>Cell Expansion |
| Seeding density for the gas permeable rapid expansion system culture vessel | Seeding densities between $3 \times 10^5$ cells/cm$^2$ to $5 \times 10^5$ cells/cm$^2$ after electroporation were examined. Cells seeded between 3-5 $\times 10^5$ cells/cm$^2$ achieved a final cell density about $30 \times 10^6$ cells/cm$^2$ and up to $50 \times 10^6$ cells/cm$^2$ after culture for 7-9 days. |
| Cell Expansion in different sized gas permeable rapid expansion system culture vessels | The scalability of cell expansion with the gas permeable rapid expansion system was assessed by comparing cell expansion when seeded in 60 cm$^2$, 100 cm$^2$, and 500 cm$^2$ gas permeable membrane surface gas permeable cell culture devices. Results indicate that modified T cells can achieve comparable fold-expansion in different vessel sizes with the same cell density at harvest, thus supporting the procedure of using satellite plating in 60 cm$^2$ gas permeable membrane surface gas permeable cell culture device to monitor cell expansion in the 500 cm$^2$ gas permeable membrane surface gas permeable cell culture device for the CTX110 manufacturing process.<br>TCRαβ$^+$ Cell Depletion |
| Evaluation of depletion performance | A customized program for TCRαβ depletion was developed using an automated cell processing system. The performance of the depletion process with this program was evaluated over 4 batches, demonstrating high depletion efficiency (input 2% → output < LOQ TCRαβ$^+$ cells) with an average of 70% cell recovery and > 90% viability. |

Example 8: Methods for Manufacturing Genetically Engineered T Cells Expressing an Anti-BCMA CAR and Having Genetically Disrupted TRAC and β2M Genes (CTX120)

CTX120 is a BCMA-directed T cell immunotherapy comprised of human allogeneic T cells that are genetically modified ex vivo using CRISPR/Cas9 (Clustered Regularly Interspaced Short Palindromic Repeats/CRISPR associated protein 9) gene editing components (sgRNA (single guide RNA) and Cas9 nuclease).

The modifications include targeted disruption of the TRAC and B2M loci, and the insertion of an anti-BCMA chimeric antigen receptor (CAR) transgene into the TRAC locus using a recombinant adeno-associated virus vector (rAAV166, a serotype 6 rAAV encoding anti-BCMA directed chimeric T cell antigen receptor).

The CAR is composed of a humanized single-chain variable fragment (scFv) specific for BCMA, followed by a CD8 hinge and transmembrane region that is fused to the intracellular signaling domains for CD137 (4-1BB) and CD3ζ. Expression of the CTX120 CAR is driven by the elongation factor 1 alpha (EF-1a) promoter.

Figure 8A:
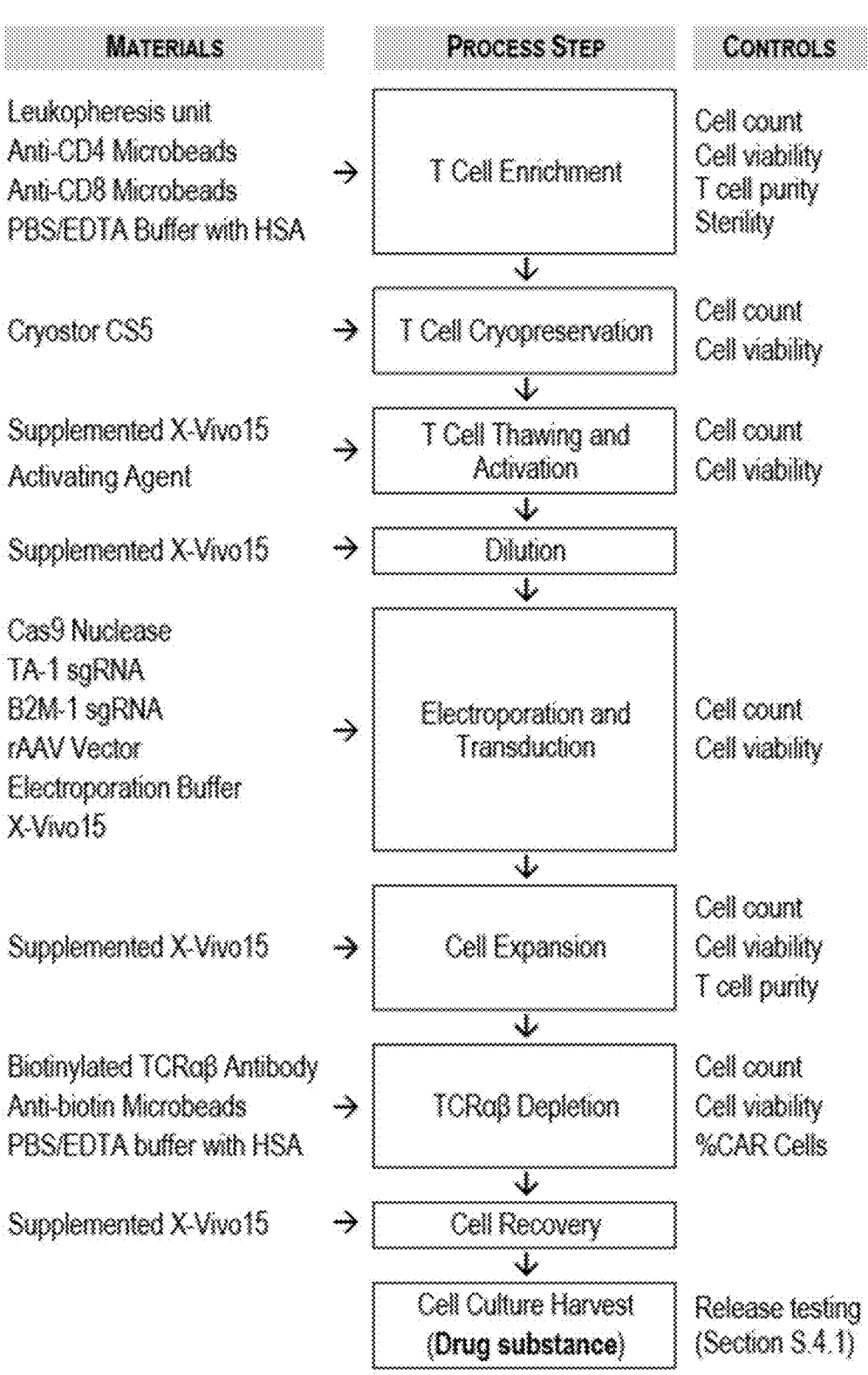

The manufacturing process of CTX120 is illustrated in FIG. 8A. Structural information of the starting materials, including bacterially-derived Cas9 nuclease; two single guide RNAs (sgRNA), TA-1 which targets the TRAC locus and B2M-1 which targets the β2M locus, is provided in Example 7 above Amino acid sequences and nucleotide sequences of the anti-BCMA CAR in a rAAV vector are provided below (Tables 16 and 17):

TABLE 16

Nucleotide Sequences of Anti-BCMA CAR Construct Components.

| Name Description | Nucleotide Sequence | SEQ ID NO: |
|---|---|---|
| CTX-166b rAAV | CCTGCAGGCAGCTGCGCGCTCGCTCGCTCACTGAGGCCGCCCGGGCG TCGGGCGACCTTTGGTCGCCCGGCCTCAGTGAGCGAGCGAGCGCGCA GAGAGGGAGTGGCCAACTCCATCACTAGGGGTTCCTGCGGCCGCACG CGTGAGATGTAAGGAGCTGCTGTGACTTGCTCAAGGCCTTATATCGA GTAAACGGTAGTGCTGGGGCTTAGACGCAGGTGTTCTGATTTATAGT TCAAAACCTCTATCAATGAGAGAGCAATCTCCTGGTAATGTGATAGA | 55 |

TABLE 16-continued

Nucleotide Sequences of Anti-BCMA CAR Construct Components.

| Name Description | Nucleotide Sequence | SEQ ID NO: |
|---|---|---|
| | TTTCCCAACTTAATGCCAACATACCATAAACCTCCCATTCTGCTAAT GCCCAGCCTAAGTTGGGGAGACCACTCCAGATTCCAAGATGTACAGT TTGCTTTGCTGGGCCTTTTTCCCATGCCTGCCTTTACTCTGCCAGAG TTATATTGCTGGGGTTTTGAAGAAGATCCTATTAAATAAAAGAATAA GCAGTATTATTAAGTAGCCCTGCATTTCAGGTTTCCTTGAGTGGCAG GCCAGGCCTGGCCGTGAACGTTCACTGAAATCATGGCCTCTTGGCCA AGATTGATAGCTTGTGCCTGTCCCTGAGTCCCAGTCCATCACGAGCA GCTGGTTTCTAAGATGCTATTTCCCGTATAAAGCATGAGACCGTGAC TTGCCAGCCCCACAGAGCCCCGCCCTTGTCCATCACTGGCATCTGGA CTCCAGCCTGGGTTGGGGCAAAGAGGGAAATGAGATCATGTCCTAAC CCTGATCCTCTTGTCCCACAGATATCCAGAACCCTGACCCTGCCGTG TACCAGCTGAGAGACTCTAAATCCAGTGACAAGTCTGTCTGCCTATT CACCGATTTTGATTCTCAAACAAATGTGTCACAAGTAAGGATTCTG ATGTGTATATCACAGACAAAACTGTGCTAGACATGAGGTCTATGGAC TTCAGGCTCCGGTGCCCGTCAGTGGGCAGAGCGCACATCGCCCACAG TCCCCGAGAAGTTGGGGGGAGGGGTCGGCAATTGAACCGGTGCCTAG AGAAGGTGGCGCGGGGTAAACTGGGAAAGTGATGTCGTGTACTGGCT CCGCCTTTTTCCCGAGGGTGGGGGAGAACCGTATATAAGTGCAGTAG TCGCCGTGAACGTTCTTTTTCGCAACGGGTTTGCCGCCAGAACACAG GTAAGTGCCGTGTGTGGTTCCCGCGGGCCTGGCCTCTTTACGGGTTA TGGCCCTTGCGTGCCTTGAATTACTTCCACTGGCTGCAGTACGTGAT TCTTGATCCCGAGCTTCGGGTTGGAAGTGGGTGGGAGAGTTCGAGGC CTTGCGCTTAAGGAGCCCCTTCGCCTCGTGCTTGAGTTGAGGCCTGG CCTGGGCGCTGGGGCCGCCGCGTGCGAATCTGGTGGCACCTTCGCGC CTGTCTCGCTGCTTTCGATAAGTCTCTAGCCATTTAAAATTTTTGAT GACCTGCTGCGACGCTTTTTTTCTGGCAAGATAGTCTTGTAAATGCG GGCCAAGATCTGCACACTGGTATTTCGGTTTTTGGGGCCGCGGGCGG CGACGGGGCCCGTGCGTCCCAGCGCACATGTTCGGCGAGGCGGGGCC TGCGAGCGCGGCCACCGAGAATCGGACGGGGGTAGTCTCAAGCTGGC CGGCCTGCTCTGGTGCCTGGCCTCGCGCCGCCGTGTATCGCCCCGCC CTGGGCGGCAAGGCTGGCCCGGTCGGCACCAGTTGCGTGAGCGGAAA GATGGCCGCTTCCCGGCCCTGCTGCAGGGAGCTCAAAATGGAGGACG CGGCGCTCGGGAGAGCGGGCGGGTGAGTCACCCACACAAAGGAAAAG GGCCTTTCCGTCCTCAGCCGTCGCTTCATGTGACTCCACGGAGTACC GGGCGCCGTCCAGGCACCTCGATTAGTTCTCGAGCTTTTGGAGTACG TCGTCTTTAGGTTGGGGGGAGGGGTTTTATGCGATGGAGTTTCCCCA CACTGAGTGGGTGGAGACTGAAGTTAGGCCAGCTTGGCACTTGATGT AATTCTCCTTGGAATTTGCCCTTTTTGAGTTTGGATCTTGGTTCATT CTCAAGCCTCAGACAGTGGTTCAAAGTTTTTTTTCTTCCATTTCAGGT GTCGTGACCACCATGGCGCTTCCGGTGACAGCACTGCTCCTCCCCTT GGCGCTGCTGCTCCACGCAGCAAGGCCGCAGGTGCAGCTGGTGCAGA GCGGAGCCGAGCTCAAGAAGCCCGGAGCCTCCGTGAAGGTGAGCTGC AAGGCCAGCGGCAACACCCTGACCAACTACGTGATCCACTGGGTGAG ACAAGCCCCCGGCCAAAGGCTGGAGTGGATGGGCTACATCCTGCCCT ACAACGACCTGACCAAGTACAGCCAGAAGTTCCAGGGCAGGGTGACC ATCACCAGGGATAAGAGCGCCTCCACCGCCTATATGGAGCTGAGCAG CCTGAGGAGCGAGGACACCGCTGTGTACTACTGTACAAGGTGGGACT GGGACGGCTTCTTTGACCCCTGGGGCCAGGGCACAACAGTGACCGTC AGCAGCGGCGGCGGAGGCAGCGGCGGCGGCGGCAGCGGCGGAGGCGG AAGCGAAATCGTGATGACCCAGAGCCCCGCCACACTGAGCGTGAGCC CTGGCGAGAGGGCCAGCATCTCCTGCAGGGCTAGCCAAAGCCTGGTG CACAGCAACGGCAACACCCACCTGCACTGGTACCAGCAGAGACCCGG ACAGGCTCCCAGGCTGCTGATCTACAGCGTGAGCAACAGGTTCTCCG AGGTGCCTGCCAGGTTTAGCGGCAGCGGAAGCGGCACCGACTTTACC CTGACCATCAGCAGCGTGGAGTCCGAGGACTTCGCCGTGTATTACTG CAGCCAGACCAGCCACATCCCTTACACCTTCGGCGGCGGCACCAAGC TGGAGATCAAAAGTGCTGCTGCCTTTGTCCCGGTATTTCTCCCAGCC AAACCGACCACGACTCCCGCCCCCGCGCCCTCCGACACCCGCTCCCAC CATCGCCTCTCAACCTCTTAGTCTTCGCCCCGAGGCATGCCGACCCG CCGCCGGGGGTGCTGTTCATACGAGGGGCTTGGACTTCGCTTGTGAT ATTTACATTTGGGCTCCGTTGGCGGGTACGTGCGGCGTCCTTTTGTT GTCACTCGTTATTACTTTGTATTGTAATCACAGGAATCGCAAACGGG GCAGAAAGAAACTCCTGTATATATTCAAACAACCATTTATGAGACCA GTACAAACTACTCAAGAGGAAGATGGCTGTAGCTGCCGATTTCCAGA AGAAGAAGAAGGAGGATGTGAACTGCGAGTGAAGTTTTCCCGAAGCG CAGACGCTCCGGCATATCAGCAAGGACAGAATCAGCTGTATAACGAA CTGAATTTGGGACGCCGCGAGGAGTATGACGTGCTTGATAAACGCCG GGGGAGAGACCCGGAAATGGGGGGTAAACCCCGAAGAAAGAATCCCC AAGAAGGACTCTACAATGAACTCCAGAAGGATAAGATGGCGGAGGCC TACTCAGAAATAGGTATGAAGGGCGAACGACGACGGGGAAAAGGTCA CGATGGCCTCTACCAAGGGTTGAGTACGGCAACCAAAGATACGTACG ATGCACTGCATATGCAGGCCCTGCCTCCCAGATAATAATAAAATCGC TATCCATCGAAGATGGATGTGTGTTGGTTTTTTGTGTGTGGAGCAAC AAATCTGACTTTGCATGTGCAAACGCCTTCAACAACAGCATTATTCC | |

TABLE 16-continued

Nucleotide Sequences of Anti-BCMA CAR Construct Components.

| Name Description | Nucleotide Sequence | SEQ ID NO: |
|---|---|---|
| | AGAAGACACCTTCTTCCCCAGCCCAGGTAAGGGCAGCTTTGGTGCCT TCGCAGGCTGTTTCCTTGCTTCAGGAATGGCCAGGTTCTGCCCAGAG CTCTGGTCAATGATGTCTAAAACTCCTCTGATTGGTGGTCTCGGCCT TATCCATTGCCACCAAAACCCTCTTTTTACTAAGAAACAGTGAGCCT TGTTCTGGCAGTCCAGAGAATGACACGGGAAAAAAGCAGATGAAGAG AAGGTGGCAGGAGAGGGCACGTGGCCCAGCCTCAGTCTCTCCAACTG AGTTCCTGCCTGCCTGCCTTTGCTCAGACTGTTTGCCCCTTACTGCT CTTCTAGGCCTCATTCTAAGCCCCTTCTCCAAGTTGCCTCTCCTTAT TTCTCCCTGTCTGCCAAAAAATCTTTCCCAGCTCACTAAGTCAGTCT CACGCAGTCACTCATTAACCCACCAATCACTGATTGTGCCGGCACAT GAATGCACCAGGTGTTGAAGTGGAGGAATTAAAAAGTCAGATGAGGG GTGTGCCCAGAGGAAGCACCATTCTAGTTGGGGGAGCCCATCTGTCA GCTGGGAAAGTCCAAATAACTTCAGATTGGAATGTGTTTTAACTCA GGGTTGAGAAAACAGCTACCTTCAGGACAAAAGTCAGGGAAGGGCTC TCTGAAGAAATGCTACTTGAAGATACCAGCCCTACCAAGGGCAGGA GAGGACCCTATAGAGGCCTGGGACAGGAGCTCAATGAGAAAGGTAAC CACGTGCGGACCGAGGCTGCAGCGTCGTCCTCCCTAGGAACCCCTAG TGATGGAGTTGGCCACTCCCTCTCTGCGCGCTCGCTCGCTCACTGAG GCCGGGCGACCAAAGGTCGCCCGACGCCCGGGCTTTGCCCGGGCGGC CTCAGTGAGCGAGCGAGCGCGCAGCTGCCTGCAGG | |
| 5' ITR | CCTGCAGGCAGCTGCGCGCTCGCTCGCTCACTGAGGCCGCCCGGGCG TCGGGCGACCTTTGGTCGCCCGGCCTCAGTGAGCGAGCGAGCGCGCA GAGAGGGAGTGGCCAACTCCATCACTAGGGGTTCCT | 38 |
| 3' ITR | AGGAACCCCTAGTGATGGAGTTGGCCACTCCCTCTCTGCGCGCTCGC TCGCTCACTGAGGCCGGGCGACCAAAGGTCGCCCGACGCCCGGGCTT TGCCCGGGCGGCCTCAGTGAGCGAGCGAGCGCGCAGCTGCCTGCAGG | 39 |
| LHA to RHA | GAGATGTAAGGAGCTGCTGTGACTTGCTCAAGGCCTTATATCGAGTA AACGGTAGTGCTGGGGCTTAGACGCAGGTGTTCTGATTTATAGTTCA AAACCTCTATCAATGAGAGAGCAATCTCCTGGTAATGTGATAGATTT CCCAACTTAATGCCAACATACCATAAACCTCCCATTCTGCTAATGCC CAGCCTAAGTTGGGGAGACCACTCCAGATTCCAAGATGTACAGTTTG CTTTGCTGGGCCTTTTTCCCATGCCTGCCTTTACTCTGCCAGAGTTA TATTGCTGGGGTTTTGAAGAAGATCCTATTAAATAAAAGAATAAGCA GTATTATTAAGTAGCCCTGCATTTCAGGTTTCCTTGAGTGGCAGGCC AGGCCTGGCCGTGAACGTTCACTGAAATCATGGCCTCTTGGCCAAGA TTGATAGCTTGTGCCTGTCCCTGAGTCCCAGTCCATCACGAGCAGCT GGTTTCTAAGATGCTATTTCCCGTATAAAGCATGAGACCGTGACTTG CCAGCCCCACAGAGCCCCGCCCTTGTCCATCACTGGCATCTGGACTC CAGCCTGGGTTGGGGCAAAGAGGGAAATGAGATCATGTCCTAACCCT GATCCTCTTGTCCCACAGATATCCAGAACCCTGACCCTGCCGTGTAC CAGCTGAGAGACTCTAAATCCAGTGACAAGTCTGTCTGCCTATTCAC CGATTTTGATTCTCAAACAAATGTGTCACAAAGTAAGGATTCTGATG TGTATATCACAGACAAAACTGTGCTAGACATGAGGTCTATGGACTTC AGGCTCCGGTGCCCGTCAGTGGGCAGAGCGCACATCGCCCACAGTCC CCGAGAAGTTGGGGGAGGGGTCGGCAATTGAACCGGTGCCTAGAGA AGGTGGCGCGGGGTAAACTGGGAAAGTGATGTCGTGTACTGGCTCCG CCTTTTTCCCGAGGGTGGGGGAGAACCGTATATAAGTGCAGTAGTCG CCGTGAACGTTCTTTTTCGCAACGGGTTTGCCGCCAGAACACAGGTA AGTGCCGTGTGTGGTTCCCGCGGGCCTGGCCTCTTTACGGGTTATGG CCCTTGCGTGCCTTGAATTACTTCCACTGGCTGCAGTACGTGATTCT TGATCCCGAGCTTCGGGTTGGAAGTGGGTGGGAGAGTTCGAGGCCTT GCGCTTAAGGAGCCCCTTCGCCTCGTGCTTGAGTTGAGGCCTGGCCT GGGCGCTGGGGCCGCCGCGTGCGAATCTGGTGGCACCTTCGCGCCTG TCTCGCTGCTTTCGATAAGTCTCTAGCCATTTAAAATTTTTGATGAC CTGCTGCGACGCTTTTTTTCTGGCAAGATAGTCTTGTAAATGCGGGC CAAGATCTGCACACTGGTATTTCGGTTTTTGGGGCCGCGGGCGGCGA CGGGGCCCGTGCGTCCCAGCGCACATGTTCGGCGAGGCGGGGCCTGC GAGCGCGGCCACCGAGAATCGGACGGGGGTAGTCTCAAGCTGGCCGG CCTGCTCTGGTGCCTGGCCTCGCGCCGCCGTGTATCGCCCCGCCCTG GGCGGCAAGGCTGGCCCGGTCGGCACCAGTTGCGTGAGCGGAAAGAT GGCCGCTTCCCGGCCCTGCTGCAGGGAGCTCAAAATGGAGGACGCGG CGCTCGGGAGAGCGGGCGGGTGAGTCACCCACACAAAGGAAAAGGGC CTTTCCGTCCTCAGCCGTCGCTTCATGTGACTCCACGGAGTACCGGG CGCCGTCCAGGCACCTCGATTAGTTCTCGAGCTTTTGGAGTACGTCG TCTTTAGGTTGGGGGGAGGGGTTTTATGCGATGGAGTTTCCCCACAC TGAGTGGGTGGGAGACTGAAGTTAGGCCAGCTTGGCACTTGATGTAAT TCTCCTTGGAATTTGCCCTTTTTTGAGTTTGGATCTTGGTTCATTCTC AAGCCTCAGACAGTGGTTCAAAGTTTTTTTCTTCCATTTCAGGTGTC GTGACCACCATGGCGCTTCCGGTGACAGCACTGCTCCTCCCCTTGGC GCTGTTGCTCCACGCAGCAAGGCCGCAGGTGCAGCTGGTGCAGAGCG GAGCCGAGCTCAAGAAGCCCGGAGCCTCCGTGAAGGTGAGCTGCAAG | 76 |

TABLE 16-continued

Nucleotide Sequences of Anti-BCMA CAR Construct Components.

| Name Description | Nucleotide Sequence | SEQ ID NO: |
|---|---|---|
| | GCCAGCGGCAACACCCTGACCAACTACGTGATCCACTGGGTGAGACA<br>AGCCCCCGGCCAAAGGCTGGAGTGGATGGGCTACATCCTGCCCTACA<br>ACGACCTGACCAAGTACAGCCAGAAGTTCCAGGGCAGGGTGACCATC<br>ACCAGGGATAAGAGCGCCTCCACCGCCTATATGGAGCTGAGCAGCCT<br>GAGGAGCGAGGACACCGCTGTGTACTACTGTACAAGGTGGGACTGGG<br>ACGGCTTCTTTGACCCCTGGGGCCAGGGCACAACAGTGACCGTCAGC<br>AGCGGCGGCGGAGGCAGCGGCGGCGGCGGCAGCGGCGGAGGCGGAAG<br>CGAAATCGTGATGACCCAGAGCCCCGCCACACTGAGCGTGAGCCCTG<br>GCGAGAGGGCCAGCATCTCCTGCAGGGCTAGCCAAAGCCTGGTGCAC<br>AGCAACGGCAACACCCACCTGCACTGGTACCAGCAGAGACCCGGACA<br>GGCTCCCAGGCTGCTGATCTACAGCGTGAGCAACAGGTTCTCCGAGG<br>TGCCTGCCAGGTTTAGCGGCAGCGGAAGCGGCACCGACTTTACCCTG<br>ACCATCAGCAGCGTGGAGTCCGAGGACTTCGCCGTGTATTACTGCAG<br>CCAGACCAGCCACATCCCTTACACCTTCGGCGGCGGCACCAAGCTGG<br>AGATCAAAAGTGCTGCTGCCTTTGTCCCGGTATTTCTCCCAGCCAAA<br>CCGACCACGACTCCCGCCCCGCGCCCCTCCGACACCCGCTCCCACCAT<br>CGCCTCTCAACCTCTTAGTCTTCGCCCCGAGGCATGCCGACCCGCCG<br>CCGGGGGTGCTGTTCATACGAGGGGCTTGGACTTCGCTTGTGATATT<br>TACATTTGGGCTCCGTTGGCGGGTACGTGCGGCGTCCTTTTGTTGTC<br>ACTCGTTATTACTTTGTATTGTAATCACAGGAATCGCAAACGGGGCA<br>GAAAGAAACTCCTGTATATATTCAAACAACCATTTATGAGACCAGTA<br>CAAACTACTCAAGAGGAAGATGGCTGTAGCTGCCGATTTCCAGAAGA<br>AGAAGAAGGAGGATGTGAACTGCGAGTGAAGTTTTCCCGAAGCGCAG<br>ACGCTCCGGCATATCAGCAAGGACAGAATCAGCTGTATAACGAACTG<br>AATTTGGGACGCCGCGAGGAGTATGACGTGCTTGATAAACGCCGGGG<br>GAGAGACCCGGAAATGGGGGGTAAACCCCGAAGAAAGAATCCCCAAG<br>AAGGACTCTACAATGAACTCCAGAAGGATAAGATGGCGGAGGCCTAC<br>TCAGAAATAGGTATGAAGGGCGAACGACGACGGGGAAAAGGTCACGA<br>TGGCCTCTACCAAGGGTTGAGTACGGCAACCAAAGATACGTACGATG<br>CACTGCATATGCAGGCCCTGCCTCCCAGATAATAATAAAATCGCTAT<br>CCATCGAAGATGGATGTGTGTTGGTTTTTTGTGTGTGGAGCAACAAA<br>TCTGACTTTGCATGTGCAAACGCCTTCAACAACAGCATTATTCCAGA<br>AGACACCTTCTTCCCCAGCCCAGGTAAGGGCAGCTTTGGTGCCTTCG<br>CAGGCTGTTTCCTTGCTTCAGGAATGGCCAGGTTCTGCCCAGAGCTC<br>TGGTCAATGATGTCTAAAACTCCTCTGATTGGTGGTCTCGGCCTTAT<br>CCATTGCCACCAAAACCCTCTTTTTACTAAGAAACAGTGAGCCTTGT<br>TCTGGCAGTCCAGAGAATGACACGGGAAAAAAGCAGATGAAGAGAAG<br>GTGGCAGGAGAGGGCACGTGGCCCAGCCTCAGTCTCTCCAACTGAGT<br>TCCTGCCTGCCTGCCTTTGCTCAGACTGTTTGCCCCTTACTGCTCTT<br>CTAGGCCTCATTCTAAGCCCCTTCTCCAAGTTGCCTCTCCTTATTTC<br>TCCCTGTCTGCCAAAAAATCTTTCCCAGCTCACTAAGTCAGTCTCAC<br>GCAGTCACTCATTAACCCACCAATCACTGATTGTGCCGGCACATGAA<br>TGCACCAGGTGTTGAAGTGGAGGAATTAAAAAGTCAGATGAGGGGTG<br>TGCCCAGAGGAAGCACCATTCTAGTTGGGGGAGCCCATCTGTCAGCT<br>GGGAAAAGTCCAAATAACTTCAGATTGGAATGTGTTTTAACTCAGGG<br>TTGAGAAAACAGCTACCTTCAGGACAAAAGTCAGGGAAGGGCTCTCT<br>GAAGAAATGCTACTTGAAGATACCAGCCCTACCAAGGGCAGGGAGAG<br>GACCCTATAGAGGCCTGGGACAGGAGCTCAATGAGAAAGG | |
| TRAC-<br>LHA<br>(800 bp) | GAGATGTAAGGAGCTGCTGTGACTTGCTCAAGGCCTTATATCGAGTA<br>AACGGTAGTGCTGGGGCTTAGACGCAGGTGTTCTGATTTATAGTTCA<br>AAACCTCTATCAATGAGAGAGCAATCTCCTGGTAATGTGATAGATTT<br>CCCAACTTAATGCCAACATACCATAAACCTCCCATTCTGCTAATGCC<br>CAGCCTAAGTTGGGGAGACCACTCCAGATTCCAAGATGTACAGTTTG<br>CTTTGCTGGGCCTTTTTCCCATGCCTGCCTTTACTCTGCCAGAGTTA<br>TATTGCTGGGGTTTTGAAGAAGATCCTATTAAATAAAAGAATAAGCA<br>GTATTATTAAGTAGCCCTGCATTTCAGGTTTCCTTGAGTGGCAGGCC<br>AGGCCTGGCCGTGAACGTTCACTGAAATCATGGCCTCTTGGCCAAGA<br>TTGATAGCTTGTGCCTGTCCCTGAGTCCCAGTCCATCACGAGCAGCT<br>GGTTTCTAAGATGCTATTTCCCGTATAAAGCATGAGACCGTGACTTG<br>CCAGCCCCACAGAGCCCCGCCCTTGTCCATCACTGGCATCTGGACTC<br>CAGCCTGGGTTGGGGCAAAGAGGGAAATGAGATCATGTCCTAACCCT<br>GATCCTCTTGTCCCACAGATATCCAGAACCCTGACCCTGCCGTGTAC<br>CAGCTGAGAGACTCTAAATCCAGTGACAAGTCTGTCTGCCTATTCAC<br>CGATTTTGATTCTCAAACAAATGTGTCACAAAGTAAGGATTCTGATG<br>TGTATATCACAGACAAAACTGTGCTAGACATGAGGTCTATGGACTTC<br>A | 40 |
| TRAC-<br>RHA<br>(800 bp) | TGGAGCAACAAATCTGACTTTGCATGTGCAAACGCCTTCAACAACAG<br>CATTATTCCAGAAGACACCTTCTTCCCCAGCCCAGGTAAGGGCAGCT<br>TTGGTGCCTTCGCAGGCTGTTTCCTTGCTTCAGGAATGGCCAGGTTC<br>TGCCCAGAGCTCTGGTCAATGATGTCTAAAACTCCTCTGATTGGTGG<br>TCTCGGCCTTATCCATTGCCACCAAAACCCTCTTTTTACTAAGAAAC<br>AGTGAGCCTTGTTCTGGCAGTCCAGAGAATGACACGGGAAAAAAGCA | 41 |

TABLE 16-continued

Nucleotide Sequences of Anti-BCMA CAR Construct Components.

| Name Description | Nucleotide Sequence | SEQ ID NO: |
|---|---|---|
| | GATGAAGAGAAGGTGGCAGGAGAGGGCACGTGGCCCAGCCTCAGTCT CTCCAACTGAGTTCCTGCCTGCCTGCCTTTGCTCAGACTGTTTGCCC CTTACTGCTCTTCTAGGCCTCATTCTAAGCCCCTTCTCCAAGTTGCC TCTCCTTATTTCTCCCTGTCTGCCAAAAAATCTTTCCCAGCTCACTA AGTCAGTCTCACGCAGTCACTCATTAACCCACCAATCACTGATTGTG CCGGCACATGAATGCACCAGGTGTTGAAGTGGAGGAATTAAAAAGTC AGATGAGGGGTGTGCCCAGAGGAAGCACCATTCTAGTTGGGGGAGCC CATCTGTCAGCTGGGAAAAGTCCAAATAACTTCAGATTGGAATGTGT TTTAACTCAGGGTTGAGAAAACAGCTACCTTCAGGACAAAAGTCAGG GAAGGGCTCTCTGAAGAAATGCTACTTGAAGATACCAGCCCTACCAA GGGCAGGGAGAGGACCCTATAGAGGCCTGGGACAGGAGCTCAATGAG AAAGG | |
| Anti-BCMA CAR (CTX-166b) | ATGGCGCTTCCGGTGACAGCACTGCTCCTCCCCTTGGCGCTGTTGCT CCACGCAGCAAGGCCGCAGGTGCAGCTGGTGCAGAGCGGAGCCGAGC TCAAGAAGCCCGGAGCCTCCGTGAAGGTGAGCTGCAAGGCCAGCGGC AACACCCTGACCAACTACGTGATCCACTGGGTGAGACAAGCCCCCGG CCAAAGGCTGGAGTGGATGGGCTACATCCTGCCCTACAACGACCTGA CCAAGTACAGCCAGAGTTCCAGGGCAGGGTGACCATCACCAGGGAT AAGAGCGCCTCCACCGCCTATATGGAGCTGAGCAGCCTGAGGAGCGA GGACACCGCTGTGTACTACTGTACAAGGTGGGACTGGGACGGCTTCT TTGACCCCTGGGGCCAGGGCACAACAGTGACCGTCAGCAGCGGCGGC GGAGGCAGCGGCGGCGGCGGCAGCGGCGGAGGCGGAAGCGAAATCGT GATGACCCAGAGCCCCGCCACACTGAGCGTGAGCCCTGGCGAGAGGG CCAGCATCTCCTGCAGGGCTAGCCAAAGCCTGGTGCACAGCAACGGC AACACCCACCTGCACTGGTACCAGCAGAGACCCGGACAGGCTCCCAG GCTGCTGATCTACAGCGTGAGCAACAGGTTCTCCGAGGTGCCTGCCA GGTTTAGCGGCAGCGGAAGCGGCACCGACTTTACCCTGACCATCAGC AGCGTGGAGTCCGAGGACTTCGCCGTGTATTACTGCAGCCAGACCAG CCACATCCCTTACACCTTCGGCGGCGGCACCAAGCTGGAGATCAAAA GTGCTGCTGCCTTTGTCCCGGTATTTCTCCCAGCCAAACCGACCACG ACTCCCGCCCCGCGCCCTCCGACACCCGCTCCCACCATCGCCTCTCA ACCTCTTAGTCTTCGCCCCGAGGCATGCCGACCCGCCGCCGGGGGTG CTGTTCATACGAGGGGCTTGGACTTCGCTTGTGATATTTACATTTGG GCTCCGTTGGCGGGTACGTGCGGCGTCCTTTTGTTGTCACTCGTTAT TACTTTGTATTGTAATCACAGGAATCGCAAACGGGGCAGAAAGAAAC TCCTGTATATATTCAAACAACCATTTATGAGACCAGTACAAACTACT CAAGAGGAAGATGGCTGTAGCTGCCGATTTCCAGAAGAAGAAGAAGG AGGATGTGAACTGCGAGTGAAGTTTTCCCGAAGCGCAGACGCTCCGG CATATCAGCAAGGACAGAATCAGCTGTATAACGAACTGAATTTGGGA CGCCGCGAGGAGTATGACGTGCTTGATAAACGCCGGGGGGAGAGACCC GGAAATGGGGGGTAAACCCCGAAGAAAGAATCCCCAAGAAGGACTCT ACAATGAACTCCAGAAGGATAAGATGGCGGAGGCCTACTCAGAAATA GGTATGAAGGGCAACGACGACGGGGAAAAGGTCACGATGGCCTCTA CCAAGGGTTGAGTACGGCAACCAAAGATACGTACGATGCACTGCATA TGCAGGCCCTGCCTCCCAGA | 56 |
| Anti-BCMA scFv (CTX-166 & CTX-166b) | CAGGTGCAGCTGGTGCAGAGCGGAGCCGAGCTCAAGAAGCCCGGAGC CTCCGTGAAGGTGAGCTGCAAGGCCAGCGGCAACACCCTGACCAACT ACGTGATCCACTGGGTGAGACAAGCCCCCGGCCAAAGGCTGGAGTGG ATGGGCTACATCCTGCCCTACAACGACCTGACCAAGTACAGCCAGAA GTTCCAGGGCAGGGTGACCATCACCAGGGATAAGAGCGCCTCCACCG CCTATATGGAGCTGAGCAGCCTGAGGAGCGAGGACACCGCTGTGTAC TACTGTACAAGGTGGGACTGGGACGGCTTCTTTGACCCCTGGGGCCA GGGCACAACAGTGACCGTCAGCAGCGGCGGCGGAGGCAGCGGCGGCG GCGGCAGCGGCGGAGGCGGAAGCGAAATCGTGATGACCCAGAGCCCC GCCACACTGAGCGTGAGCCCTGGCGAGAGGGCCAGCATCTCCTGCAG GGCTAGCCAAAGCCTGGTGCACAGCAACGGCAACACCCACCTGCACT GGTACCAGCAGAGACCCGGACAGGCTCCCAGGCTGCTGATCTACAGC GTGAGCAACAGGTTCTCCGAGGTGCCTGCCAGGTTTAGCGGCAGCGG AAGCGGCACCGACTTTACCCTGACCATCAGCAGCGTGGAGTCCGAGG ACTTCGCCGTGTATTACTGCAGCCAGACCAGCCACATCCCTTACACC TTCGGCGGCGGCACCAAGCTGGAGATCAAA | 57 |
| 4-1BB nucleotide sequence | AAACGGGGGCAGAAAGAAACTCCTGTATATATTCAAACAACCATTTAT GAGACCAGTACAAACTACTCAAGAGGAAGATGGCTGTAGCTGCCGAT TTCCAGAAGAAGAAGAAGGAGGATGTGAACTG | 58 |
| 4-1BB amino acid sequence | KRGRKKLLYIFKQPFMRPVQTTQEEDGCSCREPEEEEGGCEL | 59 |

TABLE 16-continued

Nucleotide Sequences of Anti-BCMA CAR Construct Components.

| Name Description | Nucleotide Sequence | SEQ ID NO: |
|---|---|---|
| CD3-zeta | CGAGTGAAGTTTTCCCGAAGCGCAGACGCTCCGGCATATCAGCAAGG ACAGAATCAGCTGTATAACGAACTGAATTTGGGACGCCGCGAGGAGT ATGACGTGCTTGATAAACGCCGGGGGAGAGACCCGGAAATGGGGGGT AAACCCCGAAGAAAGAATCCCCAAGAAGGACTCTACAATGAACTCCA GAAGGATAAGATGGCGGAGGCCTACTCAGAAATAGGTATGAAGGGCG AACGACGACGGGGAAAAGGTCACGATGGCCTCTACCAAGGGTTGAGT ACGGCAACCAAAGATACGTACGATGCACTGCATATGCAGGCCCTGCC TCCCAGA | 31 |
| EF-1α promoter | GGCTCCGGTGCCCGTCAGTGGGCAGAGCGCACATCGCCCACAGTCCC CGAGAAGTTGGGGGGGAGGGGTCGGCAATTGAACCGGTGCCTAGAGAA GGTGGCGCGGGGTAAACTGGGAAAGTGATGTCGTGTACTGGCTCCGC CTTTTTCCCGAGGGTGGGGGAGAACCGTATATAAGTGCAGTAGTCGC CGTGAACGTTCTTTTTCGCAACGGGTTTGCCGCCAGAACACAGGTAA GTGCCGTGTGTGGTTCCCGCGGGCCTGGCCTCTTTACGGGTTATGGC CCTTGCGTGCCTTGAATTACTTCCACTGGCTGCAGTACGTGATTCTT GATCCCGAGCTTCGGGTTGGAAGTGGGTGGGAGAGTTCGAGGCCTTG CGCTTAAGGAGCCCCTTCGCCTCGTGCTTGAGTTGAGGCCTGGCCTG GGCGCTGGGGCCGCCGCGTGCGAATCTGGTGGCACCTTCGCGCCTGT CTCGCTGCTTTCGATAAGTCTCTAGCCATTTAAAATTTTTGATGACC TGCTGCGACGCTTTTTTTCTGGCAAGATAGTCTTGTAAATGCGGGCC AAGATCTGCACACTGGTATTTCGGTTTTTGGGGCCGCGGGCGGCGAC GGGGCCCGTGCGTCCCAGCGCACATGTTCGGCGAGGCGGGGCCTGCG AGCGCGGCCACCGAGAATCGGACGGGGGTAGTCTCAAGCTGGCCGGC CTGCTCTGGTGCCTGGCCTCGCGCCGCCGTGTATCGCCCCGCCCTGG GCGGCAAGGCTGGCCCGGTCGGCACCAGTTGCGTGAGCGGAAAGATG GCCGCTTCCCGGCCCTGCTGCAGGGAGCTCAAAATGGAGGACGCGGC GCTCGGGAGAGCGGGCGGGTGAGTCACCCACACAAAGGAAAAGGGCC TTTCCGTCCTCAGCCGTCGCTTCATGTGACTCCACGGAGTACCGGGC GCCGTCCAGGCACCTCGATTAGTTCTCGAGCTTTTGGAGTACGTCGT CTTTAGGTTGGGGGGAGGGGTTTTATGCGATGGAGTTTCCCCACACT GAGTGGGTGGAGACTGAAGTTAGGCCAGCTTGGCACTTGATGTAATT CTCCTTGGAATTTGCCCTTTTTGAGTTTGGATCTTGGTTCATTCTCA AGCCTCAGACAGTGGTTCAAAGTTTTTTTCTTCCATTTCAGGTGTCG TGA | 42 |
| 3' poly A | AATAAAATCGCTATCCATCGAAGATGGATGTGTGTTGGTTTTTTGTG TG | 60 |

TABLE 17

Amino Acid Sequences of Anti-BCMA CAR Construct Components.

| Name Description | Amino Acid Sequence | SEQ ID NO: |
|---|---|---|
| CAR (CTX-166b) | MALPVTALLLPLALLLHAARPQVQLVQSGAELKKPGASVKVSC KASGNTLTNYVIHWVRQAPGQRLEWMGYILPYNDLTKYSQKFQ GRVTITRDKSASTAYMELSSLRSEDTAVYYCTRWDWDGFFDPW GQGTTVTVSSGGGGSGGGGSGGGGSEIVMTQSPATLSVSPGER ASISCRASQSLVHSNGMTHLHWYQQRPGQAPRLLIYSVSNRFS EVPARFSGSGSGTDFTLTISSVESEDFAVYYCSQTSHIPYTFG GGTKLEIKSAAAFVPVFLPAKPTTTPAPRPPTPAPTIASQPLS LRPEACRPAAGGAVHTRGLDFACDIYIWAPLAGTCGVLLLSLV ITLYCNHRNRKRGRKKLLYIFKQPFMRPVQTTQEEDGCSCRFP EEEEGGCELRVKFSRSADAPAYQQGQNQLYNELNLGRREEYDV LDKRRGRDPEMGGKPRRKNPQEGLYNELQKDKMAEAYSEIGMK GERRRGKGHDGLYQGLSTATKDTYDALHMQALPPR | 61 |
| scFv (CTX-166 (BCMA-11, & CTX-166b) | QVQLVQSGAELKKPGASVKVSCKASGNTLTNYVIHWVRQAPGQ RLEWMGYILPYNDLTKYSQKFQGRVTITRDKSASTAYMELSSL RSEDTAVYYCTRWDWDGFFDPWGQGTTVTVSSGGGGSGGGGSG GGGSEIVMTQSPATLSVSPGERASISCRASQSLVHSNGNTHLH WYQQRPGQAPRLLIYSVSNRFSEVPARFSGSGSGTDFTLTISS VESEDFAVYYCSQTSHIPYTFGGGTKLEIK | 62 |
| V_H (CTX-166) | QVQLVQSGAELKKPGASVKVSCKASGNTLTNYVIHWVRQAPGQ RLEWMGYILPYNDLTKYSQKFQGRVTITRDKSASTAYMELSSL RSEDTAVYYCTRWDWDGFFDPWGQGTTVTVSS | 63 |

TABLE 17-continued

Amino Acid Sequences of Anti-BCMA CAR Construct Components.

| Name | Description | Amino Acid Sequence | SEQ ID NO: |
|---|---|---|---|
| $V_L$ | (CTX-166) | EIVMTQSPATLSVSPGERASISCRASQSLVHSNGNTHLHWYQQ RPGQAPRLLIYSVSNRFSEVPARFSGSGSGTDFTLTISSVESE DFAVYYCSQTSHIPYTFGGGTKLEIK | 64 |
| $V_L$ CDR1 | (Kabat or | RASQSLVHSNGNTHLH | 65 |
| $V_L$ CDR2 | Chothia) | SVSNR | 66 |
| $V_L$ CDR3 | | SQTSHIPYT | 67 |
| $V_H$ CDR1 | (Kabat) | NYVIH | 68 |
| $V_H$ CDR2 | | YILPYNDLTKYSQKFQG | 69 |
| $V_H$ CDR3 | | WDWDGFFDP | 70 |
| $V_H$ CDR1 | (Chothia) | GNTLTNY | 71 |
| $V_H$ CDR2 | | LPYNDL | 72 |
| $V_H$ CDR3 | | WDWDGFFDP | 73 |
| linker | | GGGGSGGGGSGGGGS | 74 |
| CD8 signal peptide | | MALPVTALLLPLALLLHAARP | 75 |
| CD8a transmembrane domain | | IYIWAPLAGTCGVLLLSLVITLY | 34 |
| 4-1BB | | KRGRKKLLYIFKQPFMRPVQTTQEEDGCSCRFPEEEEGGCEL | 59 |
| CD3-zeta | | RVKFSRSADAPAYQQGQNQLYNELNLGRREEYDVLDKRRGRDP EMGGKPRRKNPQEGLYNELQKDKMAEAYSEIGMKGERRRGKGH DGLYQGLSTATKDTYDALHMQALPPR | 35 |

Manufacture of the CTX120 Drug Substance involved thawing enriched T cells followed by activation and electroporation/transduction, at which point cells were expanded. After expansion, TCRαβ⁺ cells were depleted. Cells were cultured overnight, harvested and sampled for Drug Substance testing. See FIG. 8A. Reprocessing was not performed in any step of CTX120 manufacturing.

T Cell Enrichment

T cells were enriched from the leukapheresis materials (Leukopaks) via magnetic separation using a mixture of anti-CD8 and anti-CD4 antibody-coated magnetic beads using the automated cell processing system. Prior to enrichment, leukopaks were sampled for cell count and viability (≥80%). Enriched cells were isolated in PBS/EDTA Buffer with HSA, and then sampled for cell count, viability (≥80%), T cell purity (≥70% CD3), and sterility. The cells were then centrifuged at 4±1° C. and resuspended in CryoStor CS5 at a target concentration of $50 \times 10^6$ viable cells/mL.

T Cell Cryopreservation

Cells were sampled for cell count, viability (≥80%) and then aliquoted into ethyl vinyl acetate cryobags at the target cell number of $2,500 \times 10^6$ cells/bag (30-70 mL of cell suspension). One Leukopak was sufficient to produce 1-2 bags of T cells. Each bag was heat-sealed, labeled, stored at 2-8° C. until transferred to a controlled-rate freezer and subsequently transferred to vapor phase liquid nitrogen for storage.

T Cell Thawing and Activation

One frozen bag of enriched T cells was thawed, transferred into a 3 L bag and diluted into Supplemented X-VIVO™ 15 media (X-VIVO™ 15, 5% Human Serum, 100 IU/mL rhIL2, 100 IU/mL rhIL7). Cells were sampled for cell count and viability (≥70%). Cells were centrifuged at 540 g at 20±1° C. for 15 minutes. Cells were then resuspended in the Supplemented X-VIVO™ 15 media and sampled for cell count and viability (≥70%). Soluble colloidal polymeric nanomatrix conjugated to recombinant humanized CD3 and CD28 agonists solution was added at the ratio of 1:12.5 (v/v) to activate the cells.

Cells were seeded to a target density $2 \times 10^6$ viable cells/mL into two static cell culture vessels, each at a total volume of approximately 500 mL of Supplemented X-VIVO™ 15 media/colloidal polymeric nanomatrix conjugated to recombinant humanized CD3 and CD28 agonists. Static culture vessels were incubated at 37±1° C. and 5±1% $CO_2$ for 48±4 hours. Throughout the process, whenever the static culture vessels were handled, they were inspected for tears and leaks, and the presence of clear, yellow medium.

Dilution

Two (2) days later, supplemented X-VIVO™ 15 media was added to each static culture vessel to 5 L. Cells were further incubated at 37±1° C. and 5±1% $CO_2$ overnight.

Electroporation and Transduction

The volume of Supplemented X-VIVO™ 15 media was reduced to a final volume of approximately 500 mL using a pump connected to dip-tube in the static culture vessel, which was gently swirled to allow resuspension of cells to in the media. Cells were sampled for cell count, and viability (≥70%). Cells were transferred to 500 mL centrifuge tubes and centrifuged at 540 g, at 20±1° C. for 15 minutes. Cell pellets were resuspended in Electroporation Buffer and centrifuged again under the same conditions. Cells were resuspended in Electroporation Buffer a second time to a target concentration of $300 \times 10^6$ cells/mL.

Cas9 nuclease was mixed with TA-1 sgRNA (targeting TCR) and with B2M-1 sgRNA (targeting β2M) in separate microcentrifuge tubes. Each solution was incubated for no less than 10 minutes at room temperature to form each ribonucleoprotein complex. The two Cas9/gRNA mixtures were combined, and mixed with the cells, bringing Cas9, TA-1 and B2M-1 to a final concentration of 0.3 mg/mL, 0.08 mg/mL and 0.2 mg/mL, respectively. The mixture was aliquoted and loaded into an electroporation cassette by pipetting. Cassettes were capped and sequentially electroporated using the transfection system based on flow electroporation. After electroporation, cells were pooled from each cassette in a 125 mL Erlenmeyer flask and incubated at 37° C. for no less than 20 minutes. Cells were sampled for viability (≥70%) and count. Cells were diluted to $10^7$ cells/mL with X-VIVO™ 15 media and freshly thawed rAAV-166b was added at a MOI of 20,000 vg/cell. Cells were incubated at 37° C. 5% $CO_2$ for no less than 60 minutes.

Figure 8B:
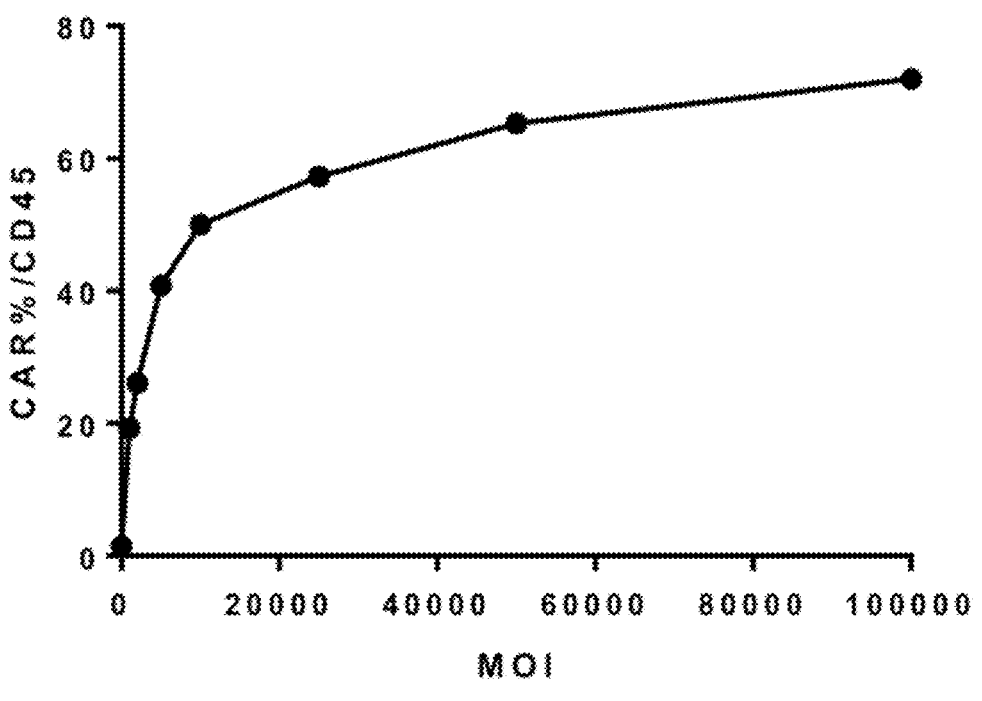

The impact of MOI to achieve desired $CAR^+$ expression, was assessed using a development lot of vector (rAAV-166b). Cells were transduced with increasing MOI and % $CAR^+$ was quantified. As shown in FIG. 8B, AAV dose-dependent CAR expression was observed. Expression of CAR was saturated around MOI of 10,000, supporting the selection of a MOI of 20,000.

Formation of the two ribonucleoprotein complexes (RNP) in situ was performed following the descriptions in Example 7 above. See also results provided in Table 13 above.

Homology directed-repair (HDR) is a high-fidelity cell repair mechanism for DNA double strand breaks. HDR is used to introduce a CAR gene from the AAV template into the desired TRAC locus by using a homologous sequence on each end of the CAR gene.

To assess the anti-BCMA CAR at the TRAC locus, a ddPCR assay was developed. A TRACsite specific PCR primer set was designed to amplify the integrated anti-BCMA CAR sequence and determine the percent of cells with the CAR gene insertion. Three lots of CTX120 were evaluated by ddPCR and the % HDR is shown in Table 18. These results confirm insertion of the anti-BCMA CAR at the TRAC locus.

TABLE 18

| Percent HDR in Development Lots of CTX120 | |
|---|---|
| Lot Number | % HDR |
| CTX120-L-3 | 46.2% |
| CTX120-L-4 | 43.2% |
| P22T090 | 34.6% |

Cell Expansion

Cells were diluted with Supplemented X-VIVO™ 15 media, sampled for cell viability (≥70%) and count, and seeded to a density between $0.2\text{-}0.5\times10^6$ viable cells/cm² into two static culture vessels, and one additional static culture vessel (satellite culture for cell monitoring). The static culture vessels were incubated at 37±1° C. and 5±1% $CO_2$. The cell cultures were incubated for up to 9 days. During this time, the cultures were supplemented every 3 to 4 days with 100 IU of rhIL2 and rhIL7 per mL of culture volume. The satellite static cell culture vessel was tested for cell count, viability, and T cell purity throughout expansion. When the cell density in the satellite culture vessel reached approximately $30\times10^6$/cm², the TCRαβ depletion was performed. If cell density in the satellite culture vessel did not reach $30\times10^6$/cm², TCRαβ depletion on the main cultures was performed on Day 9.

TCRαβ Depletion

The medium of each static cell culture vessel was reduced to a final volume of approximately 500 mL using a pump connected to the dip-tube in the static culture vessel. After the bulk of the media was removed, the static culture vessels were gently swirled to resuspend the cells in the media.

The cells were transferred to 500 mL centrifuge tubes fitted with dip-tubes that connect to the static culture vessels. Cells were sampled for viability (>70%), count, and % $CAR^+$ cells. Cells were then centrifuged at 540×g at 20±1° C. for 15 minutes. Cell pellets were resuspended and pooled in less than 650 mL PBS/EDTA containing 0.5% HSA. Cell suspensions were transferred to a sterile bag which is connected to the automated cell processing system. The automated cell processing system incubated cells with a biotin-conjugated anti-TCRαβ antibody. Cells were washed and incubated with anti-biotin magnetic beads to allow for depletion of the $TCR\alpha\beta^+$ cells using the automated cell processing system. Cells were tested for cell count, viability (>70%), and % $CAR^+$ cells.

Cell Recovery

The depleted cells were resuspended in Supplemented X-VIVO™ 15 media and transferred into 3 L bag(s), seeded into static cell culture vessel(s) and incubated overnight at 37±1° C. and 5±1% $CO_2$.

Cell Harvest (Drug Substance)

To harvest cells, static culture vessels were removed from the incubator and allowed to rest for sedimentation of cells. Growth medium was removed from each static culture vessel to a final volume of approximately 500 mL using a pump. Removed media was sampled for sterility. Static culture vessels were gently swirled to allow the cells to resuspend in the media. The contents of each static culture vessel were transferred in a 3 L transfer bag using a pump and was filtered through a 40 μm blood transfusion filter by gravity into a separate sterile 3 L bag. Cells were sampled for concentration and viability.

Cell Phenotypes of CTX120 Produced by the Manufacturing Process Disclosed Herein CTX120 Drug Product development lots were analyzed for T cell populations. Flow panels are shown in Table 19.

TABLE 19

| Flow Panels for Characterization of T Cell Populations | |
|---|---|
| Exhaustion | Subset |
| CD4 | CD4 |
| CD8 | CD8 |
| CD95 | CD45RO |
| CAR | CD45RA |
| CD57 | CD62L |
| Lag3 | CD27 |
| PD1 | CCR7 |

Exhaustion Markers

Figure 8C:
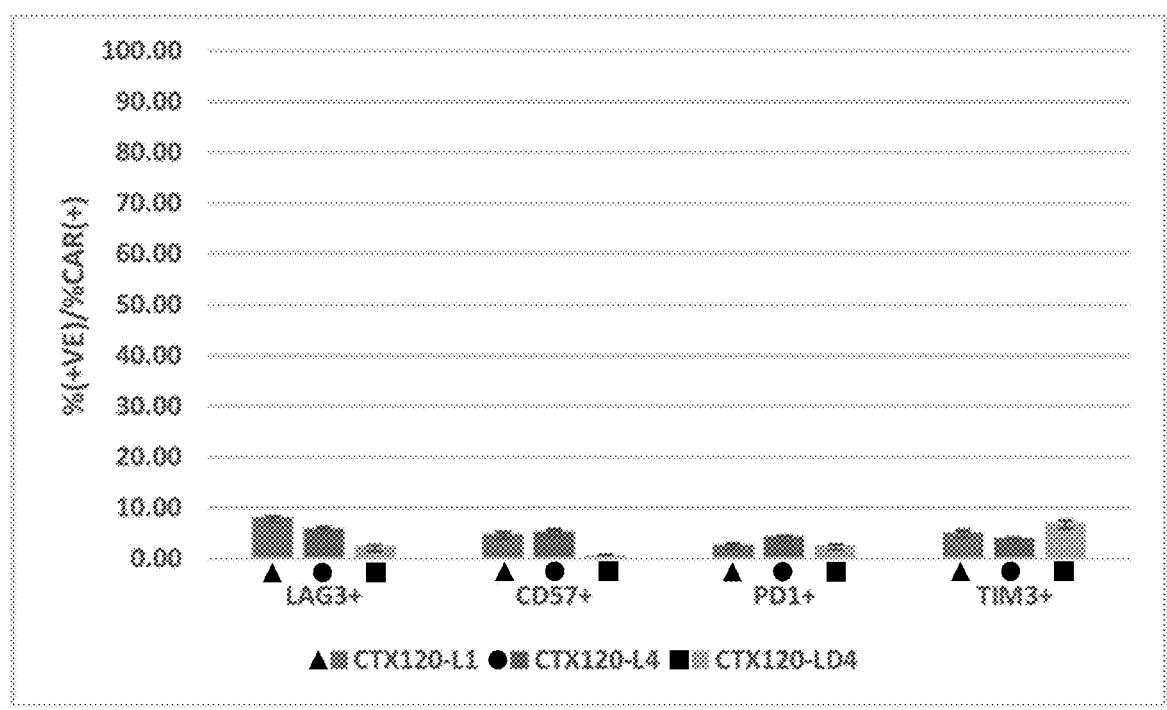

CD57, Lag3 and PD1 are markers associated with T cell exhaustion. The exhaustion status of the CTX120 Drug Product was assessed using the markers defined in Table 19. As shown in FIG. 8C and Table 20, low levels of exhaustion markers were found in $CAR^+$ CTX120 Drug Product cells.

TABLE 20

| Percent CAR⁺ Cells with Various Exhaustion Markers | | | |
|---|---|---|---|
| Marker | CTX120-L-3 | CTX120-L-4 | P22T090 |
| % Lag3⁺ | 8.19 | 5.99 | 2.46 |
| % CD57⁺ | 4.86 | 5.31 | 0.62 |
| % PD1⁺ | 2.83 | 4.36 | 2.66 |
| % Tim3⁺ | 5.15 | 4.03 | 7.01 |

Figure 8D:
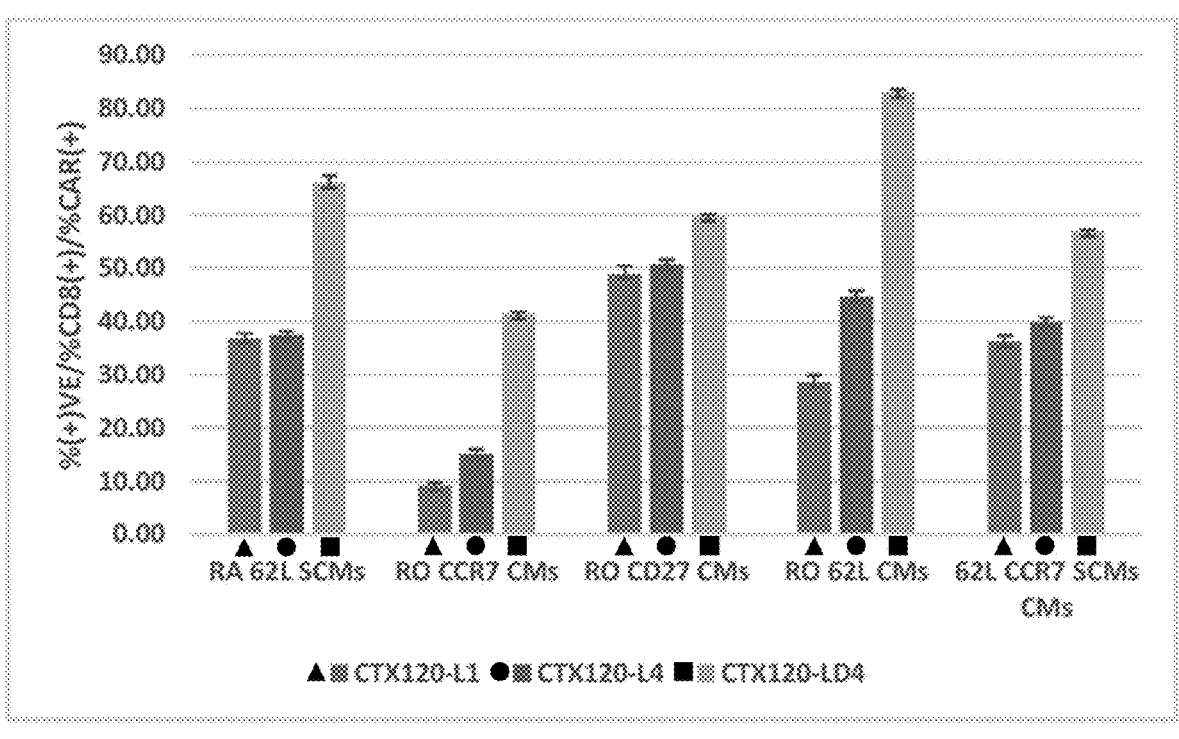
Figure 8E:
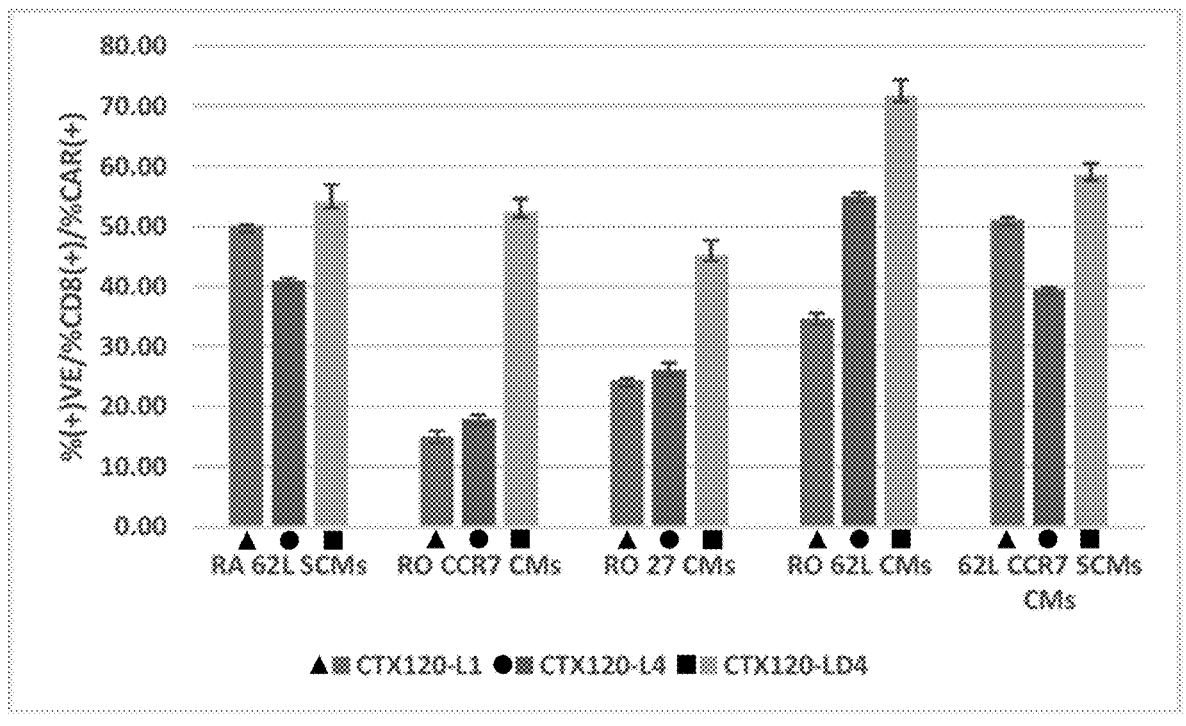

The CTX120 Drug product was assessed for memory cell markers. In the CD45RO gate, CD62 L, CCR7, and CD27 were markers associated with central memory. In the CD45RA gate CD62 L was a marker for stem cell memory. Cells that were CD62 L and CCR7$^+$ were markers for central memory and stem cell memory. The results for CD8$^+$ T cells are shown in FIG. 8D and Table 21. The results for CD4$^+$ T cells are shown in FIG. 8E and Table 22.

TABLE 21

Central Memory and Stem Cell
Memory Markers in CD8$^+$ T Cells

| Marker | T Cell Population | CTX120-L-3 | CTX120-L-4 | P22T090 |
|---|---|---|---|---|
| CD45RA/ CD62L | Stem Cell Memory | 36.97 | 37.63 | 66.13 |
| CD45RO/ CD27 | Central Memory | 48.93 | 50.77 | 59.90 |
| CD45RO/ CD62L | Central Memory | 28.63 | 44.63 | 83.03 |
| CD45RO/ CCR7 | Central Memory | 9.28 | 15.20 | 41.47 |
| CD62L/ CCR7 | Stem Cell Memory/ Central Memory | 36.40 | 39.93 | 57.03 |

TABLE 22

Central Memory and Stem Cell Memory Markers in CD4$^+$ T Cells

| Marker | T Cell Population | CTX120-L-3 | CTX120-L-4 | P22T090 |
|---|---|---|---|---|
| CD45RA/ CD62L | Stem Cell Memory | 50.13 | 41.00 | 54.10 |
| CD45RO/ CD27 | Central Memory | 24.30 | 26.13 | 45.33 |
| CD45RO/ CD62L | Central Memory | 34.63 | 55.03 | 71.87 |
| CD45RO/ CCR7 | Central Memory | 15.03 | 17.90 | 52.53 |
| CD62L/CCR7 | Stem Cell Memory/ Central Memory | 51.17 | 39.60 | 58.73 |

Biological Activities of CTX120

Figure 8F:
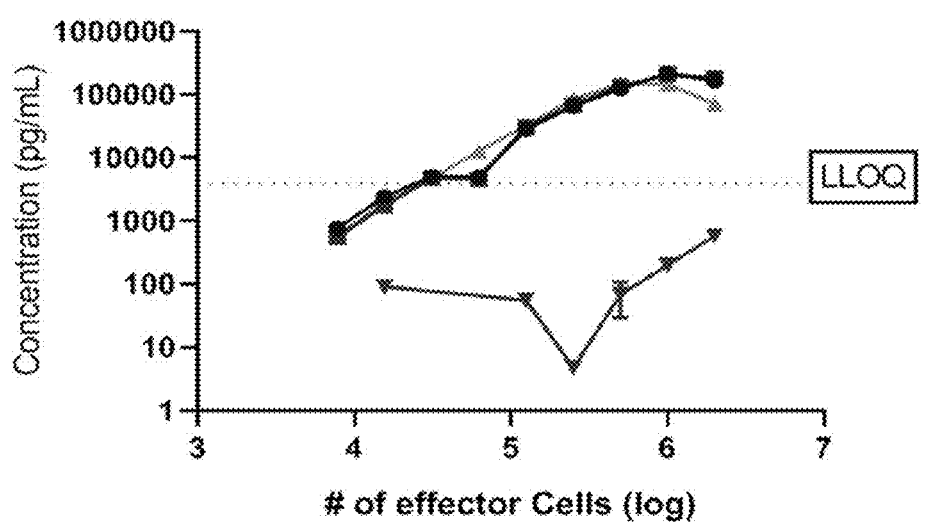

Two assays which measure the biological activity of the CAR T cell Drug Product upon stimulation with BCMA antigen were developed. First, IFNγ secretion upon T cell activation was determined. In brief, CAR T cells were incubated with recombinant human BCMA. Upon CAR T cell activation, the level of secreted IFNγ was measured by Meso-Scale Delivery (MSD). Results are shown in FIG. 8F.

Figure 8G:
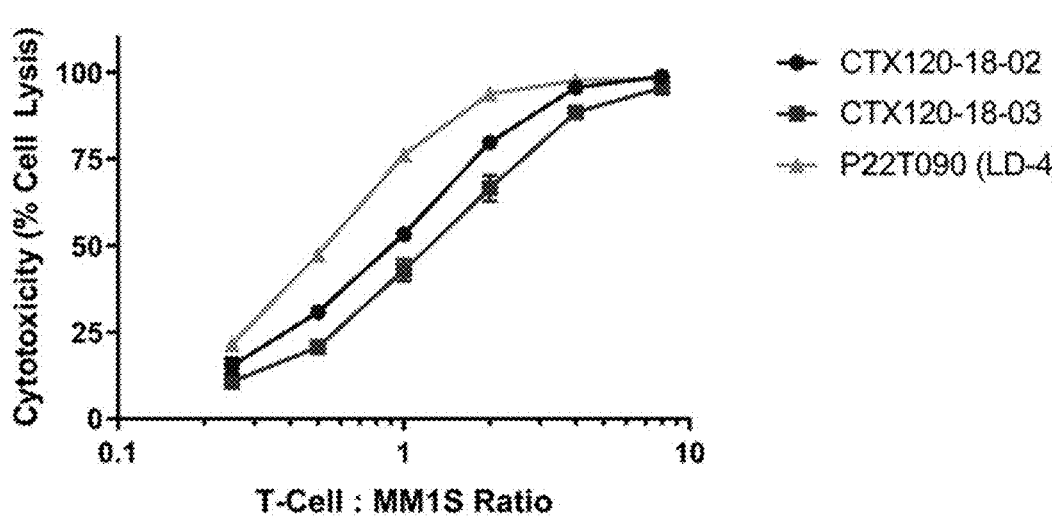

Next, the ability of CTX120 CAR-T cells to kill BCMA positive MM.1S target cells was assessed using a flow cytometry-based cytotoxicity assay. In brief, target cells were labeled with eFluor670 and incubated with CTX120 cells at varying ratios. CTX120 cytotoxicity was analyzed at 4 hours by assessing labeled cells in the live gate compared to control sample. The results are shown in FIG. 8G. All 3 development lots of CTX120 showed dose dependent target cell cytotoxicity.

Taken together, these results demonstrated production of anti-BCMA CAR expressing T cells. The anti-BCMA CAR expressing T cells manufactured, as described herein, displayed low expression levels of TCR and β2M, thereby reducing the probability of host rejection. Further, the anti- BCMA CAR expressing T cells displayed targeted cell killing of BCMA positive cells upon T cell activation.

Example 9: Identification of Optimized Conditions for T Cell Expansion for Scale Up This Example reports identification of optimal plating or replating conditions for superior T cell expansion and increasing yields. In this Example, T cells were either plated at lower density than 500 K/cm$^2$ on the same day post editing or seeded with 500 K/cm$^2$ densities and replated at different days post editing. Cell expansion was monitored over time.

In brief, cryopreserved T cells from healthy donor leukopak were thawed and activated for 48 hours. Cells were then electroporated in the presence of RNP complexes comprising Cas9 (150 µg/mL) and sgRNA targeting TCR (TA-1; SEQ ID NO: 2/Cas9; SEQ ID NO: 1) (80 µg/mL) and Cas9 (150 µg/mL) and sgRNA targeting β2M (B2M-1; SEQ ID NO: 6/Cas9; SEQ ID NO: 1) (200 µg/mL). After electroporation, cells were transduced with the rAAV at MOI of 20,000, and then expanded in a static culture vessel. See Examples 1-4 above for details.

After editing, cells were seeded at 166 K/cm$^2$, 125 K/cm$^2$, or 83 K/cm$^2$ in a static culture vessel for expansion. Another set of cells were seeded at 500 K/cm$^2$ post editing and replated at day 3, 4, 5, 6, or 7 post editing at a 1:4 ratio (1 vessel split into 4 new vessels) for further expansion. Cells that replated at 500 K/cm$^2$ without replating were used as CTX110 reference group. All groups expanded until the cell density reached 3-4×10$^6$/mL at which point the cells were harvested (Table 23). Cell count and viability were assessed every 1-3 days.

TABLE 23

| Groups | | Harvest point | Expected Yield | Harvest date |
|---|---|---|---|---|
| 1 | CTX110 500K reference | 3 × 10$^6$/mL 4 × 10$^6$/mL | 1× | day 7 |
| 2 | CTX110 166K | 4 × 10$^6$/mL | 3× | day 10 (+3 days) |
| 3 | CTX110 125K | 4 × 10$^6$/mL | 4× | day 11 (+3 days) |
| 4 | CTX110 83K | 4 × 10$^6$/mL | 6× | day 14 (+7 days) |
| 5 | CTX110 D3 replate 1:4 split | 4 × 10$^6$/mL | 4× | day 10 (+3 days) |
| 6 | CTX110 D4 replate 1:4 split | 4 × 10$^6$/mL | | day 10 (+3 days) |
| 7 | CTX110 D5 replate 1:4 split | 3 × 10$^6$/mL 4 × 10$^6$/mL | | day 10 (+3 days) |
| 8 | CTX110 D6 replate 1:4 split | 3 × 10$^6$/mL 4 × 10$^6$/mL | | day 18 (+11 days) day 14 (+7 days) |
| 9 | CTX110 D7 replate 1:4 split | 3 × 10$^6$/mL 4 × 10$^6$/mL | | day 17 (+10 days) day 18 (+11 days) |

Figure 9A:
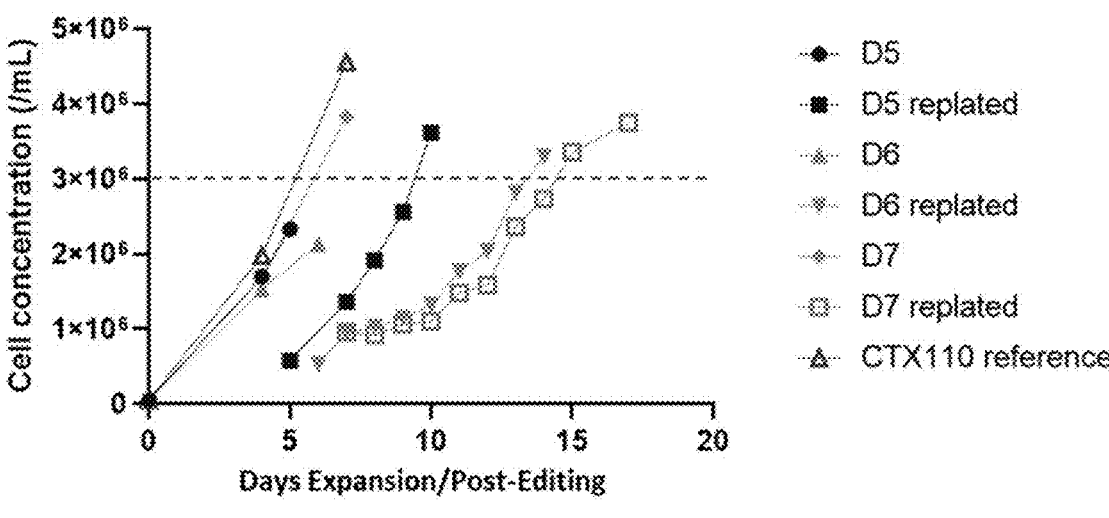
Figure 9B:
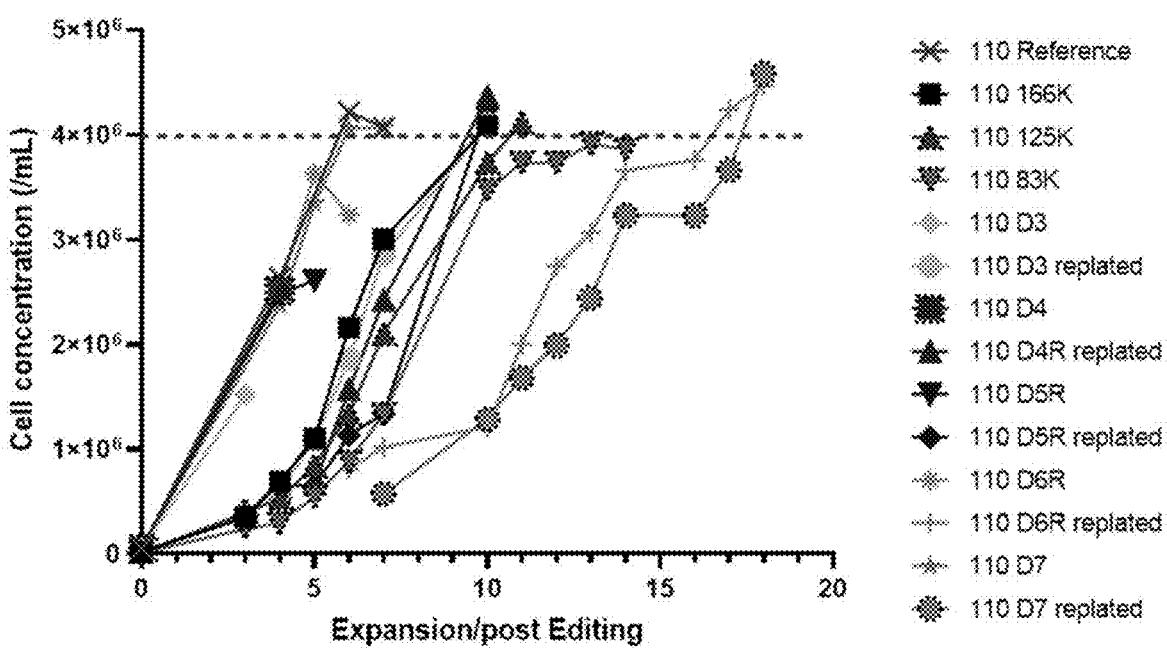

The control CTX110 reference (which was not replated) reached a concentration of 3-4×10$^6$/mL in 7 days (FIGS. 9A-9B). Cells replated at Day 3, 4 and 5 ("D3, D4, D5") reached 3-4×10$^6$/mL cell concentration in 10 days (FIGS. 9A-9B). Cells replated at Day 6 ("D6") and Day 7 ("D7") reached 3-4×10$^6$/mL cell concentration at about 14 to 18 days (FIGS. 9A-9B). The D3, D4, and D5 reached the target of 3.0-4.0×10$^6$/mL cell concentration about 4 to 8 days earlier than the D6 and D7. Cells plated at 166 K/cm$^2$, 125 K/cm$^2$, or 83 K/cm$^2$ took 10, 11 and 14 days to reach harvest point, which were 3, 4, and 7 days longer than the reference group.

Figure 10A:
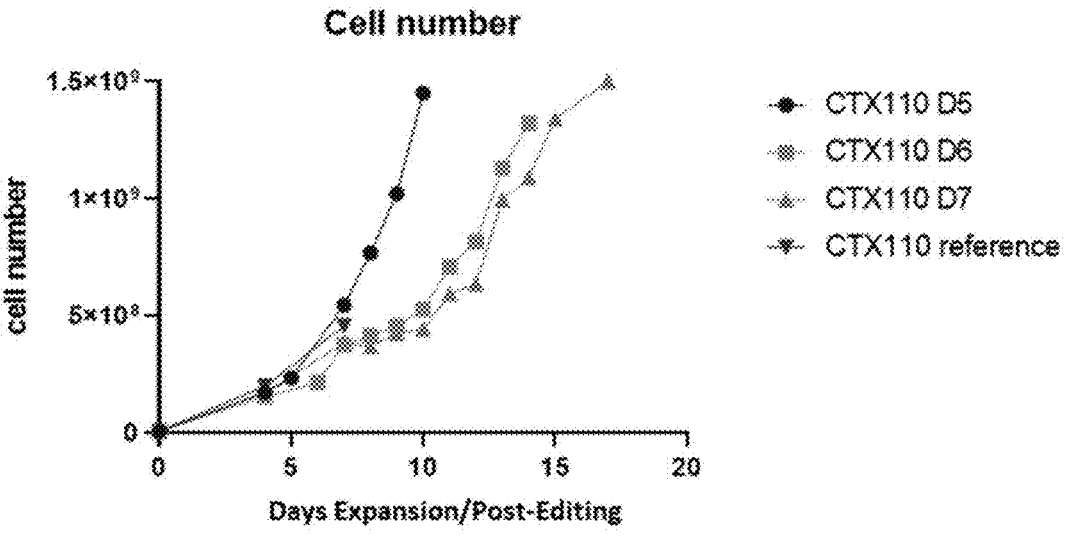
Figure 10B:
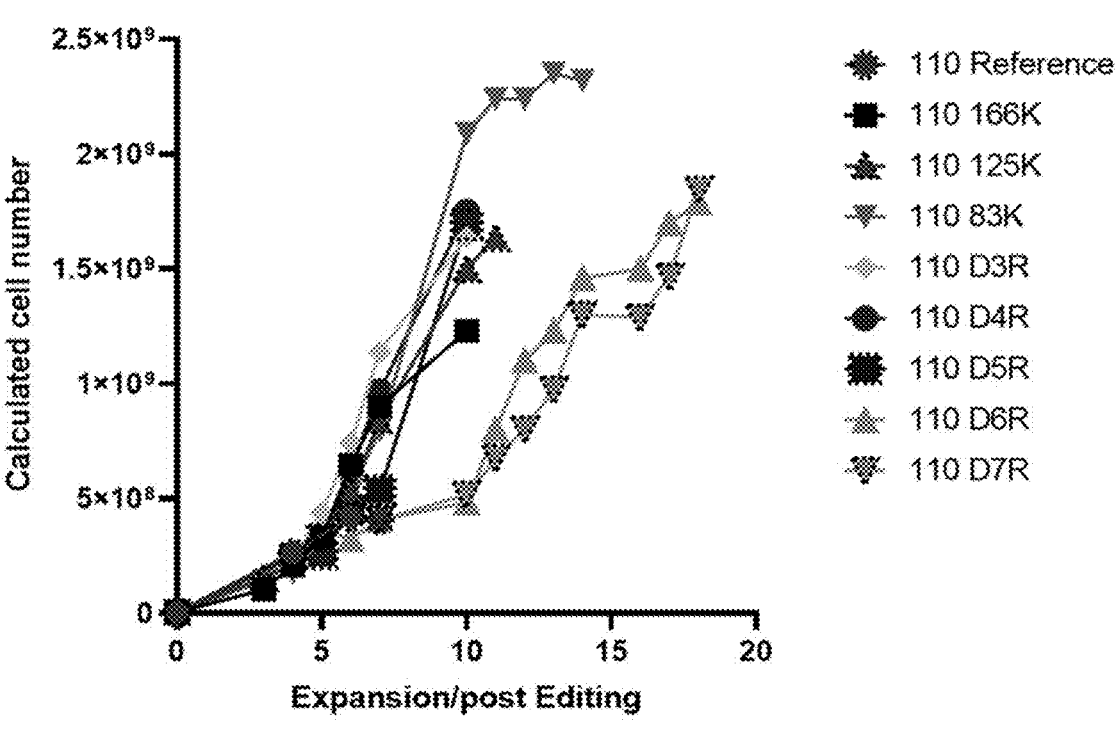

FIGS. 10A and 10B show that a total of 4.-4.5e8 cells were harvested from the CTX110 reference at day 7 while the total cell number harvested from day 3, 4, 5, 6, and 7 replated groups were between 1.3e9 to 2e9, which were 3-5 fold more cells than CTX110 control reference.

Total 1.2e9, 1.64e9 and 2.32e9 cells were harvested from 166 K/cm², 125 K/cm², or 83 K/cm² plated groups, which were 3-6 fold more cells compared with CTX110 control reference.

Figures 11A, 11B:
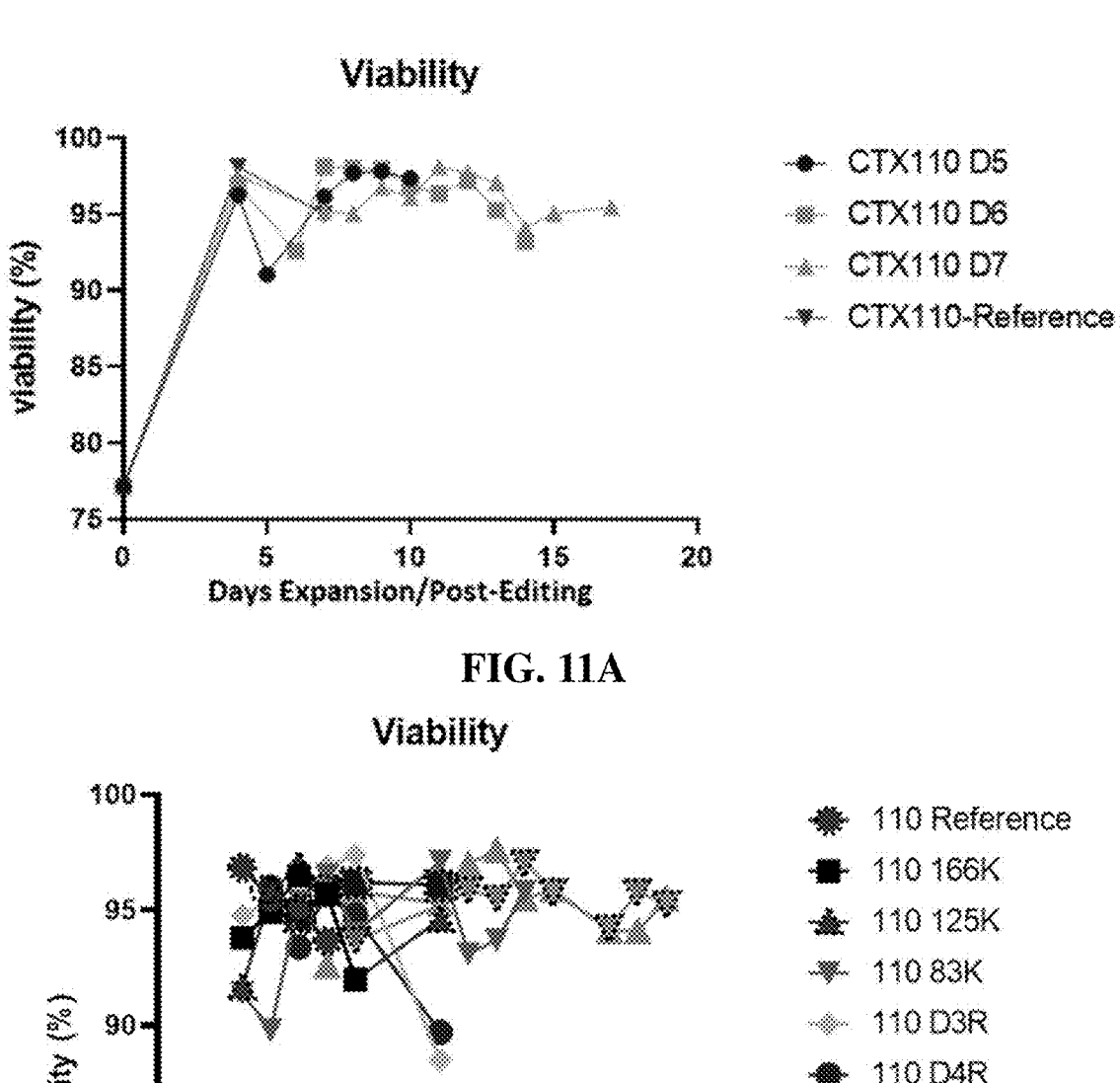

Cell viability from all the replated groups and low-density plating groups were similar to the CTX110 reference. (FIGS. 11A and 11B)

It was determined that the D3, D4, and D5 replating, 166 K/cm² plating and 125 K/cm² plating, provided the expected number of cells in the lowest number of days.

Figure 12A:
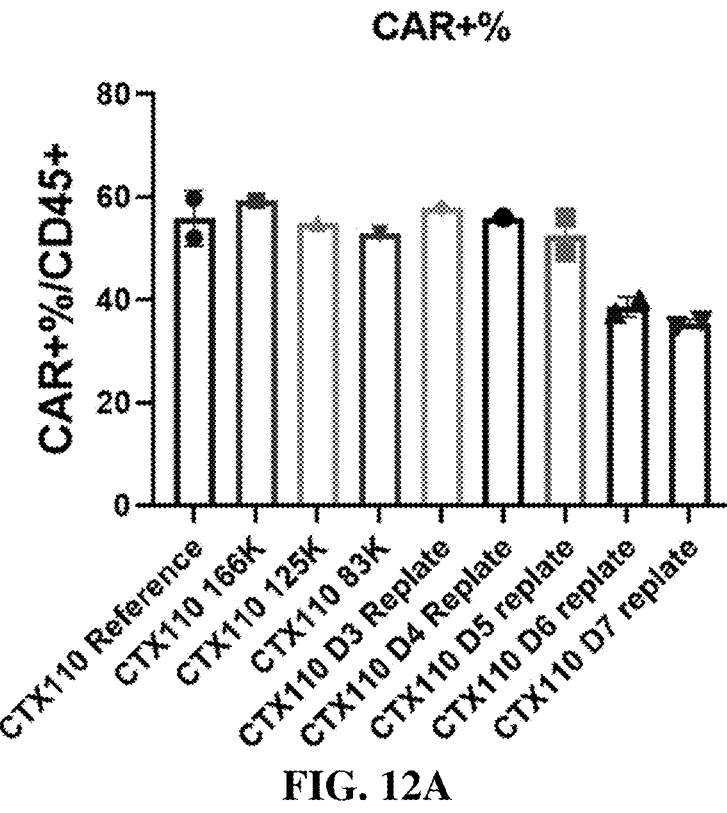
Figure 12B:
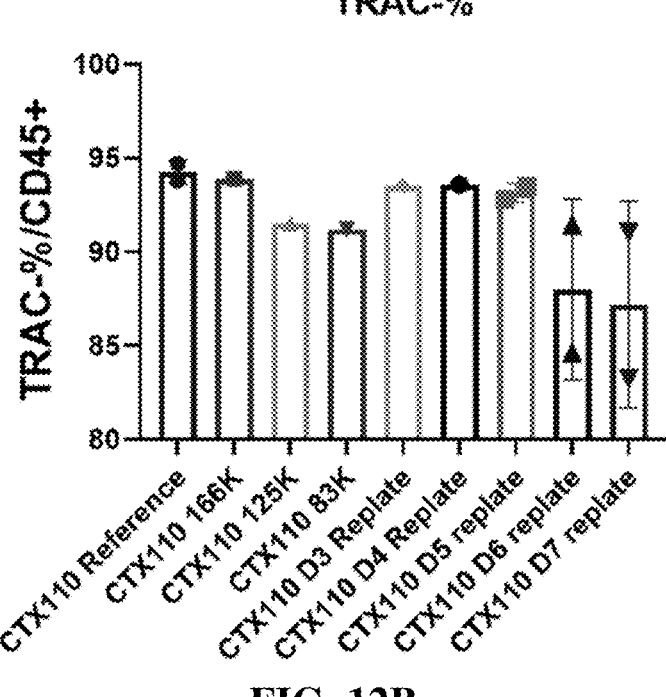
Figure 12C:
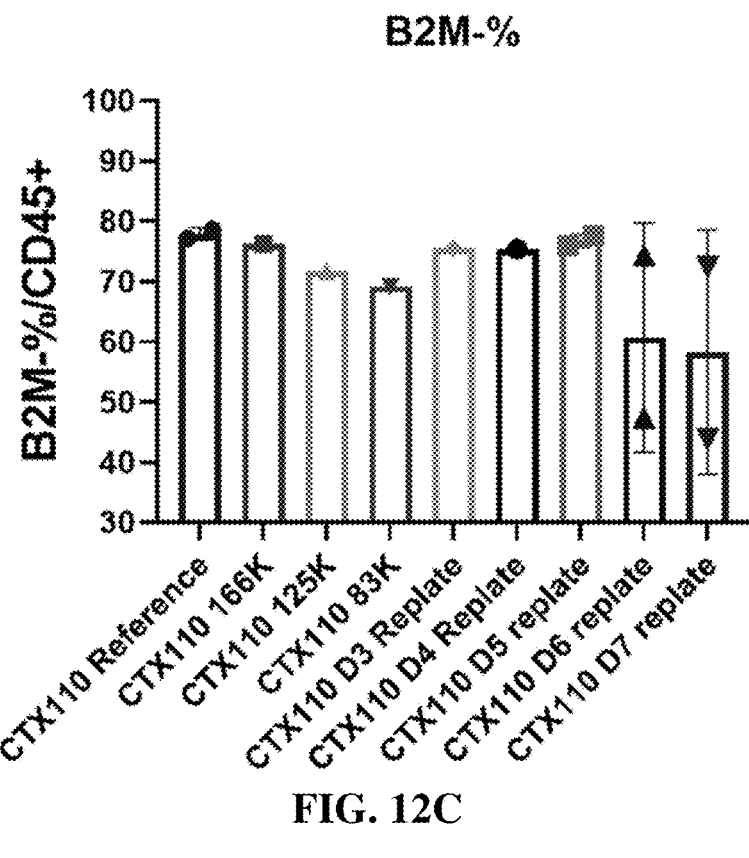

Editing efficiency including CAR⁺ %, TRAC⁻ % and B2M⁻% were assessed from all the replating and low-plating groups. (FIGS. 12A-12C) CAR⁺ % in CTX110 reference was 55.9%. D3, D4, and D5 replated groups maintained CAR+ % at 57.9%, 56% and 52.62% while D6 and D7 resulted in the decreased CAR+ % at 38.65% and 35.45%. CAR⁺ % from 166 K/cm², 125 K/cm², or 83 K/cm² were 59.3%, 54.9% and 52.9% without significant changes from CTX110 reference. TRAC⁻ % in CTX110 reference group was 94.24%. D3, D4, and D5 replated groups and 166 K/cm² plating group maintained comparable TRAC-% as 93.5%, 93.6%, 93.15% and 93.9%. Slight decreases in TRAC⁻% were observed in 125 K/cm² and 83 K/cm² at 91.5% and 91.2%. Greater decreases in TRAC⁻% were seen in D6 and D7 replating groups as 88% and 87.2%. The similar trend was demonstrated in B2M⁻ % as well. B2M⁻ % of CTX110 reference group was 77.93%. D3, D4, and D5 replated groups and 166 K/cm² plating group maintained comparable TRAC⁻ % as 75.51%, 75.39%, 76.77% and 76.31%. Slight decreases in B2M⁻ % were observed in 125 K/cm² and 83 K/cm² at 71.74% and 69.19%. Greater decreases in B2M⁻ % were seen in D6 and D7 replating groups as 60.37% and 58.29%.

It was determined that the D3, D4, and D5 replating, 166 K/cm² plating and 125 K/cm² plating provided the most comparable editing efficiency as CTX110 reference.

Figure 13A:
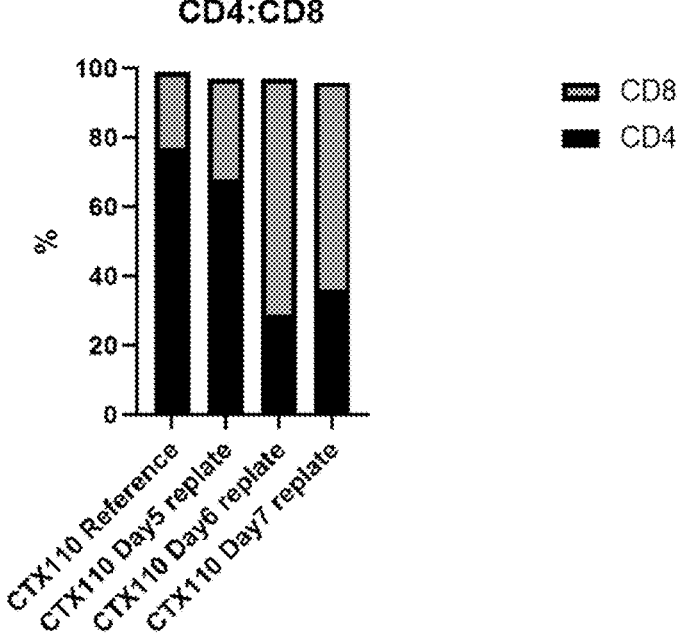
Figures 13B, 14A:
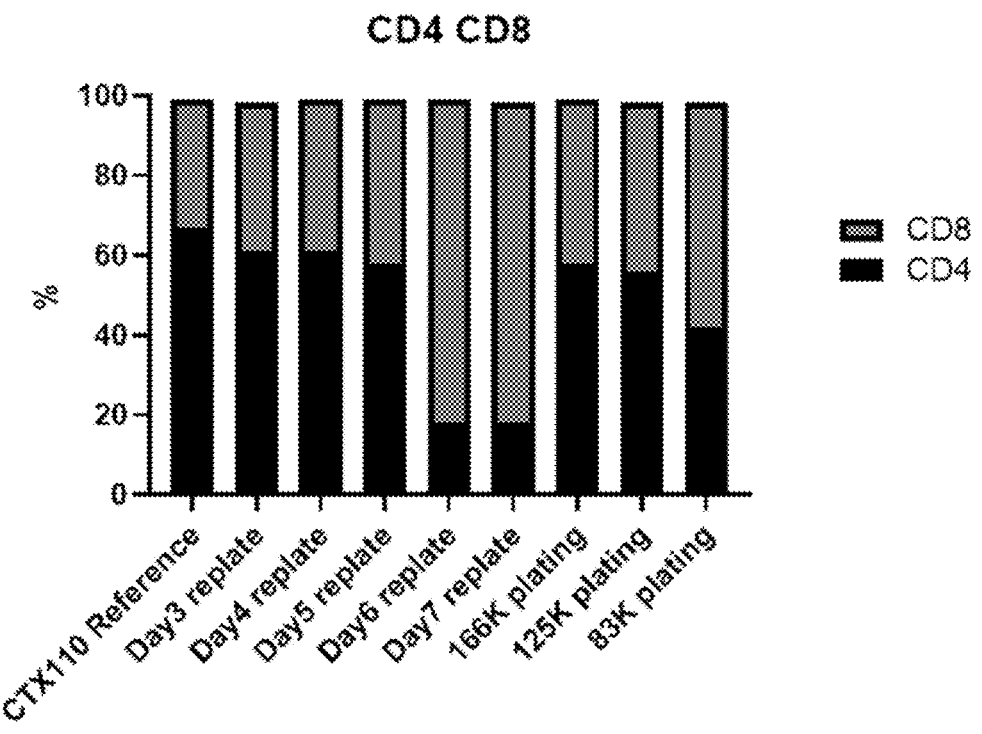
Figure 14B:
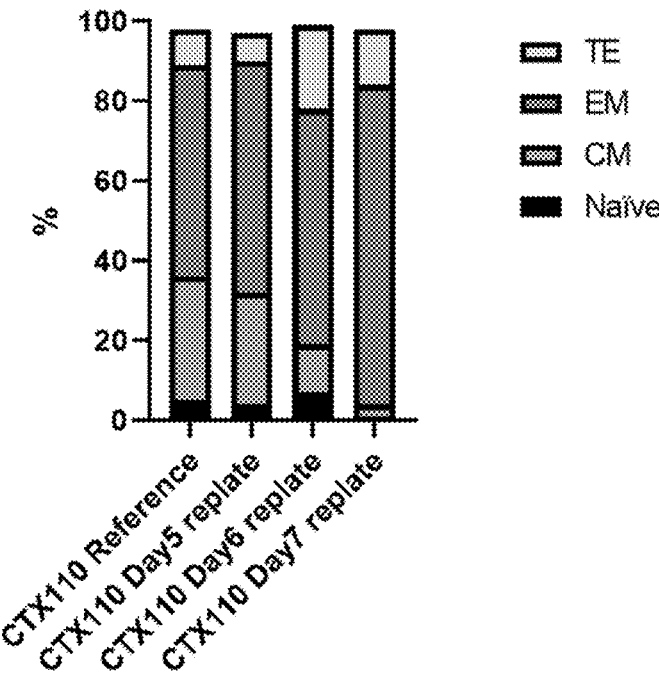
Figure 14C:
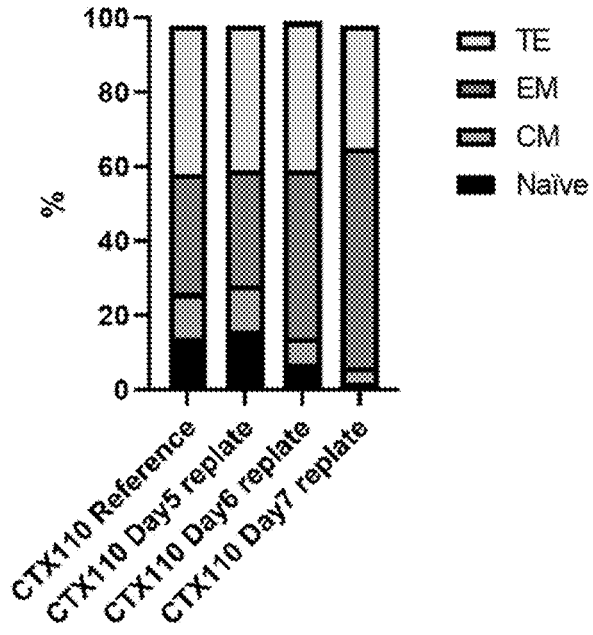
Figures 14D, 14E:
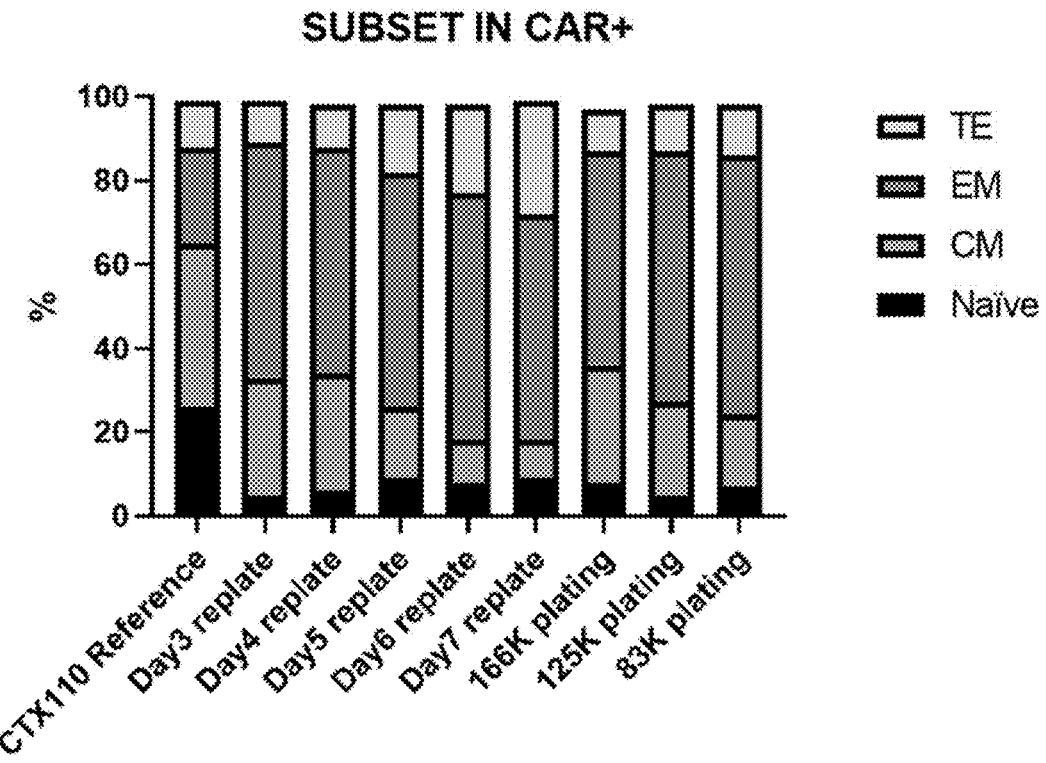
Figure 14F:
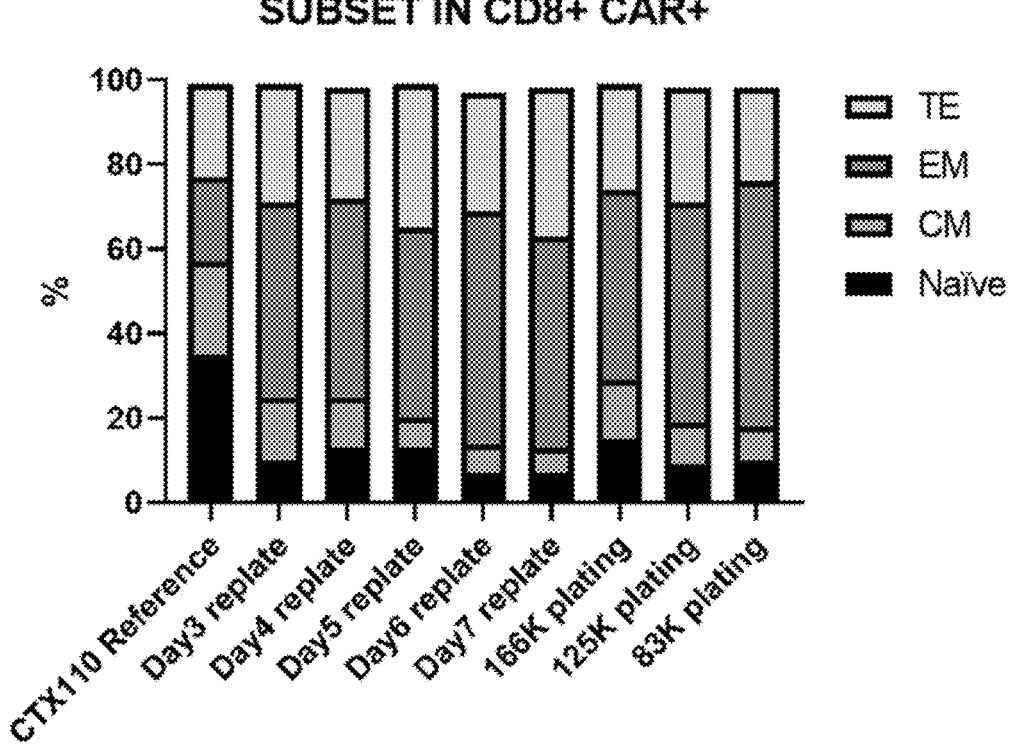
Figure 15A:
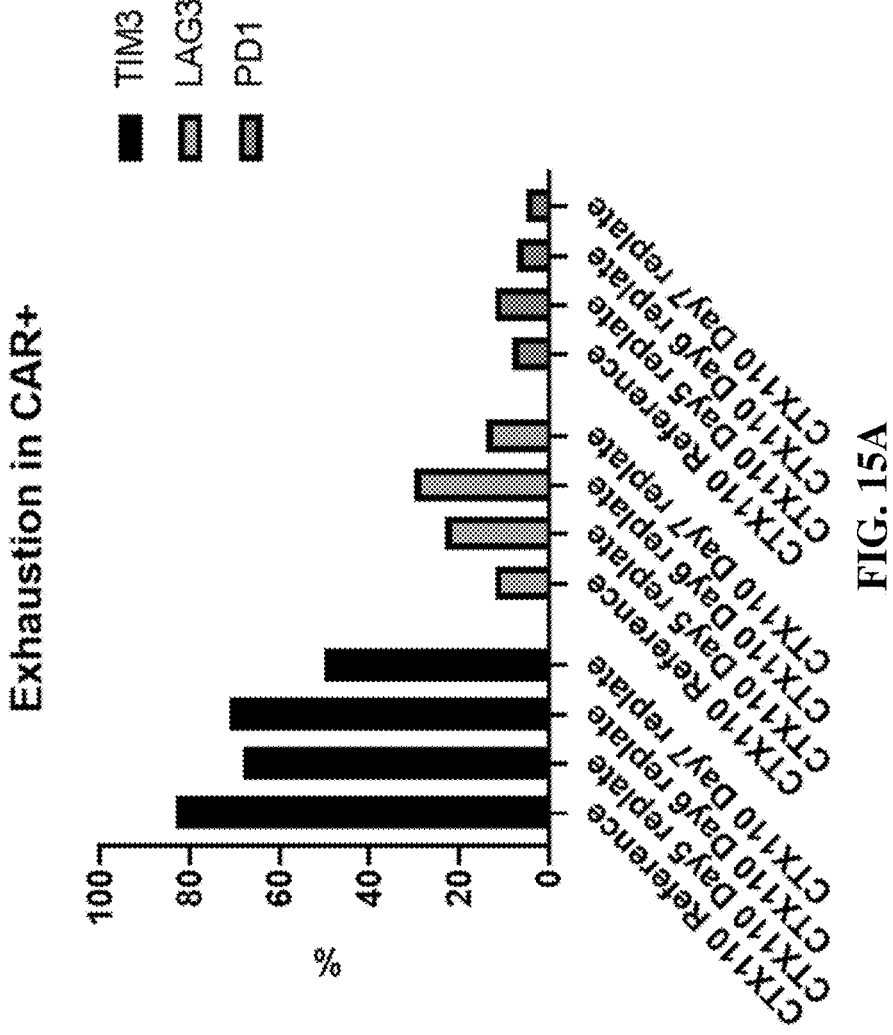
Figure 15B:
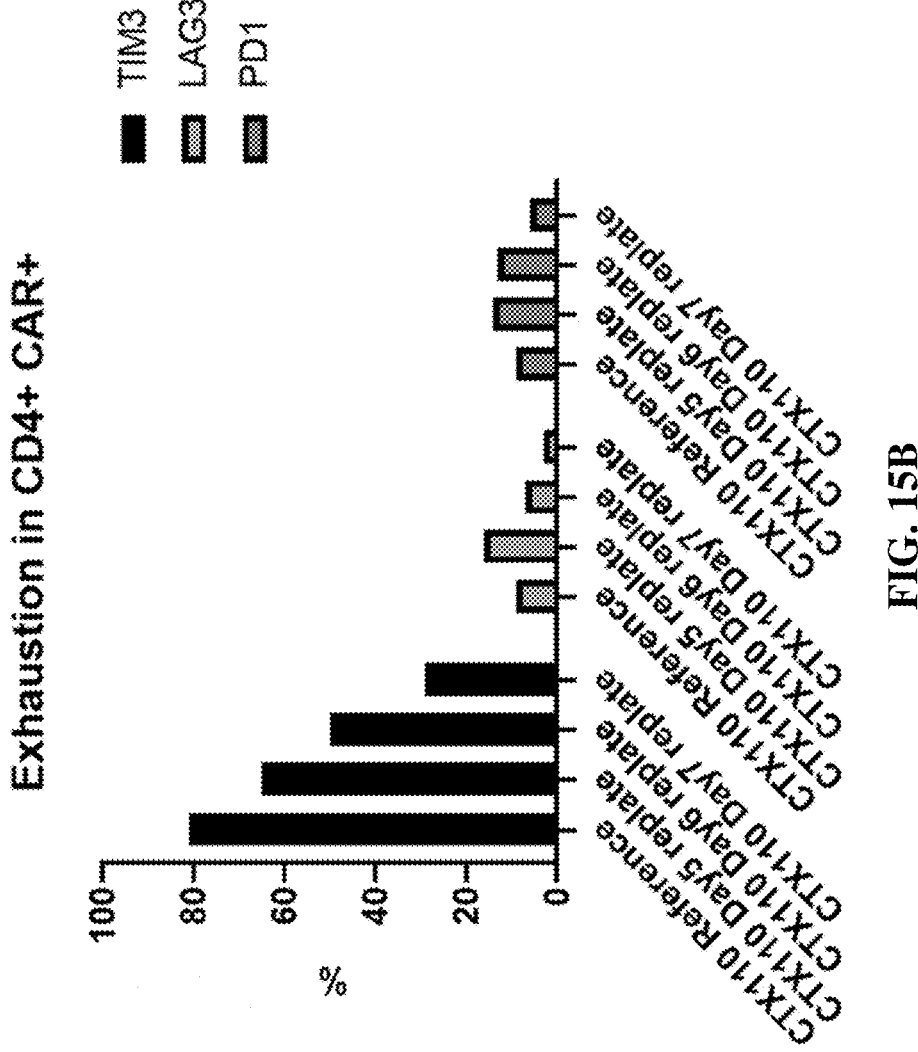
Figure 15C:
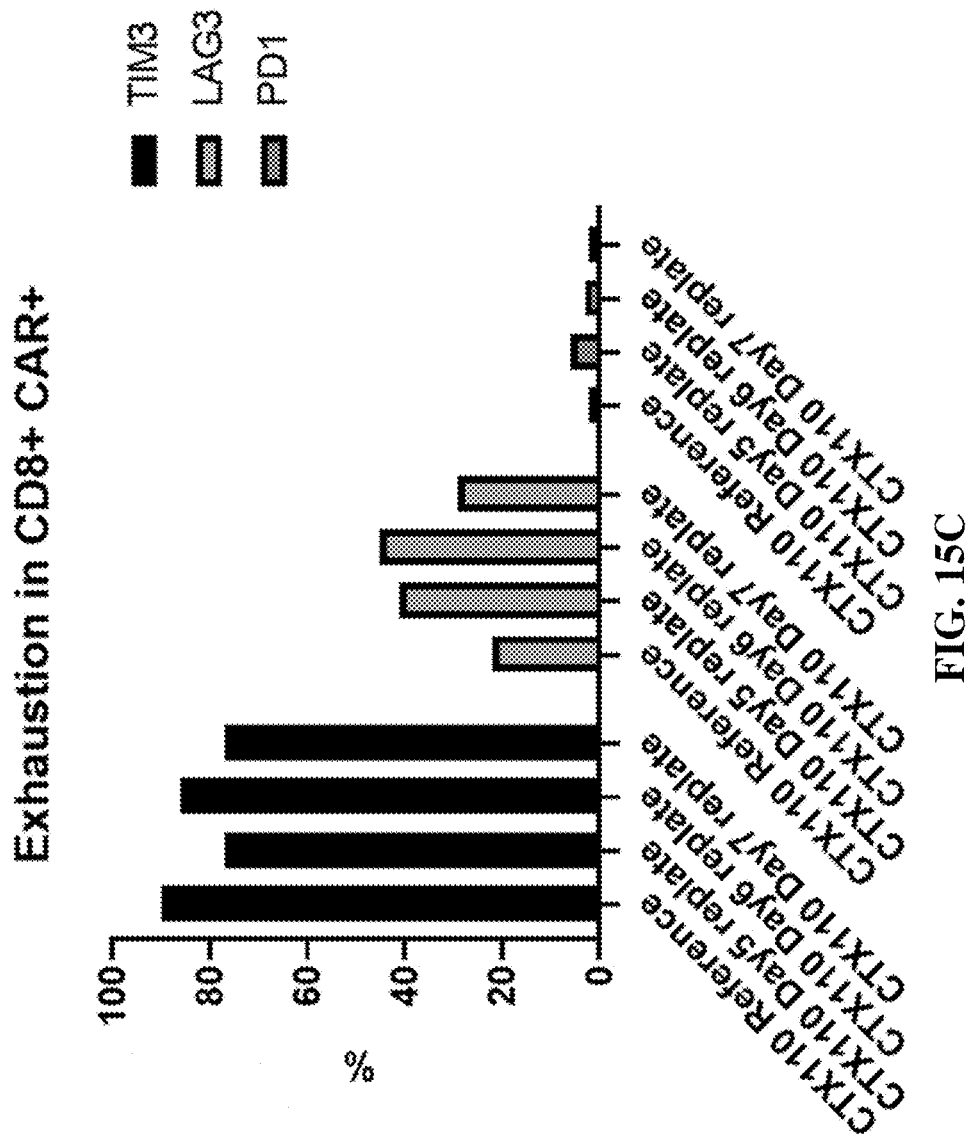
Figure 15D:
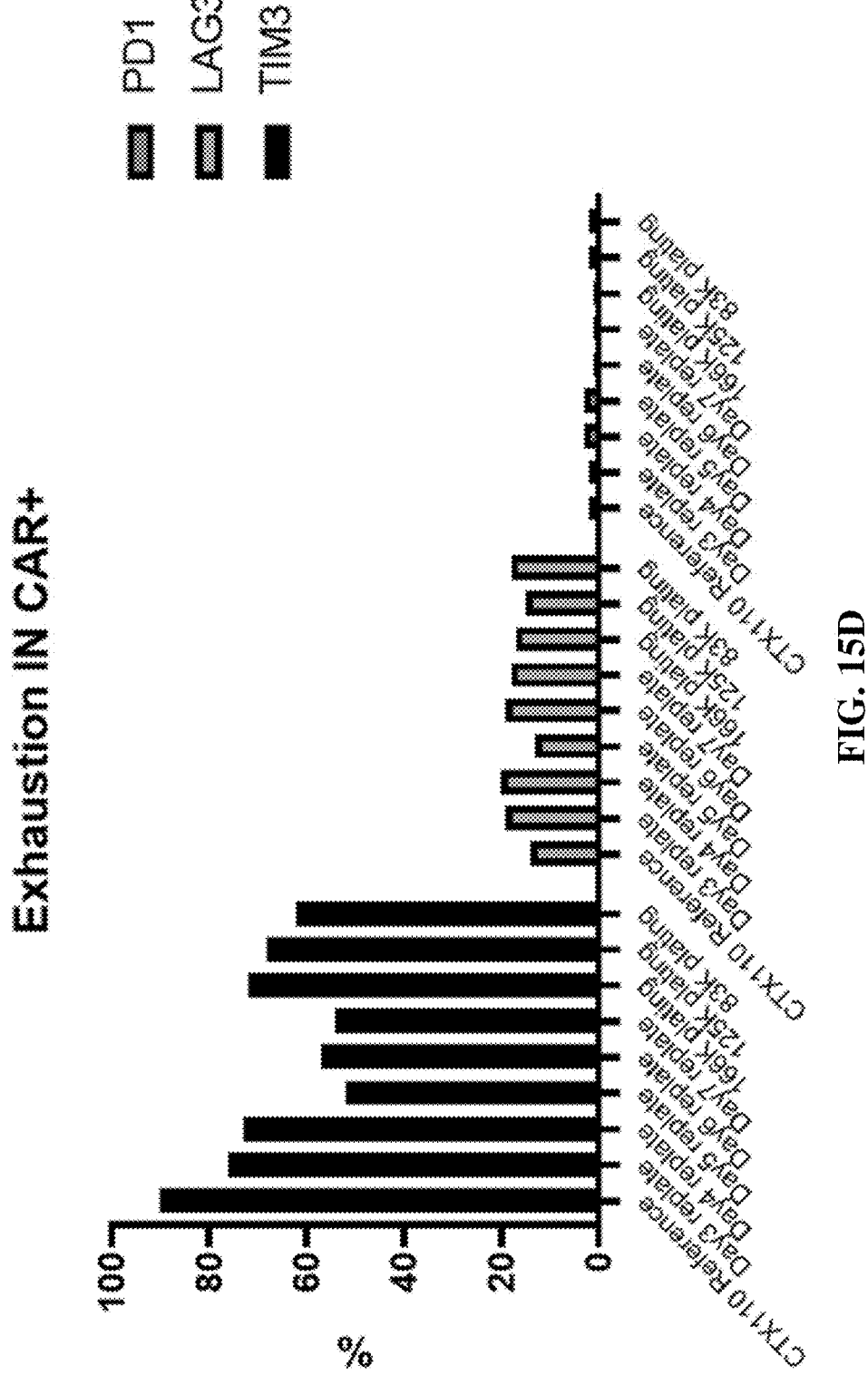
Figure 15E:
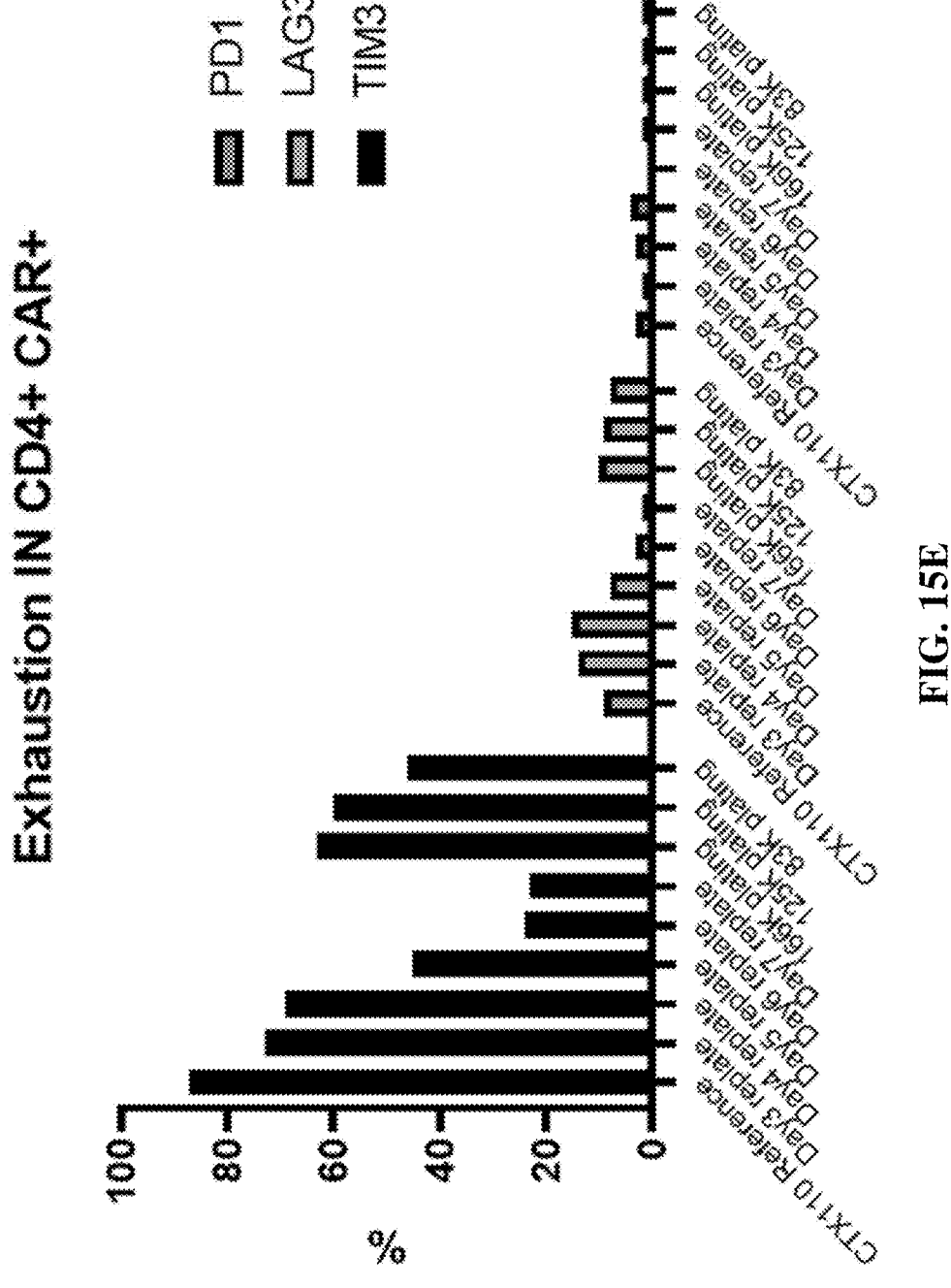
Figure 15F:
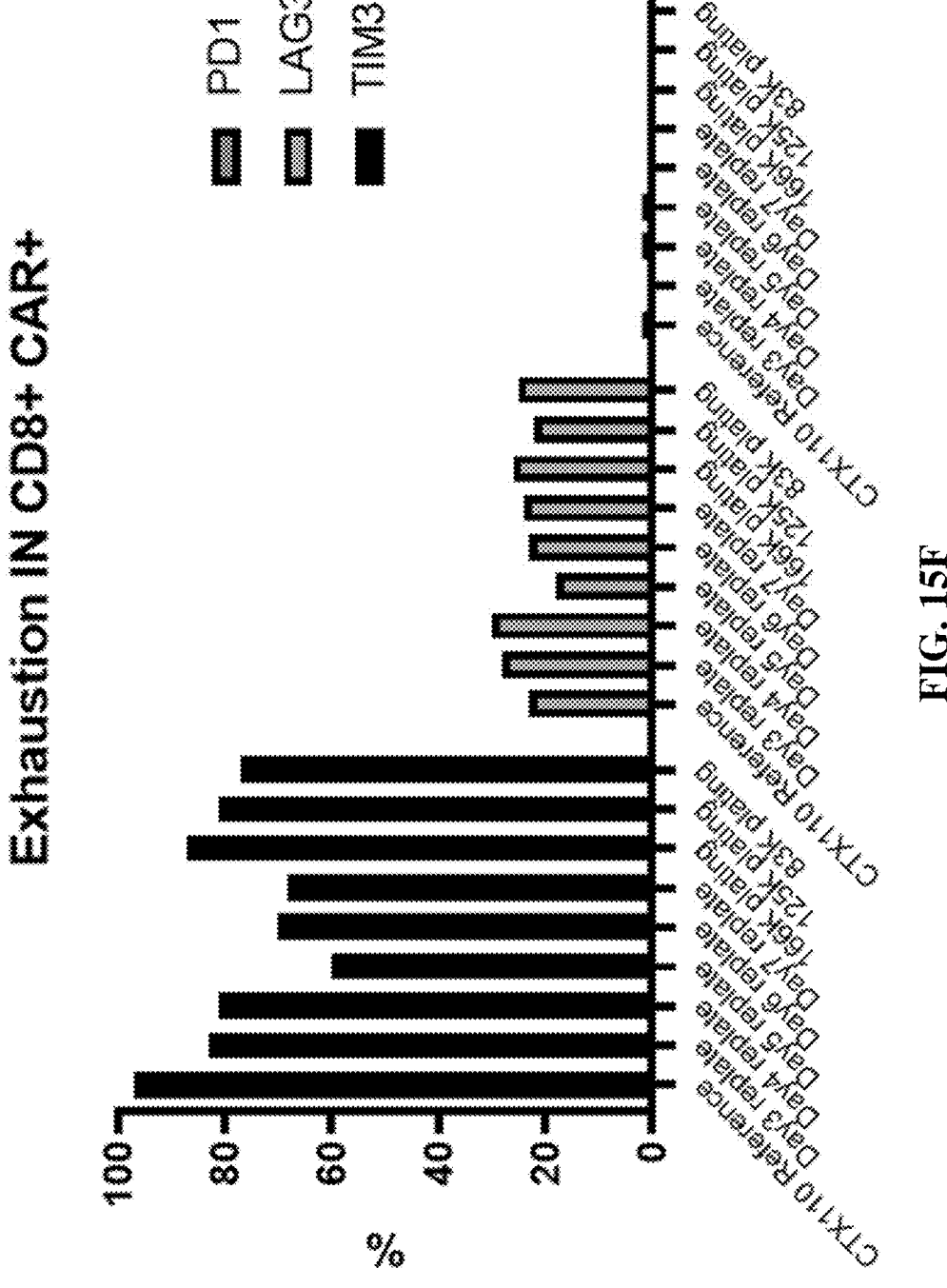

The cellular phenotypes of the replated populations were determined using the flow panels, as described in Example 8 and Table 19 excluding CD95, CD45RO, CD57, CD27 and CCR7, and including Tim3. FIGS. 13A and 13B show the ratio of CD4⁺ and CD8⁺ cells in the replated populations as well as CTX110 reference. Ratio of CD4 and CD8 was well maintained in D3, D4, and D5 replate groups and 166k and 125k low density plating groups. Increased CD8⁺ cells were seen in D6 and D7 replating groups as well as 83K low density plating group.

The replated populations were assessed for memory cell markers. Within CAR⁺, CD4⁺CAR⁺, and CD8⁺CAR⁺ population, CD45RA⁺CD62 L⁺ cells, CD45RA⁻CD62 L⁺ cells, CD45RA⁻CD62 L⁻ cells, and CD45RA⁺CD62 L⁻ cells were defined as Naïve T cells, central memory (CM) T cells, effector memory (EM) T cells, and terminal effector (TE) T cells, respectively. These populations within the CTX110 product were defined as subsets. FIGS. 14A-14F show the subset composition found in the replated populations and low density plating groups. Within CAR⁺, CD4⁺CAR⁺ and CD8⁺CAR⁺ populations, most of replated and low density plating groups demonstrated reduced naïve T cells. Decreased central memory T cells was detected in D6 and D7 replated groups but not significant in D3, D4, and D5 replated groups. Most groups showed increased effector memory T cells. Increased terminal differentiated cells were seen in CAR⁺ and CD8⁺CAR⁺ cells but not in most of CD4⁺CAR⁺ cells.

As shown in FIGS. 15A-15F, low levels of exhaustion markers were found in the CAR⁺, CD4⁺/CAR⁺, and CD8⁺/CAR⁺ replated populations. Compared with CTX110 reference, there were increased LAG3 expression on D6 and D7 replated cells (FIGS. 15A and 15C) in one of the experiments. Overall, there was not increased expression of all three exhaustion markers (PD1, LAG3 and TIM3). There was no or very low PD1 expression in all groups.

In Vitro Cell Kill Assay

Figure 16A:
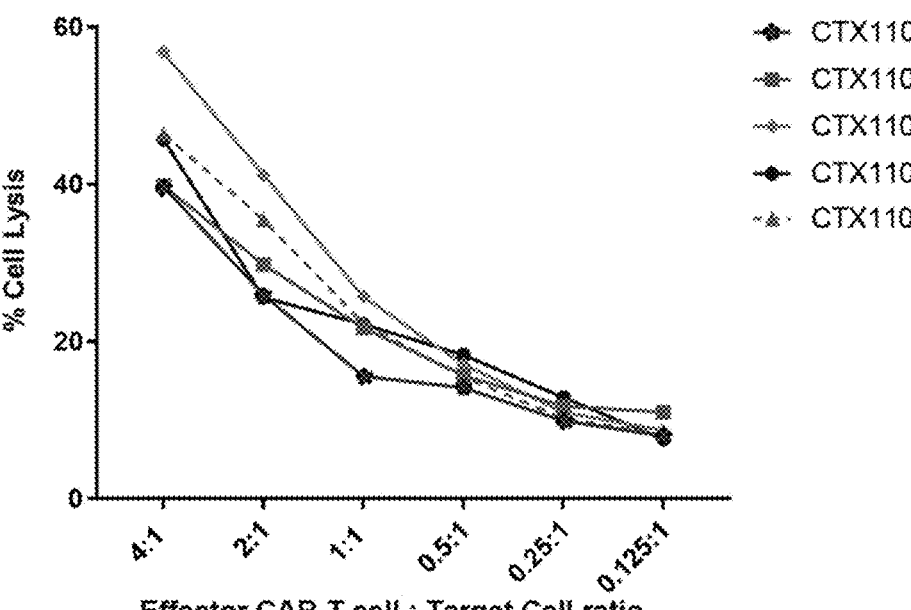
Figure 16B:
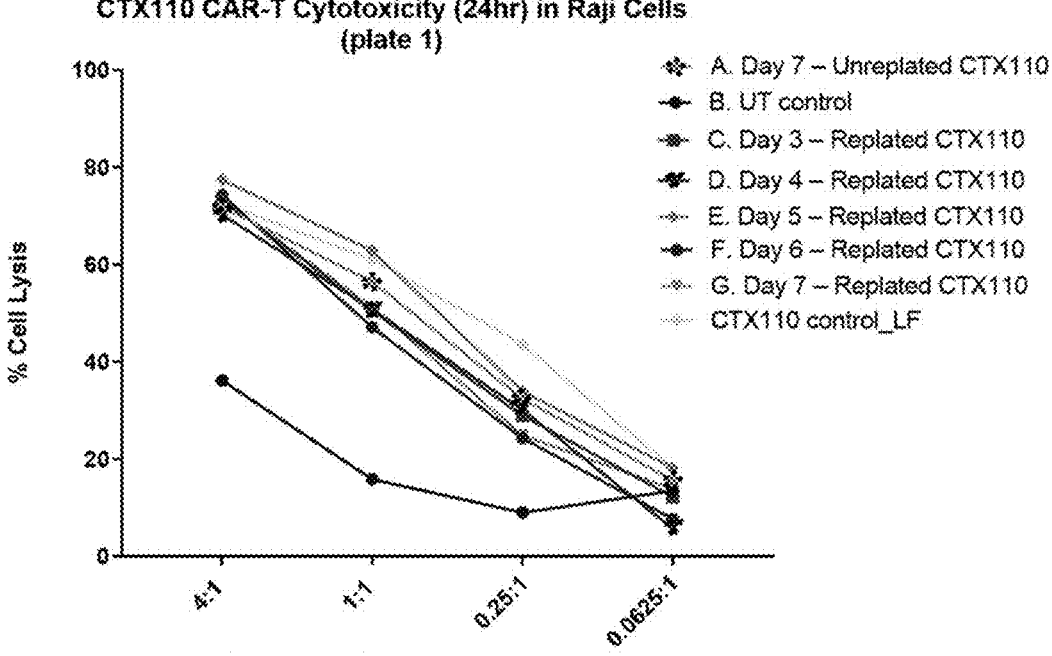
Figure 16C:
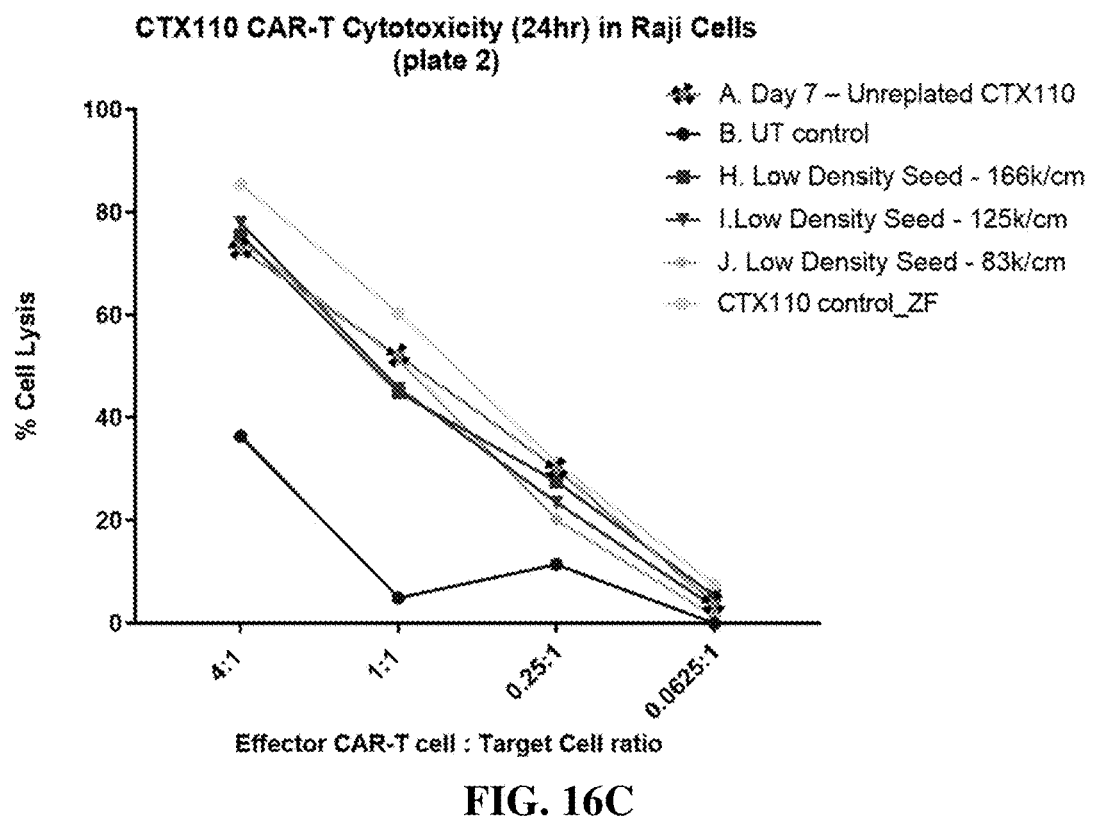

Next, the ability of the CAR-T cells in replated and low-plating density groups to kill CD19 positive Raji target cells was assessed using a flow cytometry-based cytotoxicity assay. In brief, target cells were labeled with eFluor670 and incubated with CAR-T cells at varying ratios. CTX110 cytotoxicity was analyzed at 24 hours by assessing labeled cells in the live gate compared to control sample. The results are shown in FIGS. 16A-16C. All replated and low-density plating groups of CTX110 showed dose dependent target cell cytotoxicity at comparable level as CTX110 reference.

In sum, these in vitro results demonstrate that D3, D4, and D5 replating and seeding densities of 166 K/cm² and 125 K/cm² provided sufficient expansion, editing efficiency and cytotoxicity as CTX110 reference.

In Vivo Study

Next, the ability of the CAR-T cells in the replated and low-density plating groups to kill tumors in mice was studied in vivo in two independent studies (Tables 24 and 25). Nalm6-Fluc-GFP tumor cells were inoculated into CIEA NOG mice 4 days prior to CAR-T administration. Weekly Bioluminescence (BLI, photons/s) assessment allows to assess tumor burden in mice. In in vivo study #1, D5, D6 and D7 replated, as well as CTX110 reference, were administered at dose of 2e6, 4e6, and 10e6 CAR⁺ cells per mouse. Six mice were included per group and per dose. Untreated mice were used as negative control. In in vivo study #2, low-density plating group (166 K/cm², 125 K/cm², and 83 K/cm²) and replating groups (D3, D4, and D6 replating) were administered at dose of 4e6 CAR⁺ cells per mouse. 4 recipients were included per group.

TABLE 24

| | | In vivo study 1 | |
|---|---|---|---|
| | Groups | Dose | No. of recipient |
| 1 | Untreated | 0 | 5 |
| 2 | CTX110 | 2 × 10⁶ CAR⁺ | 6 |
| 3 | Reference | 4 × 10⁶ CAR⁺ | 6 |
| 4 | | 10 × 10⁶ CAR⁺ | 6 |
| 5 | day 5 replating | 2 × 10⁶ CAR⁺ | 6 |
| 6 | 1:4 split | 4 × 10⁶ CAR⁺ | 6 |
| 7 | | 10 × 10⁶ CAR⁺ | 6 |
| 8 | day 6 replating | 2 × 10⁶ CAR⁺ | 6 |
| 9 | 1:4 split | 4 × 10⁶ CAR⁺ | 6 |
| 10 | | 10 × 10⁶ CAR⁺ | 6 |
| 11 | day 7 replating | 2 × 10⁶ CAR⁺ | 6 |
| 12 | 1:4 split | 4 × 10⁶ CAR⁺ | 6 |
| 13 | | 10 × 10⁶ CAR⁺ | 6 |

TABLE 25

| | | In vivo study 2 | |
|---|---|---|---|
| | Groups | Dose | No. of recipient |
| 1 | Untreated | | 3 |
| 2 | 110 Reference | 4 × 10⁶ CAR⁺ | 4 |
| 3 | 166K/cm² (3×) | | 4 |
| 4 | 125K/cm² (4×) | | 4 |

TABLE 25-continued

| | Groups | Dose | No. of recipient |
|---|---|---|---|
| | In vivo study 2 | | |
| 5 | 83K/cm² (6×) | | 4 |
| 6 | day 3 replating 1:4 split | | 4 |
| 7 | day 4 replating 1:4 split | | 4 |
| 8 | day 5 replating 1:4 split | | 4 |

Figure 17A:
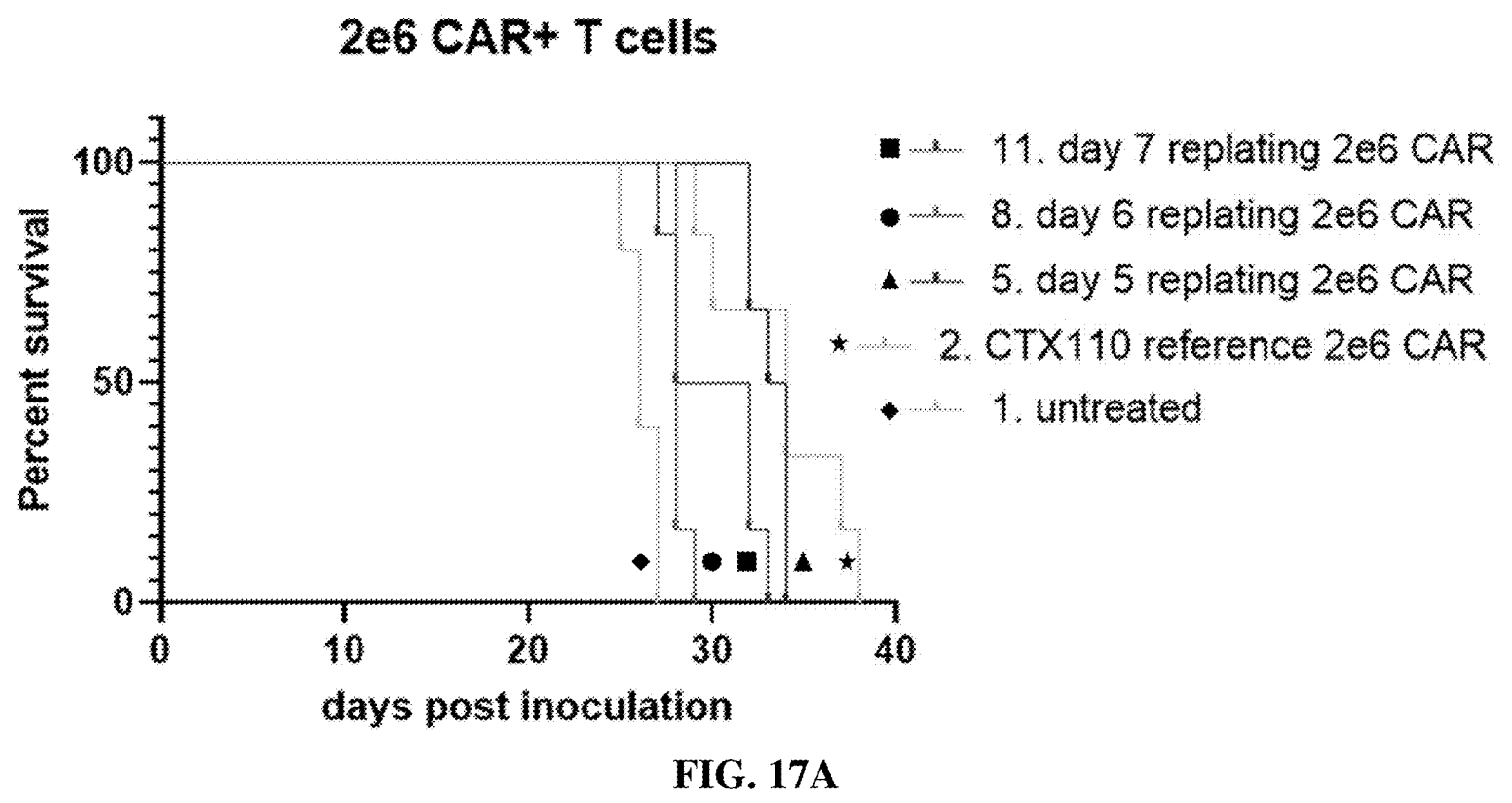
Figure 17B:
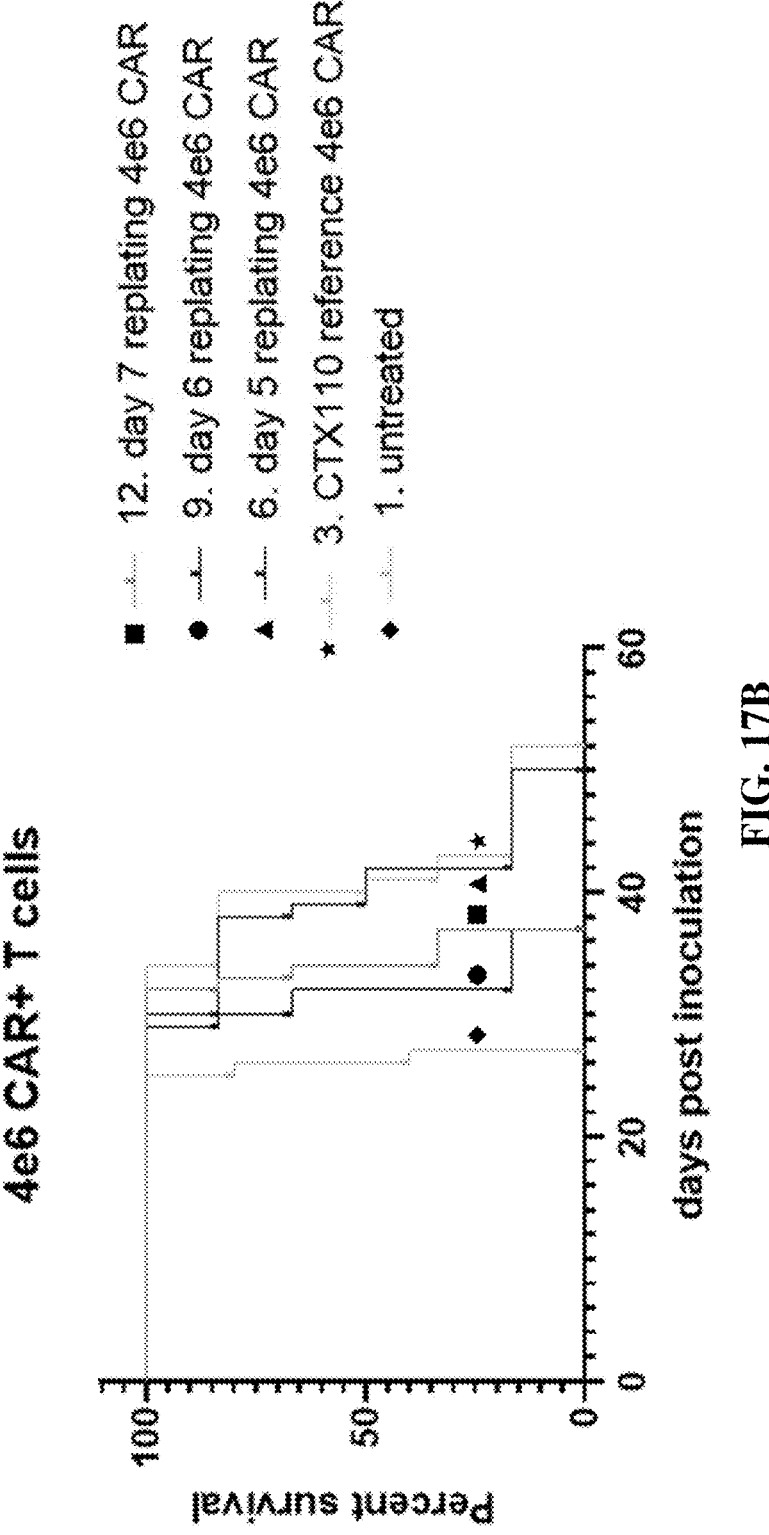
Figure 17C:
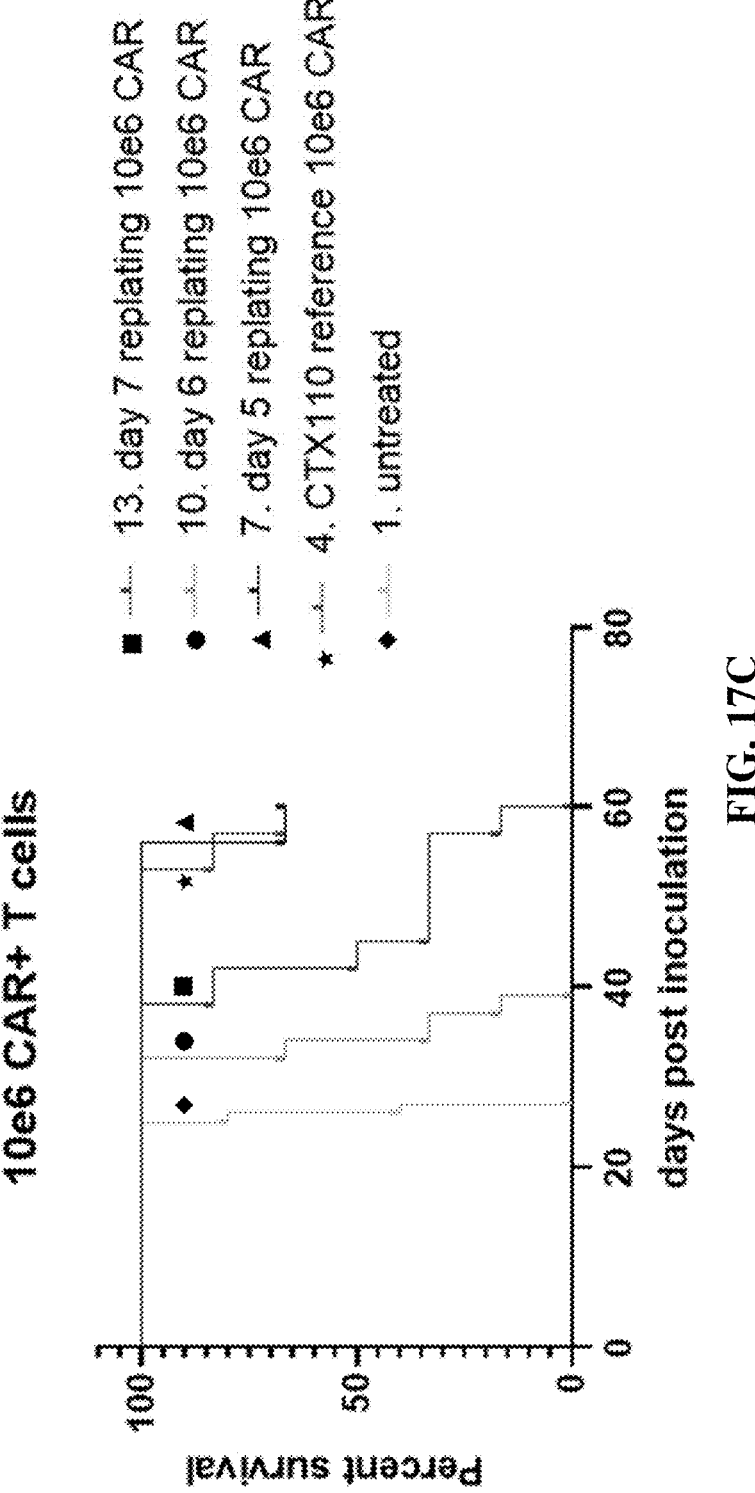

In vivo study #1 indicated comparable survival between D5 replating group and CTX110 reference at all three doses. (FIGS. 17A-17C) The 83 K/cm² and 166 K/cm² plating group and D4 replating group had compromised survival compared with other testing groups as well as CTX110 reference. (FIG. 17D) Medium survival is listed in Tables 26 and 27.

TABLE 26

| | Groups | Dose | Medium Survival |
|---|---|---|---|
| | In vivo study 1 | | |
| 1 | Untreated | 0 | 26 |
| 2 | CTX110 Reference | 2 × 10⁶ CAR⁺ | 34 |
| 3 | | 4 × 10⁶ CAR⁺ | 40.5 |
| 4 | | 10 × 10⁶ CAR⁺ | 66.5 |
| 5 | day 5 replating | 2 × 10⁶ CAR⁺ | 33.5 |
| 6 | 1:4 split | 4 × 10⁶ CAR⁺ | 40.5 |
| 7 | | 10 × 10⁶ CAR⁺ | 79 |
| 8 | day 6 replating | 2 × 10⁶ CAR⁺ | 28 |
| 9 | 1:4 split | 4 × 10⁶ CAR⁺ | 32 |
| 10 | | 10 × 10⁶ CAR⁺ | 34 |
| 11 | day 7 replating | 2 × 10⁶ CAR⁺ | 30 |
| 12 | 1:4 split | 4 × 10⁶ CAR⁺ | 34 |
| 13 | | 10 × 10⁶ CAR⁺ | 43.5 |

TABLE 27

| | Groups | Dose | Medium Survival |
|---|---|---|---|
| | In vivo study 2 | | |
| 1 | Untreated | | 25 |
| 2 | 110 Reference | 4 × 10⁶ | 70.5 |
| 3 | 166K/cm² (3×) | CAR⁺ | 68.5 |
| 4 | 125K/cm² (4×) | | Undefined |
| 5 | 83K/cm² (6×) | | 51.5 |
| 6 | day 3 replating 1:4 split | | 68.5 |
| 7 | day 4 replating 1:4 split | | 61.5 |
| 8 | day 5 replating 1:4 split | | Undefined |

Figure 18A:
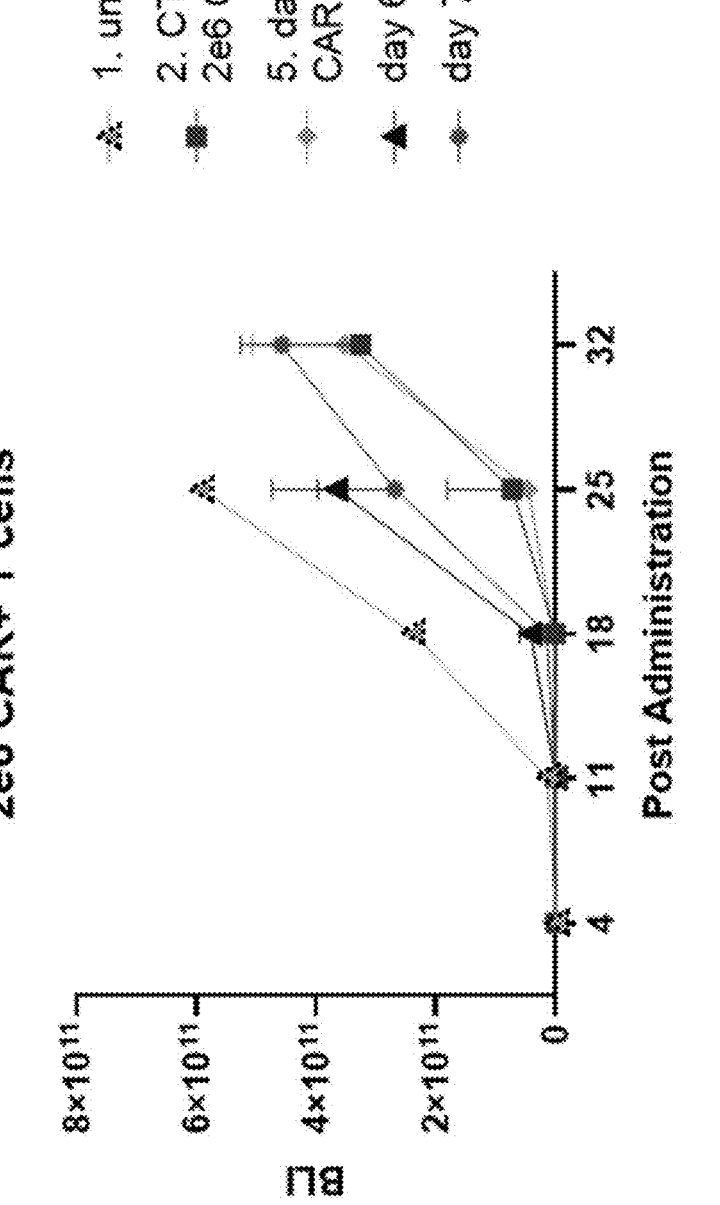

BLI from untreated mice in both studies reached peri-morbidity condition indicating high tumor burden on day 25 and day 18. In study #1, D6 and D7 replated groups demonstrated earlier increase in BLI compared with D5 and CTX110 reference at all 3 doses (2e6, 4e6 and 10e6 CAR⁺ cells per mouse; FIGS. 18A-18C, respectively). D5 and CTX110 reference demonstrated the similar tumor growth kinetics. In study #2, 83 K/cm² plating group showed quicker tumor growth than CTX110 reference. All other testing groups demonstrated similar or even delayed tumor growth compared with CTX110 reference (FIG. 18D).

According to medium survival and BLI, D5 replating group but not D6 and D7 replating groups maintained the in vivo efficacy as CTX110 reference.

Expansion duration, yield, editing, exhaustion/subset markers, in vitro and in vivo potency were used to determine optimal seeding densities and/or replating conditions. A summary of the analysis is shown in Table 28. Replating at 1:4 ratio at Day 5 provided beneficial expansion and editing efficiency.

TABLE 28

| Group | Yield | Expansion period | Editing | Exhaustion (CAR⁺) | Subsets (CAR⁺) | In vitro efficacy | In vivo efficacy & persistency |
|---|---|---|---|---|---|---|---|
| CTX110 166K | 3x | +3 days | Maintained | | | Maintained | Maintained |
| CTX110 125K | 4x | +3 days | Decreased but within spec | | | | Maintained |
| CTX110 83K | 6x | +7 days | Decreased, slightly below spec | | | | Compromised |
| CTX110 D3 replate 1:4 split | | +3 days | Maintained | | | | Maintained |
| CTX110 D4 replate 1:4 split | | +3 days | Maintained | | | | Pending Compromised |
| CTX110 D5 replate 1:4 split | 4x | +3 days | Maintained | Decrease TIM3; increase TAG3, Increase PD1 | Comparable | Maintained | Maintained |
| CTX110 D6 replate 1:4 split | | +7 or 11 days | Decreased | Decrease Tim3, Increase LAG3 | Increase TE | Maintained | Compromised |
| CTX110 D7 replate 1:4 split | | +10 or 11 days | Decreased | Decrease Tim3 | Decrease Naive | Maintained | Compromised |

Example 10: Improved Cell Expansion (A) Optimized Electroporation for Increased CTX110 & CTX 120 Cell Expansion Output The methods as described in the present disclosure utilize electroporation to deliver various nucleic acids and polypeptides to recipient T-cells, including, for example, various ribonucleoprotein (RNP) complexes comprising Cas9 and guide RNA complexes. The instrumentation used in the electroporation process is not particularly limited, as any suitable electroporation instrument from various manufacturers can find use in the methods described herein. The cell seeding density used in the electroporation is not particularly limited.

The present example uses an electroporation instrument capable of electroporating increased numbers of cells in cassettes capable of retaining larger volumes while maintaining efficient editing. The larger electroporation capacity increases, for example as much as doubling, the output of any given engineered T-cell, for example the CTX110 or CTX120 engineered T-cell product, by providing a greater number of edited cells for transduction and expansion. This is a benefit in manufacturing, as this increased capacity comes without the need to extend the process duration and or cell doublings.

For example, additional cells are available to seed additional T-cell culture vessels (500 cm² gas permeable membrane surface area with 5000 mL media capacity), such as 2 or more additional culture vessels. For example, with the increase number of cells, up to 4× culture vessels can be seeded, where 300e6≤x≤600e6 cells can be seeded in 2× culture vessels, 600e6≤x≤800e6 cells can be seeded in 3× culture vessels, or ≤800e6 cells can be seeded in 4× culture vessels.

In some aspects, between about 400,000 cells/cm² and 500,000 cells/cm² are seeded per culture vessel. Alternatively, between about 250,000 cells/cm² and 500,000 cells/cm² are seeded per culture vessel, or between about 300,000 cells/cm² and 500,000 cells/cm² are seeded per culture vessel, or between about 150,000 cells/cm² and 250,000 cells/cm² are seeded per culture vessel, or between about 150,000 cells/cm² and 500,000 cells/cm² are seeded per culture vessel, or between about 150,000 cells/cm² and 600,000 cells/cm² are seeded per culture vessel.

In some aspects, a target seeding density is at least about 150,000 cells/cm², or at least about 250,000 cells/cm², or at least about 300,000 cells/cm², or at least about 400,000 cells/cm², or at least about 500,000 cells/cm².

In some aspects, a target seeding density is about 250,000 cells/cm². In other aspects, a target seeding density is about 500,000 cells/cm².

Electroporation cassettes capable of retaining volumes of up to 1 mL can be used. Using this system, $2.7 \times 10^9$ cells can be electroporated in up to seven G1000 cassettes. Retrieval of the cells from cassettes with a single-use blunt tip needles attached to a 3 mL syringe will also eliminate the risk of micropipette tip ejection into the Erlenmeyer.

Use of a system with larger capacity also facilitates the cell transduction step. Doubling the current maximum of 7e8 cells for transduction to 1.4e9 cells produces sufficient material to seed up to four cell culture vessels for expansion. Therefore, a fixed day 9 depletion can be maintained, effectively up to doubling the output per run in the same amount of processing time.

Other steps in the example were unchanged from above.

(B) Method Optimization and Comparison Using Three T-Cell Donor Lots to Increase Drug Product Yield This section describes the generation of CAR T cells at 1×, 2×, 4×, and 4× with day 4 split to demonstrate robustness of increased expansion methods and generate material for comparability analysis between current drug product (DP) like material and selected cell culture conditions.

Starting material for this batch was CD4/CD8 T cell selection from three healthy donor apheresis lots. Selected expansion conditions of CTX110 CAR T cells were seeded in G-Rex 500M-CS chambers.

Previous CTX110 CAR T expansion seeding and harvest cell density in the G-Rex500M-CS was 500,000/cm² and $30 \times 10^6/cm^2$, respectively, producing $\leq 30 \times 10^9$ CAR T cells. To increase the DP yield of CAR T cells in the G-Rex500M-CS culture vessel, the present example was developed. Three select conditions, described in Table 29 below, were selected to evaluate CTX110 DP-like comparability with three different donors, and to generate enough sample cells for multiple downstream analytical assays.

TABLE 29

Selected cell culture conditions to increase CAR T yield during expansion unit operation

| Sample ID | Condition | Seeding density (total cells to seed) | Split (Days of Expansion) | Passage 1 (volume seeded) | Harvest for TCRab Depletion (days of expansion) |
|---|---|---|---|---|---|
| S1 | 1 × manufacturing process | $250.0 \times 10^6$ | — | — | 7 |
| S2 | 2× | $125.0 \times 10^6$ | — | — | 8 |
| S3 | 4× | $62.5 \times 10^6$ | — | — | 9 |
| S4 | 4 × with day 4 split | $250.0 \times 10^6$ | 4 | ¼ harvested volume | 9 |

The detailed protocol is provided below.

a. Prepared all culture medium, GMP IL-2 and GMP IL-7 for the entire CTX110 DS process, where:
    1. T cells were activated according to the Full Large Scale (3×G-Rex500M-CS)
    2. CAR T cells were seeded for expansion in 1× G-Rex500M-CS and Small Scale (1× Well GRex6M) with 1× well at the selected seeding density.
    3. CAR T cells were seeded post depletion according to one-half large scale, 1×G-Rex500M-CS per condition.

b. Thawed the appropriate number of T cells to perform Full Large Scale (3×G-Rex500M-CS).

c. Activated the appropriate number of T cells to perform Full Large Scale (3×G-Rex500M-CS).

d. Diluted the activating agent.

e. Harvested cells for electroporation (EP) at Full Large Scale (3×G-Rex500M-CS).

f. Electroporation of $2,040 \times 10^6$ to $2,160 \times 10^6$ of T cells (17-18 OC400 cassettes).

g. Transferred cells equally between 2× wells of a 6 well Falcon plate and incubated for 20 minutes.

h. Diluted EP T cells and seeded $5.0 \times 10^6$ total cells in Small Scale (1× well G-Rex6M) for in vitro efficacy+ EP-AAV control.

i. Transduced $1,000 \times 10^6$ T cells.

j. Seeded the appropriate number of T cells in the appropriate culture vessel for expansion:
    1. S1: $250 \times 10^6$ total cells seeded into G-Rex500M-CS, $5.0 \times 10^6$ total cells in Small Scale (1× well G-Rex6M).

83

2. S2: 125×10⁶ total cells seeded into G-Rex500M-CS, 2.5×10⁶ total cells in Small Scale (1× well G-Rex6M).

3. S3: 62.5×10⁶ total cells seeded into G-Rex500M-CS, 1.25×10⁶ total cells in Small Scale (1× well G-Rex6M).

4. S4: 250×10⁶ total cells seeded into G-Rex500M-CS, 5.0×10⁶ total cells in Small Scale (1× well G-Rex6M)

k. Performed CAR T expansion according to each condition specifications:

1. S1: supplement 100 IU/mL of IL-2 and 100 IU/mL of IL-7 to the G-Rex500M-CS and G-Rex6M well once every three days. Pulled a sample from the G-Rex6M for TCRab Flow panel and proceeded to TCRab depletion on day 7 of expansion.

2. S2: supplement 100 IU/mL of IL-2 and 100 IU/mL of IL-7 to the G-Rex500M-CS and G-Rex6M well once every three days. Pulled a sample from the G-Rex6M for TCRab flow panel and proceeded to TCRab depletion on day 8 of expansion.

3. S3: supplement 100 IU/mL of IL-2 and 100 IU/mL of IL-7 to the G-Rex500M-CS and G-Rex6M well once every three days. Pulled a sample from the G-Rex6M for TCRab flow panel and proceed to TCRab depletion on day 9 of expansion.

4. S4:

a. Day 4 of expansion:

a. Removed supernatant and harvested cells from G-Rex500M-CS using a GathRex pump, recorded volume of cells.

b. By gravity, filled a new G-Rex500M-CS with 5000 mL of culture medium and seeded one quarter of harvested cell volume into the filled culture vessel. Returned culture vessel to incubator.

c. With a serological pipet, filled a new single well of a G-Rex6M with 75 mL of culture medium. With a serological pipet, homogenized cells in G-Rex6M well and transferred 25 mL of cells to filled culture vessel. Returned culture vessel to incubator.

b. Supplemented 100 IU/mL of IL-2 and 100 IU/mL of IL-7 to the G-Rex500M-CS and G-Rex6M well once every three days. Pulled a sample from the G-Rex6M for TCRab flow panel and proceeded to TCRab depletion on day 9 of expansion posttransduction.

l. Performed TCRab depletion at one-half large scale (1× G-Rex500M-CS). Obtained a pre-depletion sample for the appropriate flow analysis.

m. Obtained a post-depletion sample for the appropriate flow analysis and seeded post-depletion target T cells to perform one-half Large Scale (1× G-Rex500M-CS).

n. Performed harvest at one-half large scale (1× G-Rex500M-CS). Based on harvest cell counts and post-depletion obtained % CAR⁺:

1. Calculated DP formulation viable cell concentration:

*Pre* – Spin Harvest $$\frac{\text{total viable cell number}}{1} * \frac{\% \text{ CAR}}{25 \times 10^6 \text{ CAR} + \text{cells/mL}} =$$

DP formulation concentration

[total viable cells]

2. Divided the harvest total viable cell number by DP formulation concentration to calculated the volume needed to reach target cell concentration:

84

*Pre* – Spin Harvest $$\frac{\text{total viable cell number}}{1} * \frac{\text{mL}}{\text{DP formulation total viable cells}} =$$

target volume *CS5*

3. Resuspended cells to 0.5× target volume.

4. Performed second cell count on resuspended cell pellet.

5. Calculated remaining volume to resuspend cells to reach target viable cell concentration.

6. Diluted down to target cell concentration based on harvest cell count calculation.

o. Cryopreserved the appropriate number of cells for additional flow characterization, and comparability analysis.

(C) In Vitro Efficacy of Cell Expansion Optimization Assessed by a Cell Toxicity Assay This example describes an in vitro efficacy cell toxicity assay of the cells prepared in the example (B) above. The assay measured the absolute amount of viable cells in a co-culture assay.

Raji target cancer cells (CD19⁺) were labeled with eFluor 670 (APC channel) proliferation dye and plated @ 50K cells per well. Various ratios of unlabeled effector CAR T cells were added for each condition tested. Cell killing of target cells by effector CAR T cells was measured following 24 hours of culture by DAPI live/dead staining (Pacific Blue channel). Counting beads were added during flow analysis to normalize between samples. The number of viable cells (DAPI negative) in the test samples were enumerated and normalized to the number of viable cell in wells containing target cells alone to calculate percentage of cell lysis. Cytokine release into the culture media by CAR-T was analyzed in a multiplex ELISA assay (Luminex).

These experiments evaluated 1× versus 2× and 4×CTX110 manufacturing conditions. T-cells from three different donors were analyzed in parallel. In vitro efficacy was ascertained by two metrics, which were the 24 hour cell toxicity assay and by cytokine production.

TABLE 30

| Sample ID | Sample Description | Seeding Density (k cells/cm²) | Day Split (if applicable) | %CAR⁺ (Fresh) | % CAR⁺ (post thaw) |
|---|---|---|---|---|---|
| DP20-07-S1 | Donor #1-Std. (1×) | 500 | N/A | 64.16 | 66.6 |
| DP20-07-S2 | Donor #1-2× | 250 | N/A | 63.13 | 58.5 |
| DP20-07-S3 | Donor #1-4× | 125 | N/A | 54.28 | 67.6 |
| DP20-07-S4 | Donor #1-HY D4 split | 500 | Day 4 | 62.70 | |
| DP20-08-S1 | Donor #2-Std. (1×) | 500 | N/A | 34.65 | 36.6 |
| DP20-08-S2 | Donor #2-2× | 250 | N/A | 34.07 | 35.8 |
| DP20-08-S3 | Donor #2-4× | 125 | N/A | 33.99 | 34.0 |
| DP20-09-S1 | Donor #3-Std. (1×) | 500 | N/A | 68.66 | 64.7 |
| DP20-09-S2 | Donor #3-2× | 250 | N/A | 66.70 | 68.9 |
| DP20-09-S3 | Donor #3-4× | 125 | N/A | 65.34 | 63.9 |

Figure 20:
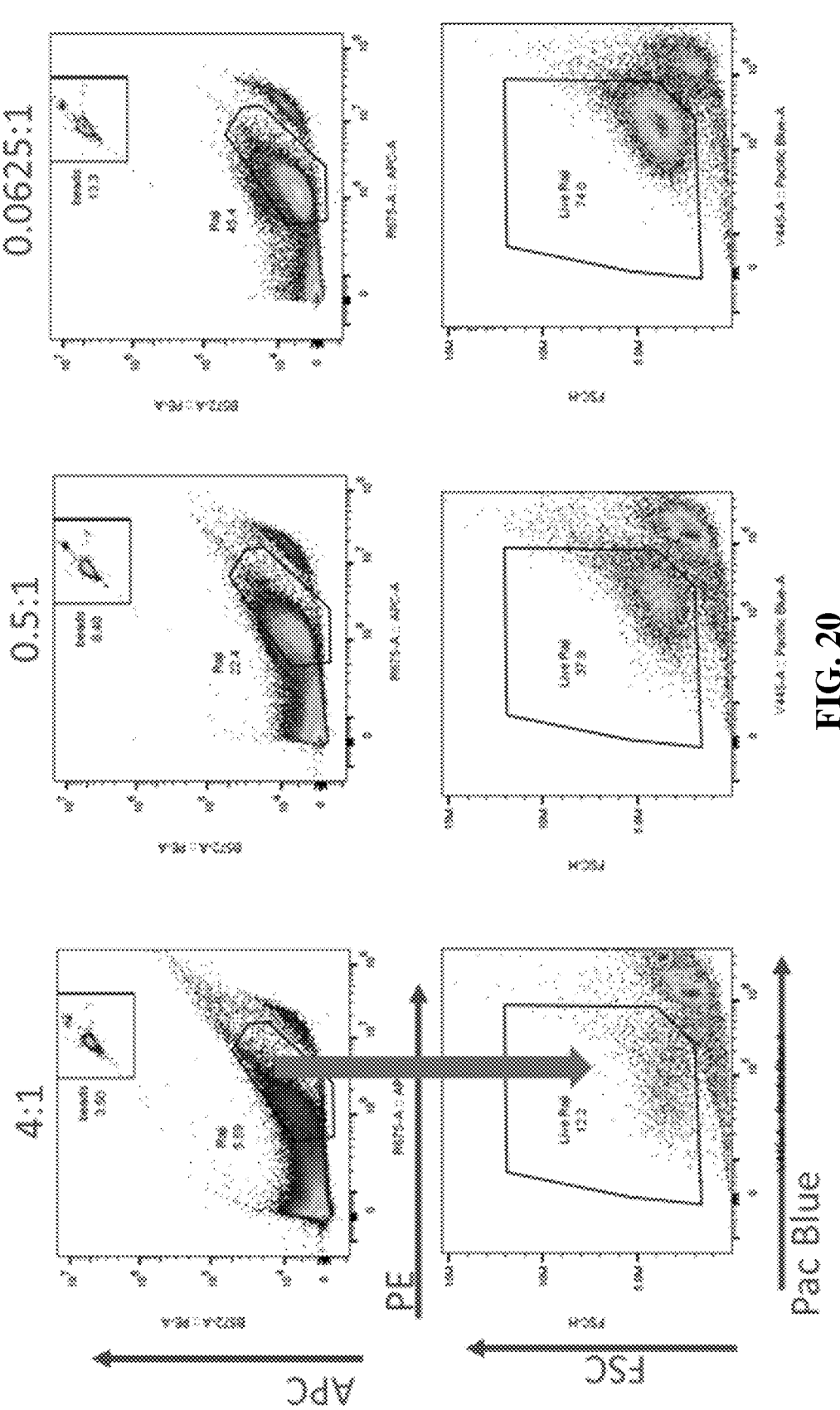
FIG. 20 shows an assay control FACS analysis by measuring CAR T-cell lysis. The CAR T-cells were CTX110 CAR T-cells. 81% of the T-cells were CAR$^+$.

FIG. 20 shows an assay control FACS analysis by measuring CAR T-cell lysis. The CAR T-cells were CTX110 CAR T-cells. 81% of the T-cells were CAR⁺.

FIGS. 21A-21C show the results of an assay control experiment measuring cell lysis and cytokine production in vitro. The assay used CTX110 CAR-T cells thawed from frozen stock. The T-cells were 80% CAR⁺ day 6 post HDR.

FIGS. 22A-22C show the results of an in vitro efficacy analysis showing that T-cells derived from each of the three donors had varying degrees of in vitro efficacy among 1×, 2× and 4× culture conditions.

FIGS. 23A-23C show the results of an analysis of cell lysis at different cell concentrations, demonstrating that cells derived from donors 1 and 2 showed similar responses despite differing percentages of CAR⁺ cells.

FIGS. 24A-24B show the results of an analysis of cell lysis from the three donors when normalized for CAR⁺ cells. Donors 2 and 3 behaved similarly in the assay when CAR cells are normalized. The assay was repeated with 2×CAR-T cell number for donor 2 at the same E:T ratios.

IFNγ production was also measure in the supernatant by ELISA. The IFNγ cytokine analysis mirrored the cell killing results in terms of dose response related to E:T ratios and there was some variability between donor responses. IL2 measurement was more variable among the donors. Significantly less IL2 production was observed in the media for donor 2 cells.

In summary, for each donor assessed, both 2× and 4× culture conditions show similar in vitro efficacy to the 1× manufacturing protocol.

(D) In Vivo Efficacy of Cell Expansion Optimization (In Vivo Survival Analysis)

CTX110 cells prepared according to the Example (C) above and were administered at a dose of 4e6 CAR⁺ T cells to mice in a Nalm6 xenograft tumor model, as shown in Table 31, below. Nalm6-Fluc-GFP tumor cells were inoculated into CIEA NOG mice 4 days prior to CAR-T administration. Weekly Bioluminescence (BLI, photons/s) assessment allows to assess tumor burden in mice.

TABLE 31

| Group | Group description | Tumor Cells | Cells to be dosed | Recipient per group |
|---|---|---|---|---|
| 1 | No treatment | 5.0e5 | 4.0e6 CAR-T | 10 |
| 2 | DP20-07-S1 | 5.0e5 | 4.0e6 CAR-T | 10 |
| 3 | DP20-07-S2 | 5.0e5 | 4.0e6 CAR-T | 10 |
| 4 | DP20-07-S3 | 5.0e5 | 4.0e6 CAR-T | 10 |
| 5 | DP20-07-S4 | 5.0e5 | 4.0e6 CAR-T | 10 |
| 6 | DP20-08-S1 | 5.0e5 | 4.0e6 CAR-T | 10 |
| 7 | DP20-08-S2 | 5.0e5 | 4.0e6 CAR-T | 10 |
| 8 | DP20-08-S3 | 5.0e5 | 4.0e6 CAR-T | 10 |
| 9 | DP20-09-S1 | 5.0e5 | 4.0e6 CAR-T | 10 |
| 10 | DP20-09-S2 | 5.0e5 | 4.0e6 CAR-T | 10 |
| 11 | DP20-09-S3 | 5.0e5 | 4.0e6 CAR-T | 10 |
| Total | | | | 110 |

For all three donors and expansion conditions, the animals dosed with CAR⁺ cells continue to survive at day 38, unlike animals dosed with untreated control cells, which did not survive beyond day 23 (see FIGS. 25A-25C), as shown in Table 32, below. BLI from mice dosed with CAR⁺ cells had similar tumor growth kinetics. (see FIGS. 26A-26C),

TABLE 32

| Median Survival | |
|---|---|
| Donor Type | Survival |
| 1. Untreated | 23 |
| 2. Donor #1, 1× | Undefined |
| 3. Donor #1, 2× | Undefined |

TABLE 32-continued

| Median Survival | |
|---|---|
| Donor Type | Survival |
| 4. Donor #1, 4× | 38.5 |
| 5. Donor #1, HY 4×, D4 | 39 |
| 6. Donor #2, 1× | Undefined |
| 7. Donor #2, 2× | Undefined |
| 8. Donor #2, 4× | Undefined |
| 9. Donor #3, 1× | Undefined |
| 10. Donor #3, 2× | Undefined |
| 11. Donor #3, 4× | Undefined |

Example 11: Methods for Manufacturing Genetically Engineered T Cells Expressing a Chimeric Antigen Receptor and Having Genetically Disrupted TRAC and β2M Genes The following describes an exemplary process for the manufacture of a T cell immunotherapy comprised of human allogeneic T cells that are genetically modified ex vivo using CRISPR/Cas9 (Clustered Regularly Interspaced Short Palindromic Repeats/CRISPR associated protein 9) gene editing components (sgRNA (single guide RNA) and Cas9 nuclease).

The modifications included targeted disruption of the TRAC and β2M loci, and the insertion of an chimeric antigen receptor (CAR) transgene into the TRAC locus using a recombinant adeno-associated virus vector (e.g.: a serotype 6 rAAV encoding an antigen directed chimeric T cell antigen receptor).

The manufacturing process is illustrated in FIG. 19. Structural information of the starting materials, including bacterially-derived Cas9 nuclease; two single guide RNAs (sgRNA), one sgRNA which targets the TRAC locus (e.g.: TA-1) and a second sgRNA which targets the β2M locus (e.g.: B2M-1), is provided herein. Exemplary amino acid sequences and nucleotide sequences of CARs in a rAAV vector are also provided.

T Cell Enrichment

T cells were enriched from the leukapheresis materials (Leukopaks) via magnetic separation using a mixture of anti-CD8 and anti-CD4 antibody-coated magnetic beads using an automated cell processing system. Prior to enrichment, leukopaks were sampled for cell count and viability (≥80%). Enriched cells were isolated in PBS/EDTA buffer with HSA, and then sampled for cell count, viability (≥80%), T cell purity (≥70% CD3), and sterility.

T Cell Cryopreservation

The cells were then centrifuged at 4±1° C. and resuspended in CryoStor CS5 at a target concentration of 50×10⁶ viable cells/mL. Cells were sampled for cell count, viability (≥80%) and then aliquoted into ethyl vinyl acetate cryobags at the target cell number of 2,500×10⁶ cells/bag (30-70 mL of cell suspension). One Leukopak was sufficient to produce 1-2 bags of T cells. Each bag was heat-sealed, labeled, stored at 2-8° C. until transferred to a controlled-rate freezer and subsequently transferred to vapor phase liquid nitrogen for storage.

T Cell Thawing and Activation

One frozen bag of enriched T cells was thawed, transferred into a 3 L bag and diluted into Supplemented X-VIVO™ 15 media (X-VIVO™ 15, 5% Human Serum, 100 IU/mL rhIL2, 100 IU/mL rhIL7). Cells were sampled for cell count and viability (≥70%). Cells were centrifuged at 540 g at 20±1° C. for 15 minutes. Cells were then resuspended in the Supplemented X-VIVO™ 15 media and sampled for cell count and viability (≥70%). Soluble colloidal polymeric nanomatrix conjugated to recombinant humanized CD3 and CD28 agonists solution was added at the ratio of 1:12.5 (v/v) to activate the cells.

Cells were seeded to a target density 2×10^6 viable cells/mL into two static cell culture vessels, each at a total volume of approximately 500 mL of Supplemented X-VIVO™ 15 media/colloidal polymeric nanomatrix conjugated to recombinant humanized CD3 and CD28 agonists. Static culture vessels were incubated at 37±1° C. and 5±1% $CO_2$ for 48±4 hours. Throughout the process, whenever the static culture vessels were handled, they were inspected for tears and leaks, and the presence of clear, yellow medium.

Dilution

Two (2) days later, supplemented X-VIVO™ 15 media was added to each static culture vessel to 5 L. Cells were further incubated at 37±1° C. and 5±1% $CO_2$ overnight.

Electroporation and Transduction

In preparation for electroporation, the volume of Supplemented X-VIVO™ 15 media was reduced to a final volume of approximately 500 mL using a pump connected to dip-tube in the static culture vessel, which was gently swirled to allow resuspension of cells into the media. Cells were sampled for cell count, and viability (≥70%). Cells were transferred to 500 mL centrifuge tubes and centrifuged at 540 g, at 20±1° C. for 15 minutes. Cell pellets were resuspended in Electroporation Buffer and centrifuged again under the same conditions. Cells were resuspended in Electroporation Buffer a second time to a target concentration of 300×10^6 cells/mL.

Cas9 nuclease was mixed with an sgRNA targeting TRAC or Cas9 nuclease was mixed with an sgRNA targeting β2M in separate microcentrifuge tubes. Each solution was incubated for no less than 10 minutes at room temperature to form each ribonucleoprotein complex (RNPs). The two Cas9/gRNA mixtures were combined, and mixed with the cells, bringing Cas9, TRAC sgRNA and B2M sgRNA to a final concentration of 0.3 mg/mL, 0.08 mg/mL and 0.2 mg/mL, respectively. The mixture was aliquoted and loaded into an electroporation cassette by pipetting. Cassettes were capped and sequentially electroporated by static electroporation using a transfection system. After electroporation, cells were pooled from each cassette in a 125 mL Erlenmeyer flask and incubated at 37° C. for no less than 20 minutes. Cells were sampled for viability (≥70%) and count.

Transduction was carried out as follows. Cells were diluted to 10^7 cells/mL with X-VIVO™ 15 media and freshly thawed rAAV was added at a MOI of 20,000 vg/cell. Cells were incubated at 37° C. 5% $CO_2$ for no less than 60 minutes.

Homology directed-repair (HDR) is a high-fidelity cell repair mechanism for DNA double strand breaks. HDR is used to introduce a CAR gene from the AAV template into the desired TRAC locus by using a homologous sequence on each end of the CAR gene.

Cell Expansion

Cells were diluted with Supplemented X-VIVO™ 15 media, sampled for cell viability (≥70%) and count, and seeded to a density between 0.2-0.5×10^6 viable cells/cm^2 into two static culture vessels, and one additional static culture vessel (satellite culture for cell monitoring). The static culture vessels were incubated at 37±1° C. and 5±1% $CO_2$. The cell cultures were incubated for up to 9 days. During this time, the cultures were supplemented every 3 to 4 days with 100 IU of rhIL2 and rhIL7 per mL of culture volume. The satellite static cell culture vessel was tested for cell count, viability, and T cell purity throughout expansion. When the cell density in the satellite culture vessel reached approximately 30×10^6/cm^2, the TCRαβ depletion was performed. If cell density in the satellite culture vessel did not reach 30×10^6/cm^2, TCRαβ depletion on the main cultures was performed on Day 9.

TCRαβ Depletion

The medium of each static cell culture vessel was reduced to a final volume of approximately 500 mL using a pump connected to the dip-tube in the static culture vessel. After the bulk of the media was removed, the static culture vessels were gently swirled to resuspend the cells in the media.

The cells were transferred to 500 mL centrifuge tubes fitted with dip-tubes that connect to the static culture vessels. Cells were sampled for viability (≥70%), count, and % CAR^+ cells. Cells were then centrifuged at 540×g at 20±1° C. for 15 minutes. Cell pellets were resuspended and pooled in less than 650 mL PBS/EDTA containing 0.5% HSA. Cell suspensions were transferred to a sterile bag which is connected to the automated cell processing system. The automated cell processing system incubated cells with a biotin-conjugated anti-TCRαβ antibody. Cells were washed and incubated with anti-biotin magnetic beads to allow for depletion of the TCRαβ^+ cells using the automated cell processing system. Cells were tested for cell count, viability (≥70%), and % CAR^+ cells (≥30-40%).

Cell Recovery

The depleted cells were resuspended in Supplemented X-VIVO™ 15 media and transferred into 3 L bag(s), seeded into static cell culture vessel(s) and incubated overnight at 37±1° C. and 5±1% $CO_2$.

Cell Harvest (Drug Substance)

To harvest cells, static culture vessels were removed from the incubator and allowed to rest for sedimentation of cells. Growth medium was removed from each static culture vessel to a final volume of approximately 500 mL using a pump. Removed media was sampled for sterility. Static culture vessels were gently swirled to allow the cells to resuspend in the media. The contents of each static culture vessel were transferred in a 3 L transfer bag using a pump and was filtered through a 40 μm blood transfusion filter by gravity into a separate sterile 3 L bag. Cells were sampled for concentration and viability.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

---

What is claimed is:

1. A method for manufacturing genetically engineered T cells, the method comprising:

(i) providing a first population of T cells obtained from human blood cells;

(ii) incubating the first population of T cells in the presence of a T cell activating agent in a cell culture vessel to produce a second population of T cells, wherein the second population of T cells comprises activated T cells;

(iii) introducing into the second population of T cells a first ribonucleoprotein (RNP) complex comprising a first Cas9 enzyme and a first guide RNA (gRNA) targeting a T cell receptor alpha chain constant region (TRAC) gene, and a second RNP complex comprising a second Cas9 enzyme and a second gRNA targeting a beta-2 microglobulin ($\beta$2M) gene to produce a third population of T cells, wherein the third population of T cells comprises T cells having the TRAC gene disrupted and the $\beta$2M gene disrupted, wherein the first RNP complex and the second RNP complex are introduced into the second population of T cells in one electroporation event;

(iv) incubating the third population of T cells with an adeno-associated viral (AAV) vector to produce a fourth population of T cells, wherein the AAV vector comprises a nucleic acid sequence encoding a chimeric antigen receptor (CAR) and wherein the nucleic acid sequence is flanked by homologous sequences to the TRAC gene locus, and wherein the fourth population of T cells comprises activated T cells expressing the CAR and having the TRAC gene disrupted and the $\beta$2M gene disrupted;

(v) expanding the fourth population of T cells thereby producing an expanded T cell population;

(vi) removing TCR$\alpha\beta^+$ T cells from the expanded T cell population to produce a population of genetically engineered T cells, wherein the population of genetically engineered T cells comprises T cells expressing the CAR and having the TRAC gene and the $\beta$2M gene disrupted; and (vii) harvesting the population of genetically engineered T cells.

2. The method of claim 1, wherein the first population of T cells is derived from cryopreserved T cells enriched from human blood cells.

3. The method of claim 1, wherein the first population of T cells is prepared by a process comprising: (a) obtaining blood cells from a human donor; and (b) enriching CD4$^+$ T cells and/or CD8$^+$ T cells from the blood cells.

4. The method of claim 3, wherein step (b) is performed using magnetic beads conjugated with anti-CD4 and/or anti-CD8 antibodies.

5. The method of claim 3, further comprising (c) cryopreserving the enriched CD4$^+$ T cells and CD8$^+$ T cells produced in step (b).

6. The method of claim 1, wherein the first population of T cells has a cell viability of at least 80% and/or a purity of at least 80% of CD4$^+$ and CD8$^+$ T cells.

7. The method of claim 1, wherein the T cell activating agent comprises a CD3 agonist and a CD28 agonist, and wherein the CD3 agonist and CD28 agonist are attached to a nanomatrix particle.

8. The method of claim 1, wherein step (ii) is performed by incubating the first population of T cells with the T cell activating agent in the cell culture vessel at a cell seeding density of $2\times10^6$/cm$^2$ and a cell concentration of $2\times10^6$ cells/mL for 48 hours.

9. The method of claim 1, wherein the ratio of the T cell activating agent to medium in the mixture is 1:12.5 (v/v).

10. The method of claim 1, further comprising diluting the T cell activating agent in the second population of T cells after step (ii) to reduce activation and to allow cells to recover before step (iii).

11. The method of claim 1, wherein the amount of the first Cas9 enzyme in the first RNP complex is the same as the amount of the second Cas9 enzyme in the second RNP complex.

12. The method of claim 1, wherein the concentration of the first Cas9 enzyme is 0.15 mg/mL, the concentration of the second Cas9 enzyme is 0.15 mg/mL, the concentration of the first gRNA targeting the TRAC gene is 0.08 mg/mL, and the concentration of the second gRNA targeting the $\beta$2M gene is 0.2 mg/mL.

13. The method of claim 1, wherein the cell concentration in step (iii) is $100\times10^6$ cells/mL to $300\times10^6$ cells/mL.

14. The method of claim 1, wherein the cell number in each vessel in step (iii) is $3\times10^8$ cells.

15. The method of claim 1, wherein the AAV vector has a multiplicity of infection (MOI) value of 10,000 to 80,000.

16. The method of claim 15, wherein the MOI of the AAV vector is 20,000.

17. The method of claim 15, wherein the AAV vector is AAV serotype 6 (AAV6) vector.

18. The method of claim 1, wherein step (v) is performed by culturing the fourth population of T cells in a cell culture vessel at a seeding density of $2\times10^5$ cells/cm$^2$ to $7\times10^5$ cells/cm$^2$ for 6 days to 12 days.

19. The method of claim 18, wherein the cell culture vessel is a static cell culture vessel allowing for cell expansion for 7 days to 9 days without medium change.

20. The method of claim 1, wherein step (v) is performed by culturing the fourth population of T cells in a cell culture vessel at a seeding density of $2\times10^5$ cells/cm$^2$ to $5\times10^5$ cells/cm$^2$ for 7 days to 9 days.

21. The method of claim 20, wherein the fourth population of T cells is cultured at a seeding density of $3\times10^5$ cells/cm$^2$ to $5\times10^5$ cells/cm$^2$.

22. The method of claim 20, wherein the cell culture vessel is a static cell culture vessel allowing for cell expansion for 10 days to 12 days without medium change.

23. The method of claim 1, wherein step (vi) is performed by contacting the expanded cells to beads on which anti-TCR$\alpha\beta$ antibodies are immobilized, and collecting unbound cells.

24. The method of claim 1, wherein the expanding step comprises seeding the T cells at a density between 150,000 cells/cm$^2$ and 500,000 cells/cm$^2$, in a cell vessel.

25. The method of claim 24, wherein the expanding step comprises seeding the T cells at a density between 300,000 cells/cm$^2$ and 500,000 cells/cm$^2$ in a cell vessel.

26. The method of claim 1, wherein the first Cas9 enzyme, the second Cas9 enzyme, or both are *Streptococcus pyogenes* Cas9 nuclease (spCas9).

27. The method of claim 1, wherein the first Cas9 enzyme and the second Cas9 enzyme are the same.

28. The method of claim 1, wherein the first Cas9 enzyme comprises the amino acid sequence of SEQ ID NO: 1, and/or wherein the second Cas9 enzyme comprises the amino acid sequence of SEQ ID NO: 1.

29. The method of claim 1, wherein the first gRNA targeting the TRAC gene comprises a spacer sequence of SEQ ID NO: 4.

30. The method of claim 29, wherein the first gRNA targeting the TRAC gene comprises the nucleotide sequence of SEQ ID NO: 2.

31. The method of claim 30, wherein the first gRNA, the second gRNA, or both comprise one or more 2'-O-methyl phosphorothioate modification.

32. The method of claim 1, wherein the second gRNA targeting the β2M gene comprises a spacer sequence of SEQ ID NO: 8.

33. The method of claim 32, wherein the second gRNA targeting the β2M gene comprises the nucleotide sequence of SEQ ID NO: 6.

34. The method of claim 1, wherein the CAR comprises an extracellular domain targeting a cancer antigen, a transmembrane domain, a co-stimulatory domain, and a CD3z cytoplasmic signaling domain.

35. The method of claim 1, wherein the CAR binds CD19.

36. The method of claim 35, wherein the extracellular domain comprises a single-chain variable fragment (scFv), the transmembrane domain is derived from CD8a, and/or the co-stimulatory domain is derived from CD28.

37. The method of claim 36, wherein the CAR comprises the amino acid sequence of SEQ ID NO: 37.

38. The method of claim 1, wherein the CAR binds BCMA.

39. The method of claim 38, wherein the extracellular domain comprises a single-chain variable fragment (scFv), the transmembrane domain is derived from CD8a, and/or the co-stimulatory domain is derived from 4-1BB.

40. The method of claim 39 wherein the CAR comprises the amino acid sequence of SEQ ID NO: 61.

* * * * *

SEQUENCE LISTING

```
<160> NUMBER OF SEQ ID NOS: 76

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95
```

```
Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
            210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510
```

-continued

```
Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
```

```
              930              935              940
Glu Asn Asp Lys Leu Ile Arg Glu Val Lys Val Ile Thr Leu Lys Ser
945              950              955              960

Lys Leu Val Ser Asp Phe Arg Lys Asp Phe Gln Phe Tyr Lys Val Arg
              965              970              975

Glu Ile Asn Asn Tyr His His Ala His Asp Ala Tyr Leu Asn Ala Val
              980              985              990

Val Gly Thr Ala Leu Ile Lys Lys  Tyr Pro Lys Leu Glu  Ser Glu Phe
         995              1000              1005

Val Tyr  Gly Asp Tyr Lys Val  Tyr Asp Val Arg Lys  Met Ile Ala
    1010              1015              1020

Lys Ser  Glu Gln Glu Ile Gly  Lys Ala Thr Ala Lys  Tyr Phe Phe
    1025              1030              1035

Tyr Ser  Asn Ile Met Asn Phe  Phe Lys Thr Glu Ile  Thr Leu Ala
    1040              1045              1050

Asn Gly  Glu Ile Arg Lys Arg  Pro Leu Ile Glu Thr  Asn Gly Glu
    1055              1060              1065

Thr Gly  Glu Ile Val Trp Asp  Lys Gly Arg Asp Phe  Ala Thr Val
    1070              1075              1080

Arg Lys  Val Leu Ser Met Pro  Gln Val Asn Ile Val  Lys Lys Thr
    1085              1090              1095

Glu Val  Gln Thr Gly Gly Phe  Ser Lys Glu Ser Ile  Leu Pro Lys
    1100              1105              1110

Arg Asn  Ser Asp Lys Leu Ile  Ala Arg Lys Lys Asp  Trp Asp Pro
    1115              1120              1125

Lys Lys  Tyr Gly Gly Phe Asp  Ser Pro Thr Val Ala  Tyr Ser Val
    1130              1135              1140

Leu Val  Val Ala Lys Val Glu  Lys Gly Lys Ser Lys  Lys Leu Lys
    1145              1150              1155

Ser Val  Lys Glu Leu Leu Gly  Ile Thr Ile Met Glu  Arg Ser Ser
    1160              1165              1170

Phe Glu  Lys Asn Pro Ile Asp  Phe Leu Glu Ala Lys  Gly Tyr Lys
    1175              1180              1185

Glu Val  Lys Lys Asp Leu Ile  Ile Lys Leu Pro Lys  Tyr Ser Leu
    1190              1195              1200

Phe Glu  Leu Glu Asn Gly Arg  Lys Arg Met Leu Ala  Ser Ala Gly
    1205              1210              1215

Glu Leu  Gln Lys Gly Asn Glu  Leu Ala Leu Pro Ser  Lys Tyr Val
    1220              1225              1230

Asn Phe  Leu Tyr Leu Ala Ser  His Tyr Glu Lys Leu  Lys Gly Ser
    1235              1240              1245

Pro Glu  Asp Asn Glu Gln Lys  Gln Leu Phe Val Glu  Gln His Lys
    1250              1255              1260

His Tyr  Leu Asp Glu Ile Ile  Glu Gln Ile Ser Glu  Phe Ser Lys
    1265              1270              1275

Arg Val  Ile Leu Ala Asp Ala  Asn Leu Asp Lys Val  Leu Ser Ala
    1280              1285              1290

Tyr Asn  Lys His Arg Asp Lys  Pro Ile Arg Glu Gln  Ala Glu Asn
    1295              1300              1305

Ile Ile  His Leu Phe Thr Leu  Thr Asn Leu Gly Ala  Pro Ala Ala
    1310              1315              1320

Phe Lys  Tyr Phe Asp Thr Thr  Ile Asp Arg Lys Arg  Tyr Thr Ser
    1325              1330              1335
```

-continued

```
Thr Lys  Glu Val Leu Asp Ala  Thr Leu Ile His Gln  Ser Ile Thr
    1340             1345              1350

Gly Leu  Tyr Glu Thr Arg Ile  Asp Leu Ser Gln Leu  Gly Gly Asp
    1355             1360              1365

<210> SEQ ID NO 2
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with a 2'-O-methyl phosphorothioate
<220> FEATURE:
<221> NAME/KEY: misc_feature
<222> LOCATION: (97)..(100)
<223> OTHER INFORMATION: modified with a 2'-O-methyl phosphorothioate

<400> SEQUENCE: 2
agagcaacag ugcuguggcc guuuuagagc uagaaauagc aaguuaaaau aaggcuaguc      60
cguuaucaac uugaaaaagu ggcaccgagu cggugcuuuu                          100

<210> SEQ ID NO 3
<211> LENGTH: 100
<212> TYPE: RNA
<213> ORGANISM: Artificial Sequence
<220> FEATURE:
<223> OTHER INFORMATION: Synthetic

<400> SEQUENCE: 3
agagcaacag ugcuguggcc guuuuagagc uagaaauagc aaguuaaaau aaggcuaguc      60
cguuaucaac uugaaaaagu ggcaccgagu cggugcuuuu                          100

<210> SEQ ID NO 4
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with a 2'-O-methyl phosphorothioate

<400> SEQUENCE: 4
agagcaacag ugcuguggcc                                                 20

<210> SEQ ID NO 5
<211> LENGTH: 20
<212> TYPE: RNA
<213> ORGANISM: Artificial Sequence
<220> FEATURE:
<223> OTHER INFORMATION: Synthetic

<400> SEQUENCE: 5
agagcaacag ugcuguggcc                                                 20

<210> SEQ ID NO 6
<211> LENGTH: 100
<212> TYPE: RNA
<213> ORGANISM: Artificial Sequence
<220> FEATURE:
<223> OTHER INFORMATION: Synthetic
<220> FEATURE:
```

-continued

```
<221> NAME/KEY: misc_feature
<222> LOCATION: (1)..(4)
<223> OTHER INFORMATION: modified with a 2'-O-methyl phosphorothioate
<220> FEATURE:
<221> NAME/KEY: misc_feature
<222> LOCATION: (97)..(100)
<223> OTHER INFORMATION: modified with a 2'-O-methyl phosphorothioate

<400> SEQUENCE: 6
gcuacucucu cuuucuggcc guuuuagagc uagaaauagc aaguuaaaau aaggcuaguc        60
cguuaucaac uugaaaaagu ggcaccgagu cggugcuuuu                            100

<210> SEQ ID NO 7
<211> LENGTH: 100
<212> TYPE: RNA
<213> ORGANISM: Artificial Sequence
<220> FEATURE:
<223> OTHER INFORMATION: Synthetic

<400> SEQUENCE: 7
gcuacucucu cuuucuggcc guuuuagagc uagaaauagc aaguuaaaau aaggcuaguc        60
cguuaucaac uugaaaaagu ggcaccgagu cggugcuuuu                            100

<210> SEQ ID NO 8
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with a 2'-O-methyl phosphorothioate

<400> SEQUENCE: 8
gcuacucucu cuuucuggcc                                                   20

<210> SEQ ID NO 9
<211> LENGTH: 20
<212> TYPE: RNA
<213> ORGANISM: Artificial Sequence
<220> FEATURE:
<223> OTHER INFORMATION: Synthetic

<400> SEQUENCE: 9
gcuacucucu cuuucuggcc                                                   20

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
agagcaacag tgctgtggcc tgg                                               23

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
agagcaacag tgctgtggcc                                                   20
```

-continued

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12
gctactctct ctttctggcc tgg                                              23

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gctactctct ctttctggcc                                                  20

<210> SEQ ID NO 14
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 14
nnnnnnnnnn nnnnnnnnnn guuuuagagc uagaaauagc aaguuaaaau aaggcuaguc      60
cguuaucaac uugaaaaagu ggcaccgagu cggugcuuuu                            100

<210> SEQ ID NO 15
<211> LENGTH: 96
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 15
nnnnnnnnnn nnnnnnnnnn guuuuagagc uagaaauagc aaguuaaaau aaggcuaguc      60
cguuaucaac uugaaaaagu ggcaccgagu cggugc                                96

<210> SEQ ID NO 16
<211> LENGTH: 114
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: n is a, c, g, or u
<220> FEATURE:
<221> NAME/KEY: misc_feature
<222> LOCATION: (17)..(30)
<223> OTHER INFORMATION: may be absent
<220> FEATURE:
<221> NAME/KEY: misc_feature
<222> LOCATION: (108)..(114)

<223> OTHER INFORMATION: may be absent

<400> SEQUENCE: 16
nnnnnnnnnn nnnnnnnnnn nnnnnnnnnn guuuuagagc uagaaauagc aaguuaaaau      60
aaggcuaguc cguuaucaac uugaaaaagu ggcaccgagu cggugcuuuu uuuu      114

<210> SEQ ID NO 17
<211> LENGTH: 19
<212> TYPE: DNA
<213> ORGANISM: Artificial Sequence
<220> FEATURE:
<223> OTHER INFORMATION: Synthetic

<400> SEQUENCE: 17
aagagcaaca aatctgact      19

<210> SEQ ID NO 18
<211> LENGTH: 39
<212> TYPE: DNA
<213> ORGANISM: Artificial Sequence
<220> FEATURE:
<223> OTHER INFORMATION: Synthetic

<400> SEQUENCE: 18
aagagcaaca gtgctgtgcc tggagcaaca aatctgact      39

<210> SEQ ID NO 19
<211> LENGTH: 33
<212> TYPE: DNA
<213> ORGANISM: Artificial Sequence
<220> FEATURE:
<223> OTHER INFORMATION: Synthetic

<400> SEQUENCE: 19
aagagcaaca gtgctggagc aacaaatctg act      33

<210> SEQ ID NO 20
<211> LENGTH: 34
<212> TYPE: DNA
<213> ORGANISM: Artificial Sequence
<220> FEATURE:
<223> OTHER INFORMATION: Synthetic

<400> SEQUENCE: 20
aagagcaaca gtgcctggag caacaaatct gact      34

<210> SEQ ID NO 21
<211> LENGTH: 19
<212> TYPE: DNA
<213> ORGANISM: Artificial Sequence
<220> FEATURE:
<223> OTHER INFORMATION: Synthetic

<400> SEQUENCE: 21
aagagcaaca gtgctgact      19

<210> SEQ ID NO 22
<211> LENGTH: 41
<212> TYPE: DNA
<213> ORGANISM: Artificial Sequence
<220> FEATURE:
<223> OTHER INFORMATION: Synthetic

<400> SEQUENCE: 22
aagagcaaca gtgctgtggg cctggagcaa caaatctgac t      41

```
<210> SEQ ID NO 23
<211> LENGTH: 38
<212> TYPE: DNA
<213> ORGANISM: Artificial Sequence
<220> FEATURE:
<223> OTHER INFORMATION: Synthetic

<400> SEQUENCE: 23
aagagcaaca gtgctggcct ggagcaacaa atctgact                              38

<210> SEQ ID NO 24
<211> LENGTH: 41
<212> TYPE: DNA
<213> ORGANISM: Artificial Sequence
<220> FEATURE:
<223> OTHER INFORMATION: Synthetic

<400> SEQUENCE: 24
aagagcaaca gtgctgtgtg cctggagcaa caaatctgac t                         41

<210> SEQ ID NO 25
<211> LENGTH: 79
<212> TYPE: DNA
<213> ORGANISM: Artificial Sequence
<220> FEATURE:
<223> OTHER INFORMATION: Synthetic

<400> SEQUENCE: 25
cgtggcctta gctgtgctcg cgctactctc tctttctgcc tggaggctat ccagcgtgag     60
tctctcctac cctcccgct                                                  79

<210> SEQ ID NO 26
<211> LENGTH: 78
<212> TYPE: DNA
<213> ORGANISM: Artificial Sequence
<220> FEATURE:
<223> OTHER INFORMATION: Synthetic

<400> SEQUENCE: 26
cgtggcctta gctgtgctcg cgctactctc tctttcgcct ggaggctatc cagcgtgagt     60
ctctcctacc ctcccgct                                                   78

<210> SEQ ID NO 27
<211> LENGTH: 75
<212> TYPE: DNA
<213> ORGANISM: Artificial Sequence
<220> FEATURE:
<223> OTHER INFORMATION: Synthetic

<400> SEQUENCE: 27
cgtggcctta gctgtgctcg cgctactctc tctttctgga ggctatccag cgtgagtctc     60
tcctaccctc ccgct                                                      75

<210> SEQ ID NO 28
<211> LENGTH: 84
<212> TYPE: DNA
<213> ORGANISM: Artificial Sequence
<220> FEATURE:
<223> OTHER INFORMATION: Synthetic

<400> SEQUENCE: 28
cgtggcctta gctgtgctcg cgctactctc tctttctgga tagcctggag gctatccagc     60
```

-continued gtgagtctct cctaccctcc cgct                                               84

<210> SEQ ID NO 29
<211> LENGTH: 55
<212> TYPE: DNA
<213> ORGANISM: Artificial Sequence
<220> FEATURE:
<223> OTHER INFORMATION: Synthetic

<400> SEQUENCE: 29
cgtggcctta gctgtgctcg cgctatccag cgtgagtctc tcctaccctc ccgct           55

<210> SEQ ID NO 30
<211> LENGTH: 82
<212> TYPE: DNA
<213> ORGANISM: Artificial Sequence
<220> FEATURE:
<223> OTHER INFORMATION: Synthetic

<400> SEQUENCE: 30
cgtggcctta gctgtgctcg cgctactctc tctttctgtg gcctggaggc tatccagcgt       60
gagtctctcc taccctcccg ct                                                 82

<210> SEQ ID NO 31
<211> LENGTH: 23
<212> TYPE: PRT
<213> ORGANISM: Artificial Sequence
<220> FEATURE:
<223> OTHER INFORMATION: Synthetic

<400> SEQUENCE: 31

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 32
<211> LENGTH: 120
<212> TYPE: DNA
<213> ORGANISM: Artificial Sequence
<220> FEATURE:
<223> OTHER INFORMATION: Synthetic

<400> SEQUENCE: 32
tcaaagcgga gtaggttgtt gcattccgat tacatgaata tgactcctcg ccggcctggg        60
ccgacaagaa aacattacca accctatgcc cccccacgag acttcgctgc gtacaggtcc       120

<210> SEQ ID NO 33
<211> LENGTH: 40
<212> TYPE: PRT
<213> ORGANISM: Artificial Sequence
<220> FEATURE:
<223> OTHER INFORMATION: Synthetic

<400> SEQUENCE: 33

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 34

-continued

```
<211> LENGTH: 336
<212> TYPE: DNA
<213> ORGANISM: Artificial Sequence
<220> FEATURE:
<223> OTHER INFORMATION: Synthetic

<400> SEQUENCE: 34
cgagtgaagt tttcccgaag cgcagacgct ccggcatatc agcaaggaca gaatcagctg        60
tataacgaac tgaatttggg acgccgcgag gagtatgacg tgcttgataa acgccggggg       120
agagacccgg aaatgggggg taaaccccga agaaagaatc cccaagaagg actctacaat       180
gaactccaga aggataagat ggcggaggcc tactcagaaa taggtatgaa gggcgaacga       240
cgacggggaa aaggtcacga tggcctctac caagggttga gtacggcaac caaagatacg       300
tacgatgcac tgcatatgca ggccctgcct cccaga                                 336

<210> SEQ ID NO 35
<211> LENGTH: 112
<212> TYPE: PRT
<213> ORGANISM: Artificial Sequence
<220> FEATURE:
<223> OTHER INFORMATION: Synthetic

<400> SEQUENCE: 35

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 36
<211> LENGTH: 1518
<212> TYPE: DNA
<213> ORGANISM: Artificial Sequence
<220> FEATURE:
<223> OTHER INFORMATION: Synthetic

<400> SEQUENCE: 36
atgcttcttt tggttacgtc tctgttgctt tgcgaacttc ctcatccagc gttcttgctg        60
atccccgata ttcagatgac tcagaccacc agtagcttgt ctgcctcact gggagaccga       120
gtaacaatct cctgcagggc aagtcaagac attagcaaat acctcaattg gtaccagcag       180
aagcccgacg gaacggtaaa actcctcatc tatcatacgt caaggttgca ttccggagta       240
ccgtcacgat tttcaggttc tgggagcgga actgactatt ccttgactat ttcaaacctc       300
gagcaggagg acattgcgac atattttttgt caacaaggta ataccctccc ttacactttc       360
ggaggaggaa ccaaactcga aattaccggg tccaccagtg gctctgggaa gcctggcagt       420
ggagaaggtt ccactaaagg cgaggtgaag ctccaggaga gcggccccgg tctcgttgcc       480
cccagtcaaa gcctctctgt aacgtgcaca gtgagtggtg tatcattgcc tgattatggc       540
```

```
gtctcctgga taaggcagcc cccgcgaaag ggtcttgaat ggcttggggt aatatggggc        600
tcagagacaa cgtattataa ctccgctctc aaaagtcgct tgacgataat aaaagataac        660
tccaagagtc aagttttcct taaaatgaac agtttgcaga ctgacgatac cgctatatat        720
tattgtgcta aacattatta ctacggcggt agttacgcga tggattattg ggggcagggg        780
acttctgtca cagtcagtag tgctgctgcc tttgtcccgg tatttctccc agccaaaccg        840
accacgactc ccgccccgcg ccctccgaca cccgctccca ccatcgcctc tcaacctctt        900
agtcttcgcc ccgaggcatg ccgacccgcc gccgggggtg ctgttcatac gaggggcttg        960
gacttcgctt gtgatattta catttgggct ccgttggcgg gtacgtgcgg cgtccttttg       1020
ttgtcactcg ttattacttt gtattgtaat cacaggaatc gctcaaagcg gagtaggttg       1080
ttgcattccg attacatgaa tatgactcct cgccggcctg ggccgacaag aaaacattac       1140
caaccctatg cccccccacg agacttcgct gcgtacaggt cccgagtgaa gttttcccga       1200
agcgcagacg ctccggcata tcagcaagga cagaatcagc tgtataacga actgaatttg       1260
ggacgccgcg aggagtatga cgtgcttgat aaacgccggg ggagagaccc ggaaatgggg       1320
ggtaaacccc gaagaaagaa tccccaagaa ggactctaca atgaactcca gaaggataag       1380
atggcggagg cctactcaga aataggtatg aagggcgaac gacgacgggg aaaaggtcac       1440
gatggcctct accaagggtt gagtacggca accaaagata cgtacgatgc actgcatatg       1500
caggccctgc ctcccaga                                                     1518
```

```
<210> SEQ ID NO 37
<211> LENGTH: 506
<212> TYPE: PRT
<213> ORGANISM: Artificial Sequence
<220> FEATURE:
<223> OTHER INFORMATION: Synthetic

<400> SEQUENCE: 37

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190
```

-continued

```
Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Phe Val
                260                 265                 270

Pro Val Phe Leu Pro Ala Lys Pro Thr Thr Thr Pro Ala Pro Arg Pro
            275                 280                 285

Pro Thr Pro Ala Pro Thr Ile Ala Ser Gln Pro Leu Ser Leu Arg Pro
        290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
                340                 345                 350

Asn Arg Ser Lys Arg Ser Arg Leu Leu His Ser Asp Tyr Met Asn Met
            355                 360                 365

Thr Pro Arg Arg Pro Gly Pro Thr Arg Lys His Tyr Gln Pro Tyr Ala
        370                 375                 380

Pro Pro Arg Asp Phe Ala Ala Tyr Arg Ser Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
            435                 440                 445

Gln Glu Gly Leu Tyr Asn Glu Leu Gln Lys Asp Lys Met Ala Glu Ala
        450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
            500                 505
```

```
<210> SEQ ID NO 38
<211> LENGTH: 130
<212> TYPE: DNA
<213> ORGANISM: Artificial Sequence
<220> FEATURE:
<223> OTHER INFORMATION: Synthetic

<400> SEQUENCE: 38
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct                                                            130

<210> SEQ ID NO 39
```

-continued

```
<211> LENGTH: 141
<212> TYPE: DNA
<213> ORGANISM: Artificial Sequence
<220> FEATURE:
<223> OTHER INFORMATION: Synthetic

<400> SEQUENCE: 39
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag ctgcctgcag g                                               141

<210> SEQ ID NO 40
<211> LENGTH: 800
<212> TYPE: DNA
<213> ORGANISM: Artificial Sequence
<220> FEATURE:
<223> OTHER INFORMATION: Synthetic

<400> SEQUENCE: 40
gagatgtaag gagctgctgt gacttgctca aggccttata tcgagtaaac ggtagtgctg      60
gggcttagac gcaggtgttc tgatttatag ttcaaaacct ctatcaatga gagagcaatc     120
tcctggtaat gtgatagatt tcccaactta atgccaacat accataaacc tcccattctg     180
ctaatgccca gcctaagttg gggagaccac tccagattcc aagatgtaca gtttgctttg     240
ctgggccttt ttcccatgcc tgcctttact ctgccagagt tatattgctg gggttttgaa     300
gaagatccta ttaaataaaa gaataagcag tattattaag tagccctgca tttcaggttt     360
ccttgagtgg caggccaggc ctggccgtga acgttcactg aaatcatggc ctcttggcca     420
agattgatag cttgtgcctg tccctgagtc ccagtccatc acgagcagct ggtttctaag     480
atgctatttc ccgtataaag catgagaccg tgacttgcca gccccacaga gccccgccct     540
tgtccatcac tggcatctgg actccagcct gggttggggc aaagagggaa atgagatcat     600
gtcctaaccc tgatcctctt gtcccacaga tatccagaac cctgaccctg ccgtgtacca     660
gctgagagac tctaaatcca gtgacaagtc tgtctgccta ttcaccgatt ttgattctca     720
aacaaatgtg tcacaaagta aggattctga tgtgtatatc acagacaaaa ctgtgctaga     780
catgaggtct atggacttca                                                 800

<210> SEQ ID NO 41
<211> LENGTH: 804
<212> TYPE: DNA
<213> ORGANISM: Artificial Sequence
<220> FEATURE:
<223> OTHER INFORMATION: Synthetic

<400> SEQUENCE: 41
tggagcaaca aatctgactt tgcatgtgca aacgccttca acaacagcat tattccagaa      60
gacaccttct tccccagccc aggtaagggc agctttggtg ccttcgcagg ctgtttcctt     120
gcttcaggaa tggccaggtt ctgcccagag ctctggtcaa tgatgtctaa aactcctctg     180
attggtggtc tcggccttat ccattgccac caaaaccctc tttttactaa gaaacagtga     240
gccttgttct ggcagtccag agaatgacac gggaaaaaag cagatgaaga gaaggtggca     300
ggagagggca cgtggcccag cctcagtctc tccaactgag ttcctgcctg cctgcctttg     360
ctcagactgt ttgcccctta ctgctcttct aggcctcatt ctaagcccct tctccaagtt     420
gcctctcctt atttctccct gtctgccaaa aaatctttcc cagctcacta agtcagtctc     480
acgcagtcac tcattaaccc accaatcact gattgtgccg gcacatgaat gcaccaggtg     540
```

-continued

```
ttgaagtgga ggaattaaaa agtcagatga ggggtgtgcc cagaggaagc accattctag      600
ttgggggagc ccatctgtca gctgggaaaa gtccaaataa cttcagattg gaatgtgttt      660
taactcaggg ttgagaaaac agctaccttc aggacaaaag tcaggaagg gctctctgaa       720 gaaatgctac ttgaagatac cagccctacc aagggcaggg agaggaccct atagaggcct      780
gggacaggag ctcaatgaga aagg                                            804

<210> SEQ ID NO 42
<211> LENGTH: 1178
<212> TYPE: DNA
<213> ORGANISM: Artificial Sequence
<220> FEATURE:
<223> OTHER INFORMATION: Synthetic

<400> SEQUENCE: 42
ggctccggtg cccgtcagtg ggcagagcgc acatcgccca cagtccccga gaagttgggg      60
ggaggggtcg gcaattgaac cggtgcctag agaaggtggc gcggggtaaa ctgggaaagt      120
gatgtcgtgt actggctccg cctttttccc gagggtgggg gagaaccgta tataagtgca      180
gtagtcgccg tgaacgttct ttttcgcaac gggtttgccg ccagaacaca ggtaagtgcc      240
gtgtgtggtt cccgcgggcc tggcctcttt acgggttatg gcccttgcgt gccttgaatt      300
acttccactg gctgcagtac gtgattcttg atcccgagct tcgggttgga agtgggtggg      360
agagttcgag gccttgcgct taaggagccc cttcgcctcg tgcttgagtt gaggcctggc      420
ctgggcgctg gggccgccgc gtgcgaatct ggtggcacct tcgcgcctgt ctcgctgctt      480
tcgataagtc tctagccatt taaaattttt gatgacctgc tgcgacgctt tttttctggc      540
aagatagtct tgtaaatgcg ggccaagatc tgcacactgg tatttcggtt tttggggccg      600
cgggcggcga cggggcccgt gcgtcccagc gcacatgttc ggcgaggcgg ggcctgcgag      660
cgcggccacc gagaatcgga cggggtagt ctcaagctgg ccggcctgct ctggtgcctg       720
gcctcgcgcc gccgtgtatc gccccgccct gggcggcaag gctggcccgg tcggcaccag      780
ttgcgtgagc ggaaagatgg ccgcttcccg gccctgctgc agggagctca aaatggagga      840
cgcggcgctc gggagagcgg gcgggtgagt cacccacaca aaggaaaagg gcctttccgt      900
cctcagccgt cgcttcatgt gactccacgg agtaccgggc gccgtccagg cacctcgatt      960
agttctcgag cttttggagt acgtcgtctt taggttgggg ggaggggttt tatgcgatgg      1020
agtttcccca cactgagtgg gtggagactg aagttaggcc agcttggcac ttgatgtaat      1080
tctccttgga atttgccctt tttgagtttg gatcttggtt cattctcaag cctcagacag      1140
tggttcaaag ttttttctt ccatttcagg tgtcgtga                              1178

<210> SEQ ID NO 43
<211> LENGTH: 66
<212> TYPE: DNA
<213> ORGANISM: Artificial Sequence
<220> FEATURE:
<223> OTHER INFORMATION: Synthetic

<400> SEQUENCE: 43
atgcttcttt tggttacgtc tctgttgctt tgcgaacttc ctcatccagc gttcttgctg      60
atcccc                                                                 66

<210> SEQ ID NO 44
<211> LENGTH: 22
<212> TYPE: PRT
```

<213> ORGANISM: Artificial Sequence
<220> FEATURE:
<223> OTHER INFORMATION: Synthetic

<400> SEQUENCE: 44

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 45
<211> LENGTH: 735
<212> TYPE: DNA
<213> ORGANISM: Artificial Sequence
<220> FEATURE:
<223> OTHER INFORMATION: Synthetic

<400> SEQUENCE: 45
gatattcaga tgactcagac caccagtagc ttgtctgcct cactgggaga ccgagtaaca      60
atctcctgca gggcaagtca agacattagc aaatacctca attggtacca gcagaagccc     120
gacggaacgg taaaactcct catctatcat acgtcaaggt tgcattccgg agtaccgtca     180
cgattttcag gttctgggag cggaactgac tattccttga ctatttcaaa cctcgagcag     240
gaggacattg cgacatattt ttgtcaacaa ggtaataccc tcccttacac tttcggagga     300
ggaaccaaac tcgaaattac cgggtccacc agtggctctg gaagcctgg cagtggagaa      360 ggttccacta aaggcgaggt gaagctccag gagagcggcc ccggtctcgt tgcccccagt     420
caaagcctct ctgtaacgtg cacagtgagt ggtgtatcat tgcctgatta tggcgtctcc     480
tggataaggc agcccccgcg aaagggtctt gaatggcttg gggtaatatg gggctcagag     540
acaacgtatt ataactccgc tctcaaaagt cgcttgacga taataaaaga taactccaag     600
agtcaagttt tccttaaaat gaacagtttg cagactgacg ataccgctat atattattgt     660
gctaaacatt attactacgg cggtagttac gcgatggatt attgggggca ggggacttct     720
gtcacagtca gtagt                                                      735

<210> SEQ ID NO 46
<211> LENGTH: 245
<212> TYPE: PRT
<213> ORGANISM: Artificial Sequence
<220> FEATURE:
<223> OTHER INFORMATION: Synthetic

<400> SEQUENCE: 46

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

-continued

```
Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
        130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
            195                 200                 205

Ser Leu Gln Thr Asp Asp Thr Ala Ile Tyr Tyr Cys Ala Lys His Tyr
        210                 215                 220

Tyr Tyr Gly Gly Ser Tyr Ala Met Asp Tyr Trp Gly Gln Gly Thr Ser
225                 230                 235                 240

Val Thr Val Ser Ser
                245
```

<210> SEQ ID NO 47
<211> LENGTH: 261
<212> TYPE: DNA
<213> ORGANISM: Artificial Sequence
<220> FEATURE:
<223> OTHER INFORMATION: Synthetic

<400> SEQUENCE: 47

```
gctgctgcct ttgtcccggt atttctccca gccaaaccga ccacgactcc cgccccgcgc      60
cctccgacac ccgctcccac catcgcctct caacctctta gtcttcgccc cgaggcatgc     120
cgacccgccg ccggggggtgc tgttcatacg aggggcttgg acttcgcttg tgatatttac     180
atttgggctc cgttggcggg tacgtgcggc gtccttttgt tgtcactcgt tattactttg     240
tattgtaatc acaggaatcg c                                               261
```

<210> SEQ ID NO 48
<211> LENGTH: 252
<212> TYPE: DNA
<213> ORGANISM: Artificial Sequence
<220> FEATURE:
<223> OTHER INFORMATION: Synthetic

<400> SEQUENCE: 48

```
tttgtcccgg tatttctccc agccaaaccg accacgactc ccgccccgcg ccctccgaca      60
cccgctccca ccatcgcctc tcaacctctt agtcttcgcc ccgaggcatg ccgacccgcc     120 gccggggggtg ctgttcatac gaggggcttg gacttcgctt gtgatattta catttgggct     180
ccgttggcgg gtacgtgcgg cgtccttttg ttgtcactcg ttattacttt gtattgtaat     240
cacaggaatc gc                                                         252
```

<210> SEQ ID NO 49
<211> LENGTH: 84
<212> TYPE: PRT
<213> ORGANISM: Artificial Sequence
<220> FEATURE:
<223> OTHER INFORMATION: Synthetic

<400> SEQUENCE: 49

```
Phe Val Pro Val Phe Leu Pro Ala Lys Pro Thr Thr Thr Pro Ala Pro
1               5                   10                  15
```

Arg Pro Pro Thr Pro Ala Pro Thr Ile Ala Ser Gln Pro Leu Ser Leu
         20             25             30

Arg Pro Glu Ala Cys Arg Pro Ala Ala Gly Gly Ala Val His Thr Arg
         35             40             45

Gly Leu Asp Phe Ala Cys Asp Ile Tyr Ile Trp Ala Pro Leu Ala Gly
         50             55             60

Thr Cys Gly Val Leu Leu Leu Ser Leu Val Ile Thr Leu Tyr Cys Asn
65             70             75             80

His Arg Asn Arg

<210> SEQ ID NO 50
<211> LENGTH: 120
<212> TYPE: PRT
<213> ORGANISM: Artificial Sequence
<220> FEATURE:
<223> OTHER INFORMATION: Synthetic

<400> SEQUENCE: 50

Glu Val Lys Leu Gln Glu Ser Gly Pro Gly Leu Val Ala Pro Ser Gln
1             5             10             15

Ser Leu Ser Val Thr Cys Thr Val Ser Gly Val Ser Leu Pro Asp Tyr
         20             25             30

Gly Val Ser Trp Ile Arg Gln Pro Pro Arg Lys Gly Leu Glu Trp Leu
         35             40             45

Gly Val Ile Trp Gly Ser Glu Thr Thr Tyr Tyr Asn Ser Ala Leu Lys
         50             55             60

Ser Arg Leu Thr Ile Ile Lys Asp Asn Ser Lys Ser Gln Val Phe Leu
65             70             75             80

Lys Met Asn Ser Leu Gln Thr Asp Asp Thr Ala Ile Tyr Tyr Cys Ala
         85             90             95

Lys His Tyr Tyr Tyr Gly Gly Ser Tyr Ala Met Asp Tyr Trp Gly Gln
         100           105          110

Gly Thr Ser Val Thr Val Ser Ser
         115           120

<210> SEQ ID NO 51
<211> LENGTH: 107
<212> TYPE: PRT
<213> ORGANISM: Artificial Sequence
<220> FEATURE:
<223> OTHER INFORMATION: Synthetic

<400> SEQUENCE: 51

Asp Ile Gln Met Thr Gln Thr Thr Ser Ser Leu Ser Ala Ser Leu Gly
1             5             10             15

Asp Arg Val Thr Ile Ser Cys Arg Ala Ser Gln Asp Ile Ser Lys Tyr
         20             25             30

Leu Asn Trp Tyr Gln Gln Lys Pro Asp Gly Thr Val Lys Leu Leu Ile
         35             40             45

Tyr His Thr Ser Arg Leu His Ser Gly Val Pro Ser Arg Phe Ser Gly
         50             55             60

Ser Gly Ser Gly Thr Asp Tyr Ser Leu Thr Ile Ser Asn Leu Glu Gln
65             70             75             80

Glu Asp Ile Ala Thr Tyr Phe Cys Gln Gln Gly Asn Thr Leu Pro Tyr
         85             90             95

Thr Phe Gly Gly Gly Thr Lys Leu Glu Ile Thr
         100           105

```
<210> SEQ ID NO 52
<211> LENGTH: 18
<212> TYPE: PRT
<213> ORGANISM: Artificial Sequence
<220> FEATURE:
<223> OTHER INFORMATION: Synthetic

<400> SEQUENCE: 52

Gly Ser Thr Ser Gly Ser Gly Lys Pro Gly Ser Gly Glu Gly Ser Thr
1               5                   10                  15

Lys Gly

<210> SEQ ID NO 53
<211> LENGTH: 4682
<212> TYPE: DNA
<213> ORGANISM: Artificial Sequence
<220> FEATURE:
<223> OTHER INFORMATION: Synthetic

<400> SEQUENCE: 53
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgcac gcgtgagatg taaggagctg ctgtgacttg ctcaaggcct     180
tatatcgagt aaacggtagt gctggggctt agacgcaggt gttctgattt atagttcaaa     240
acctctatca atgagagagc aatctcctgg taatgtgata gatttcccaa cttaatgcca     300
acataccata aacctcccat tctgctaatg cccagcctaa gttggggaga ccactccaga     360
ttccaagatg tacagtttgc tttgctgggc cttttttccca tgcctgcctt tactctgcca     420
gagttatatt gctggggttt tgaagaagat cctattaaat aaaagaataa gcagtattat     480
taagtagccc tgcatttcag gtttccttga gtggcaggcc aggcctggcc gtgaacgttc     540
actgaaatca tggcctcttg gccaagattg atagcttgtg cctgtccctg agtcccagtc     600
catcacgagc agctggtttc taagatgcta tttcccgtat aaagcatgag accgtgactt     660
gccagcccca cagagccccg cccttgtcca tcactggcat ctggactcca gcctgggttg     720
gggcaaagag ggaaatgaga tcatgtccta accctgatcc tcttgtccca cagatatcca     780
gaaccctgac cctgccgtgt accagctgag agactctaaa tccagtgaca gtctgtctg     840 cctattcacc gatttttgatt ctcaaacaaa tgtgtcacaa agtaaggatt ctgatgtgta     900
tatcacagac aaaactgtgc tagacatgag gtctatggac ttcaggctcc ggtgcccgtc     960
agtgggcaga gcgcacatcg cccacagtcc ccgagaagtt gggggagggg tcggcaatt    1020 gaaccggtgc ctagagaagg tggcgcgggg taaactggga aagtgatgtc gtgtactggc    1080 tccgccttttt tcccgagggt gggggagaac cgtatataag tgcagtagtc gccgtgaacg    1140 ttcttttttcg caacgggttt gccgccagaa cacaggtaag tgccgtgtgt ggttcccgcg    1200
ggcctggcct ctttacgggt tatggccctt gcgtgccttg aattacttcc actggctgca    1260
gtacgtgatt cttgatcccg agcttcgggt tggaagtggg tgggagagtt cgaggccttg    1320
cgcttaagga gccccttcgc ctcgtgcttg agttgaggcc tggcctgggc gctgggccg    1380 ccgcgtgcga atctggtggc accttcgcgc ctgtctcgct gctttcgata agtctctagc    1440
catttaaaat ttttgatgac ctgctgcgac gctttttttttc tggcaagata gtcttgtaaa    1500
tgcgggccaa gatctgcaca ctggtatttc ggtttttggg gccgcgggcg cgacgggggc    1560
ccgtgcgtcc cagcgcacat gttcggcgag gcggggcctg cgagcgcggc caccgagaat    1620
```

-continued

```
cggacggggg tagtctcaag ctggccggcc tgctctggtg cctggcctcg cgccgccgtg    1680
tatcgccccg ccctgggcgg caaggctggc ccggtcggca ccagttgcgt gagcggaaag    1740
atggccgctt cccggccctg ctgcagggag ctcaaaatgg aggacgcggc gctcgggaga    1800
gcgggcgggt gagtcaccca cacaaaggaa aagggccttt ccgtcctcag ccgtcgcttc    1860
atgtgactcc acggagtacc gggcgccgtc caggcacctc gattagttct cgagcttttg    1920
gagtacgtcg tctttaggtt ggggggaggg gttttatgcg atggagtttc cccacactga    1980
gtgggtggag actgaagtta ggccagcttg gcacttgatg taattctcct tggaatttgc    2040 ccttttgag tttggatctt ggttcattct caagcctcag acagtggttc aaagtttttt    2100
tcttccattt caggtgtcgt gaccaccatg cttcttttgg ttacgtctct gttgctttgc    2160
gaacttcctc atccagcgtt cttgctgatc cccgatattc agatgactca gaccaccagt    2220
agcttgtctg cctcactggg agaccgagta acaatctcct gcagggcaag tcaagacatt    2280
agcaaatacc tcaattggta ccagcagaag cccgacggaa cggtaaaact cctcatctat    2340
catacgtcaa ggttgcattc cggagtaccg tcacgatttt caggttctgg gagcggaact    2400
gactattcct tgactatttc aaacctcgag caggaggaca ttgcgacata tttttgtcaa    2460
caaggtaata ccctccctta cactttcgga ggaggaacca aactcgaaat taccgggtcc    2520
accagtggct ctgggaagcc tggcagtgga gaaggttcca ctaaaggcga ggtgaagctc    2580
caggagagcg gccccggtct cgttgccccc agtcaaagcc tctctgtaac gtgcacagtg    2640
agtggtgtat cattgcctga ttatggcgtc tcctggataa ggcagccccc gcgaaagggt    2700
cttgaatggc ttggggtaat atggggctca gagacaacgt attataactc cgctctcaaa    2760
agtcgcttga cgataataaa agataactcc aagagtcaag ttttccttaa aatgaacagt    2820
ttgcagactg acgataccgc tatatattat tgtgctaaac attattacta cggcggtagt    2880
tacgcgatgg attattgggg gcaggggact tctgtcacag tcagtagtgc tgctgccttt    2940
gtcccggtat ttctcccagc caaaccgacc acgactcccg ccccgcgccc tccgacaccc    3000
gctcccacca tcgcctctca acctcttagt cttcgccccg aggcatgccg acccgccgcc    3060
gggggtgctg ttcatacgag gggcttggac ttcgcttgtg atatttacat ttgggctccg    3120
ttggcgggta cgtgcggcgt cctttttgttg tcactcgtta ttactttgta ttgtaatcac    3180
aggaatcgct caaagcggag taggttgttg cattccgatt acatgaatat gactcctcgc    3240
cggcctgggc cgacaagaaa acattaccaa ccctatgccc ccccacgaga cttcgctgcg    3300
tacaggtccc gagtgaagtt ttcccgaagc gcagacgctc cggcatatca gcaaggacag    3360
aatcagctgt ataacgaact gaatttggga cgccgcgagg agtatgacgt gcttgataaa    3420
cgccggggga gagaccgga aatgggggggt aaaccccgaa gaaagaatcc ccaagaagga    3480
ctctacaatg aactccagaa ggataagatg gcggaggcct actcagaaat aggtatgaag    3540
ggcgaacgac gacggggaaa aggtcacgat ggcctctacc aagggttgag tacggcaacc    3600
aaagatacgt acgatgcact gcatatgcag gccctgcctc ccagataata ataaaatcgc    3660
tatccatcga agatggatgt gtgttggttt tttgtgtgtg gagcaacaaa tctgactttg    3720
catgtgcaaa cgccttcaac aacagcatta ttccagaaga caccttcttc cccagcccag    3780
gtaagggcag ctttggtgcc ttcgcaggct gtttccttgc ttcaggaatg gccaggttct    3840
gcccagagct ctggtcaatg atgtctaaaa ctcctctgat tggtggtctc ggccttatcc    3900
attgccacca aaaccctctt tttactaaga aacagtgagc cttgttctgg cagtccagag    3960
```

```
aatgacacgg gaaaaaagca gatgaagaga aggtggcagg agagggcacg tggcccagcc      4020
tcagtctctc caactgagtt cctgcctgcc tgcctttgct cagactgttt gccccttact      4080
gctcttctag gcctcattct aagccccttc tccaagttgc ctctccttat ttctccctgt      4140
ctgccaaaaa atctttccca gctcactaag tcagtctcac gcagtcactc attaacccac      4200
caatcactga ttgtgccggc acatgaatgc accaggtgtt gaagtggagg aattaaaaag      4260
tcagatgagg ggtgtgccca gaggaagcac cattctagtt gggggagccc atctgtcagc      4320
tgggaaaagt ccaaataact tcagattgga atgtgtttta actcagggtt gagaaaacag      4380
ctaccttcag gacaaaagtc agggaagggc tctctgaaga aatgctactt gaagatacca      4440
gccctaccaa gggcagggag aggaccctat agaggcctgg gacaggagct caatgagaaa      4500
ggtaaccacg tgcggaccga ggctgcagcg tcgtcctccc taggaacccc tagtgatgga      4560
gttggccact ccctctctgc gcgctcgctc gctcactgag gccgggcgac caaaggtcgc      4620
ccgacgcccg ggctttgccc gggcggcctc agtgagcgag cgagcgcgca gctgcctgca      4680
gg                                                                    4682

<210> SEQ ID NO 54
<211> LENGTH: 4358
<212> TYPE: DNA
<213> ORGANISM: Artificial Sequence
<220> FEATURE:
<223> OTHER INFORMATION: Synthetic

<400> SEQUENCE: 54
gagatgtaag gagctgctgt gacttgctca aggccttata tcgagtaaac ggtagtgctg        60
gggcttagac gcaggtgttc tgatttatag ttcaaaacct ctatcaatga gagagcaatc       120
tcctggtaat gtgatagatt tcccaactta atgccaacat accataaacc tcccattctg       180
ctaatgccca gcctaagttg gggagaccac tccagattcc aagatgtaca gtttgctttg       240
ctgggccttt ttcccatgcc tgcctttact ctgccagagt tatattgctg gggtttttgaa      300 gaagatccta ttaaataaaa gaataagcag tattattaag tagccctgca tttcaggttt       360
ccttgagtgg caggccaggc ctggccgtga acgttcactg aaatcatggc ctcttggcca       420
agattgatag cttgtgcctg tccctgagtc ccagtccatc acgagcagct ggtttctaag       480
atgctatttc ccgtataaag catgagaccg tgacttgcca gccccacaga gccccgccct       540
tgtccatcac tggcatctgg actccagcct gggttggggc aaagagggaa atgagatcat       600
gtcctaaccc tgatcctctt gtcccacaga tatccagaac cctgaccctg ccgtgtacca       660
gctgagagac tctaaatcca gtgacaagtc tgtctgccta ttcaccgatt ttgattctca       720
aacaaatgtg tcacaaagta aggattctga tgtgtatatc acagacaaaa ctgtgctaga       780
catgaggtct atggacttca ggctccggtg cccgtcagtg ggcagagcgc acatcgccca       840
cagtccccga gaagttgggg ggaggggtcg gcaattgaac cggtgcctag agaaggtggc       900
gcggggtaaa ctgggaaagt gatgtcgtgt actggctccg cctttttccc gagggtgggg       960
gagaaccgta tataagtgca gtagtcgccg tgaacgttct ttttcgcaac gggtttgccg      1020
ccagaacaca ggtaagtgcc gtgtgtggtt cccgcgggcc tggcctcttt acgggttatg      1080
gcccttgcgt gccttgaatt acttccactg ctgcagtac gtgattcttg atcccgagct       1140
tcgggttgga agtgggtggg agagttcgag gccttgcgct taaggagccc cttcgcctcg      1200
tgcttgagtt gaggcctggc ctgggcgctg gggccgccgc gtgcgaatct ggtggcacct      1260
tcgcgcctgt ctcgctgctt tcgataagtc tctagccatt taaaattttt gatgacctgc      1320
```

-continued

```
tgcgacgctt ttttctggc aagatagtct tgtaaatgcg ggccaagatc tgcacactgg        1380
tatttcggtt tttggggccg cgggcggcga cgggccccgt gcgtcccagc gcacatgttc        1440
ggcgaggcgg ggcctgcgag cgcggccacc gagaatcgga cggggtagt ctcaagctgg         1500 ccggcctgct ctggtgcctg gcctcgcgcc gccgtgtatc gccccgccct gggcggcaag        1560
gctggcccgg tcggcaccag ttgcgtgagc ggaaagatgg ccgcttcccg gccctgctgc        1620
agggagctca aaatggagga cgcggcgctc gggagagcgg gcgggtgagt cacccacaca        1680
aaggaaaagg gcctttccgt cctcagccgt cgcttcatgt gactccacgg agtaccgggc        1740
gccgtccagg cacctcgatt agttctcgag cttttggagt acgtcgtctt taggttgggg        1800
ggaggggttt tatgcgatgg agtttcccca cactgagtgg gtggagactg aagttaggcc        1860
agcttggcac ttgatgtaat tctccttgga atttgccctt tttgagtttg gatcttggtt        1920
cattctcaag cctcagacag tggttcaaag ttttttttctt ccatttcagg tgtcgtgacc       1980
accatgcttc ttttggttac gtctctgttg ctttgcgaac ttcctcatcc agcgttcttg        2040
ctgatccccg atattcagat gactcagacc accagtagct tgtctgcctc actgggagac        2100
cgagtaacaa tctcctgcag ggcaagtcaa gacattagca aatacctcaa ttggtaccag        2160
cagaagcccg acggaacggt aaaactcctc atctatcata cgtcaaggtt gcattccgga        2220
gtaccgtcac gattttcagg ttctgggagc ggaactgact attccttgac tatttcaaac        2280
ctcgagcagg aggacattgc gacatatttt tgtcaacaag gtaatacct cccttacact         2340 ttcggaggag gaaccaaact cgaaattacc gggtccacca gtggctctgg gaagcctggc        2400
agtggagaag gttccactaa aggcgaggtg aagctccagg agagcggccc cggtctcgtt        2460
gcccccagtc aaagcctctc tgtaacgtgc acagtgagtg gtgtatcatt gcctgattat        2520
ggcgtctcct ggataaggca gccccgcgca aagggtcttg aatggcttgg ggtaatatgg        2580
ggctcagaga caacgtatta taactccgct ctcaaaagtc gcttgacgat aataaaagat        2640
aactccaaga gtcaagtttt ccttaaaatg aacagtttgc agactgacga taccgctata        2700
tattattgtg ctaaacatta ttactacggc ggtagttacg cgatggatta ttgggggcag        2760
gggacttctg tcacagtcag tagtgctgct gcctttgtcc cggtatttct cccagccaaa        2820
ccgaccacga ctcccgcccc gcgccctccg acacccgctc ccaccatcgc ctctcaacct        2880
cttagtcttc gccccgaggc atgccgaccc gccgccgggg gtgctgttca tacgaggggc        2940
ttggacttcg cttgtgatat ttacatttgg gctccgttgg cgggtacgtg cggcgtcctt        3000
ttgttgtcac tcgttattac tttgtattgt aatcacagga atcgctcaaa gcggagtagg        3060
ttgttgcatt ccgattacat gaatatgact cctcgccggc ctgggccgac aagaaaacat        3120
taccaaccct atgccccccc acgagacttc gctgcgtaca ggtcccgagt gaagtttcc         3180 cgaagcgcag acgctccggc atatcagcaa ggacagaatc agctgtataa cgaactgaat        3240
ttgggacgcc gcgaggagta tgacgtgctt gataaacgcc gggggagaga cccgaaatg         3300 gggggtaaac cccgaagaaa gaatccccaa gaaggactct acaatgaact ccagaaggat        3360
aagatggcgg aggcctactc agaaataggt atgaagggcg aacgacgacg gggaaaaggt        3420
cacgatggcc tctaccaagg gttgagtacg gcaaccaaag atacgtacga tgcactgcat        3480
atgcaggccc tgcctcccag ataataataa aatcgctatc catcgaagat ggatgtgtgt        3540 tggtttttg tgtgtggagc aacaaatctg actttgcatg tgcaaacgcc ttcaacaaca        3600
gcattattcc agaagacacc ttcttcccca gcccaggtaa gggcagcttt ggtgccttcg        3660
```

-continued

```
caggctgttt ccttgcttca ggaatggcca ggttctgccc agagctctgg tcaatgatgt    3720
ctaaaactcc tctgattggt ggtctcggcc ttatccattg ccaccaaaac cctcttttta    3780
ctaagaaaca gtgagccttg ttctggcagt ccagagaatg acacgggaaa aaagcagatg    3840
aagagaaggt ggcaggagag ggcacgtggc ccagcctcag tctctccaac tgagttcctg    3900
cctgcctgcc tttgctcaga ctgtttgccc cttactgctc ttctaggcct cattctaagc    3960
cccttctcca agttgcctct ccttatttct ccctgtctgc caaaaaatct ttcccagctc    4020
actaagtcag tctcacgcag tcactcatta acccaccaat cactgattgt gccggcacat    4080
gaatgcacca ggtgttgaag tggaggaatt aaaaagtcag atgaggggtg tgcccagagg    4140
aagcaccatt ctagttgggg gagcccatct gtcagctggg aaaagtccaa ataacttcag    4200
attggaatgt gttttaactc agggttgaga aaacagctac cttcaggaca aaagtcaggg    4260
aagggctctc tgaagaaatg ctacttgaag ataccagccc taccaagggc agggagagga    4320
ccctatagag gcctgggaca ggagctcaat gagaaagg                            4358
```

<210> SEQ ID NO 55
<211> LENGTH: 4688
<212> TYPE: DNA
<213> ORGANISM: Artificial Sequence
<220> FEATURE:
<223> OTHER INFORMATION: Synthetic

<400> SEQUENCE: 55

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtgagatg taaggagctg ctgtgacttg ctcaaggcct    180
tatatcgagt aaacggtagt gctggggctt agacgcaggt gttctgattt atagttcaaa    240
acctctatca atgagagagc aatctcctgg taatgtgata gatttcccaa cttaatgcca    300
acataccata aacctcccat tctgctaatg cccagcctaa gttggggaga ccactccaga    360
ttccaagatg tacagtttgc tttgctgggc ctttttccca tgcctgcctt tactctgcca    420
gagttatatt gctggggttt tgaagaagat cctattaaat aaaagaataa gcagtattat    480
taagtagccc tgcatttcag gtttccttga gtggcaggcc aggcctggcc gtgaacgttc    540
actgaaatca tggcctcttg gccaagattg atagcttgtg cctgtccctg agtcccagtc    600
catcacgagc agctggtttc taagatgcta tttcccgtat aaagcatgag accgtgactt    660
gccagcccca cagagccccg cccttgtcca tcactggcat ctggactcca gcctgggttg    720
gggcaaagag ggaaatgaga tcatgtccta accctgatcc tcttgtccca cagatatcca    780
gaaccctgac cctgccgtgt accagctgag agactctaaa tccagtgaca agtctgtctg    840
cctattcacc gattttgatt ctcaaacaaa tgtgtcacaa agtaaggatt ctgatgtgta    900
tatcacagac aaaactgtgc tagacatgag gtctatggac ttcaggctcc ggtgcccgtc    960
agtgggcaga gcgcacatcg cccacagtcc ccgagaagtt gggggagggg gtcggcaatt   1020
gaaccggtgc ctagagaagg tggcgcgggg taaactggga aagtgatgtc gtgtactggc   1080
tccgcctttt tcccgagggt gggggagaac cgtatataag tgcagtagtc gccgtgaacg   1140 ttcttttttcg caacgggttt gccgccagaa cacaggtaag tgccgtgtgt ggttcccgcg   1200
ggcctggcct ctttacgggt tatggccctt gcgtgccttg aattacttcc actggctgca   1260
gtacgtgatt cttgatcccg agcttcgggt tggaagtggg tgggagagtt cgaggccttg   1320
cgcttaagga gccccttcgc ctcgtgcttg agttgaggcc tggcctgggc gctggggccg   1380
```

-continued

```
ccgcgtgcga atctggtggc accttcgcgc ctgtctcgct gctttcgata agtctctagc     1440
catttaaaat ttttgatgac ctgctgcgac gcttttttc tggcaagata gtcttgtaaa     1500
tgcgggccaa gatctgcaca ctggtatttc ggtttttggg gccgcgggcg gcgacggggc     1560
ccgtgcgtcc cagcgcacat gttcggcgag gcggggcctg cgagcgcggc caccgagaat     1620
cggacggggg tagtctcaag ctggccggcc tgctctggtg cctggcctcg cgccgccgtg     1680
tatcgccccg ccctgggcgg caaggctggc ccggtcggca ccagttgcgt gagcggaaag     1740
atggccgctt cccggccctg ctgcaggag ctcaaaatgg aggacgcggc gctcgggaga     1800
gcgggcgggt gagtcaccca cacaaaggaa aagggccttt ccgtcctcag ccgtcgcttc     1860
atgtgactcc acggagtacc gggcgccgtc caggcacctc gattagttct cgagcttttg     1920
gagtacgtcg tctttaggtt gggggggaggg gttttatgcg atggagtttc cccacactga     1980
gtgggtggag actgaagtta ggccagcttg gcacttgatg taattctcct tggaatttgc     2040 ccttttgag tttggatctt ggttcattct caagcctcag acagtggttc aaagtttttt     2100
tcttccattt caggtgtcgt gaccaccatg gcgcttccgg tgacagcact gctcctcccc     2160
ttggcgctgt tgctccacgc agcaaggccg caggtgcagc tggtgcagag cggagccgag     2220
ctcaagaagc ccggagcctc cgtgaaggtg agctgcaagg ccagcggcaa caccctgacc     2280
aactacgtga tccactgggt gagacaagcc cccggccaaa ggctggagtg gatgggctac     2340
atcctgccct acaacgacct gaccaagtac agccagaagt tccagggcag ggtgaccatc     2400
accagggata gagcgcctc caccgcctat atggagctga gcagcctgag gagcgaggac     2460
accgctgtgt actactgtac aaggtgggac tgggacggct tctttgaccc ctggggccag     2520
ggcacaacag tgaccgtcag cagcggcggc ggaggcagcg gcggcggcgg cagcggcgga     2580
ggcggaagcg aaatcgtgat gacccagagc cccgccacac tgagcgtgag ccctggcgag     2640
agggccagca tctcctgcag ggctagccaa agcctggtgc acagcaacgg caacacccac     2700
ctgcactggt accagcagag acccggacag gctcccaggc tgctgatcta cagcgtgagc     2760
aacaggttct ccgaggtgcc tgccaggttt agcggcagcg gaagcggcac cgactttacc     2820
ctgaccatca gcagcgtgga gtccgaggac ttcgccgtgt attactgcag ccagaccagc     2880
cacatcccct acaccttcgg cggcggcacc aagctggaga tcaaaagtgc tgctgccttt     2940
gtcccggtat ttctcccagc caaaccgacc acgactcccg ccccgcgccc tccgacaccc     3000
gctcccacca tcgcctctca acctcttagt cttcgccccg aggcatgccg acccgccgcc     3060
gggggtgctg ttcatacgag gggcttggac ttcgcttgtg atatttacat ttgggctccg     3120
ttggcgggta cgtgcggcgt cctttttgttg tcactcgtta ttactttgta ttgtaatcac     3180
aggaatcgaa aacggggcag aaagaaactc ctgtatatat tcaaacaacc atttatgaga     3240
ccagtacaaa ctactcaaga ggaagatggc tgtagctgcc gatttccaga agaagaagaa     3300
ggaggatgtg aactgcgagt gaagttttcc cgaagcgcag acgctccggc atatcagcaa     3360
ggacagaatc agctgtataa cgaactgaat ttgggacgcc gcgaggagta tgacgtgctt     3420
gataaacgcc gggggagaga cccggaaatg gggggtaaac cccgaagaaa gaatccccaa     3480
gaaggactct acaatgaact ccagaaggat aagatggcgg aggcctactc agaaataggt     3540
atgaagggcg aacgacgacg gggaaaaggt cacgatggcc tctaccaagg gttgagtacg     3600
gcaaccaaag atacgtacga tgcactgcat atgcaggccc tgcctcccag ataataataa     3660
aatcgctatc catcgaagat ggatgtgtgt tggtttttttg tgtgtggagc aacaaatctg     3720
```

-continued

```
actttgcatg tgcaaacgcc ttcaacaaca gcattattcc agaagacacc ttcttcccca    3780
gcccaggtaa gggcagcttt ggtgccttcg caggctgttt ccttgcttca ggaatggcca    3840
ggttctgccc agagctctgg tcaatgatgt ctaaaactcc tctgattggt ggtctcggcc    3900
ttatccattg ccaccaaaac cctctttttta ctaagaaaca gtgagccttg ttctggcagt    3960
ccagagaatg acacgggaaa aaagcagatg aagagaaggt ggcaggagag ggcacgtggc    4020
ccagcctcag tctctccaac tgagttcctg cctgcctgcc tttgctcaga ctgtttgccc    4080
cttactgctc ttctaggcct cattctaagc cccttctcca agttgcctct ccttatttct    4140
ccctgtctgc caaaaaatct ttcccagctc actaagtcag tctcacgcag tcactcatta    4200
acccaccaat cactgattgt gccggcacat gaatgcacca ggtgttgaag tggaggaatt    4260
aaaaagtcag atgaggggtg tgcccagagg aagcaccatt ctagttgggg gagcccatct    4320
gtcagctggg aaaagtccaa ataacttcag attggaatgt gttttaactc agggttgaga    4380
aaacagctac cttcaggaca aaagtcaggg aagggctctc tgaagaaatg ctacttgaag    4440
ataccagccc taccaagggc agggagagga ccctatagag gcctgggaca ggagctcaat    4500
gagaaaggta accacgtgcg gaccgaggct gcagcgtcgt cctccctagg aaccctagt    4560 gatggagttg gccactccct ctctgcgcgc tcgctcgctc actgaggccg ggcgaccaaa    4620
ggtcgcccga cgcccgggct ttgcccgggc ggcctcagtg agcgagcgag cgcgcagctg    4680
cctgcagg                                                              4688
```

<210> SEQ ID NO 56
<211> LENGTH: 1524
<212> TYPE: DNA
<213> ORGANISM: Artificial Sequence
<220> FEATURE:
<223> OTHER INFORMATION: Synthetic

<400> SEQUENCE: 56

```
atggcgcttc cggtgacagc actgctcctc cccttggcgc tgttgctcca cgcagcaagg      60
ccgcaggtgc agctggtgca gagcggagcc gagctcaaga agcccggagc ctccgtgaag     120
gtgagctgca aggccagcgg caacaccctg accaactacg tgatccactg ggtgagacaa     180 gccccggcc aaaggctgga gtggatgggc tacatcctgc cctacaacga cctgaccaag     240
tacagccaga gttccagggg cagggtgacc atcaccaggg ataagagcgc ctccaccgcc     300
tatatggagc tgagcagcct gaggagcgag gacaccgctg tgtactactg tacaaggtgg     360
gactgggacg gcttcttttga cccctggggc caggggcacaa cagtgaccgt cagcagcggc    420
ggcggaggca gcggcggcgg cggcagcggc ggaggcggaa gcgaaatcgt gatgacccag     480
agccccgcca cactgagcgt gagccctggc gagagggcca gcatctcctg cagggctagc     540
caaagcctgg tgcacagcaa cggcaacacc cacctgcact ggtaccagca gagacccgga     600
caggctccca ggctgctgat ctacagcgtg agcaacaggt tctccgaggt gcctgccagg     660
tttagcggca gcggaagcgg caccgacttt accctgacca tcagcagcgt ggagtccgag     720
gacttcgccg tgtattactg cagccagacc agccacatcc cttacacctt cggcggcggc     780
accaagctgg agatcaaaag tgctgctgcc tttgtcccgg tatttctccc agccaaaccg     840
accacgactc ccgccccgcg ccctccgaca cccgctccca ccatcgcctc tcaacctctt     900
agtcttcgcc ccgaggcatg ccgacccgcc gccggggggtg ctgttcatac gagggggcttg    960 gacttcgctt gtgatattta catttgggct ccgttggcgg gtacgtgcgg cgtcctttttg    1020 ttgtcactcg ttattacttt gtattgtaat cacaggaatc gcaaacgggg cagaaagaaa    1080
```

-continued

```
ctcctgtata tattcaaaca accatttatg agaccagtac aaactactca agaggaagat    1140
ggctgtagct gccgatttcc agaagaagaa gaaggaggat gtgaactgcg agtgaagttt    1200
tcccgaagcg cagacgctcc ggcatatcag caaggacaga atcagctgta taacgaactg    1260
aatttgggac gccgcgagga gtatgacgtg cttgataaac gccggggggag agacccggaa    1320 atgggggggta aaccccgaag aaagaatccc caagaaggac tctacaatga actccagaag    1380
gataagatgg cggaggccta ctcagaaata ggtatgaagg cgaacgacg acggggaaaa    1440 ggtcacgatg gcctctacca agggttgagt acggcaacca aagatacgta cgatgcactg    1500
catatgcagg ccctgcctcc caga                                          1524
```

<210> SEQ ID NO 57
<211> LENGTH: 735
<212> TYPE: DNA
<213> ORGANISM: Artificial Sequence
<220> FEATURE:
<223> OTHER INFORMATION: Synthetic

<400> SEQUENCE: 57

```
caggtgcagc tggtgcagag cggagccgag ctcaagaagc ccggagcctc cgtgaaggtg      60
agctgcaagg ccagcggcaa caccctgacc aactacgtga tccactgggt gagacaagcc     120
cccggccaaa ggctggagtg gatgggctac atcctgcccc acaacgacct gaccaagtac     180
agccagaagt tccagggcag ggtgaccatc accagggata gagcgcctc caccgcctat     240 atggagctga gcagcctgag gagcgaggac accgctgtgt actactgtac aaggtgggac     300
tgggacggct tctttgaccc ctgggggccag ggcacaacag tgaccgtcag cagcggcggc     360
ggaggcagcg gcggcggcgg cagcggcgga ggcggaagcg aaatcgtgat gacccagagc     420
cccgccacac tgagcgtgag ccctggcgag agggccagca tctcctgcag ggctagccaa     480
agcctggtgc acagcaacgg caacacccac ctgcactggt accagcagag acccggacag     540
gctcccaggc tgctgatcta cagcgtgagc aacaggttct ccgaggtgcc tgccaggttt     600
agcggcagcg gaagcggcac cgactttacc ctgaccatca gcagcgtgga gtccgaggac     660
ttcgccgtgt attactgcag ccagaccagc cacatccctt acaccttcgg cggcggcacc     720
aagctggaga tcaaa                                                      735
```

<210> SEQ ID NO 58
<211> LENGTH: 126
<212> TYPE: DNA
<213> ORGANISM: Artificial Sequence
<220> FEATURE:
<223> OTHER INFORMATION: Synthetic

<400> SEQUENCE: 58

```
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126
```

<210> SEQ ID NO 59
<211> LENGTH: 42
<212> TYPE: PRT
<213> ORGANISM: Artificial Sequence
<220> FEATURE:
<223> OTHER INFORMATION: Synthetic

<400> SEQUENCE: 59

-continued

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
        35                  40
```

```
<210> SEQ ID NO 60
<211> LENGTH: 49
<212> TYPE: DNA
<213> ORGANISM: Artificial Sequence
<220> FEATURE:
<223> OTHER INFORMATION: Synthetic

<400> SEQUENCE: 60
aataaaatcg ctatccatcg aagatggatg tgtgttggtt ttttgtgtg                    49
```

```
<210> SEQ ID NO 61
<211> LENGTH: 508
<212> TYPE: PRT
<213> ORGANISM: Artificial Sequence
<220> FEATURE:
<223> OTHER INFORMATION: Synthetic

<400> SEQUENCE: 61

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Leu
                20                  25                  30

Lys Lys Pro Gly Ala Ser Val Lys Val Ser Cys Lys Ala Ser Gly Asn
        35                  40                  45

Thr Leu Thr Asn Tyr Val Ile His Trp Val Arg Gln Ala Pro Gly Gln
    50                  55                  60

Arg Leu Glu Trp Met Gly Tyr Ile Leu Pro Tyr Asn Asp Leu Thr Lys
65                  70                  75                  80

Tyr Ser Gln Lys Phe Gln Gly Arg Val Thr Ile Thr Arg Asp Lys Ser
                85                  90                  95

Ala Ser Thr Ala Tyr Met Glu Leu Ser Ser Leu Arg Ser Glu Asp Thr
                100                 105                 110

Ala Val Tyr Tyr Cys Thr Arg Trp Asp Trp Asp Gly Phe Phe Asp Pro
            115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Glu Ile Val Met Thr Gln
145                 150                 155                 160

Ser Pro Ala Thr Leu Ser Val Ser Pro Gly Glu Arg Ala Ser Ile Ser
                165                 170                 175

Cys Arg Ala Ser Gln Ser Leu Val His Ser Asn Gly Asn Thr His Leu
                180                 185                 190

His Trp Tyr Gln Gln Arg Pro Gly Gln Ala Pro Arg Leu Leu Ile Tyr
            195                 200                 205

Ser Val Ser Asn Arg Phe Ser Glu Val Pro Ala Arg Phe Ser Gly Ser
        210                 215                 220

Gly Ser Gly Thr Asp Phe Thr Leu Thr Ile Ser Ser Val Glu Ser Glu
225                 230                 235                 240

Asp Phe Ala Val Tyr Tyr Cys Ser Gln Thr Ser His Ile Pro Tyr Thr
                245                 250                 255
```

-continued

```
Phe Gly Gly Gly Thr Lys Leu Glu Ile Lys Ser Ala Ala Ala Phe Val
            260             265             270

Pro Val Phe Leu Pro Ala Lys Pro Thr Thr Thr Pro Ala Pro Arg Pro
            275             280             285

Pro Thr Pro Ala Pro Thr Ile Ala Ser Gln Pro Leu Ser Leu Arg Pro
            290             295             300

Glu Ala Cys Arg Pro Ala Ala Gly Gly Ala Val His Thr Arg Gly Leu
305             310             315             320

Asp Phe Ala Cys Asp Ile Tyr Ile Trp Ala Pro Leu Ala Gly Thr Cys
                325             330             335

Gly Val Leu Leu Leu Ser Leu Val Ile Thr Leu Tyr Cys Asn His Arg
            340             345             350

Asn Arg Lys Arg Gly Arg Lys Lys Leu Leu Tyr Ile Phe Lys Gln Pro
            355             360             365

Phe Met Arg Pro Val Gln Thr Thr Gln Glu Glu Asp Gly Cys Ser Cys
    370             375             380

Arg Phe Pro Glu Glu Glu Glu Gly Gly Cys Glu Leu Arg Val Lys Phe
385             390             395             400

Ser Arg Ser Ala Asp Ala Pro Ala Tyr Gln Gln Gly Gln Asn Gln Leu
                405             410             415

Tyr Asn Glu Leu Asn Leu Gly Arg Arg Glu Glu Tyr Asp Val Leu Asp
            420             425             430

Lys Arg Arg Gly Arg Asp Pro Glu Met Gly Gly Lys Pro Arg Arg Lys
            435             440             445

Asn Pro Gln Glu Gly Leu Tyr Asn Glu Leu Gln Lys Asp Lys Met Ala
    450             455             460

Glu Ala Tyr Ser Glu Ile Gly Met Lys Gly Glu Arg Arg Arg Gly Lys
465             470             475             480

Gly His Asp Gly Leu Tyr Gln Gly Leu Ser Thr Ala Thr Lys Asp Thr
            485             490             495

Tyr Asp Ala Leu His Met Gln Ala Leu Pro Pro Arg
            500             505
```

```
<210> SEQ ID NO 62
<211> LENGTH: 245
<212> TYPE: PRT
<213> ORGANISM: Artificial Sequence
<220> FEATURE:
<223> OTHER INFORMATION: Synthetic

<400> SEQUENCE: 62
```

```
Gln Val Gln Leu Val Gln Ser Gly Ala Glu Leu Lys Lys Pro Gly Ala
1               5               10              15

Ser Val Lys Val Ser Cys Lys Ala Ser Gly Asn Thr Leu Thr Asn Tyr
            20              25              30

Val Ile His Trp Val Arg Gln Ala Pro Gly Gln Arg Leu Glu Trp Met
        35              40              45

Gly Tyr Ile Leu Pro Tyr Asn Asp Leu Thr Lys Tyr Ser Gln Lys Phe
    50              55              60

Gln Gly Arg Val Thr Ile Thr Arg Asp Lys Ser Ala Ser Thr Ala Tyr
65              70              75              80

Met Glu Leu Ser Ser Leu Arg Ser Glu Asp Thr Ala Val Tyr Tyr Cys
                85              90              95

Thr Arg Trp Asp Trp Asp Gly Phe Phe Asp Pro Trp Gly Gln Gly Thr
            100             105             110
```

-continued

```
Thr Val Thr Val Ser Ser Gly Gly Gly Ser Gly Gly Gly Ser
        115             120             125

Gly Gly Gly Gly Ser Glu Ile Val Met Thr Gln Ser Pro Ala Thr Leu
    130             135             140

Ser Val Ser Pro Gly Glu Arg Ala Ser Ile Ser Cys Arg Ala Ser Gln
145             150             155             160

Ser Leu Val His Ser Asn Gly Asn Thr His Leu His Trp Tyr Gln Gln
            165             170             175

Arg Pro Gly Gln Ala Pro Arg Leu Leu Ile Tyr Ser Val Ser Asn Arg
            180             185             190

Phe Ser Glu Val Pro Ala Arg Phe Ser Gly Ser Gly Ser Gly Thr Asp
            195             200             205

Phe Thr Leu Thr Ile Ser Ser Val Glu Ser Glu Asp Phe Ala Val Tyr
    210             215             220

Tyr Cys Ser Gln Thr Ser His Ile Pro Tyr Thr Phe Gly Gly Gly Thr
225             230             235             240

Lys Leu Glu Ile Lys
            245

<210> SEQ ID NO 63
<211> LENGTH: 118
<212> TYPE: PRT
<213> ORGANISM: Artificial Sequence
<220> FEATURE:
<223> OTHER INFORMATION: Synthetic

<400> SEQUENCE: 63

Gln Val Gln Leu Val Gln Ser Gly Ala Glu Leu Lys Lys Pro Gly Ala
1               5               10              15

Ser Val Lys Val Ser Cys Lys Ala Ser Gly Asn Thr Leu Thr Asn Tyr
            20              25              30

Val Ile His Trp Val Arg Gln Ala Pro Gly Gln Arg Leu Glu Trp Met
        35              40              45

Gly Tyr Ile Leu Pro Tyr Asn Asp Leu Thr Lys Tyr Ser Gln Lys Phe
    50              55              60

Gln Gly Arg Val Thr Ile Thr Arg Asp Lys Ser Ala Ser Thr Ala Tyr
65              70              75              80

Met Glu Leu Ser Ser Leu Arg Ser Glu Asp Thr Ala Val Tyr Tyr Cys
            85              90              95

Thr Arg Trp Asp Trp Asp Gly Phe Phe Asp Pro Trp Gly Gln Gly Thr
            100             105             110

Thr Val Thr Val Ser Ser
        115

<210> SEQ ID NO 64
<211> LENGTH: 112
<212> TYPE: PRT
<213> ORGANISM: Artificial Sequence
<220> FEATURE:
<223> OTHER INFORMATION: Synthetic

<400> SEQUENCE: 64

Glu Ile Val Met Thr Gln Ser Pro Ala Thr Leu Ser Val Ser Pro Gly
1               5               10              15

Glu Arg Ala Ser Ile Ser Cys Arg Ala Ser Gln Ser Leu Val His Ser
            20              25              30

Asn Gly Asn Thr His Leu His Trp Tyr Gln Gln Arg Pro Gly Gln Ala
        35              40              45
```

-continued

```
Pro Arg Leu Leu Ile Tyr Ser Val Ser Asn Arg Phe Ser Glu Val Pro
    50                  55                  60

Ala Arg Phe Ser Gly Ser Gly Ser Gly Thr Asp Phe Thr Leu Thr Ile
65                  70                  75                  80

Ser Ser Val Glu Ser Glu Asp Phe Ala Val Tyr Tyr Cys Ser Gln Thr
                85                  90                  95

Ser His Ile Pro Tyr Thr Phe Gly Gly Gly Thr Lys Leu Glu Ile Lys
            100                 105                 110

<210> SEQ ID NO 65
<211> LENGTH: 16
<212> TYPE: PRT
<213> ORGANISM: Artificial Sequence
<220> FEATURE:
<223> OTHER INFORMATION: Synthetic

<400> SEQUENCE: 65

Arg Ala Ser Gln Ser Leu Val His Ser Asn Gly Asn Thr His Leu His
1               5                   10                  15

<210> SEQ ID NO 66
<211> LENGTH: 5
<212> TYPE: PRT
<213> ORGANISM: Artificial Sequence
<220> FEATURE:
<223> OTHER INFORMATION: Synthetic

<400> SEQUENCE: 66

Ser Val Ser Asn Arg
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic

<400> SEQUENCE: 67

Ser Gln Thr Ser His Ile Pro Tyr Thr
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic

<400> SEQUENCE: 68

Asn Tyr Val Ile His
1               5

<210> SEQ ID NO 69
<211> LENGTH: 17
<212> TYPE: PRT
<213> ORGANISM: Artificial Sequence
<220> FEATURE:
<223> OTHER INFORMATION: Synthetic

<400> SEQUENCE: 69

Tyr Ile Leu Pro Tyr Asn Asp Leu Thr Lys Tyr Ser Gln Lys Phe Gln
1               5                   10                  15

Gly
```

```
<210> SEQ ID NO 70
<211> LENGTH: 9
<212> TYPE: PRT
<213> ORGANISM: Artificial Sequence
<220> FEATURE:
<223> OTHER INFORMATION: Synthetic

<400> SEQUENCE: 70

Trp Asp Trp Asp Gly Phe Phe Asp Pro
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic

<400> SEQUENCE: 71

Gly Asn Thr Leu Thr Asn Tyr
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic

<400> SEQUENCE: 72

Leu Pro Tyr Asn Asp Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic

<400> SEQUENCE: 73

Trp Asp Trp Asp Gly Phe Phe Asp Pro
1               5

<210> SEQ ID NO 74
<211> LENGTH: 15
<212> TYPE: PRT
<213> ORGANISM: Artificial Sequence
<220> FEATURE:
<223> OTHER INFORMATION: Synthetic

<400> SEQUENCE: 74

Gly Gly Gly Gly Ser Gly Gly Gly Gly Ser Gly Gly Gly Gly Ser
1               5                   10                  15

<210> SEQ ID NO 75
<211> LENGTH: 21
<212> TYPE: PRT
<213> ORGANISM: Artificial Sequence
<220> FEATURE:
<223> OTHER INFORMATION: Synthetic

<400> SEQUENCE: 75

Met Ala Leu Pro Val Thr Ala Leu Leu Leu Pro Leu Ala Leu Leu Leu
1               5                   10                  15
```

-continued

His Ala Ala Arg Pro
                20

<210> SEQ ID NO 76
<211> LENGTH: 4364
<212> TYPE: DNA
<213> ORGANISM: Artificial Sequence
<220> FEATURE:
<223> OTHER INFORMATION: Synthetic

<400> SEQUENCE: 76
gagatgtaag gagctgctgt gacttgctca aggccttata tcgagtaaac ggtagtgctg      60
gggcttagac gcaggtgttc tgatttatag ttcaaaacct ctatcaatga gagagcaatc     120
tcctggtaat gtgatagatt tcccaactta atgccaacat accataaacc tcccattctg     180
ctaatgccca gcctaagttg gggagaccac tccagattcc aagatgtaca gtttgctttg     240
ctgggccttt ttcccatgcc tgcctttact ctgccagagt tatattgctg gggttttgaa     300
gaagatccta ttaaataaaa gaataagcag tattattaag tagccctgca tttcaggttt     360
ccttgagtgg caggccaggc ctggccgtga acgttcactg aaatcatggc ctcttggcca     420
agattgatag cttgtgcctg tccctgagtc ccagtccatc acgagcagct ggtttctaag     480
atgctatttc ccgtataaag catgagaccg tgacttgcca gccccacaga gccccgccct     540
tgtccatcac tggcatctgg actccagcct gggttggggc aaagagggaa atgagatcat     600
gtcctaaccc tgatcctctt gtcccacaga tatccagaac cctgaccctg ccgtgtacca     660
gctgagagac tctaaatcca gtgacaagtc tgtctgccta ttcaccgatt ttgattctca     720
aacaaatgtg tcacaaagta aggattctga tgtgtatatc acagacaaaa ctgtgctaga     780
catgaggtct atggacttca ggctccggtg cccgtcagtg ggcagagcgc acatcgccca     840
cagtccccga gaagttgggg ggaggggtcg gcaattgaac cggtgcctag agaaggtggc     900
gcggggtaaa ctgggaaagt gatgtcgtgt actggctccg cctttttccc gagggtgggg     960
gagaaccgta tataagtgca gtagtcgccg tgaacgttct ttttcgcaac gggtttgccg    1020
ccagaacaca ggtaagtgcc gtgtgtggtt cccgcgggcc tggcctcttt acgggttatg    1080
gcccttgcgt gccttgaatt acttccactg gctgcagtac gtgattcttg atcccgagct    1140
tcgggttgga agtgggtggg agagttcgag gccttgcgct taaggagccc cttcgcctcg    1200
tgcttgagtt gaggcctggc ctgggcgctg gggccgccgc gtgcgaatct ggtggcacct    1260
tcgcgcctgt ctcgctgctt tcgataagtc tctagccatt taaaattttt gatgacctgc    1320
tgcgacgctt tttttctggc aagatagtct tgtaaatgcg ggccaagatc tgcacactgg    1380
tatttcggtt tttggggccg cgggcggcga cggggcccgt gcgtcccagc gcacatgttc    1440
ggcgaggcgg ggcctgcgag cgcggccacc gagaatcgga cggggtagt ctcaagctgg     1500 ccggcctgct ctggtgcctg gcctcgcgcc gccgtgtatc gccccgccct gggcggcaag    1560
gctggcccgg tcggcaccag ttgcgtgagc ggaaagatgg ccgcttccg gccctgctgc     1620 agggagctca aaatggagga cgcggcgctc gggagagcgg cgggtgagt cacccacaca     1680 aaggaaaagg gcctttccgt cctcagccgt cgcttcatgt gactccacgg agtaccgggc    1740
gccgtccagg cacctcgatt agttctcgag cttttggagt acgtcgtctt taggttgggg    1800
ggaggggttt tatgcgatgg agtttcccca cactgagtgg gtggagactg aagttaggcc    1860
agcttggcac ttgatgtaat tctccttgga atttgccctt tttgagtttg gatcttggtt    1920
cattctcaag cctcagacag tggttcaaag ttttttttctt ccatttcagg tgtcgtgacc    1980

-continued

```
accatggcgc ttccggtgac agcactgctc ctcccttgg cgctgttgct ccacgcagca      2040
aggccgcagg tgcagctggt gcagagcgga gccgagctca agaagcccgg agcctccgtg      2100
aaggtgagct gcaaggccag cggcaacacc ctgaccaact acgtgatcca ctgggtgaga      2160
caagcccccg gccaaaggct ggagtggatg ggctacatcc tgccctacaa cgacctgacc      2220
aagtacagcc agaagttcca gggcagggtg accatcacca gggataagag cgcctccacc      2280
gcctatatgg agctgagcag cctgagggc gaggacaccg ctgtgtacta ctgtacaagg      2340
tgggactggg acggcttctt tgacccctgg ggccagggca acagtgac cgtcagcagc      2400 ggcggcggag gcagcggcgg cggcggcagc ggcggaggcg gaagcgaaat cgtgatgacc      2460
cagagccccg ccacactgag cgtgagccct ggcgagaggg ccagcatctc ctgcagggct      2520
agccaaagcc tggtgcacag caacggcaac acccacctgc actggtacca gcagagaccc      2580
ggacaggctc ccaggctgct gatctacagc gtgagcaaca ggttctccga ggtgcctgcc      2640
aggtttagcg gcagcggaag cggcaccgac tttaccctga ccatcagcag cgtggagtcc      2700
gaggacttcg ccgtgtatta ctgcagccag accagccaca tcccttacac cttcggcggc      2760
ggcaccaagc tggagatcaa aagtgctgct gcctttgtcc cggtatttct cccagccaaa      2820
ccgaccacga ctcccgcccc gcgccctccg acacccgctc ccaccatcgc ctctcaacct      2880
cttagtcttc gccccgaggc atgccgaccc gccgccgggg gtgctgttca tacgaggggc      2940
ttggacttcg cttgtgatat ttacatttgg gctccgttgg cgggtacgtg cggcgtcctt      3000
ttgttgtcac tcgttattac tttgtattgt aatcacagga atcgcaaacg gggcagaaag      3060
aaactcctgt atatattcaa acaaccattt atgagaccag tacaaactac tcaagaggaa      3120
gatggctgta gctgccgatt tccagaagaa gaagaaggag gatgtgaact gcgagtgaag      3180
ttttcccgaa gcgcagacgc tccggcatat cagcaaggac agaatcagct gtataacgaa      3240
ctgaatttgg gacgccgcga ggagtatgac gtgcttgata acgccggggg gagagacccg      3300
gaaatggggg gtaaacccg aagaaagaat ccccaagaag gactctacaa tgaactccag      3360
aaggataaga tggcggaggc ctactcagaa ataggtatga agggcgaacg acgacgggga      3420
aaaggtcacg atggcctcta ccaagggttg agtacggcaa ccaaagatac gtacgatgca      3480
ctgcatatgc aggccctgcc tcccagataa taataaaatc gctatccatc gaagatggat      3540
gtgtgttggt ttttgtgtg tggagcaaca aatctgactt tgcatgtgca aacgccttca      3600
acaacagcat tattccagaa gacaccttct tccccagccc aggtaagggc agctttggtg      3660
ccttcgcagg ctgtttcctt gcttcaggaa tggccaggtt ctgcccagag ctctggtcaa      3720
tgatgtctaa aactcctctg attggtggtc tcggccttat ccattgccac caaaaccctc      3780
tttttactaa gaaacagtga gccttgttct ggcagtccag agaatgacac gggaaaaaag      3840
cagatgaaga gaaggtggca ggagagggca cgtggcccag cctcagtctc tccaactgag      3900
ttcctgcctg cctgcctttg ctcagactgt ttgcccctta ctgctcttct aggcctcatt      3960
ctaagcccct tctccaagtt gcctctcctt atttctccct gtctgccaaa aaatctttcc      4020
cagctcacta agtcagtctc acgcagtcac tcattaaccc accaatcact gattgtgccg      4080
gcacatgaat gcaccaggtg ttgaagtgga ggaattaaaa agtcagatga ggggtgtgcc      4140
cagaggaagc accattctag ttggggggagc ccatctgtca gctgggaaaa gtccaaataa      4200
cttcagattg gaatgtgttt taactcaggg ttgagaaaac agctaccttc aggacaaaag      4260
```

-continued

```
tcagggaagg gctctctgaa gaaatgctac ttgaagatac cagccctacc aagggcaggg    4320
agaggaccct atagaggcct gggacaggag ctcaatgaga aagg                     4364
```